US008415382B2

(12) United States Patent
Costales et al.

(10) Patent No.: US 8,415,382 B2
(45) Date of Patent: Apr. 9, 2013

(54) SUBSTITUTED BENZAZOLES AND METHODS OF THEIR USE AS INHIBITORS OF RAF KINASE

(75) Inventors: Abran Costales, El Cerrito, CA (US); Teresa Hansen, Danville, CA (US); Barry H. Levine, Lafayette, CA (US); Christopher McBride, Oakland, CA (US); Daniel J. Poon, Oakland, CA (US); Savithri Ramurthy, Walnut Creek, CA (US); Paul A. Renhowe, Danville, CA (US); Cynthia M. Shafer, El Sobrante, CA (US); Sharadha Subramanian, San Ramon, CA (US); Joelle Verhagen, Richmond, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 575 days.

(21) Appl. No.: 12/205,028

(22) Filed: Sep. 5, 2008

(65) Prior Publication Data

US 2009/0035309 A1    Feb. 5, 2009

Related U.S. Application Data

(62) Division of application No. 10/967,089, filed on Oct. 15, 2004, now Pat. No. 7,423, 150.

(60) Provisional application No. 60/511,966, filed on Oct. 16, 2003.

(51) Int. Cl.
*A61K 31/44* (2006.01)
(52) U.S. Cl.
USPC .......................................................... 514/338
(58) Field of Classification Search ........................ None
See application file for complete search history.

(56) References Cited

U.S. PATENT DOCUMENTS

| | | | |
|---|---|---|---|
| 5,717,100 | A | 2/1998 | Selnick |
| 6,211,177 | B1 | 4/2001 | Sperl |
| 6,248,771 | B1 | 6/2001 | Shenoy |
| 6,268,391 | B1 | 7/2001 | Dickerson |
| 6,358,932 | B1 | 3/2002 | Monia |
| 6,399,603 | B1 | 6/2002 | Jacobs |
| 6,417,194 | B1 | 7/2002 | Fox |
| 6,458,813 | B1 | 10/2002 | Mantlo |
| 7,071,216 | B2 | 7/2006 | Renhowe |
| 7,423,150 | B2 | 9/2008 | Costales |
| 7,531,553 | B2 * | 5/2009 | Di Pietro et al. .............. 514/312 |
| 2001/0014679 | A1 | 8/2001 | Tang |
| 2004/0087626 | A1 | 5/2004 | Renhowe |
| 2004/0122237 | A1 | 6/2004 | Amiri |
| 2005/0192287 | A1 | 9/2005 | Costales |

FOREIGN PATENT DOCUMENTS

| | | |
|---|---|---|
| WO | 00/42012 A1 | 7/2000 |
| WO | WO 00/62778 A1 | 10/2000 |
| WO | WO00/62778 A1 | 10/2000 |
| WO | 01/66539 A1 | 9/2001 |
| WO | WO 01/66539 A1 | 9/2001 |
| WO | 02/42273 A2 | 5/2002 |
| WO | WO 02/42273 A2 | 5/2002 |
| WO | 02/44156 A2 | 6/2002 |
| WO | WO 02/44156 A2 | 6/2002 |
| WO | 02/076960 A1 | 10/2002 |
| WO | WO 02/076960 A1 | 10/2002 |
| WO | 02/094808 A1 | 11/2002 |
| WO | WO 02/094808 A1 | 11/2002 |
| WO | 03/082272 A1 | 10/2003 |
| WO | WO 03/082272 A1 | 10/2003 |
| WO | 2004/085425 A1 | 10/2004 |
| WO | WO 2004/085425 A1 | 10/2004 |

OTHER PUBLICATIONS

Lambert et al., Expert Opinion on Therapeutic Targets, 2007, 11(5), 589-99.*
Patani et al. Chemical Reviews, 1996, 96, 3147-76.*
Andreyev, H.J.N., et al., "Kirsten Ras Mutations in Patients With Colorectal Cancer: the Multicenter 'RASCAL' Study," Journal of the National Cancer Institute 90(9):675-684, May 6, 1998.
Banker, G.S., and C.T. Rhodes (eds.), "Modern Pharmaceutics," 3rd ed., Marcel Dekker, Inc., New York, 1996, p. 451 and p. 596.
Bos, J.L., "Ras Oncogenes in Human Cancer: A Review," Cancer Research 49(17):4682-4689, Sep. 1, 1989.
Brose, M.S., et. al., "BRAF and RAS Mutations in Human Lung Cancer and Melanoma," Cancer Research 62:6997-7000, Dec. 1, 2002.
Davies, H., et al., "Mutations of the BRAF Gene in Human Cancer," Nature 417:949-954, Jun. 27, 2002.
De Bono, J.S., and E.K. Rowinsky, "Therapeutics Targeting Signal Transduction for Patients With Colorectal Carcinoma," British Medical Bulletin 64:227-254, 2002.
Hoshino, R., et al., "Constitutive Activation of the 41-/43-kDa Mitogen-Activated Protein Kinase Signaling Pathway in Human Tumors," Oncogene 18(3):813-822, Jan. 21, 1999.
Office Action dated Jun. 15, 2004, and Response (Amendment) dated Dec. 14, 2004, from U.S. Appl. No. 10/405,945, filed Mar. 31, 2003.
Office Action (Final) dated Apr. 5, 2005, and Response (Amendment After Final) dated Jul. 21, 2005, from U.S. Appl. No. 10/405,945, filed Mar. 31, 2003.
Office Action (Advisory Action) dated Aug. 3, 2005, and Response (Supplemental Amendment After Final) dated Aug. 23, 2005, and further Response (Third Amendment After Final) dated Sep. 1, 2005, from U.S. Appl. No. 10/405,945, filed Mar. 31, 2003.
Office Action (Notice of Allowance) dated Sep. 14, 2005, from U.S. Appl. No. 10/405,945, filed Mar. 31, 2003.
Office Action dated Nov. 15, 2005, and Response (Amendment and Response) dated May 15, 2006, from U.S. Appl. No. 10/675,927, filed Sep. 29, 2003.
Office Action (Final) dated Sep. 11, 2006, and Response (Amendment and Response to Final Office Action) dated Mar. 12, 2007, from U.S. Appl. No. 10/675,927, filed Sep. 29, 2003.

(Continued)

*Primary Examiner* — Noble Jarrell
(74) *Attorney, Agent, or Firm* — Michael G. Smith

(57) ABSTRACT

New substituted benzazole compounds, compositions and methods of inhibition of Raf kinase activity in a human or animal subject are provided. The new compounds compositions may be used either alone or in combination with at least one additional agent for the treatment of a Raf kinase mediated disorder, such as cancer.

16 Claims, No Drawings

OTHER PUBLICATIONS

Office Action dated Jun. 6, 2007, and Response (Amendment After Non-Final Rejection) dated Dec. 3, 2007, from U.S. Appl. No. 10/675,927, filed Sep. 29, 2003.

Office Action (Final) dated Feb. 27, 2008, and Response (Amendment Submitted With RCE) dated Aug. 27, 2008, from U.S. Appl. No. 10/675,927, filed Sep. 29, 2003.

Office Action dated Sep. 30, 2008, and Response (Amendment After Non-Final Rejection) dated Jan. 15, 2009, from U.S. Appl. No. 10/675,927, filed Sep. 29, 2003.

Office Action (Final) dated Mar. 31, 2009, and Response (Amendment Submitted With RCE) dated Jul. 30, 2009, from U.S. Appl. No. 10/675,927, filed Sep. 29, 2003.

Office Action dated Mar. 28, 2007, and Response (Amendment and Response to Restriction Requirement) dated Apr. 13, 2007, from U.S. Appl. No. 10/967,089, filed Oct. 15, 2004.

Office Action dated May 17, 2007, and Response (Amendment After Non-Final Rejection) dated Nov. 15, 2007, from U.S. Appl. No. 10/967,089, filed Oct. 15, 2004.

Office Action (Supplemental Notice of Allowability and Examiner Interview Summary) dated Oct. 27, 2008, from U.S. Appl. No. 10/967,089, filed Oct. 15, 2004.

Pollack, RM., et al., "High Frequency of BRAF Mutations in Nevi," in "Brief Communications," Nature Genetics 33:19-20, 2002.

Rowinsky, E.K., et al., "Ras Protein Farnesyltransferase: a Strategic Target for Anticancer Therapeutic Development," Journal of Clinical Oncology 17(11):3631-3652, 1999.

Scharovsky, O.G., et al., "Inhibition of Ras Oncogene: a Novel Approach to Antineoplastic Therapy," Journal of Biomedical Science 7:292-298, 2000.

Wolff, M.E. (ed.(, "Burger's Medicinal Chemistry and Drug Discovery, vol. 1: Principles and Practice," 5th ed., John Wiley & Sons, New York, 1995, pp. 975-977.

Yuen, S.T., et al., "Similarity of the Phenotypic Patterns Associated with BRAF and KRAS Mutations in Colorectal Neophasia," Cancer Research 62:6451-6455, Nov. 15, 2002.

Moore, M., et al., "Phase I Study of the Raf-1 Kinase Inhibitor Bay 43-9006 in Patients With Advanced Refractory Solid Tumors," Proceedings of the American Society of Clinical Oncology 21:2002 (Abstract 1816), <http://www.asco.org/portal/site/ASCO/template.RAW/menuitem.34d60f5624ba07fd506fe . . . > [retrieved Dec. 3, 2008], 2 pages.

Strumberg, D., et al., "Final Results of a Phase I Pharmocokinetic and Pharmocodynamic Study of the Raf Kinase Inhibitor BAY 43-9006 in Patients With Solid Tumors," Proceedings of American Society of Clinical Oncology 21:2002 (Abstract 121), <http://www.asco.org/portal/site/ASCO/template.RAW/menuitem.34d60f5624ba07fd506fe . . . > [retrieved Dec. 3, 2008], 2 pages.

English Translation of Patentability Examination Report issued Oct. 26, 2010, in related Ecuadorian Patent Application No. 04-5407 PCT, filed Mar. 31, 2003, provided by Ecuadorian foreign associate on Jan. 3, 2011, 3 pages.

* cited by examiner

SUBSTITUTED BENZAZOLES AND METHODS OF THEIR USE AS INHIBITORS OF RAF KINASE

CROSS-REFERENCE(S) TO RELATED APPLICATION(S)

This application is a divisional of U.S. application Ser. No. 10/967,089 filed on 15 Oct. 2004, which is a nonprovisional filing of U.S. Provisional Application Ser. No. 60/511,966 filed on 16 Oct. 2003, the contents of which are incorporated herein by reference in their entirety.

FIELD OF THE INVENTION

The present invention relates to new substituted benzazole compounds and pharmaceutically acceptable salts, esters or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND OF THE INVENTION

The Raf serine/threonine kinases are essential components of the Ras Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase) (Crews et al. (1993) Cell 74:215). The Raf serine/threonine kinases are considered to be the primary Ras effectors involved in the proliferation of animal cells (Avruch et al. (1994) Trends Biochem Sci. 19:279).

Raf kinase has three distinct isoforms, Raf-1 (c-Raf), A-Raf, and B-Raf, distinguished by their ability to interact with Ras, to activate MAPK kinase pathway, tissue distribution and sub-cellular localization (Marias et. al., Biochem. J. 351: 289-305, 2000; Weber et al., Oncogene 19:169-176, 2000; Pritchard et al., Mol. Cell. Biol. 15:6430-6442, 1995). Raf kinases are activated by Ras and phosphorylate and activate two isoforms of Mitogen-Activated Protein Kinase Kinase (called Mek1 and Mek2) that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including cytosolic proteins and ETS family of transcription factors. Raf kinase participation in the Ras/MAPK pathway influences and regulates many cellular functions such as proliferation, differentiation, survival, cell cycle progression and apoptosis.

Activating mutation of one of the Ras genes can be seen in ~20% of all tumors and the Raf/MEK/ERK pathway is activated in ~30% of all tumors (Bos et. al., Cancer Res. 49:4682-4689, 1989) (Hoshino et. al., Oncogene 18:813-822, 1999). Recent studies have shown that B-Raf mutation in the skin nevi is a critical step in the initiation of melanocytic neoplasia (Pollock et. al., Nature Genetics 25:1-2, 2002). Furthermore, most recent studies have emerged that activating mutation in the kinase domain of B-Raf occurs in ~66% of melanomas, 12% of colon carcinoma and 14% of liver cancer (Davies et. al., Nature 417:949-954, 2002) (Yuen et. al., Cancer Research 62:6451-6455, 2002) (Brose et. al., Cancer Research 62:6997-7000, 2002).

Inhibitors of Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Raf itself. In the early clinical trails inhibitor of Raf-1 kinase that also inhibit B-Raf have shown promise as therapeutic agents in cancer therapy (Crump, Current Pharmaceutical Design 8: 2243-2248, 2002; Sebastien et. al., Current Pharmaceutical Design 8: 2249-2253, 2002). In addition, an orally administered Raf kinase inhibitor that inhibits both B-Raf and C-Raf, BAY 43-9006, is currently undergoing worldwide clinical evaluation in phase I and II clinical studies in patients with a variety of malignancies, including melanomas (Tuveson et al., Cancer Cell 4: 95-98, 2003).

Disruption of Raf expression in cell lines through the application of RNA antisense technology has been shown to suppress both Ras and Raf-mediated tumorigenicity (Kolch et al., Nature 349:416-428, 1991; Monia et al., Nature Medicine 2(6):668-675, 1996). In recent studies, reduction in B-Raf levels with RNA interference in melanoma cells resulted in a profound inhibition of the MAP kinase cascade, diminished proliferative capacity, and the inability to support anchorage-independent cell growth (Tuveson et al., Cancer Cell 4: 95-98, 2003).

Several Raf kinase inhibitors have been described as exhibiting efficacy in inhibiting tumor cell proliferation in vitro and or in vivo assays (see, e.g., U.S. Pat. Nos. 6,391,636, 6,358, 932, 6,037,136, 5,717,100, 6,458,813, 6,204,467, and 6,268, 391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932, 5,717,100, 6,458,813, 6,268,391, and 6,204,467, and published U.S. Patent Application No. 20010014679).

Certain benzazole compounds and their use as Raf kinase inhibitors are disclosed in WO03082272 and published U.S. Patent Application No. 20040122237 A1. However, these published applications do not disclose the carboxamide compounds of the present invention.

SUMMARY OF THE INVENTION

New substituted benzazole compounds and pharmaceutically acceptable salts thereof or esters having a solubility enhancing moieties or prodrugs thereof are provided of the formula (I):

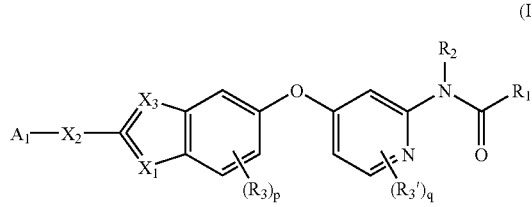

(I)

wherein, $X_1$ and $X_3$ are independently selected from N, —$NR_4$—, —O— or —S—, wherein $R_4$ is hydrogen or loweralkyl, provided that at least one of $X_1$ and $X_3$ must be N or —$NR_4$—;

$X_2$ is —NH— or —$(CH_2)_m$—, wherein m is 0, 1, 2, 3 or 4;

$A_1$ is substituted or unsubstituted alkyl, cycloalkyl, heterocycloalkyl, aryl, polycyclic aryl, polycyclic arylalkyl, heteroaryl, biaryl, heteroarylaryl, or heteroarylheteroaryl;

$R_1$ is hydrogen or substituted or unsubstituted loweralkyl, alkoxyalkyl, loweralkyloxy, amino, aminoalkyl, cycloalkyl, heterocycloalkyl, aryl, heteroaryl, alkyloxyalkylheterocycloalkyl, heteroarylalkyl, cycloalkyloweralkyl, heterocycloalkylloweralkyl, loweralkylheterocycloalkyl, aryllower-alkyl, heteroarylloweralkyl, alkyloxyalkylheterocycloloweralkyl, or heteroarylloweralkyl;

$R_2$ is hydrogen or loweralkyl;

each $R_3$ and $R_3'$ are independently selected from hydrogen, halogen, hydroxy, cyano, loweralkyl, or loweralkoxy; and p and q are independently 0, 1, 2 or 3; or a pharmaceutically acceptable salt, ester or prodrug thereof.

In other embodiments, new substituted benzimidazole compounds are provided of the formula (II):

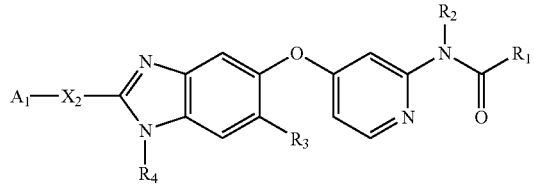

(II)

wherein and $X_2$, $A_1$, $R_1$, $R_2$, $R_3$, and $R_4$ are as defined above; or a pharmaceutically acceptable salt, ester or prodrug thereof.

In other embodiments, new substituted benzazole compounds are provided of the formula (III):

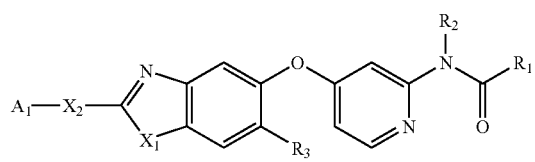

(III)

wherein and $X_1$, $X_2$, $A_1$, $R_1$, $R_2$, and $R_3$ are as defined above; or a pharmaceutically acceptable salt, ester or prodrug thereof.

In other embodiments, new substituted benzazole compounds are provided of the formula (IV):

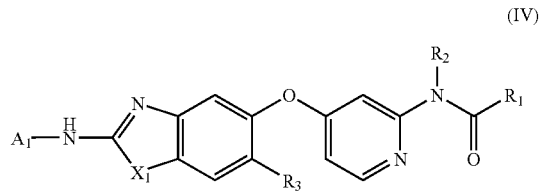

(IV)

wherein $X_1$, $A_1$, $R_1$, $R_2$, and $R_3$ are as defined above; or a pharmaceutically acceptable salt, ester or prodrug thereof.

In yet other embodiments, new substituted benzimidazole compounds are provided of the formula (V):

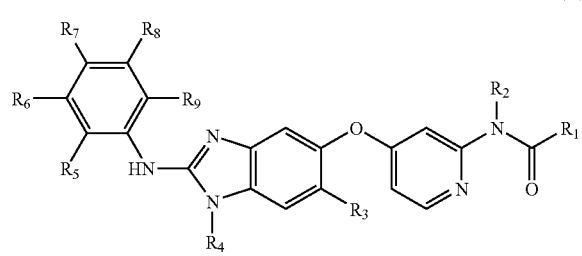

(V)

wherein $R_1$, $R_2$, $R_3$ and $R_4$ are as defined above; and $R_5$, $R_6$, $R_7$, $R_8$ and $R_9$ are independently selected from hydrogen, halo, loweralkyl, cyano, hydroxy, haloloweralkyl, loweralkyloxy, haloloweralkyloxy, loweralkylthio, haloloweralkylthio, and substituted or unsubstituted cycloalkyl, heterocycloalkyl, aryl, or heteroaryl; or a pharmaceutically acceptable salt, ester or prodrug thereof.

In yet other embodiments, new substituted benzimidazole compounds are provided of the formula (VI):

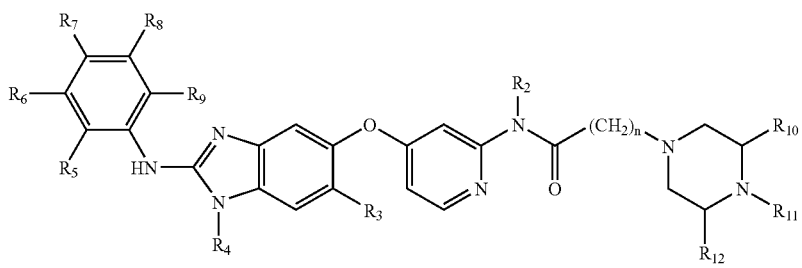

wherein $R_2$, $R_3$, $R_4$ $R_5$, $R_6$, $R_7$, $R_8$ and $R_9$ are as defined above;

n is 0, 1, 2, 3 or 4

$R_{10}$, and $R_{12}$ are independently selected from hydrogen, halo, loweralkyl, haloloweralkyl, hydroxyloweralkyl, loweralkyloxy, haloloweralkyloxy, loweralkylsulfonyl, haloloweralkylsulfonyl, and substituted or unsubstituted cycloalkyl, heterocycloalkyl, aryl, or heteroaryl; and $R_{11}$ is hydrogen, loweralkyl, haloloweralkyl, hydroxyloweralkyl, loweralkyloxy, haloloweralkyloxy, loweralkyloxyloweralkyl, and substituted or unsubstituted cycloalkyl, heterocycloalkyl, aryl, or heteroaryl; or a pharmaceutically acceptable salt, ester or prodrug thereof.

In other aspects, the present invention provides methods for treating Raf related disorders in a human or animal subject in need of such treatment comprising administering to said subject an amount of a compound of formula (I), (II), (III), (IV), (V) or (VI) effective to reduce or prevent tumor growth in the subject.

In yet other aspects, the present invention provides methods for treating Raf related disorders in a human or animal subject in need of such treatment comprising administering to said subject an amount of a compound of formula (I), (II), (III), (IV), (V) or (VI) effective to reduce or prevent tumor growth in the subject in combination with at least one additional agent for the treatment of cancer.

In yet other aspects, the present invention provides therapeutic compositions comprising at least one compound of formula (I), (II), (III), (IV), (V) or (VI) in combination with one or more additional agents for the treatment of cancer, as are commonly employed in cancer therapy.

In yet other aspects, the present invention provides a compound of formula (I), (II), (III), (IV), (V) or (VI) for use as a pharmaceutical. The present invention further provides for the use of a compound of formula (I), (II), (III), (IV), (V) or (VI) in the manufacture of a medicament for the treatment of cancer.

The compounds of the invention are useful in the treatment of cancers, including malignant melanoma, papillary thyroid cancer, cholangiocarcinoma, gallbladder carcinoma, colorectal cancer, lung cancer, pancreatic cancer, leukemias, prostate cancer, ovarian cancer, breast cancer and lung cancer.

The invention further provides compositions, methods of use, and methods of manufacture as described in the detailed description of the invention.

DETAILED DESCRIPTION OF THE PREFERRED EMBODIMENT

In accordance with one aspect of the present invention, new substituted benzazole compounds and pharmaceutically acceptable salts, esters or prodrugs thereof are provided of the formula (I):

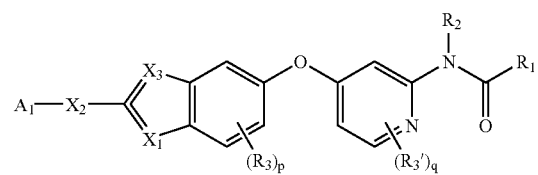

wherein, $X_1$ and $X_3$ are independently selected from N, —$NR_4$—, —O— or —S—, wherein $R_4$ is hydrogen or loweralkyl, provided that at least one of $X_1$ and $X_3$ must be N or —$NR_4$—;

$X_2$ is —NH— or —$(CH_2)_m$—, wherein m is 0, 1, 2, 3 or 4;

$A_1$ is substituted or unsubstituted alkyl, cycloalkyl, heterocycloalkyl, aryl, polycyclic aryl, polycyclic arylalkyl, heteroaryl, biaryl, heteroarylaryl, or heteroarylheteroaryl;

$R_1$ is hydrogen or substituted or unsubstituted loweralkyl, alkoxyalkyl, loweralkyloxy, amino, aminoalkyl, cycloalkyl, heterocycloalkyl, aryl, heteroaryl, alkyloxyalkylheterocycloalkyl, heteroarylalkyl, cycloalkyloweralkyl, heterocycloalkylloweralkyl, loweralkylheterocycloalkyl, aryllower-alkyl, heteroarylloweralkyl, alkyloxyalkylheterocycloloweralkyl, or heteroarylloweralkyl;

$R_2$ is hydrogen or loweralkyl;

each $R_3$ and $R_3'$ are independently selected from hydrogen, halogen, hydroxy, cyano, loweralkyl, or loweralkoxy; and p and q are independently 0, 1, 2 or 3; or a pharmaceutically acceptable salt, ester or prodrug thereof.

In some aspects of the invention, $X_1$ in formula (I) is —$NR_4$—. Thus, in some embodiments, new substituted benzimidazole compounds are provided of the formula (II):

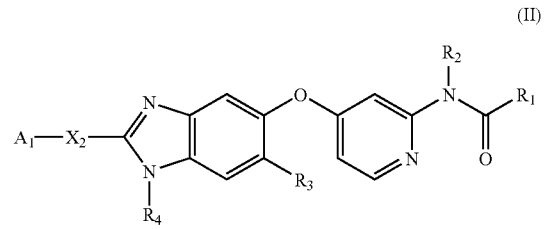

wherein and $X_2$, $A_1$, $R_1$, $R_2$, $R_3$, and $R_4$ are as defined above; or a pharmaceutically acceptable salt, ester or prodrug thereof.

In other embodiments of the invention, $X_3$ is N and $X_4$, is —CH— in formula (I). Thus, in some aspects the invention provides new substituted benzazole compounds of the formula (III):

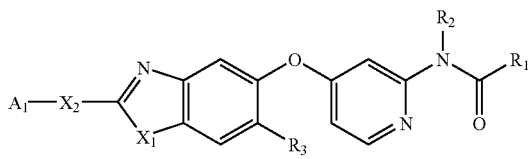

(III)

wherein and $X_1$, $X_2$, $A_1$, $R_1$, $R_2$, and $R_3$ are as defined above; or a pharmaceutically acceptable salt, ester or prodrug thereof.

In other embodiments of the invention, $X_2$ is —NH— in formula (I). Thus, in some aspects, new substituted benzazole compounds are provided of the formula (IV):

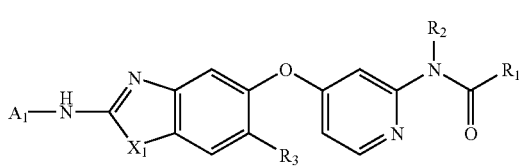

(IV)

wherein $X_1$, $A_1$, $R_1$, $R_2$, and $R_3$ are as defined above; or a pharmaceutically acceptable salt, ester or prodrug thereof.

In yet other embodiments of the invention, $X_1$ —$NR_4$—, $X_2$ is —NH—, X3 is N, $X_4$ is —CH— and $A_1$ is in formula (I) has the structure:

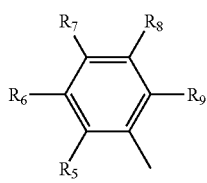

wherein $R_5$, $R_6$, $R_7$, $R_8$ and $R_9$ are independently selected from hydrogen, halo, loweralkyl, cyano, hydroxy, haloloweralkyl, loweralkyloxy, haloloweralkyloxy, loweralkylthio, haloloweralkylthio, and substituted or unsubstituted cycloalkyl, heterocycloalkyl, aryl, or heteroaryl. Thus, in some aspects, new substituted benzimidazole compounds are provided of the formula (V):

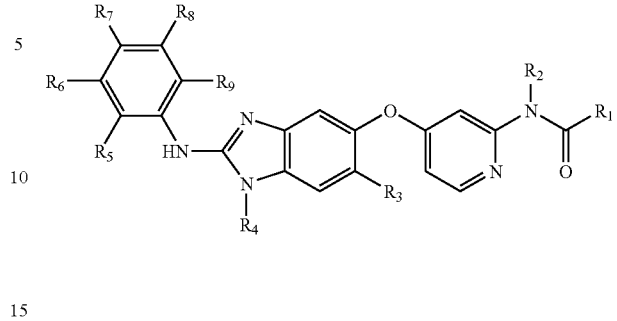

(V)

wherein $R_1$, $R_2$, $R_3$ and $R_4$ are as defined above; and $R_5$, $R_6$, $R_7$, $R_8$ and $R_9$ are independently selected from hydrogen, halo, loweralkyl, cyano, hydroxy, haloloweralkyl, loweralkyloxy, haloloweralkyloxy, loweralkylthio, haloloweralkylthio, and substituted or unsubstituted cycloalkyl, heterocycloalkyl, aryl, or heteroaryl; or a pharmaceutically acceptable salt, ester or prodrug thereof. In representative, but non-limiting embodiments, $R_5$, $R_6$, $R_7$, $R_8$ and $R_9$ may be independently selected from, for example, hydrogen, chloro, fluoro, methyl, ethyl, propyl, isopropyl, butyl, tert-butyl, methyloxy, trifluoromethyl, trifluoromethoxy, trifluoromethylthio, acetyl, and substituted or unsubstituted phenyl, phenyloxy, furyl, tetrahydrofuranyl, tetrahydropyranyl, pyridinyl, trifluoromethylpiperidinyl, thiophenyl, piperazinyl, and morpholinyl.

In yet other embodiments, $R_1$ in formula (V) has the structure:

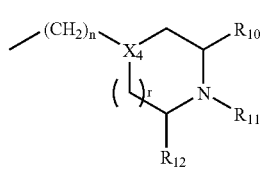

wherein n is 0, 1, 2, 3 or 4;

r is 1 or 2;

$X_4$ is —CH— or N $R_{10}$, and $R_{12}$ are independently selected from hydrogen, halo, loweralkyl, haloloweralkyl, hydroxyloweralkyl, loweralkyloxy, haloloweralkyloxy, loweralkylsulfonyl, haloloweralkylsulfonyl, and substituted or unsubstituted cycloalkyl, heterocycloalkyl, aryl, or heteroaryl; and $R_{11}$ is hydrogen, loweralkyl, haloloweralkyl, hydroxyloweralkyl, loweralkyloxy, haloloweralkyloxy, loweralkyloxyloweralkyl, and substituted or unsubstituted cycloalkyl, heterocycloalkyl, aryl, or heteroaryl. In some presently preferred embodiments, r is 1 and $X_4$ is N. Thus, in some aspects the invention provides new substituted benzimidazole compounds are provided of the formula (VI):

(VI)

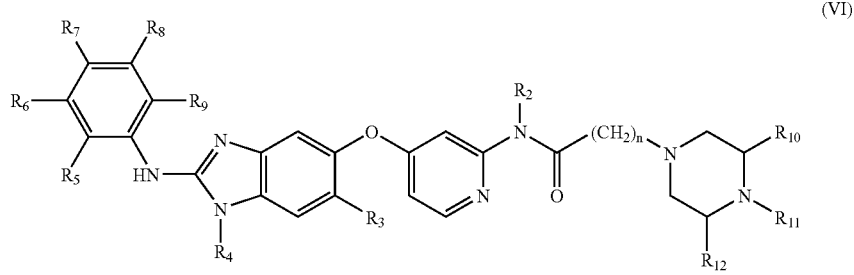

wherein $R_2$, $R_3$, $R_4$, $R_5$, $R_6$, $R_7$, $R_8$ and $R_9$ are as defined above;

n is 0, 1, 2, 3 or 4;

$R_{10}$, and $R_{12}$ are independently selected from hydrogen, halo, loweralkyl, haloloweralkyl, hydroxyloweralkyl, loweralkyloxy, haloloweralkyloxy, loweralkylsulfonyl, haloloweralkylsulfonyl, and substituted or unsubstituted cycloalkyl, heterocycloalkyl, aryl, or heteroaryl; and $R_{11}$ is hydrogen, loweralkyl, haloloweralkyl, hydroxyloweralkyl, loweralkyloxy, haloloweralkyloxy, loweralkyloxyloweralkyl, and substituted or unsubstituted cycloalkyl, heterocycloalkyl, aryl, or heteroaryl; or a pharmaceutically acceptable salt, ester or prodrug thereof.

In another aspect, the present invention provides methods of treating human or animal subjects suffering from a Raf related disorder, such as cancer. Thus, the present invention provides methods of treating a human or animal subject in need of such treatment comprising administering to the subject a therapeutically effective amount of a compound of formula (I), (II), (III), (IV), (V) or (VI) above, either alone or in combination with other anticancer agents.

In other aspects, the present invention provides methods for treating Raf related disorders in a human or animal subject in need of such treatment comprising administering to said subject an amount of a compound of formula (I), (II), (III), (IV) or (V) effective to reduce or prevent tumor growth in the subject.

In yet other aspects, the present invention provides methods for treating Raf related disorders in a human or animal subject in need of such treatment comprising administering to said subject an amount of a compound of formula (I), (II), (III), (IV) or (V) effective to reduce or prevent tumor growth in the subject in combination with at least one additional agent for the treatment of cancer. A number of suitable anticancer agents to be used as combination therapeutics are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and or radionuclides; biological response modifiers (e.g. interferons [e.g. IFN-a, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of formula (I), (II), (III), (IV), (V) or (VI) are known to those skilled in the art.

In preferred embodiments, anticancer agents to be used in combination with compounds of the present invention comprise agents that induce or stimulate apoptosis. Agents that induce apoptosis include, but are not limited to, radiation; kinase inhibitors (e.g., epidermal growth factor receptor [EGFR] kinase inhibitor, vascular endothelial growth factor receptor [VEGFR] kinase inhibitor, fibroblast growth factor receptor [FGFR] kinase inhibitor, platelet-derived growth factor receptor [PGFR] I kinase inhibitor, and Bcr-Abl kinase inhibitors such as Gleevec® [imatinib mesylate or STI-571]); antisense molecules; antibodies [e.g., Herceptin® anti-HER monoclonal antibody and Rituxan® anti-CD20 monoclonal antibody]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib®, meloxicam, NS-398, and non-steroidal antiinflammatory drugs (NSAIDs)]; and cancer chemotherapeutic drugs [e.g., irinotecan (Camptosar®), CPT-11, fludarabine (Fludara®), dacarbazine (DTIC®), dexamethasone, mitoxantrone, Mylotarg®, VP-16, cisplatinum, 5-FU, doxrubicin, docetaxel (Taxotere® or taxol, dacarbazine, aldesleukin, capecitabine, and Iressa® (gefitinib)]; cellular signaling molecules; ceramides and cytokines; and staurosprine, and the like.

In some embodiments of this aspect of the invention, anticancer agents to be used in combination with compounds of the present invention include, for example, dacarbazine, irinotecan, topotecan, gemcitabine, 5-fluorouracil, leucovorin carboplatin, cisplatin, taxanes, tezacitabine, cyclophosphamide, vinca alkaloids, imatinib, anthracyclines, rituximab and trastuzumab In other aspects, the present invention provides pharmaceutical compositions comprising at least one compound of formula I, II, III, IV or V together with a pharmaceutically acceptable carrier suitable for administration to a human or animal subject, either alone or together with other anticancer agents.

In other aspects, the present invention provides methods of manufacture of compounds of formula (I), (II), (III), (IV), (V) or (VI) as described herein.

In yet other aspects, the present invention provides compounds which are inhibitors of the enzyme raf kinase. Since the enzyme is a downstream effector of $p21^{ras}$, the instant inhibitors are useful in pharmaceutical compositions for human or veterinary use where inhibition of the raf kinase pathway is indicated, e.g., in the treatment of tumors and or cancerous cell growth mediated by raf kinase. In particular, the compounds are useful in the treatment of human or animal, e.g., murine cancer, since the progression of these cancers is dependent upon the ras protein signal transduction cascade and therefore is susceptible to treatment by interruption of the cascade by inhibiting raf kinase activity. Accordingly, the compounds of the invention are useful in treating cancers, such as, for example, malignant melanoma, papillary thyroid cancer, cholangiocarcinoma, gallbladder carcinoma, colorectal cancer, lung cancer, pancreatic cancer, leukemias, prostate cancer, ovarian cancer, breast cancer and lung cancer.

"Raf inhibitor" is used herein to refer to a compound that exhibits an $IC_{50}$ with respect to Raf Kinase activity of no more than about 100 µM and more typically not more than about 50 µM, as measured in the Raf/Mek Filtration Assay described generally hereinbelow. Preferred isoforms of Raf Kinase in which the compounds of the present invention will be shown to inhibit, include A-Raf, B-Raf, and C-Raf (Raf-1). "$IC_{50}$" is that concentration of inhibitor which reduces the activity of an enzyme (e.g., Raf kinase) to half-maximal level. Representative compounds of the present invention have been discovered to exhibit inhibitory activity against Raf. Compounds of the present invention preferably exhibit an $IC_{50}$ with respect to Raf of no more than about 10 µM, more preferably, no more than about 5 µM, even more preferably not more than about 1 µM, and most preferably, not more than about 200 nM, as measured in the Raf kinase assays described herein.

As used herein, the term "benzazoles" includes benzimidazoles, benzothiazoles and benzoxazoles.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: $CH(CH_3)_2$, —$CH(CH_3)(CH_2CH_3)$, —$CH(CH_2CH_3)_2$, —$C(CH_3)_3$, —$C(CH_2CH_3)_3$, —$CH_2$ $CH(CH_3)_2$, —$CH_2CH(CH_3)$ $(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, —$CH(CH_3)CH(CH_3)CH(CH_3)_2$, —$CH(CH_2CH_3)CH(CH_3)CH(CH_3)(CH_2CH_3)$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups includes primary alkyl groups, secondary alkyl groups, and tertiary alkyl groups. Preferred alkyl groups include straight and branched chain alkyl groups and cyclic alkyl groups having 1 to 12 carbon atoms.

As used herein "loweralkyl" includes both substituted or unsubstituted straight or branched chain alkyl groups having from 1 to 6 carbon atoms. Representative loweralkyl groups include, for example, methyl, ethyl, propyl, isopropyl, n-butyl, tert-butyl, neopentyl, trifluoromethyl, pentafluoroethyl and the like. Loweralkyl groups may be substituted, such as with halo, hydroxy, amino, nitro and or cyano groups, and the like. Representative of halo-substituted and hydroxy-substituted loweralkyl include chloromethyl, trichloromethyl, fluoromethyl, trifluoromethyl, chloroethyl, fluoroethyl, hydroxyethyl, perfluoropentyl, perfluoroheptyl and the like. Other suitable substituted loweralkyl moieties include, for example, aralkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

"Loweralkoxy" as used herein refers to RO— wherein R is loweralkyl. Representative examples of loweralkoxy groups include methoxy, ethoxy, t-butoxy, trifluoromethoxy and the like.

As used herein, the term "halogen" or "halo" refers to chloro, bromo, fluoro and iodo groups. "Haloalkyl" refers to an alkyl radical substituted with one or more halogen atoms. The term "haloloweralkyl" refers to a loweralkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Amino" refers herein to the group —$NH_2$. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term amino acid refers to both alpha and beta amino acids having D- or L-stereochemistry, and includes, but is not limited to, synthetic, non-natural amino acids having side chains other than those found in the 20 common amino acids. Non-natural amino acids are commercially available or may be prepared according to U.S. Pat. No. 5,488,131 and references therein. Amino acids may be further substituted to contain modifications to their amino, carboxy, or side chain groups. These modifications include the numerous protecting groups commonly used in peptide synthesis.

The term "alkoxyalkyl" refers to the group -$alk_1$-O-$alk_2$ where $alk_1$ is alkyl or alkenyl, and $alk_2$ is alkyl or alkenyl. The term "loweralkoxyalkyl" refers to an alkoxyalkyl where $alk_1$ is loweralkyl or loweralkenyl, and $alk_2$ is loweralkyl or loweralkenyl. The term "aryloxyalkyl" refers to the group -alkyl-O-aryl. The term "aralkoxyalkyl" refers to the group -alkylenyl-O-aralkyl, where aralkyl is a loweraralkyl.

The term "alkoxyalkylamino" refers herein to the group —NR-(alkoxyalkyl), where R is typically hydrogen, loweraralkyl, or loweralkyl. The term "aminoloweralkoxyalkyl" refers herein to an aminoalkoxyalkyl in which the alkoxyalkyl is a loweralkoxyalkyl.

The term "aminocarbonyl" refers herein to the group —C(O)—$NH_2$. "Substituted aminocarbonyl" refers herein to the group —C(O)—NRR' where R is loweralkyl and R' is hydrogen or a loweralkyl. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —$S(O)_2$—$NH_2$. "Substituted aminosulfonyl" refers herein to the group —$S(O)_2$—NRR' where R is loweralkyl and R' is hydrogen or a loweralkyl. The term "aralkylaminosulfonylaryl" refers herein to the group -aryl-$S(O)_2$—NH-aralkyl, where the aralkyl is loweraralkyl.

"Carbonyl" refers to the divalent group —C(O)—.

"Carbonyloxy" refers generally to the group —C(O)—O. Such groups include esters, —C(O)—O—R, where R is loweralkyl, cycloalkyl, aryl, or loweraralkyl. The term "carbonyloxycycloalkyl" refers generally herein to both a "carbonyloxycarbocycloalkyl" and a "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl, where the aralkyl is loweraralkyl.

The term "sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically loweralkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl" refers herein to the group —SO$_2$-aralkyl, in which the aralkyl is loweraralkyl. The term "sulfonamido" refers herein to —SO$_2$NH$_2$.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—O—R, where R is a straight or branched chain loweralkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is a lower aralkyl. As used herein, the term "aminocarbonyl" refers to the divalent group —C(O)—NH— in which the hydrogen atom of the amide nitrogen of the carbonylamino group can be replaced a loweralkyl, aryl, or loweraralkyl group, as described above.

As used herein, the term "guanidino" or "guanidyl" refers to moieties derived from guanidine, H$_2$N—C(=NH)—NH$_2$. Such moieties include those bonded at the nitrogen atom carrying the formal double bond (the "2"-position of the guanidine, e.g., diaminomethyleneamino, (H$_2$N)$_2$C=NH—) and those bonded at either of the nitrogen atoms carrying a formal single bond (the "1-" and/or "3"-positions of the guanidine, e.g., H$_2$N—C(=NH)—NH—). The hydrogen atoms at any of the nitrogens can be replaced with a suitable substituent, such as loweralkyl, aryl, or loweraralkyl.

As used herein, the term "amidino" refers to the moieties R—C(=N)—NR'— (the radical being at the "N$^1$" nitrogen) and R(NR')C=N— (the radical being at the "N$^2$" nitrogen), where R and R' can be hydrogen, loweralkyl, aryl, or loweraralkyl.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures. Examples of such polycyclic structures include bicyclic compounds having two bridgehead atoms connected by three or more arms. An example of a bicyclic structure is bicyclo[2.2.1]heptane, in which the bridgehead atoms are connected by three arms respectively having two, two, and one carbon atoms.

The term "substituted heterocycle" or "heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclic moieties can be unsubstituted or monosubstituted or disubstituted with various substituents independently selected from hydroxy, halo, oxo (C=), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl.

The heterocyclic groups may be attached at various positions as will be apparent to those having skill in the organic and medicinal chemistry arts in conjunction with the disclosure herein.

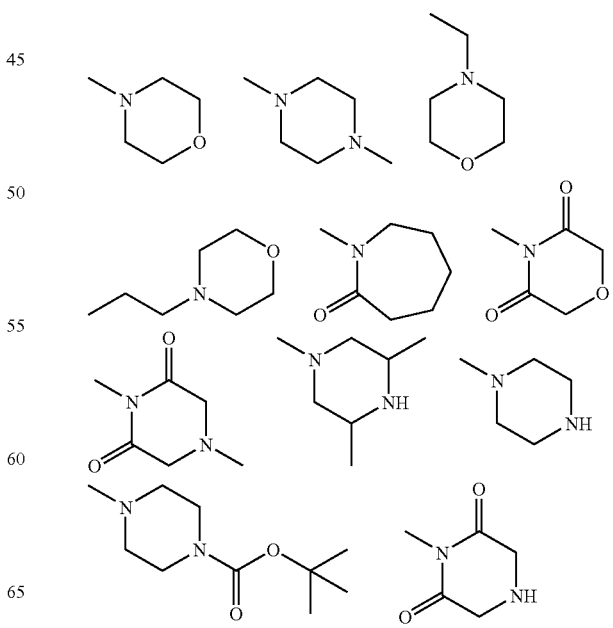

-continued

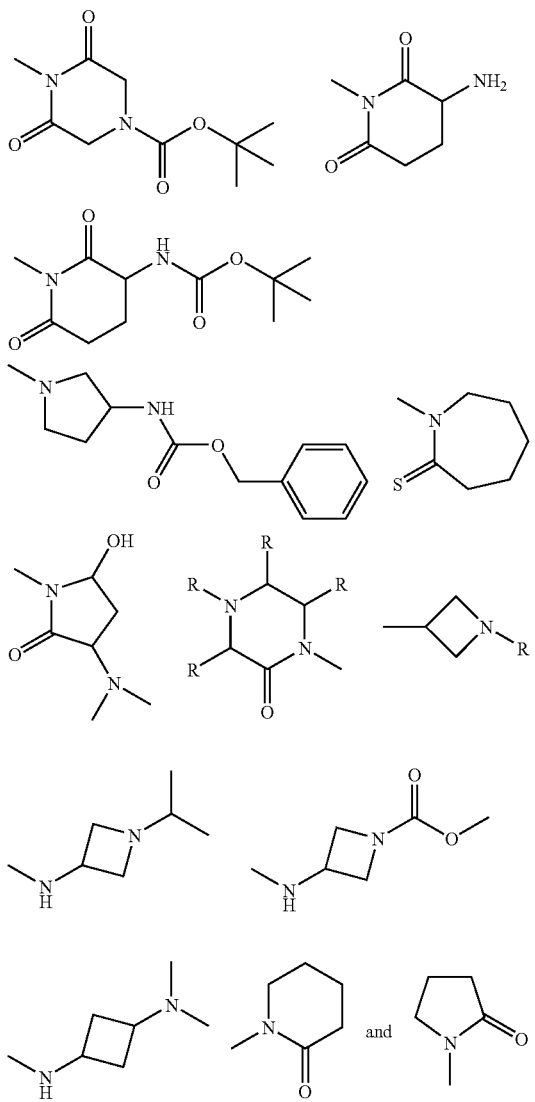

where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e.,

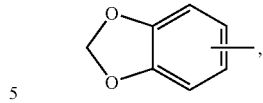

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

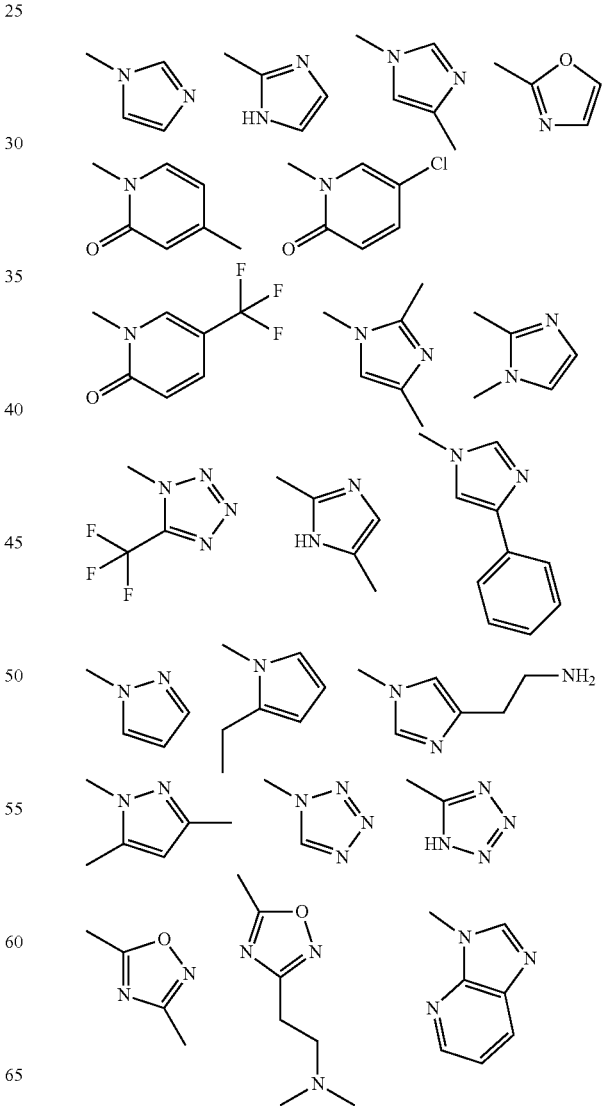

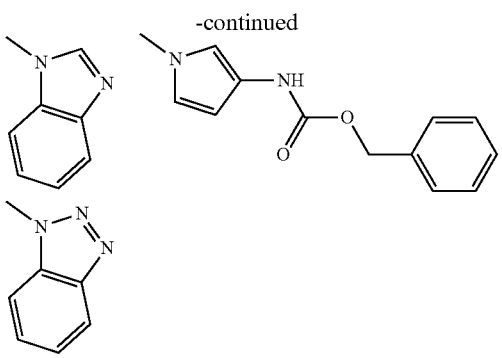

Representative heteroaryl groups include, for example, imidazolyl, pyridyl, piperazinyl, azetidinyl, thiazolyl, triazolyl benzimidazolyl, benzothiazolyl, benzoxazolyl, pyrazolyl and pyrazinyl.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)phenyl]acetamide, 1,4-diphenylbenzene, N-[4-(2-phenylethynyl)phenyl]-2-[benzylamino]acetamide, 2-amino-N-[4-(2-phenylethynyl) phenyl]propanamide, 2-amino-N-[4-(2-phenylethynyl) phenyl]acetamide, 2-(cyclopropylamino)-N-[4-(2-phenylethynyl)phenyl]acetamide, 2-(ethylamino)-N-[4-(2-phenylethynyl)phenyl]acetamide, 2-[(2-methylpropyl) amino]-N-[4-(2-phenylethynyl)phenyl]acetamide, 5-phenyl-2H-benzo[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)[4-(2-phenylethynyl) phenyl]carboxamide, 2-{[(4-fluorophenyl)methyl]amino}-N-[4-(2-phenylethynyl)phenyl]acetamide, 2-{[(4-methylphenyl)methyl]amino}-N-[4-(2-phenylethynyl) phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethylmethylamino)-N-[4-(2-phenylethynyl)phenyl]acetamide, 2-(butylamino)-N-[4-(2-phenyl ethynyl)phenyl]acetamide, N-[4-(2-phenylethynyl)phenyl]-2-(4-pyridylamino)acetamide, N-[4-(2-phenylethynyl)phenyl]-2-(quinuclidin-3-ylamino) acetamide, N-[4-(2-phenylethynyl)phenyl]pyrrolidin-2-ylcarboxamide, 2-amino-3-methyl-N-[4-(2-phenylethynyl)-phenyl]butanamide, 4-(4-phenylbuta-1,3-diynyl) phenylamine, 2-(dimethylamino)-N-[4-(4-phenylbuta-1,3-diynyl)phenyl]acetamide, 2-(ethylamino)-N-[4-(4-phenylbuta-1,3-diynyl)-phenyl]acetamide, 4-ethyl-1-phenylbenzene, 1-[4-(2-phenyl ethynyl)phenyl]ethan-1-one, N-(1-carbamoyl-2-hydroxypropyl)[4-(4-phenylbuta-1,3-diynyl)phenyl]carboxamide, N-[4-(2-phenylethynyl)phenyl] propanamide, 4-methoxyphenyl phenyl ketone, phenyl-N-benzamide, (tert-butoxy)-N-[(4-phenylphenyl)methyl] carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenylpyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl (2-thienyl))methane, 5-[(4-methylpiperazinyl)methyl]-2-phenylthiophene, 2-(4-ethylphenyl)thiophene, 4-methylthio-1-(2-thienyl)benzene, 2-(3-nitrophenyl)thiophene, (tert-butoxy)-N-[(5-phenyl(3-pyridyl))methyl]carboxamide, hydroxy-N-[(5-phenyl(3-pyridyl))methyl]-amide, 2-(phenylmethylthio)pyridine, and benzylimidazole.

The term "heteroarylheteroaryl" refers to a biaryl group where both of the aryl groups are a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl(3-pyrazin-2-yl(4-pyridyl))amine, and dimethyl {2-[2-(5-methylpyrazin-2-yl) ethynyl] (4-pyridyl)}amine.

"Optionally substituted" or "substituted" refers to the replacement of one or more hydrogen atoms with a monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like. The term substituted and unsubstituted, when introducing a list of substituents, is intended to apply to each member of that list. For instance the phrase "substituted and unsubstituted aryl, heteroaryl, or alkyl" and the phrase "substituted and unsubstituted aryl, heteroaryl, and alkyl" is intended to specify aryl, heteroaryl, and alky groups that are each substituted or unsubstituted.

The substitution group can itself be substituted. The group substituted onto the substitution group can be carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

As used herein, the term "carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, loweralkyl esters, secondary amides and the like.

As used herein, the term "pharmaceutically acceptable salts" refers to the nontoxic acid or alkaline earth metal salts of the compounds of Formula I. These salts can be prepared in situ during the final isolation and purification of the compounds of Formula I, or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylpropionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term pharmaceutically acceptable esters refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "cancer" refers to cancer diseases that can be beneficially treated by the inhibition of Raf kinase, including, for example, cancers such as malignant melanoma, papillary thyroid cancer, cholangiocarcinoma, gallbladder carcinoma, colorectal cancer, lung cancer, pancreatic cancer, leukemias, prostate cancer, ovarian cancer, breast cancer and lung cancer.

In illustrative embodiments of the invention, $A_1$ may be, for example, phenyl, phenylalkyl, pyridyl, pyrimidinyl, pyridylalkyl, pyrimidinylalkyl, alkylbenzoate, thiophene, thiophene-2-carboxylate, indenyl, 2,3-dihydroindenyl, tetralinyl, trifluorophenyl, (trifluoromethyl)-thiophenyl, morpholinyl, N-piperazinyl, N-morpholinylalkyl, piperazinylalkyl, cyclohexylalkyl, indolyl, 2,3-dihydroindolyl, 1-acetyl-2,3-dihydroindolyl, cycloheptyl, bicyclo[2.2.1]hept-2-yl, pyrrolidinyl, pyrrolidin-1-yl, pyrrolidin-1-ylalkyl, 4-amino(imino)methylphenyl, isoxazolyl, indazolyl, adamantyl, bicyclohexyl, quinuclidinyl, imidazolyl, benzimidazolyl, imidazolylphenyl, phenylimidazolyl, pthalamido, napthyl, napththalenyl, benzophenone, anilinyl, anisolyl, quinolinyl, quinolinonyl, phenylsulfonyl, phenylalkylsulfonyl, 9H-fluoren-1-yl, piperidin-1-yl, piperidin-1-ylalkyl, cyclopropyl, cyclopropylalkyl, furanyl, N-methylpiperidin-4-yl, pyrrolidin-4-ylpyridinyl, 4-diazepan-1-yl, hydroxypyrrolidin-1-yl, dialkylaminopyrrolidin-1-yl, and 1,4'-bipiperidin-1'-yl, which may be substituted by one or more substituents selected from the group consisting of hydroxyl, nitro, cyano, halo, and substituted or unsubstituted amino, imino, thio, sulfonyl, thioamido, amidino, imidino, oxo, oxamidino, methoxamidino, imidino, guanidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, loweralkylaminocarbonyl, heterocycloalkylloweralkylaminocarbonyl, carboxylloweralkylaminocarbonyl, arylcarbonyl, aralkylcarbonyl, heteroarylcarbonyl, heteroaralkylcarbonyl, alkylthio, aminoalkyl, cyanoalkyl, aryl and the like. In other embodiments, $A_1$ may be substituted phenyl, such as, for example, substituted or unsubstituted hydroxyphenyl, hydroxyalkylphenyl, alkylphenyl, dialkylphenyl, trialkylphenyl, alkoxyphenyl, dialkoxyphenyl, alkoxyalkylphenyl, halophenyl, dihalophenyl, haloalkylphenyl, haloalkoxyphenyl, alkylhalophenyl, alkoxyhalophenyl, alkylthiophenyl, aminophenyl, nitrophenyl, acetylphenyl, sulfamoylphenyl, biphenyl, alkoxybiphenyl, cyclohexylphenyl, phenyloxyphenyl, dialkylaminophenyl, morpholinylphenyl, heterocyclylcarbonylphenyl, heterocyclylphenyl, heterocyclyl alkylphenyl, furanylphenyl, (1,4'-bipiperidin-1'-ylcarbonyl)phenyl, pyrimidin-5-ylphenyl, and quinolidinylphenyl. In yet other embodiments, $A_1$ is substituted phenyl selected from the group consisting of chlorophenyl, fluorophenyl, bromophenyl, iodophenyl, dichlorophenyl, difluorophenyl, dibromophenyl, fluorochlorophenyl, bromochlorophenyl, trifluoromethylphenyl, trifluoromethoxyphenyl, alkylbromophenyl, trifluoromethylbromophenyl, alkylchlorophenyl, trifluoromethylchlorophenyl, alkylfluorophenyl, and trifluoromethylfluorophenyl.

In representative embodiments of the invention, the compounds of the invention include, for example, 4-[(2-{[4- chloro-3-(trifluoromethyl)phenyl]amino}-1H-benzimidazol-6-yl)oxy]-N-methylpyridine-2-carboxamide, 4-({2-[(3-chlorophenyl)amino]-1H-benzimidazol-6-yl}oxy)-N-methylpyridine-2-carboxamide, 4-({2-[(4-bromophenyl) amino]-1H-benzimidazol-6-yl}oxy)-N-methylpyridine-2-carboxamide, 4-({2-[(3-chloro-4-fluorophenyl)amino]-1H-benzimidazol-6-yl}oxy)-N-methylpyridine-2-carboxamide, N-methyl-4-{[2-(phenylamino)-1H-benzimidazol-6-yl]oxy}pyridine-2-carboxamide, 4-[(2-{[4-bromo-2-(trifluoromethyl)-phenyl]amino}-1H-benzimidazol-6-yl)oxy]-N-methylpyridine-2-carboxamide, N-methyl-4-({2-[(2-methylpropyl)amino]-1H-benzimidazol-6-yl}oxy)pyridine-2-carboxamide, 4-[(2-{[4-(dimethylamino)naphthalen-1-yl]amino}-1H-benzimidazol-6-yl)oxy]-N-methylpyridine-2-carboxamide, N-methyl-4-({2-[(4-nitrophenyl)amino]-1H-benzimidazol-6-yl}oxy)pyridine-2-carboxamide, N-methyl-4-({2-[(phenylcarbonyl)amino]-1H-benzimidazol-6-yl}oxy)pyridine-2-carboxamide, N-methyl-4-({2-[(phenylmethyl)amino]-1H-benzimidazol-6-yl}oxy)pyridine-2-carboxamide, methyl 4-{[6-({2-[(methylamino)carbonyl]pyridin-4-yl}oxy)-1H-benzimidazol-2-yl]amino}benzoate, 4-({2-[(4-chlorophenyl)amino]-1H-benzimidazol-6-yl}oxy)-N-methylpyridine-2-carboxamide, 4-[(2-{[2-(ethyloxy)phenyl]amino}-1H-benzimidazol-6-yl) oxy]-N-methylpyridine-2-carboxamide, N-methyl-4-({2-[(2-morpholin-4-ylethyl)amino]-1H-benzimidazol-6-yl}oxy)pyridine-2-carboxamide, 4-({2-[(4-iodophenyl) amino]-1H-benzimidazol-6-yl}oxy)-N-methylpyridine-2-carboxamide, N-methyl-4-[(2-{[4-(trifluoromethyl)phenyl]amino}-1H-benzimidazol-6-yl)oxy]pyridine-2-carboxamide, 4-({2-[(furan-2-ylmethyl)amino]-1H-benzimidazol-6-yl}oxy)-N-methylpyridine-2-carboxamide, 4-({2-[(4-bromo-3-methylphenyl)amino]-1H-benzimidazol-6-yl}oxy)-N-methylpyridine-2-carboxamide, 4-({2-[(4-acetylphenyl)amino]-1H-benzimidazol-6-yl}-oxy)-N-methylpyridine-2-carboxamide, N-methyl-4-({2-[(2,4,6-trimethylphenyl)amino]-1H-benzimidazol-6-yl}oxy)pyridine-2-carboxamide, 4-[(2-{[4-(1,1-dimethylethyl)phenyl]amino}-1H-benzimidazol-6-yl)oxy]-N-methylpyridine-2-carboxamide, 4-({2-[(2-bromophenyl)amino]-1H-benzimidazol-6-yl}oxy)-N-methylpyridine-2-carboxamide, 4-({2-[(3-bromophenyl)amino]-1H-benzimidazol-6-yl}oxy)-N-methylpyridine-2-carboxamide, 4-({2-[(2-chlorophenyl)amino]-1H-benzimidazol-6-yl}oxy)-N-methylpyridine-2-carboxamide, methyl 3-{[6-({2-[(methylamino)-carbonyl]pyridin-4-yl}oxy)-1H-benzimidazol-2-yl]amino}thiophene-2-carboxylate, 4-({2-[(4-bromophenyl)amino]-1H-benzimidazol-6-yl}oxy)-N-{(3R,5R)-5-[(methyloxy)methyl]pyrrolidin-3-yl}pyridine-2-carboxamide, 4-({2-[(4-bromophenyl)amino]-1-methyl-1H-benzimidazol-5-yl}oxy)-N-methylpyridine-2-carboxamide, 4-[(2-{[4-chloro-3-(trifluoromethyl)phenyl]amino}-1-methyl-1H-benzimidazol-5-yl)oxy]-N-methylpyridine-2-carboxamide, N-methyl-4-[(1-methyl-2-{[4-(trifluoromethyl)phenyl]amino}-1H-benzimidazol-5-yl)oxy]pyridine-2-carboxamide, 4-({2-[(4-bromophenyl)amino]-1-methyl-1H-benzimidazol-5-yl}oxy)-N-ethylpyridine-2-carboxamide, 4-({2-[(4-bromophenyl)amino]-1-methyl-1H-benzimidazol-5-yl}oxy)-N-(2-hydroxyethyl)pyridine-2-carboxamide, 4-({2-[(4-bromophenyl)amino]-1-methyl-1H-benzimidazol-5-yl}oxy)-N,N-dimethylpyridine-2-carboxamide, 4-({2-[(4-bromophenyl)amino]-1-methyl-1H-benzimidazol-5-yl}-oxy)-N-(2,2,2-trifluoroethyl)pyridine-2-carboxamide, N-(4-bromophenyl)-1-methyl-5-{[2-(pyrrolidin-1-ylcarbonyl) pyridin-4-yl]oxy}-1H-benzimidazol-2-amine, ethyl (3R)-3-(methyloxy)-4-[({4-[(2-{[4-(trifluoromethyl)phenyl] amino}-1H-benzimidazol-5-yl)oxy]pyridin-2-yl}carbonyl)amino]piperidine-1-carboxylate, 4-({2-[(4-bromophenyl) amino]-1-methyl-1H-benzimidazol-5-yl}oxy)-N-[2-(dimethylamino)ethyl]pyridine-2-carboxamide, 4-({2-[(4-bromophenyl)amino]-1-methyl-1H-benzimidazol-5-yl}oxy)-N-(tetrahydrofuran-2-ylmethyl)pyridine-2-carboxamide, 4-({2-[(4-bromophenyl)amino]-1-methyl-1H-benzimidazol-5-yl}oxy)-N-(2-morpholin-4-ylethyl)pyridine-2-carboxamide, 4-({2-[(4-bromophenyl)amino]-1-methyl-1H-benzimidazol-5-yl}oxy)-N-(piperidin-4-ylmethyl)pyridine-2-carboxamide, 5-({2-[(3-aminopyrrolidin-1-yl)carbonyl]pyridin-4-yl}oxy)-N-(4-bromophenyl)-1-methyl-1H-benzimidazol-2-amine, 4-({2-[(4-bromophenyl)amino]-1-methyl-1H-benzimidazol-5-yl}oxy)-N-[1-(diphenylmethyl) azetidin-3-yl]pyridine-2-carboxamide, 4-({2-[(4-bromophenyl)amino]-1-methyl-1H-benzimidazol-5-yl}oxy)-N-piperidin-3-ylpyridine-2-carboxamide, 4-({2-[(4-bromophenyl)amino]-1-methyl-1H-benzimidazol-5-yl}oxy)-N-(1,3-thiazol-2-yl)pyridine-2-carboxamide, and 4-({2-[(4-bromophenyl)amino]-1-methyl-1H-benzimidazol-5-yl}-oxy)-N-[(1-ethylpyrrolidin-2-yl)methyl]pyridine-2-carboxamide, (4-{2-[(4-bromophenyl)amino]-benzothiazol-5-yloxy}(2-pyridyl))-N-methylcarboxamide, (4-{2-[(4-bromophenyl)amino]-benzoxazol-5-yloxy}-(2-pyridyl))-N-methylcarboxamide, and other representative compounds set forth in the Examples.

In other aspects, the present invention relates to the processes for preparing the compounds of Formulas (I), (II), (III), (IV), (V) and (VI) and to the synthetic intermediates useful in such processes.

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

The present invention also relates to the processes for preparing the compounds of the invention and to the synthetic intermediates useful in such processes, as described in detail below.

Synthetic Methods

Compounds of the invention containing a benzimidazole core may be prepared via a number of synthetic routes using methods familiar to one of skill in the art, such as those disclosed in WO03082272 and published U.S. Patent Application No. 20040122237 A1. One such route is as shown in Scheme I below. The pyridyl ether Ig is formed by coupling 4-halopyridine Ic with phenol If under basic conditions. The resulting amide Ig is treated with KOH and bromine to form the pyridyl amine Ih that may then be coupled with various acids to form amide Ii. Reduction of Ii gives diamine Ij, which may be coupled with various thioisocyanates to form benzimidazole Ik.

Scheme I

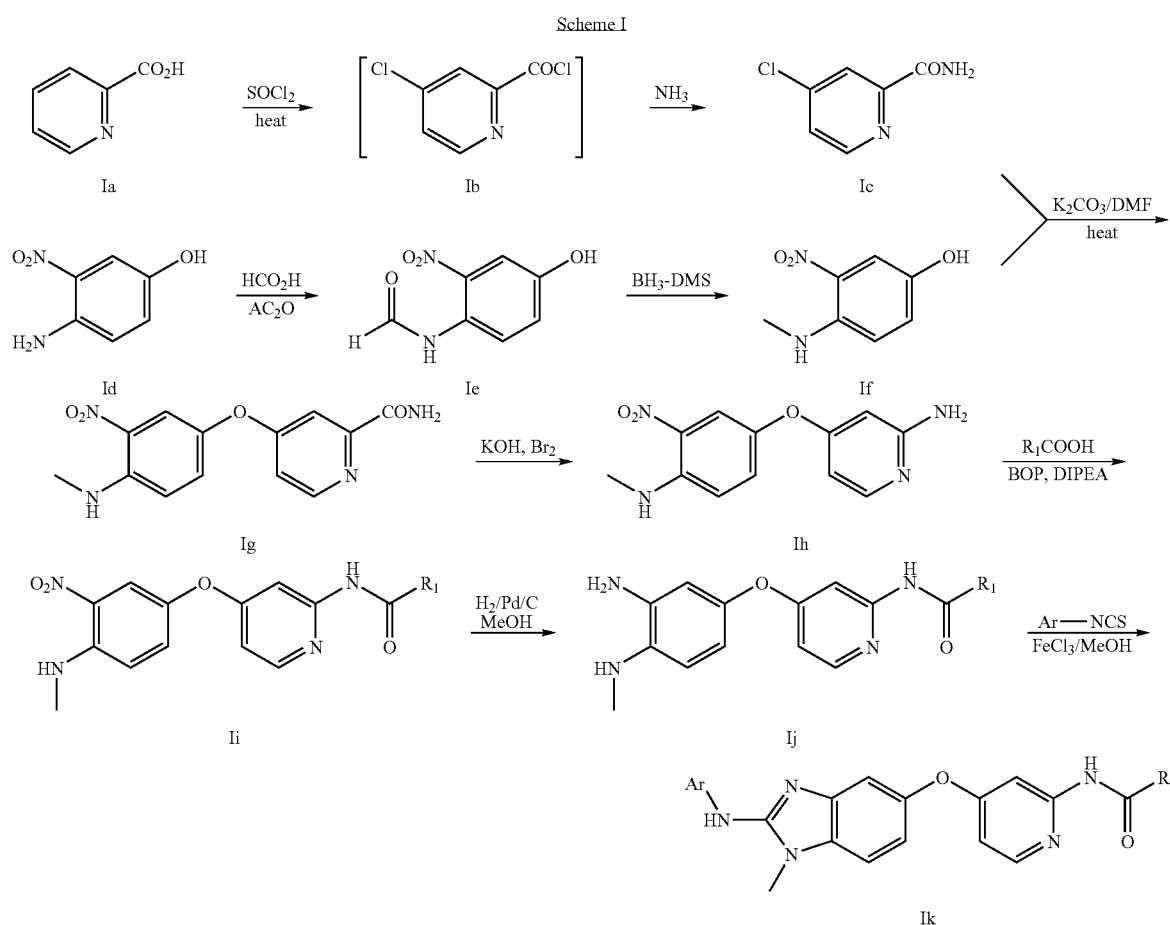

Compounds containing the oxazole structure may similarly be prepared according to the methods above or according to other known general procedures, such as those disclosed in WO03082272 and published U.S. Patent Application No. 20040122237 A1. In addition, Haviv et al. (*J. Med. Chem.* 1988, 31:1719) describes a procedure for assembling oxazole cores wherein a hydroxy aniline is treated with ethyl potassium xanthate. The resulting sulfuryl benzoxazole may then be chlorinated and coupled with an amine.

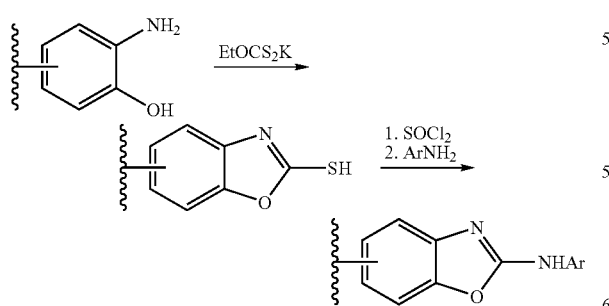

Compounds containing a benzothiazole core may also be prepared according to known methods, such as those disclosed in WO03082272 and published U.S. Patent Application No. 20040122237 A1. An ortho-haloamine may be reacted with a thioisocyanate to form a thiourea. Reduction with NaH then allows formation of the thiazole ring.

Intermediates for synthesizing benzoxazoles may generally be prepared through the following pathway:

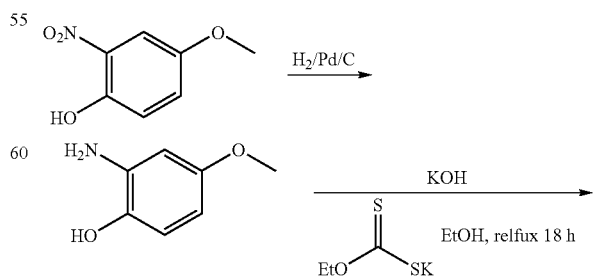

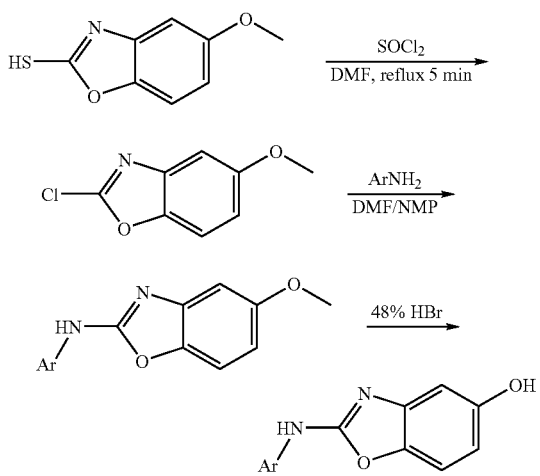

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Raf activity by any of the assays described herein, by other Raf kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al, *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formulas (I), (II), (III), (IV) and (V) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. The afflicted patients are responsive to Gleevec, a small molecule tyrosine kinase inhibitor, as a result of inhibition of Abl kinase activity. However, many patients with advanced stage disease respond to Gleevec initially, but then relapse later due to resistance-conferring mutations in the Abl kinase domain. In vitro studies have demonstrated that BCR-Avl employs the Raf kinase pathway to elicit its effects. In addition, inhibiting more than one kinase in the same pathway provides additional protection against resistance-conferring mutations. Accordingly, in another aspect of the invention, the compounds of formulas (I), (II), (III), (IV) and (V) are used in combination with at least one additional agent, such as Gleevec, in the treatment of hematological cancers, such as chronic myelogenous leukemia (CML), to reverse or prevent resistance to the at least one additional agent.

The present invention will be understood more readily by reference to the following examples, which are provided by way of illustration and are not intended to be limiting of the present invention.

Representative side chains for use in the compounds of the following examples may generally be prepared in accordance with the following procedures:

EXAMPLE 1

Synthesis of N-[4-({2-[(3-tert-butylphenyl)amino]-1-methyl-1H-benzimidazol-5-yl}oxy)pyridin-2-yl]acetamide

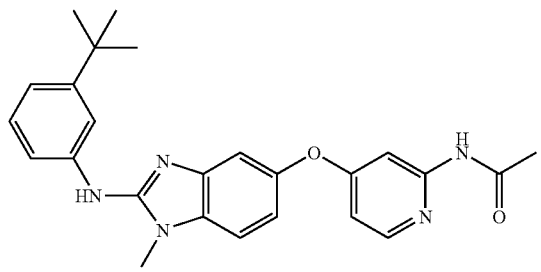 [SMILES: CC(=O)Nc1cc(Oc2ccc3c(c2)nc(Nc2cccc(C(C)(C)C)c2)n3C)ccn1]

Step 1:

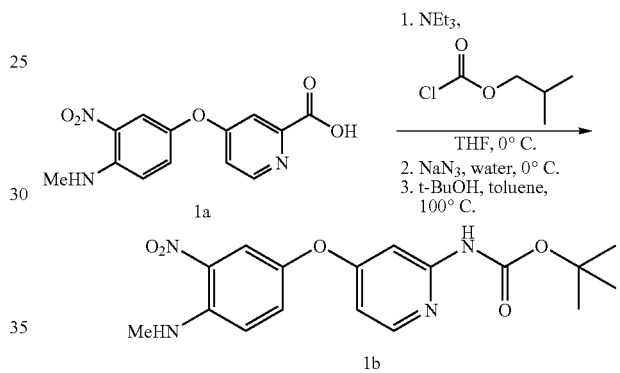

Triethylamine (5 mL, 35.6 mmol) was added to a stirring suspension of acid 1a (3.34 g, 11.6 mmol) in dry THF (44 mL) at 0° C. The reaction was maintained at 0° C. for 1 h, after which a solution of isobutylchloroformate (1.8 mL, 13.9 mmol) in cry THF (14 mL) was added dropwise. After 1 h at 0° C., a solution of sodium azide (2.28 g, 35.1 mmol) in water (8 mL) was added and the resulting reaction was maintained at 0° C. for 45 min. The reaction solution was concentrated into an aqueous slurry and partitioned between saturated aqueous $NaHCO_3$ solution and $CH_2Cl_2$. The phases were separated and the aqueous portion was extracted with $CH_2Cl_2$ (3×). The combined organics were washed with brine and the combined aqueous portions were further extracted with $CH_2Cl_2$. The combined organic phases were dried ($MgSO_4$) and concentrated to give 2.71 g (8.6 mmol, 75%) of an orange solid as crude acyl azide.

A suspension of acyl azide (322 mg, 1.02 mol) and t-butanol (0.2 mL, 2.09 mmol) in dry toluene (12 mL) was heated to 100° C. and maintained at that temperature for 1.5 h. The reaction was allowed to cool to rt and then partitioned between saturated aqueous $Na_2CO_3$ solution and $CH_2Cl_2$. The phases were separated and the aqueous portion was extracted with $CH_2Cl_2$ (3×). The combined organic portions were washed with saturated aqueous $Na_2CO_3$ solution (2×) and brine, dried ($MgSO_4$), and adsorbed onto $SiO_2$. Purification by flash chromatography (9:1, 4:1, 2:1 hexanes-EtOAc) afforded 131 mg (0.36 mmol, 36%) of an orange solid as 1b: $^1H$ NMR (300 MHz, $CDCl_3$) δ 8.18 (br s, 1 H), 8.12 (d, J=5.8 Hz, 1 H), 8.04 (br dd, 1 H), 7.95 (d, J=2.8 Hz, 1 H), 7.53 (d, J=2.2, 1H), 7.29 (dd, J=2.8, 9.1 Hz, 1 H), 6.91 (d, J=9.3 Hz, 1 H), 6.47 (dd, J=2.5, 5.8 Hz, 1 H), 3.07 (d, J=5.2 Hz, 3 H), 1.49 (s, 9 H).

Step 2:

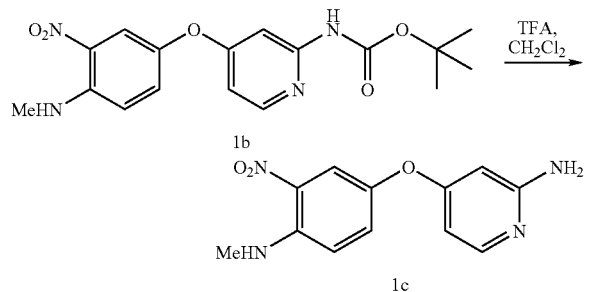

Trifluoroacetic acid (4 mL) was added to a stirring suspension of BOC carbamate 1b (181 mg, 0.5 mmol) in CH$_2$Cl$_2$ (4 mL). The resulting reaction was maintained at rt for 3.5 h and was then concentrated. The crude residue was suspended in saturated aqueous Na$_2$CO$_3$ and extracted with CH$_2$Cl$_2$ (3×). The combined organic portions were concentrated and the resulting residue was adsorbed onto SiO$_2$. Purification by flash chromatography (0.5:99.5, 0.75:99.25, 1:99, 2:98, 5:95 methanol-CH$_2$Cl$_2$) gave 94 mg (0.36 mmol, 72%) of a bright orange solid as 1c: $^1$H NMR (300 MHz, CDCl$_3$) δ 8.03 (br d, J=3.3 Hz, 1 H), 7.93 (d, J=2.8 Hz, 1 H), 7.92 (d, J=5.8 Hz, 1 H), 7.27 (dd, J=2.8, 9.4 Hz, 1 H), 6.89 (d, J=9.3 Hz, 1 H), 6.24 (dd, J=2.2, 6.0 Hz, 1 H), 5.92 (d, J=2.2 Hz, 1 H), 4.4 (br s, 2 H), 3.05 (d, J=5.0 Hz, 3 H).

Step 3:

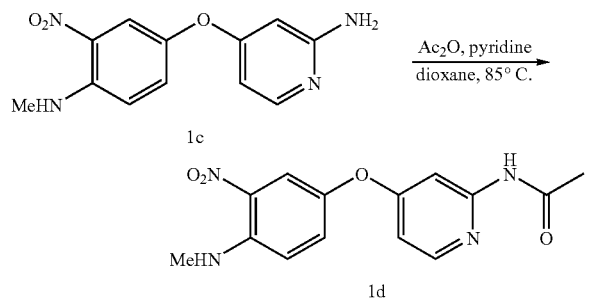

Pyridine (0.08 mL, 0.99 mmol) and acetic anhydride (0.04 mL, 0.42 mmol) was added to suspension of 2-aminopyridine 1c (94 mg, 0.36 mmol) in dry dioxane (1.71 mL). The resulting reaction mixture was heated to and maintained at 85° C. for 2 h. The reaction was allowed to cool to rt and was then partitioned between EtOAc and saturated aqueous Na$_2$CO$_3$. The layers were separated and the aqueous layer was extracted with EtOAc (3×). The combined organic portions were washed with brine, dried (MgSO$_4$), and adsorbed onto SiO$_2$. Purification by flash chromatography (2:1, 1:1, 1:2, 1:3 hexanes-EtOAc) provided 75 mg (0.25 mmol, 69%) of an orange solid as 1d: $^1$H NMR (300 MHz, CDCl$_3$) δ 8.35 (br s, 1 H), 8.10 (d, J=5.8 Hz, 1 H), 8.05 (br d, J=4.4 Hz, 1 H), 7.95 (d, J=2.8 Hz, 1 H), 7.76 (br d, J=1.7 Hz 1 H), 7.30 (dd, J=2.7, 9.1 Hz, 1 H), 6.91 (d, J=9.3 Hz, 1 H), 6.60 (dd, J=2.5, 5.8 Hz, 1 H), 3.05 (d, J=5.2 Hz 3 H), 2.16 (s, 3 H).

Step 4:

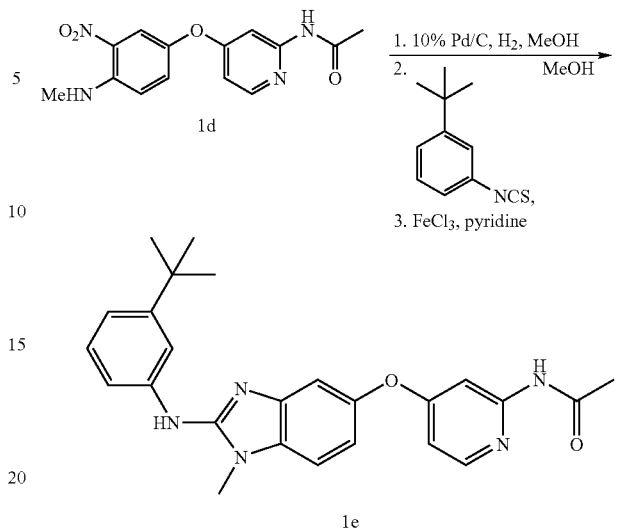

A suspension of acetamide 1d (75 mg, 0.25 mmol) and 10% Pd/C (30 mg, 0.03 mmol) in methanol (5 mL) was charged with H$_2$ and the resulting reaction mixture was maintained under a H$_2$ atmosphere for 1 h at rt. The mixture was filtered and the remaining solids washed thoroughly with EtOAc and methanol. The combined organic portions were evaporated to afford 60 mg (0.22 mmol, 88%) of a brown residue as the phenylene diamine, which was carried forward without further purification.

The above diamine (60 mg, 0.22 mmol) was dissolved in methanol (3 mL) and a solution of 3-tert-butyl phenylthioisocyanate (62 mg, 0.32 mmol) in methanol was added. The reaction was maintained for 16 h. Pyridine (0.06 mL, 0.74 mmol) was added to the reaction, followed by ferric chloride (45 mg, 0.28 mmol). The resulting dark reaction mixture was maintained at rt for 16 h, then suspended in saturated aqueous Na$_2$CO$_3$ solution, and filtered with Celite. The remaining solids were washed with EtOAc and the combined filtrate was partitioned and separated. The aqueous portion was extracted with EtOAc (3×) and the combined organic portions were washed with brine, dried (MgSO$_4$), and evaporated. Purification by semi-prep HPLC gave 1e as the TFA salt which was neutralized with saturated aqueous Na$_2$CO$_3$ solution and extracted with EtOAc (3×). The combined organic portions were washed with brine and water, dried (MgSO$_4$), and evaporated. The resulting residue was reconstituted as the mono citrate salt: LCMS m/z 430.3 (MH$^+$), t$_R$=2.24 min.

EXAMPLE 2

Synthesis of N-[4-({2-[(4-fluoro-3-tetrahydrofuran-3-ylphenyl)amino]-1-methyl-1H-benzimidazol-5-yl}oxy)pyridin-2-yl]acetamide

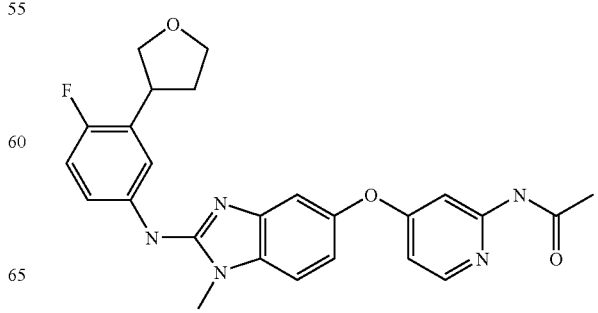

Synthesized as described above in Example 1 using 3-(2-fluoro-5-isothiocyanato-phenyl)-tetrahydro-furan. LCMS m/z 462.2 (MH⁺), R$_t$ 2.51 min.

EXAMPLE 3

Synthesis of N-(4-{[1-methyl-2-({4-[(trifluoromethyl)thio]phenyl}amino)-1H-benzimidazol-5-yl]oxy}pyridin-2-yl)acetamide

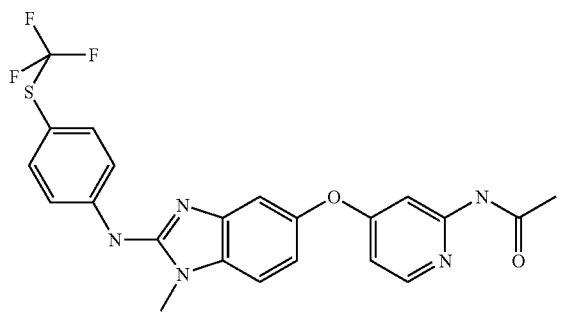 [SMILES: CC(=O)Nc1cc(Oc2ccc3c(c2)nc(Nc2ccc(SC(F)(F)F)cc2)n3C)ccn1]

Synthesized as described above in Example 1 using 4-trifluoromethylthiophenyl isothiocyanate. LCMS m/z 474.2 (MH⁺), R$_t$ 3.41 min.

EXAMPLE 4

Synthesis of N-[4-{(2-[4-fluoro-3-isopropylphenyl)amino]-1-methyl-1H-benzimidazol-5-yl}oxy)pyridin-2-yl]acetamide Synthesized as described above in Example 1 using 4-fluoro-3-isopropylphenyl isothiocyanate. LCMS m/z 434.2 (MH⁺), R$_t$ 3.28 min.

EXAMPLE 5

Synthesis of N-{4-[(2-{[4-fluoro-3-(3-furyl)phenyl]amino}-1-methyl-1H-benzimidazol-5-yl)oxy]pyridin-2-yl}acetamide

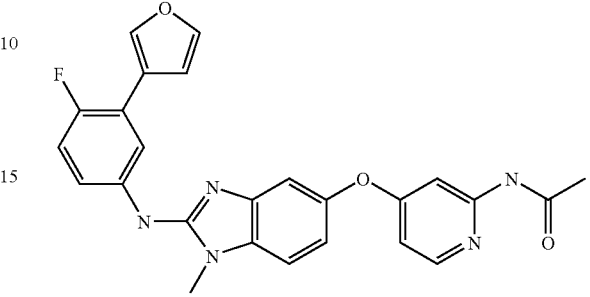

Synthesized as described above in Example 1 using 3-(2-fluoro-5-isothiocyanato-phenyl)-furan. LCMS m/z 458.3 (MH⁺), R$_t$ 2.02 min.

EXAMPLE 6

Synthesis of N-[4-({2-[(4-fluoro-3-tetrahydrofuran-2-ylphenyl)amino]-1-methyl-1H-benzimidazol-5-yl}oxy)pyridin-2-yl]acetamide

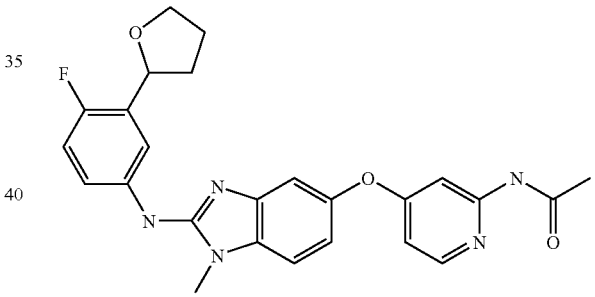

Synthesized as described above in Example 1 using 2-(2-Fluoro-5-isothiocyanato-phenyl)-tetrahydro-furan. LCMS m/z 462.3 (MH⁺), R$_t$ 1.87 min.

EXAMPLE 7

Synthesis of N-[4-({2-[(4-chloro-3-isopropylphenyl)amino]-1-methyl-1H-benzimidazol-5-yl}oxy)pyridin-2-yl]-1-methylpiperidine-4-carboxamide

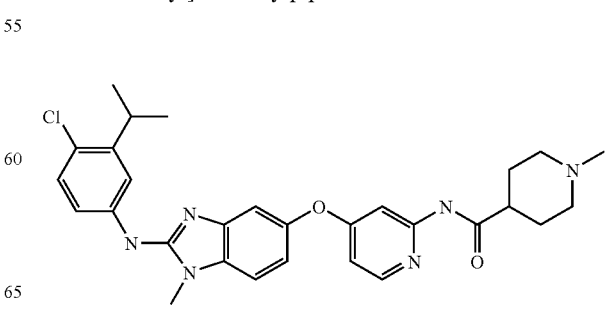

1. Synthesis of [(4-(2-amino(4-pyridyloxy))-2-nitrophenyl]methylamine

Bromine (1.3 eq) was added dropwise to a solution of potassium hydroxide (10 eq) at −10° C. 4-(4-methylamino-3-nitrophenoxy)-pyridine-2-carboxamide (1 eq) was added followed by dioxane and the mixture was heated to 60° C. for one hour. The mixture was then cooled to ambient temperature followed by slow addition of acetic acid (5 eq). The solution was heated to 60° C. for one hour. The solution was brought to pH=8 with acetic acid. [4-(2-amino(4-pyridyloxy))-2-nitrophenyl]methylamine precipitated as an orange solid on cooling which was collected by filtration and washed with water and dried. MS: MH$^+$=261.

2. Synthesis of 1-methyl-N-(4-{[4-(methylamino)-3-nitrophenyl]oxy}pyridin-2-yl)-piperidine-4-carboxamide To a mixture of 1-methylpiperidine-4-carboxylic acid (1 eq) in N,N-dimethyl formamide and N,N-disopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting 1-methyl-N-(4-{[4-(methylamino)-3-nitrophenyl]oxy}pyridin-2-yl)piperidine-4-carboxamide was purified by silica gel chromatography. MS: MH$^+$=386.2.

3. Synthesis of N-(4-{[3-amino-4-(methylamino)phenyl]oxy}pyridin-2-yl)-1-methylpiperidine-4-carboxamide The mixture containing 1-methyl-N-(4-{[4-(methylamino)-3-nitrophenyl]oxy}pyridin-2-yl)piperidine-4-carboxamide in methanol with catalytic amount of Lindlar's catalyst was hydrogenated to yield N-(4-{[3-amino-4-(methylamino)phenyl]oxy}pyridin-2-yl)-1-methylpiperidine-4-carboxamide. MS: MH$^+$=356.2.

4. Synthesis of N-[4-({2-[(4-chloro-3-isopropylphenyl)amino]-1-methyl-1H-benzimidazol-5-yl}oxy)pyridin-2-yl]-1-methylpiperidine-4-carboxamide To 4-chloro-3-(methylethyl)benzeneisothiocyanate (1 eq) in methanol was added N-(4-{[3-amino-4-(methylamino)phenyl]oxy}pyridin-2-yl)-1-methylpiperidine-4-carboxamide (1 eq) and the resulting mixture was stirred at ambient temperature for 16 h. LC/MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to yield N—N-[4-({2-[(4-chloro-3-isopropylphenyl)amino]-1-methyl-1H-benzimidazol-5-yl}oxy)pyridin-2-yl]-1-methylpiperidine-4-carboxamide. MS: MH$^+$=534.1.

EXAMPLE 8

Synthesis of 1-ethyl-N-{4-[(2-{[2-fluoro-5-(trifluoromethyl)phenyl]amino}-1-methyl-1H-benzimidazol-5-yl)oxy]pyridin-2-yl}piperidine-4-carboxamide

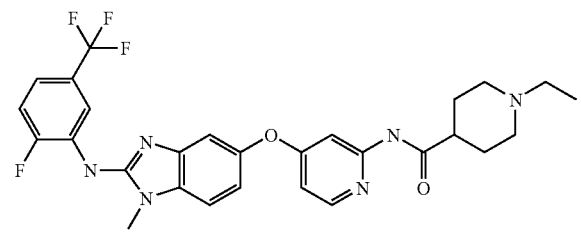 [SMILES: CCN1CCC(C(=O)Nc2cc(Oc3ccc4c(c3)nc(Nc3cc(C(F)(F)F)ccc3F)n4C)ccn2)CC1]

1. Synthesis of 1-(ethyl)piperidine-4-carboxylic acid

To ethylpiperidine-4-carboxylate (1 eq) in ethanol was added iodoethane (1.1 eq) and potassium carbonate (2 eq) and the resulting mixture was refluxed for 16 h. The mixture was then cooled to room temperature and filtered. Ethanol was concentrated and partitioned between methylene chloride and water. The organic layer was then washed with saturated sodium chloride solution, dried with sodium sulfate and concentrated. To it was then added concentrated hydrochloric acid and water (2:1) and the mixture was refluxed for 5 h. The resulting 1-(ethyl)piperidine-4-carboxylic acid was then azeotroped with toluene. MS: MH$^+$=158.

2. Synthesis of ((1-ethyl)(4-piperidyl))-N-{4-{4-(methylamino)-3-nitrophenoxy}(2-pyridyl)}carboxamide To a mixture of 1-(ethyl)piperidine-4-carboxylic acid (1 eq) in N,N-dimethyl formamide and N,N-disopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting (((1-ethyl)(4-piperidyl))-N-{4-[4-(methylamino)-3-nitrophenoxy]}(2-pyridyl))carboxamide was purified by silica gel chromatography. MS: MH$^+$=400.2.

3. Synthesis of N-[4-{3-amino-4-(methylamino)}phenoxy](2-pyridyl)-(1-ethyl(4-piperidyl))carboxamide The mixture containing ((1-ethyl)(4-piperidyl))-N-{4-[4-(methylamino)-3-nitrophenoxy]}(2-pyridyl))carboxamide in methanol with catalytic amount of Lindlar's catalyst was hydrogenated to yield N-[4-{3-amino-4-(methylamino)}phenoxy](2-pyridyl)-(1-ethyl(4-piperidyl))carboxamide. MS: MH$^+$=370.2.

4. Synthesis of 1-ethyl-N-{4-[(2-{[2-fluoro-5-(trifluoromethyl)phenyl]amino}-1-methyl-1H-benzimidazol-5-yl)oxy]pyridin-2-yl}piperidine-4-carboxamide To 2-fluoro-5-(trifluoromethyl)benzeneisothiocyanate (1 eq) in methanol was added N-[4-{3-amino-4-(methylamino)

}phenoxy](2-pyridyl)-(1-ethyl(4-piperidyl))carboxamide (1 eq) and the resulting mixture was stirred at ambient temperature for 16 h. LC/MS showed formation of the corresponding thiourea. To this in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to yield 1-ethyl-N-{4-[(2-{[2-fluoro-5-(trifluoromethyl)phenyl]amino}-1-methyl-1H-benzimidazol-5-yl)oxy]pyridin-2-yl}piperidine-4-carboxamide. MS: MH$^+$=557.6.

EXAMPLE 9

Synthesis of N-{4-[(2-{[2-fluoro-5-(trifluoromethyl) phenyl]amino}-1-methyl-1H-benzimidazol-5-yl) oxy]pyridin-2-yl}-1-isopropylpiperidine-4-carboxamide

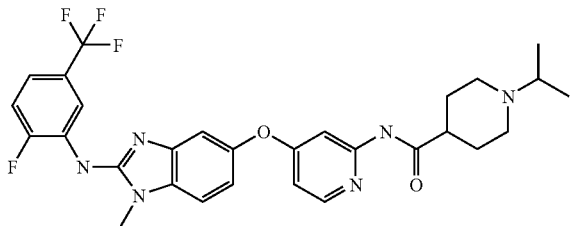 [SMILES: CC(C)N1CCC(C(=O)Nc2cc(Oc3ccc4c(c3)nc(Nc3cc(C(F)(F)F)ccc3F)n4C)ccn2)CC1]

1. Synthesis of 1-(methylethyl)piperidine-4-carboxylic acid

To ethylpiperidine-4-carboxylate (1 eq) in methanol was added acetone (1 eq) and acetic acid (5%) and the resulting mixture was stirred for 2 h at ambient temperature. To it was then added sodium cyanoborohydride (1 eq) and continued stirring for 16 h. The mixture was then concentrated and to it was added sodium bicarbonate and was partitioned between ethyl acetate and water. The organic layer was dried with sodium sulfate and concentrated to yield ethyl-1-(methylethyl)piperidine 4-carboxylate. To this was then added concentrated hydrochloric acid and water (2:1) and the mixture was refluxed for 5 h. The resulting 1-(methylethyl)piperidine-4-carboxylic acid was then azeotroped with toluene. MS: MH$^+$=172.

2. Synthesis of N-{4-[4-(methylamino)3-nitrophenoxy](2-pyridyl)}-[1-(methylethyl)(4-piperidyl)carboxamide To a mixture of 1-(methylethyl)piperidine-4-carboxylic acid (1 eq) in N,N-dimethyl formamide and N,N-diisopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting N-{4-[4-(methylamino)3-nitrophenoxy](2-pyridyl)}-[1-(methylethyl)(4-piperidyl]carboxamide was purified by silica gel chromatography. MS: MH$^+$=414.2.

3. Synthesis of N-{4-[3-amino-4-(methylamino)phenoxy](2-pyridyl)}-[1-methylethyl)(4-piperidyl)]carboxamide The mixture containing N-{4-[4-(methylamino)3-nitrophenoxy](2-pyridyl)}-[1-(methylethyl)(4-piperidyl]carboxamide in methanol with catalytic amount of Lindlar's catalyst was hydrogenated to yield N-{4-[3-amino-4-(methylamino)phenoxy](2-pyridyl)}-[1-(methylethyl)(4-piperidyl)]carboxamide. MS: MH$^+$=384.2.

4. Synthesis of N-{4-[(2-{[2-fluoro-5-(trifluoromethyl)phenyl]amino}-1-methyl-1H-benzimidazol-5-yl)oxy]pyridin-2-yl}-1-isopropylpiperidine-4-carboxamide To 2-fluoro-5-(trifluoromethyl)benzeneisothiocyanate (1 eq) in methanol was added N-{4-[3-amino-4-(methylamino) phenoxy] (2-pyridyl)}-[1-(methylethyl)(4-piperidyl)]carboxamide (1 eq) and the resulting mixture was stirred at ambient temperature for 16 h. LC MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to yield N-{4-[(2-{[2-fluoro-5-(trifluoromethyl)phenyl]amino}-1-methyl-1H-benzimidazol-5-yl)oxy]pyridin-2-yl}-1-isopropylpiperidine-4-carboxamide. MS: MH$^+$=571.6.

EXAMPLE 10

Synthesis of N-{4-[(2-{[2-fluoro-5-(trifluoromethyl) phenyl]amino}-1-methyl-1H-benzimidazol-5-yl) oxy]pyridin-2-yl}-1-(2-methoxyethyl)piperidine-4-carboxamide

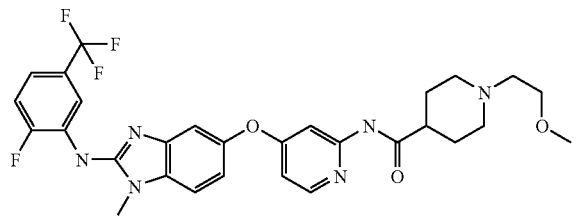 [SMILES: COCCN1CCC(C(=O)Nc2cc(Oc3ccc4c(c3)nc(Nc3cc(C(F)(F)F)ccc3F)n4C)ccn2)CC1]

1. Synthesis of 1-(2-methoxyethyl)piperidine-4-carboxylic acid

To ethylpiperidine-4-carboxylate (1 eq) in ethanol was added 2-bromo-1-methoxyethane (1 eq) and potassium carbonate 2 eq) and the resulting mixture was refluxed for 16 h. The mixture was then filtered and concentrated. To it was then added ethanol and water (3:1) and sodium hydroxide (1 eq) and it was refluxed for 16 h. The resulting 1-(2-methoxyethyl) piperidine-4-carboxylic acid was then azeotroped with toluene. MS: MH$^+$=188.

2. Synthesis of [1-(2-methoxyethyl)(4-piperidyl)]-N-{4-[4-(methylamino)-3-nitrophenoxy](2-[pyridyl)}carboxamide To a mixture of 1-(2-methoxyethyl)piperidine-4-carboxylic (1 eq) in N,N-dimethyl formamide and N,N-disopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting [1-(2-methoxyethyl)(4-piperidyl)]-N-{4-[4-(methylamino)-3-nitrophenoxy](2-[pyridyl)}carboxamide was purified by silica gel chromatography. MS: MH$^+$=430.2.

3. Synthesis of N-{4[3-amino-4-(methylamino)phenoxy](2-pyridyl)}[1-(2-methoxyethyl)(4-piperidyl)]carboxamide The mixture containing [1-(2-methoxyethyl)(4-piperidyl)}-N-{4-[4-(methylamino)-3-nitrophenoxy](2-[pyridyl)}carboxamide in methanol with catalytic amount of Lindlar's catalyst was hydrogenated to yield N-{4[3-amino-4-(methylamino)phenoxy](2-pyridyl)}[1-(2-methoxyethyl)(4-piperidyl)]carboxamide. MS: MH$^+$=400.2.

4. Synthesis of N-{4-[(2-{[2-fluoro-5-(trifluoromethyl)phenyl]amino}-1-methyl-1H-benzimidazol-5-yl)oxy]pyridin-2-yl}-1-(2-methoxyethyl)piperidine-4-carboxamide To 2-fluoro-5-(trifluoromethyl)benzeneisothiocyanate (1 eq) in methanol was added N-{4[3-amino-4-(methylamino)phenoxy](2-pyridyl)}[1-(2-methoxyethyl)(4-piperidyl)]carboxamide (1 eq) and the resulting mixture was stirred at ambient temperature for 16 h. LC/MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through elite and was then extracted with ethyl acetate and the organic layer was washed with brine and dried with sodium sulfate. The crude was then triturated with hot ether with a few drops of ethyl acetate to yield N-{4-[(2-{[2-fluoro-5-(trifluoromethyl)phenyl]amino}-1-methyl-1H-benzimidazol-5-yl)oxy]pyridin-2-yl}-1-(2-methoxyethyl)piperidine-4-carboxamide. MS: MH$^+$=587.6.

EXAMPLE 11

Synthesis of N-{4-[(2-{[2-fluoro-5-(trifluoromethyl)phenyl]amino}-1-methyl-1H-benzimidazol-5-yl)oxy]pyridin-2-yl}-1-(2-hydroxyethyl)piperidine-4-carboxamide

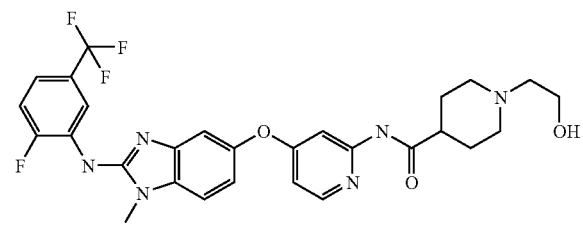 [SMILES: Cn1c(Nc2cc(C(F)(F)F)ccc2F)nc2cc(Oc3ccnc(NC(=O)C4CCN(CCO)CC4)c3)ccc21]

To N-{4-[(2-{[2-fluoro-5-(trifluoromethyl)phenyl]amino}-1-methyl-1H-benzimidazol-5-yl)oxy]pyridin-2-yl}-1-(2-methoxyethyl)piperidine-4-carboxamide (1 eq) in methylene chloride at 78° C. was added 1M borontribromide in methylene chloride (10 eq) and the resulting mixture and the resulting mixture was stirred at −78° C. for 1 h. It was then brought to ambient temperature and stirred for 2 h. LC/MS showed formation of the product. The reaction was quenched with saturated sodium carbonate solution at 0° C. The mixture was concentrated and then brought to pH=9. It was then extracted with ethyl acetate and the organic layer was dried with sodium sulfate and concentrated and purified on preparative chromatography to yield N-{4-[(2-{[2-fluoro-5-(trifluoro-methyl)phenyl]amino}-1-methyl-1H-benzimidazol-5-yl)oxy]pyridin-2-yl}-1-(2-hydroxyethyl)-piperidine-4-carboxamide. MS: MH$^+$=573.6.

EXAMPLE 12

Synthesis of N-{4-[(2-{[2-fluoro-5-(trifluoromethyl)phenyl]amino}-1-methyl-1H-benzimidazol-5-yl)oxy]pyridin-2-yl}-piperidine-4-carboxamide

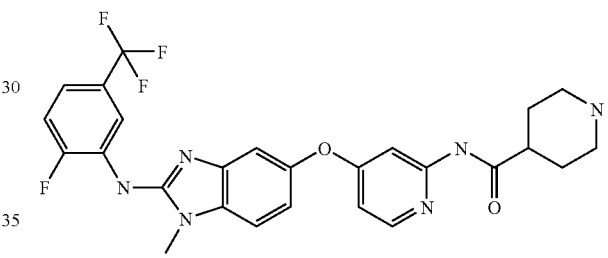

1. Synthesis of tert-butyl-4-(N-{4-[4-(methylamino)-3-nitrophenoxy]-2-pyridyl}carbamoyl)piperidinecarboxylate To a mixture of 1-(tert-butoxy)carbonylpiperidine-4-carboxylic acid (1 eq) in N,N-dimethyl formamide and N,N-disopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting tert-butyl-4-(N-{4-[4-(methylamino)-3-nitrophenoxy]-2-pyridyl}carbamoyl)piperidinecarboxylate was purified by silica gel chromatography. MS: MH$^+$=472.2.

2. Synthesis of tert-butyl-4-(N-{4-[3-amino-4-(methylamino)phenoxy]-2-pyridyl-carbamoyl)piperidinecarboxylate The mixture containing tert-butyl-4-(N-{4-[4-(methylamino)-3-nitrophenoxy]-2-pyridyl}carbamoyl)piperidinecarboxylate in methanol with catalytic amount of Lindlar's catalyst was hydrogenated to yield tert-butyl-4-(N-{4-[3-amino-4-(methylamino)phenoxy]-2-pyridylcarbamoyl)piperidinecarboxylate. MS: MH$^+$=2.2.

3. Synthesis of N-{4-[(2-{[2-fluoro-5-(trifluoromethyl)phenyl]amino}-1-methyl-1H-benzimidazol-5-yl)oxy]pyridin-2-yl}piperidine-4-carboxamide To 2-fluoro-5-(trifluoromethyl)benzeneisothiocyanate (1 eq) in methanol was added tert-butyl-4-(N-{4-[3-amino-4-(methylamino)phenoxy]-2-pyridylcarbamoyl)piperidinecarboxylate (1 eq) and the resulting mixture was stirred at ambient temperature for 16 h. LC MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to yield the product. To it in methylene chloride was then added trifluoroacetic acid to yield N-{4-[(2-{[2-fluoro-5-(trifluoromethyl)phenyl]amino}-1-methyl-1H-benzimidazol-5-yl)oxy]pyridin-2-yl}piperidine-4-carboxamide. MS: $MH^+=529.5$.

EXAMPLE 13

Synthesis of 1-acetyl-N-{4-[(2-{[2-fluoro-5-(trifluoromethyl)phenyl]amino}-1-methyl-1H-benzimidazol-5-yl)oxy]pyridin-2-yl}piperidine-4-carboxamide

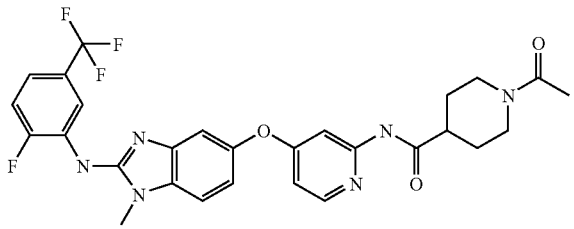 [SMILES: CC(=O)N1CCC(C(=O)Nc2cc(Oc3ccc4c(c3)nc(Nc3cc(C(F)(F)F)ccc3F)n4C)ccn2)CC1]

To N-{4-[(2-{[2-fluoro-5-(trifluoromethyl)phenyl]amino}-1-methyl-1H-benzimidazol-5-yl)oxy]pyridin-2-yl}piperidine-4-carboxamide (1 eq) in dioxane and N,N-disopropylethylamine (2 eq) was added acetic anhydride (1 eq) and the resulting mixture was stirred for 1 h. 1-acetyl-N-{4-[(2-{[2-fluoro-5-(trifluoromethyl)phenyl]amino}-1-methyl-1H-benzimidazol-5-yl)oxy]pyridin-2-yl}piperidine-4-carboxamide thus formed was purified by preparative chromatography. MS: $MH^+=571.5$.

EXAMPLE 14

Synthesis of N-{4-[(2-{[2-fluoro-5-(trifluoromethyl)phenyl]amino}-1-methyl-1H-benzimidazol-5-yl)oxy]pyridin-2-yl}-3-piperidin-4-ylpropanamide

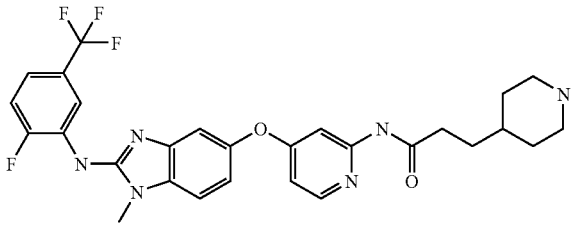 [SMILES: Cn1c(Nc2cc(C(F)(F)F)ccc2F)nc2cc(Oc3ccnc(NC(=O)CCC4CCNCC4)c3)ccc21]

1. Synthesis of tert-butyl-4-[2-(N-{4-{4-(methylamino)-3-nitrophenoxy]-2-pyridylcarbamoyl)ethyl]piperidinecarboxylate To a mixture of 3-{1-[(tert-butyl)oxycarbonyl]-4-piperidyl}propanoic acid (1 eq) in N,N-dimethyl formamide and N,N-disopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting tert-butyl-4-[2-(N-{4-{4-(methylamino)-3-nitrophenoxy]-2-pyridylcarbamoyl)ethyl]piperidinecarboxylate was purified by silica gel chromatography. MS: $MH^+=500.2$.

2. Synthesis of tert-butyl-4-[2-(N-{4-[3-amino-4-(methylamino)phenoxy]-2-pyridyl}carbamoyl)ethyl]piperidine carboxylate The mixture containing tert-butyl-4-[2-(N-{4-{4-(methylamino)-3-nitrophenoxy]-2-pyridylcarbamoyl)ethyl]piperidinecarboxylate in methanol with catalytic amount of Lindlar's catalyst was hydrogenated to yield tert-butyl-4-[2-(N-{4-[3-amino-4-(methylamino)phenoxy]-2-pyridyl}carbamoyl)ethyl]piperidine carboxylate. MS: $MH^+=470.2$.

3. Synthesis of N-[4-(2-{[2-fluoro-5-(trifluoromethyl)phenyl]amino-1-methylbenzimidazol-5-yloxy)(2-pyridyl]-3-(4-piperidyl)propanamide To 2-fluoro-5-(trifluoromethyl)benzeneisothiocyanate (1 eq) in methanol was added tert-butyl-4-[2-(N-{4-[3-amino-4-(methylamino)phenoxy]-2-pyridyl}carbamoyl)ethyl]piperidine carboxylate (1 eq) and the resulting mixture was stirred at ambient temperature for 16 h. LC/MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to yield the product. To it was then added trifluoroacetic acid to yield N-{4-[(2-{[2-fluoro-5-(trifluoromethyl)phenyl]amino}-1-methyl-1H-benzimidazol-5-yl)oxy]pyridin-2-yl}-3-piperidin-4-ylpropanamide. MS: $MH^+=557.6$.

EXAMPLE 15

Synthesis of N-{4-[(2-{[2-fluoro-5-(trifluoromethyl)phenyl]amino}-1-methyl-1H-benzimidazol-5-yl)oxy]pyridin-2-yl}-3-(1-methylpiperidin-4-yl)propanamide

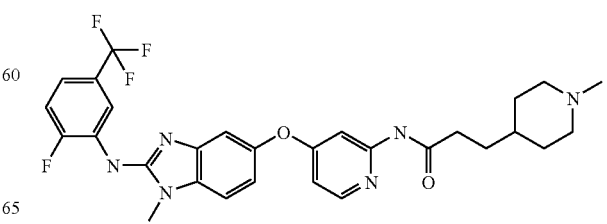

To N-{4-[(2-{[2-fluoro-5-(trifluoromethyl)phenyl]amino}-1-methyl-1H-benzimidazol-5-yl)oxy]pyridin-2-yl}-3-piperidin-4-ylpropanamide (1 eq) in methanol was added formalin (2 eq) and acetic acid (5%) followed by sodium cyanoborohydride (2 eq) and the resulting mixture was stirred at ambient temperature for 3 h. LC MS showed formation of the product. The crude mixture was then concentrated and to it was added sodium bicarbonate and the resulting mixture was partitioned between ethyl acetate and water. The organic layer was dried with sodium sulfate and purified by preparative chromatography to yield N-{4-[(2-{[2-fluoro-5-(trifluoromethyl)phenyl]amino}-1-methyl-1H-benzimidazol-5-yl)oxy]pyridin-2-yl}-3-(1-methylpiperidin-4-yl)propanamide. MS: MH$^+$=571.6.

EXAMPLE 16

Synthesis of N-{4-[(2-{[2-fluoro-5-(trifluoromethyl)phenyl]amino}-1-methyl-1H-benzimidazol-5-yl)oxy]pyridin-2-yl}-3-(1-isopropylpiperidin-4-yl)propanamide

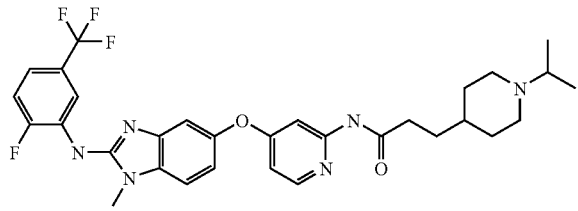 [SMILES: CC(C)N1CCC(CCC(=O)Nc2cc(Oc3ccc4c(c3)nc(Nc3cc(C(F)(F)F)ccc3F)n4C)ccn2)CC1]

1. Synthesis of N-[4-(2-{[2-fluoro-5-trifluoromethyl)phenyl]amino)-1-methylbenzimidazol-5-yloxy)(2-pyridyl)]-3-[1-(methylethyl)(4-piperidyl)]propanamide To N-[4-(2-{[2-fluoro-5-(trifluoromethyl)phenyl]amino-1-methylbenzimidazol-5-yloxy)(2-pyridyl]-3-(4-piperidyl)propanamide (1 eq) in methanol was added acetone (2 eq) and acetic acid (5%) followed by sodium cyanoborohydride (2 eq) and the resulting mixture was stirred at ambient temperature for 3 h. LC MS shows formation of the product. The crude mixture was then concentrated and to it was added sodium bicarbonate and the resulting mixture was partitioned between ethyl acetate and water. The organic layer was dried with sodium sulfate and purified by preparative chromatography to yield N-{4-[(2-{[2-fluoro-5-(trifluoromethyl)phenyl]amino}-1-methyl-1H-benzimidazol-5-yl)oxy]pyridin-2-yl}-3-(1-isopropylpiperidin-4-yl)propanamide. MS: MH$^+$=599.6.

EXAMPLE 17

Synthesis of N~1~-{4-[(2-{[2-fluoro-5-(trifluoromethyl)phenyl]amino}-1-methyl-1H-benzimidazol-5-yl)oxy]pyridin-2-yl}-N~2~-methylglycinamide

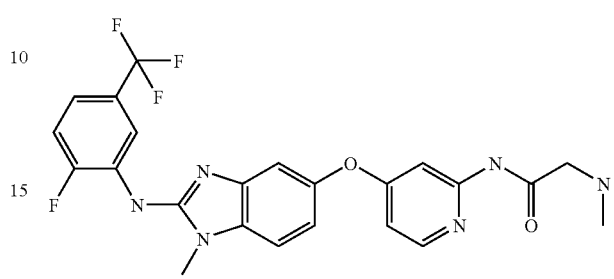

1. Synthesis of 2-[(tert-butoxy)-N-methylcarbonylamino]-N-{4-[4-(methylamino)-3-nitrophenoxy](2-pyridyl)acetamide To a mixture of 2-[(tert-butoxy)-N-methylcarbonylamino] acetic acid (1 eq) in N,N-dimethyl formamide and N,N-diisopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting 2-[(tert-butoxy)-N-methylcarbonylamino]-N-{4-[4-(methylamino)-3-nitrophenoxy] (2-pyridyl)acetamide was purified by silica gel chromatography. MS: MH$^+$=432.2.

2. Synthesis of N-{4-[3-amino-4-(methylamino)phenoxy](2-pyridyl)}-2-[(tert-butoxy)-N-methylcarbonylamino]acetamide The mixture containing 2-[(tert-butoxy)-N-methylcarbonylamino]-N-{4-[4-(methylamino)-3-nitrophenoxy](2-pyridyl)acetamide in methanol with catalytic amount of Lindlar's catalyst was hydrogenated to N-{4-[3-amino-4-(methylamino)phenoxy](2-pyridyl)}-2-[(tert-butoxy)-N-methylcarbonylamino]acetamide. MS: MH$^+$=402.2.

3. Synthesis of N~1~-{4-[(2-{[2-fluoro-5-(trifluoromethyl)phenyl]amino}-1-methyl-1H-benzimidazol-5-yl)oxy]pyridin-2-yl}-N~2~-methylglycinamide To 2-fluoro-5-(trifluoromethyl)benzeneisothiocyanate (1 eq) in methanol was added N-{4-[3-amino-4-(methylamino)phenoxy](2-pyridyl)}-2-[(tert-butoxy)-N-methylcarbonylamino]acetamide (1 eq) and the resulting mixture was stirred at ambient temperature for 16 h. LC/MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to yield the product. To it in methylene chloride was then added trifluoroacetic acid to yield N~1~-{4-[(2-{[2- fluoro-5-(trifluoromethyl)phenyl]amino}-1-methyl-1H-benzimidazol-5-yl)oxy]pyridin-2-yl}-N~2~-methylglycinamide. MS: MH+=489.4.

EXAMPLE 18

Synthesis of N-{4-[(2-{[2-fluoro-5-(trifluoromethyl)phenyl]amino}-1-methyl-1H-benzimidazol-5-yl)oxy]pyridin-2-yl}-4-morpholin-4-ylbutanamide

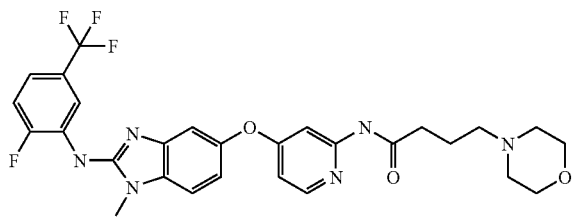 [SMILES: Cn1c(Nc2cc(C(F)(F)F)ccc2F)nc2cc(Oc3ccnc(NC(=O)CCCN4CCOCC4)c3)ccc21]

1. Synthesis of N-{4-[4-(methylamino)-3-nitrophenoxy](2-pyridyl)}-4-morpholino-4-ylbutanamide To a mixture of 4-morpholino-4-ylbutanoic acid (1 eq) in N,N-dimethyl formamide and N,N-disopropylethylamine (4 eq) was added BOP (2 eq) and the mixture was stirred at ambient temperature until homogeneous. To it was added [4-(2-amino(4-pyridyloxy))-2-nitrophenyl]methylamine (1 eq) and the resulting mixture was stirred at 60° C. for 16 h. The reaction mixture was then concentrated and partitioned between ethyl acetate and water. The organic layer was dried over sodium sulfate and the resulting N-{4-[4-(methylamino)-3-nitrophenoxy](2-pyridyl)}-4-morpholino-4-ylbutanamide was purified by silica gel chromatography. MS: MH+=416.2.

2. Synthesis of N-{4-[3-amino-4-(methylamino)phenoxy](2-pyridyl))-4-morpholin-4-ylbutanamide The mixture containing N-{4-[4-(methylamino)-3-nitrophenoxy](2-pyridyl)}-4-morpholino-4-ylbutanamide in methanol with catalytic amount of Lindlar's catalyst was hydrogenated to yield N-{4-[3-amino-4-(methylamino)phenoxy](2-pyridyl))-4-morpholin-4-ylbutanamide. MS: MH+=386.2.

3. Synthesis of N-{4-[(2-{[2-fluoro-5-(trifluoromethyl)phenyl]amino}-1-methyl-1H-benzimidazol-5-yl)oxy]pyridin-2-yl}-4-morpholin-4-ylbutanamide To 2-fluoro-5-(trifluoromethyl)benzeneisothiocyanate (1 eq) in methanol was added N-{4-[3-amino-4-(methylamino) phenoxy](2-pyridyl))-4-morpholin-4-ylbutanamide (1 eq) and the resulting mixture was stirred at ambient temperature for 16 h. LC/MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to N-{4-[(2-{[2-fluoro-5-(trifluoromethyl)phenyl]amino}-1-methyl-1H-benzimidazol-5-yl)oxy]pyridin-2-yl}-4-morpholin-4-ylbutanamide. MS: MH+=573.6.

EXAMPLE 19

Synthesis of N-{4-[(2-{[2-fluoro-5-(trifluoromethyl)phenyl]amino}-1-methyl-1H-benzimidazol-5-yl)oxy]pyridin-2-yl}-2-[4-(2-methoxyethyl)piperazin-1-yl]acetamide

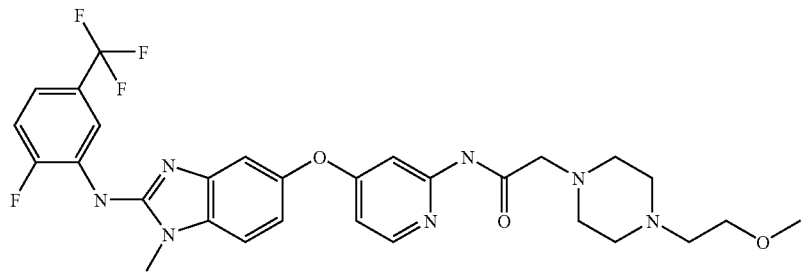 [SMILES: COCCN1CCN(CC(=O)Nc2cc(Oc3ccc4c(c3)nc(Nc3cc(C(F)(F)F)ccc3F)n4C)ccn2)CC1]

1. Synthesis of 2-[4-(2-methoxyethyl)piperizinyl]-N-{4-[4-(methylamino-3-nitrophenoxy](2-pyridyl)}acetamide To 2-chloro-N-{4-[4-(methylamino)-3-nitrophenoxy](2-pyridyl)}acetamide (1 eq) in acetonitrile was added 1-methoxy-2-piperizinylethane (1 eq) and potassium carbonate (2 eq) and the resulting mixture was heated to 60° C. for 16 h. It was then concentrated and partitioned between ethyl acetate and water. The organic layer was dried with sodium sulfate and concentrated to give 2-[4-(2-methoxyethyl)piperizinyl]-N-{4-[4-(methylamino-3-nitrophenoxy](2-pyridyl)}acetamide. MS: MH+=445.2.

2. Synthesis of N-{4-[3-amino-4-(methylamino)phenoxy] (2-pyridyl)}-2-[4-(2-methoxyethyl)piperizinyl]acetamide The mixture containing 2-[4-(2-methoxyethyl)piperizinyl]-N-{4-[4-(methylamino-3-nitrophenoxy](2-pyridyl)} acetamide in methanol with catalytic amount of Lindlar's catalyst was hydrogenated to yield N-{4-[3-amino-4-(methylamino)phenoxy](2-pyridyl)}-2-[4-(2-methoxyethyl)piperizinyl]acetamide. MS: MH+=415.2.

3. Synthesis of N-{4-[(2-{[2-fluoro-5-(trifluoromethyl)phenyl]amino}-1-methyl-1H-benzimidazol-5-yl)oxy]pyridin-2-yl}-2-[4-(2-methoxyethyl)piperazin-1-yl]acetamide To 2-fluoro-5-(trifluoromethyl)benzeneisothiocyanate (1 eq) in methanol was added N-{4-[3-amino-4-(methylamino)phenoxy](2-pyridyl)}-2-[4-(2-methoxyethyl)piperizinyl]acetamide (1 eq) and the resulting mixture was stirred at ambient temperature for 16 h. LC/MS showed formation of the corresponding thiourea. To it in methanol was then added anhydrous ferric chloride (1.5 eq) and stirred for 3 h. The reaction mixture was then concentrated to half its volume and brought to basic pH with saturated sodium carbonate solution. The aqueous solution was filtered through celite and was then extracted with ethyl acetate and the organic layer was washed with brine and dried with sodium sulfate. The crude was then triturated with hot ether with a few drops of ethyl acetate to yield N-{4-[(2-{[2-fluoro-5-(trifluoromethyl)phenyl]amino}-1-methyl-1H-benzimidazol-5-yl)oxy]pyridin-2-yl}-2-[4-(2-methoxyethyl)piperazin-1-yl]acetamide. MS: MH$^+$=602.6.

EXAMPLE 20

Synthesis of N-{4-[(2-{[2-fluoro-5-(trifluoromethyl)phenyl]amino}-1-methyl-1H-benzimidazol-5-yl)oxy]pyridin-2-yl}-2-[4-(2-hydroxyethyl)piperazin-1-yl]acetamide

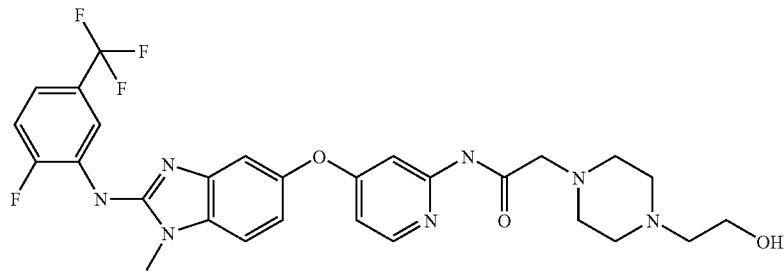 [SMILES: Cn1c(Nc2cc(C(F)(F)F)ccc2F)nc2cc(Oc3ccnc(NC(=O)CN4CCN(CCO)CC4)c3)ccc21]

To N-{4-[(2-{[2-fluoro-5-(trifluoromethyl)phenyl]amino}-1-methyl-1H-benzimidazol-5-yl)oxy]pyridin-2-yl}-2-[4-(2-methoxyethyl)piperazin-1-yl]acetamide (1 eq) in methylene chloride at 78° C. was added 1M borontribromide in methylene chloride (Oeq) and the resulting mixture was stirred at −78° C. for 1 h. It was then brought to ambient temperature and stirred for 2 h. LC/MS showed formation of the product. The reaction was quenched with saturated sodium carbonate solution at 0° C. The mixture was concentrated and then brought to pH=9. It was then extracted with ethyl acetate and the organic layer was dried with sodium sulfate and concentrated and purified on preparative chromatography to yield N-{4-[(2-{[2-fluoro-5-(trifluoromethyl)phenyl]amino}-1-methyl-1H-benzimidazol-5-yl)oxy]pyridin-2-yl}-2-[4-(2-hydroxyethyl)piperazin-1-yl]acetamide. MS: MH$^+$=588.6.

EXAMPLE 21

Synthesis of N-(4-{[2-(4-chlorobenzyl)-1-methyl-1H-benzimidazol-5-yl]oxy}pyridin-2-yl)acetamide

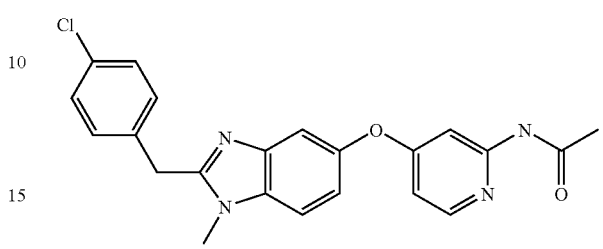

To N-{4-[3-amino-4-(methylamino)phenoxy]}-2-pyridylacetamide (1 eq) in tetra-hydrofuran added EDC (2 eq) and HOAT (1 eq) and N,N-disopropylethylamine (4 eq) and 2-(4-chlorophenyl)acetic acid (1 eq) and the resulting mixture was stirred at ambient temperature for 16 h. The reaction mixture was then partitioned between ethyl acetate and water. The organic layer was then dried with sodium sulfate and concentrated to give N-{4-[2-(acetylamino)(4-pyridyloxy)]-2-aminophenyl}-2-(4-chlorophenyl)-N-methylacetamide. To it was added acetic acid and the resulting mixture was heated to 60° C. for 4 h. The crude was purified by preparative chromatography to give N-(4-{[2-(4-chlorobenzyl)-1-methyl-1H-benzimidazol-5-yl]oxy}pyridin-2-yl)acetamide. MS: MH$^+$=407.9.

EXAMPLE 22

Synthesis of N-[4-({2-[(4-chlorophenyl)amino]-1-methyl-1H-benzimidazol-5-yl}oxy)pyridin-2-yl]benzamide

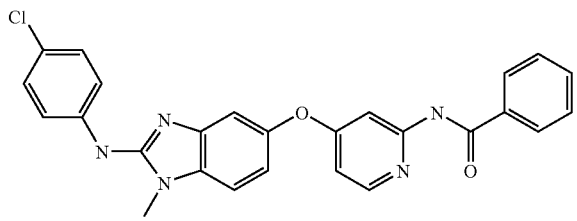 [SMILES: Cn1c(Nc2ccc(Cl)cc2)nc2cc(Oc3ccnc(NC(=O)c4ccccc4)c3)ccc21]

To [5-(2-amino(4-pyridyloxy))-1-methylbenzimidazol-2-yl] (4-chlorophenyl)amine (1 eq) in tetrahydrofuran added EDC (2 eq) and HOAT (1 eq) and N,N-disopropylethylamine (4 eq) and benzoic acid (1 eq) and the resulting mixture was stirred at ambient temperature for 16 h. The reaction mixture was then partitioned between ethyl acetate and water. The organic layer was then dried with sodium sulfate and concentrated and purified by preparative chromatography to give N-[4-({2-[(4-chlorophenyl)amino]-1-methyl-1H-benzimidazol-5-yl}oxy)pyridin-2-yl]benzamide. MS: MH$^+$=470.9.

EXAMPLE 23

Synthesis of N-[4-({2-[(3-tert-butylphenyl)amino]-1-methyl-1H-benzimidazol-5-yl}oxy)pyridin-2-yl]-N'-(2-morpholin-4-ylethyl)urea

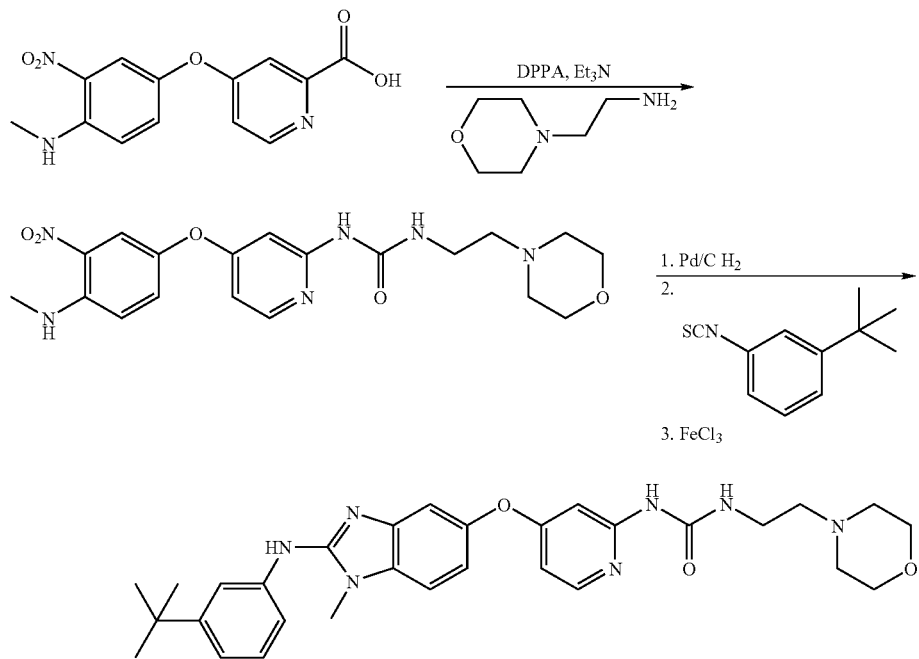

Step 1: Synthesis of N-{4-[4-(methylamino)-3-nitrophenoxy](2-pyridyl)}[(2-morpholin-4-ylethyl)amino]carboxamide A flame dried flask was charged with 4-[4-(methylamino)-3-nitrophenoxy]pyridine-2-carboxylic acid (1 eq), diphenylphosphoryl azide (1.1 eq), triethylamine (2.1 eq) and 20 ml toluene and heated for one and one half hours at 75° C. To this was added 2-morpholin-4-ylethylamine (1.2 eq) and the resulting mixture was stirred at 75° C. overnight. The reaction was then concentrated and partitioned between ethyl acetate and distilled water. The organic layer was dried with sodium sulfate and concentrated and titurated with ether then hexanes to give the purified product. MS: MH$^+$=417.

Step 2: Synthesis of N-{4-[3-amino-4-(methylamino)phenoxy](2-pyridyl)}[(2-morpholin-4-ylethyl)amino]carboxamide To a flask containing N-{4-[4-(methylamino)-3-nitrophenoxy](2-pyridyl)}[(2-morpholin-4-ylethyl)amino]carboxamide in methanol was added a catalytic amount of 10% Pd C and hydrogenated to yield in quantitative amount N-{4-[3-amino-4-(methylamino)phenoxy](2-pyridyl)}[(2-morpholin-4-ylethyl)amino]carboxamide. MS: MH$^+$=387.

Step 3: Synthesis of 3-(tert-butyl)benzenisothiocyanate

To 3-(tert-butyl)phenylamine in acetone at 0° C. was added sodium bicarbonate (2 eq) and thiophosgene (2 eq). The mixture was brought to ambient temperature and concentrated and partitioned between ethyl acetate and water. The organic layer was dried with sodium bicarbonate and sodium sulfate and concentrated to yield 3-(tert-butyl)benzenisothiocyanate. MS: MH$^+$=192.

Step 4: Synthesis of N-[4-({2-[(3-tert-butylphenyl)amino]-1-methyl-1H-benzimidazol-5-yl}oxy)pyridin-2-yl]-N'-(2-morpholin-4-ylethyl)urea To 3-(tert-butyl)benzenisothiocyanate (1 eq) in methanol was added N-{4-[3-amino-4-(methylamino)phenoxy](2-pyridyl)}[(2-morpholin-4-ylethyl)amino]carboxamide (1 eq) and the resulting mixture was stirred at ambient temperature for 16 h. LC MS showed formation of corresponding thiourea. To this was added anhydrous ferric chloride (1.5 eq) and stirred for 3 h. The reaction mixture was then concentrated to half its volume and brought to neutral pH with 1N sodium hydroxide. It was then extracted with ethyl acetate and the organic layer was washed with brine and dried with sodium sulfate. The crude material was then purified on preparative chromatography to yield N-[4-({2-[(3-tert-butylphenyl)amino]-1-methyl-1H-benzimidazol-5-yl}oxy)pyridin-2-yl]-N'-(2-morpholin-4-ylethyl)urea. MS: MH$^+$=544.

EXAMPLE 24

Synthesis of 2-(4-ethylpiperazin-1-yl)-N-{4-[(2-{[2-fluoro-5-(trifluoromethyl)phenyl]amino}-1-methyl-1H-benzimidazol-5-yl)oxy]pyridin-2-yl}acetamide

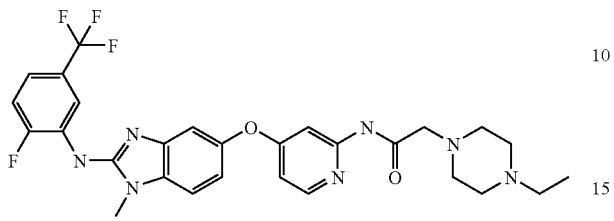

1. Synthesis of N-(4-(4-(methylamino)-3-nitrophenoxy)pyridin-2-yl)-2-chloroacetamide A solution of 4-(4-(methylamino)-3-nitrophenoxy)pyridin-2-amine (1 eq) and triethylamine (2 eq) in tetrahydrofuran was treated with 2-chloroacetyl chloride and stirred for 15 minutes at room temperature. The reaction mixture was then concentrated and partitioned between ethyl acetate and water. The organic layer was separated and washed with brine, dried over sodium sulfate and concentrated in vacuum to give crude product. Purification on silica gel with 2% methanol in methylene chloride gave N-(4-(4-(methylamino)-3-nitrophenoxy)pyridin-2-yl)-2-chloroacetamide as a bright orange solid. HPLC=3.82 min; MS: MH$^+$=337.

2. Synthesis of N-(4-(4-(methylamino)-3-nitrophenoxy)pyridin-2-yl)-2-(4-ethylpiperazin-1-yl)acetamide The mixture containing N-(4-(4-(methylamino)-3-nitrophenoxy)pyridin-2-yl)-2-chloroacetamide (1 eq), 1-ethylpiperazine (3 eq), and potassium carbonate (4 eq) was stirred in dimethylformamide at 60° C. for 1 hour. The reaction mixture was then concentrated and partitioned between ethyl acetate and water. The organic layer was separated and washed with water then brine, dried over sodium sulfate and concentrated to give orange solid. Purification on silica gel with 20% methanol in methylene chloride gave N-(4-(4-(methylamino)-3-nitrophenoxy)pyridin-2-yl)-2-(4-ethylpiperazin-1-yl)acetamide as a red solid. HPLC=3.26 min; MS: MH$^+$=415.

3. Synthesis of N-(4-(3-amino-4-(methylamino)phenoxy)pyridin-2-yl)-2-(4-ethylpiperazin-1-yl)acetamide The mixture containing N-(4-(4-(methylamino)-3-nitrophenoxy)pyridin-2-yl)-2-(4-ethylpiperazin-1-yl)acetamide in methanol with a catalytic amount of 10% Pd/C poisoned with lead was hydrogenated until the disappearance of the yellow color. The reaction was then filtered to remove the catalyst and concentrated to yield N-(4-(3-amino-4-(methylamino)phenoxy)pyridin-2-yl)-2-(4-ethylpiperazin-1-yl)acetamide as a brown oil. HPLC=2.00 min; MS: MH$^+$=385.

4. Synthesis of 2-(4-ethylpiperazin-1-yl)-N-{4-[(2-{[2-fluoro-5-(trifluoromethyl)phenyl]amino}-1-methyl-1H-benzimidazol-5-yl)oxy]pyridin-2-yl}acetamide A solution of N-(4-(3-amino-4-(methylamino)phenoxy)pyridin-2-yl)-2-(4-ethyl-piperazin-1-yl)acetamide (1 eq) in methanol was treated with 1-fluoro-4-(trifluoromethyl)-2-isothiocyanatobenzene (1 eq) and stirred at room temperature for 16 hours to form the corresponding thiourea. To it was then added iron (III) chloride (1.2 eq) and stirred for another 4 hours. The mixture was then concentrated and partitioned between saturated sodium carbonate and ethyl acetate. The organic layer was separated and washed with water and brine, dried over sodium sulfate and concentrated to give brown crude solid. Purification by trituration with 5% ethyl acetate in diethyl ether to give 2-(4-ethylpiperazin-1-yl)-N-{4-[(2-{[2-fluoro-5-(trifluoromethyl)phenyl]amino}-1-methyl-1H-benzimidazol-5-yl)oxy]pyridin-2-yl}acetamide as tan solid. HPLC=3.40 min; MS: MH$^+$=572.

EXAMPLE 25

Synthesis of N-{4-[(2-{[4-chloro-3-(3-fluoropyridin-4-yl)phenyl]amino}-1-methyl-1H-benzimidazol-5-yl)oxy]pyridin-2-yl}acetamide

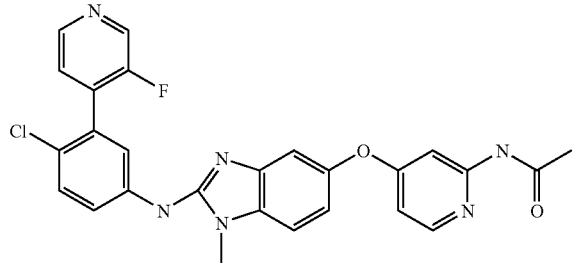 [SMILES: CC(=O)Nc1cc(Oc2ccc3c(c2)nc(Nc2ccc(Cl)c(-c4ccncc4F)c2)n3C)ccn1]

1. Synthesis of 4-(2-chloro-5-nitrophenyl)-3-fluoropyridine

A mixture of DME:H2O (3:1) was degassed with N$_2$ for one half hour. 2-bromo-1-chloro-4-nitrobenzene (1 eq) added and degassed for another 10 minutes. 1,1'-bis(diphenylphosphino)ferrocene palladium(II)chloride (0.05 eq), 3-fluoropyridin-4-yl-4-boronic acid (1 eq), and sodium carbonate (3 eq) were then added and stirred at 100° C. for 16 hours. Reaction then concentrated and partitioned between ethyl acetate and water. Organic layer washed with brine, dried over sodium sulfate and concentrated. Purification on silica gel, 10% ethyl acetate in hexanes to yield 4-(2-chloro-5-nitrophenyl)-3-fluoropyridine. HPLC=4.57 min; MS: MH$^+$=253.

2. Synthesis of 4-chloro-3-(3-fluoropyridin-4-yl)benzenamine 4-(2-chloro-5-nitrophenyl)-3-fluoropyridine (1 eq) was stirred with Iron (0), (3 eq), in acetic acid for 10 hours at room temperature. Reaction neutralized with sodium carbonate and filtered to remove iron. Reaction partitioned between ethyl acetate and water. Organic layer separated and washed with brine, dried over sodium sulfate and concentrated to give 4-chloro-3-(3-fluoropyridin-4-yl)benzenamine. HPLC=1.72 min; MS: MH$^+$=223.

3. Synthesis of 4-(2-chloro-5-isothiocyanatophenyl)-3-fluoropyridine

The mixture containing 4-chloro-3-(3-fluoropyridin-4-yl)benzenamine (1 eq) and sodium bicarbonate (2 eq) in acetone was treated with thiophosgene (2 eq) and stirred for 5 minutes at 0° C. Reaction then concentrated and partitioned between ethyl acetate and water. Organic layer dried over sodium sulfate and sodium bicarbonate and concentrated to give 4-(2-chloro-5-isothiocyanatophenyl)-3-fluoropyridine. HPLC=5.54 min; MS: MH$^+$=265.

4. Synthesis of N-{4-[(2-{[4-chloro-3-(3-fluoropyridin-4-yl)phenyl]amino}-1-methyl-1H-benzimidazol-5-yl)oxy]pyridin-2-yl}acetamide The mixture containing 4-(2-chloro-5-isothiocyanatophenyl)-3-fluoropyridine (1 eq) and N-(4-(3-amino-4-(methylamino)phenoxy)pyridin-2-yl)acetamide (1 eq) in methanol was stirred at room temperature of 16 hours to give the corresponding thiourea. To it was then added iron (III) chloride (1.2 eq) and stirred for another 4 hours. The mixture was then concentrated and partitioned between saturated sodium carbonate and ethyl acetate. The organic layer was separated and washed with water and brine, dried over sodium sulfate and concentrated to give brown crude solid. Purification on HPLC to yield N-{4-[(2-{[4-chloro-3-(3-fluoropyridin-4-yl)phenyl]amino}-1-methyl-1H-benzimidazol-5-yl)oxy]pyridin-2-yl}acetamide. HPLC=3.37 min; MS: MH$^+$=503

EXAMPLE 26

Synthesis of N-[4-({2-[(3-isopropylphenyl)amino]-1,3-benzothiazol-5-yl}oxy)pyridin-2-yl]acetamide

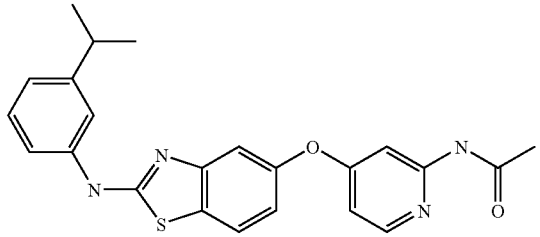 [SMILES: CC(=O)Nc1cc(Oc2ccc3sc(Nc4cccc(C(C)C)c4)nc3c2)ccn1]

1. Synthesis of N-(3-isopropylphenyl)-5-methoxybenzo[d]thiazol-2-amine

The mixture containing 2-bromo-5-methoxybenzo[d]thiazole (1 eq), 3-isopropylbnezylamine (1.5 eq) and diisopropylethylamine (4 eq) was subjected to microwave in NMP at 235° C. for 15 minutes. Reaction partitioned between ethyl acetate and water. Organic layer separated and washed with brine, dried over sodium sulfate and concentrated. Purification on silica gel, 10% ethyl acetate in hexane to give N-(3-isopropylphenyl)-5-methoxybenzo[d]thiazol-2-amine. HPLC=5.50 min; MS: MH$^+$=299.

2. Synthesis of 2-(3-isopropylphenylamino)benzo[d]thiazol-5-ol

N-(3-isopropylphenyl)-5-methoxybenzo[d]thiazol-2-amine was charged with hydrobromic acid (45%) and subjected to microwave at 170° C. for 10 minutes. Reaction was then neutralized with sodium carbonate (saturated solution) and partitioned between ethyl acetate and water. The organic layer was separated, washed with brine, dried over sodium sulfate and concentrated to give 2-(3-isopropylphenylamino)benzo[d]thiazol-5-ol. HPLC=4.63 min; MS: MH$^+$=285.

3. Synthesis of N-[4-({2-[(3-isopropylphenyl)amino]-1,3-benzothiazol-5-yl}oxy)pyridin-2-yl]acetamide The mixture containing 2-(3-isopropylphenylamino)benzo[d]thiazol-5-ol (1 eq), N-(4-chloropyridin-2-yl)acetamide (1.4 eq), potassium bis(trimethylsilyl)amide (4 eq) and potassium carbonate (1.2 eq) in dimethylformamide was subjected to the microwave at 200° C. for 15 minutes. The reaction was then partitioned between ethyl acetate and water. The organic layer was separated, washed with brine, dried over sodium sulfate and concentrated to give the crude product. Purification on HPLC to yield N-[4-({2-[(3-isopropylphenyl)amino]-1,3-benzothiazol-5-yl}oxy)pyridin-2-yl]acetamide. HPLC=4.87 min; MS: MH$^+$=419.

EXAMPLE 27

Synthesis of N-[4-({2-[(3-tert-butylphenyl)amino]-1,3-benzothiazol-5-yl}oxy)pyridin-2-yl]-1-methylpiperidine-4-carboxamide

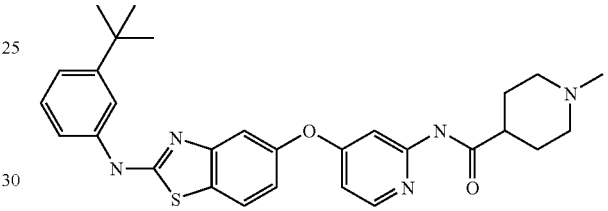

1. Synthesis of 1-methylpiperidine-4-carbonyl chloride

A flask was flame dried and placed under a nitrogen atmosphere. 1-methylpiperidine-4-carboxylic acid (1 eq) in anhydrous methylene chloride added to flask and cooled to 20° C. in a water bath. Dimethylformamide added, then oxalyl chloride (1.4 eq) in methylene chloride. Reaction refluxed for 2 hours, brought to room temperature, concentrated and azeotroped with toluene to yield 1-methylpiperidine-4-carbonyl chloride as a light yellow fluffy solid. MS: MH$^+$=162.

2. Synthesis of N-(4-chloropyridin-2-yl)-1-methylpiperidine-4-carboxamide

A flask was flame dried and placed under a nitrogen atmosphere. 1-methylpiperidine-4-carbonyl chloride (1 eq) in anhydrous methylene chloride was added to the flask and brought to 0° C. To this was added the solution containing 4-chloropyridin-2-amine (1 eq), and diisopropylethylamine (5 eq) in anhydrous methylene chloride, which was stirred for 1 hour at 0° C. Reaction concentrated and partitioned between water and ethyl acetate. The organic layer was separated, washed with brine, dried over sodium sulfate and concentrated to give the crude product. Purification on silica gel, 10% methanol in methylene chloride to yield N-(4-chloropyridin-2-yl)-1-methylpiperidine-4-carboxamide as a slightly yellow crystal solid. HPLC=2.39 min; MS: MH$^+$=254.

3. Synthesis of N-[4-({2-[(3-tert-butylphenyl)amino]-1,3-benzothiazol-5-yl}oxy)pyridin-2-yl]-1-methylpiperidine-4-carboxamide The mixture containing 2-(3-tert-butylphenylamino)benzo[d]thiazol-5-ol (1 eq), potassium bis(trimethylsilyl)amide (4 eq), and potassium carbonate (1.2 eq) in dimethylformamide was stirred at room temperature for 10 minutes. N-(4-chloropyridin-2-yl)-1-methylpiperidine-4-carboxamide (1.4 eq) was then added and mixture subjected to microwave at 220° C. for 20 minutes. Reaction partitioned between ethyl acetate and water. Organic layer separated, washed with brine, dried over sodium sulfate and concentrated to give crude product. Purification by HPLC to yield N-[4-({2-[(3-tert-butylphenyl)amino]-1,3-benzothiazol-5-yl}oxy)pyridin-2-yl]-1-methylpiperidine-4-carboxamide. HPLC=4.74 min; MS: MH$^+$=516.

EXAMPLE 28

Synthesis of N-{4-[(2-{[2-fluoro-5-(trifluoromethyl)phenyl]amino}-6-methoxy-1-methyl-1H-benzimidazol-5-yl)oxy]pyridin-2-yl}acetamide

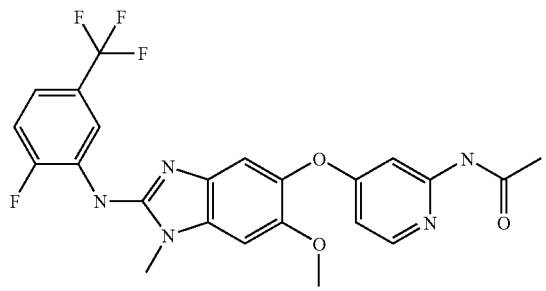 [SMILES: COc1cc2c(cc1Oc1ccnc(NC(C)=O)c1)nc(Nc1cc(C(F)(F)F)ccc1F)n2C]

1. Synthesis of 4-(2-methoxy-4-(methylamino)-5-nitrophenoxy)pyridine-2-carboxylic acid Trifluoroacetic acid was added neat to tert-butyl 4-(2-methoxy-4-(methylamino)-5-nitrophenoxy)pyridine-2-carboxylate and stirred at room temperature for 5 hours. TFA was evaporated, solid product azeotroped with toluene then placed under vacuum for 24 hours to yield 4-(2-methoxy-4-(methylamino)-5-nitrophenoxy)pyridine-2-carboxylic acid. HPLC=3.07 min; MS: MH$^+$=321

2. Synthesis of 4-(2-methoxy-4-(methylamino)-5-nitrophenoxy)pyridine-2-carboxamide The mixture containing 4-(2-methoxy-4-(methylamino)-5-nitrophenoxy)pyridine-2-carboxylic acid (1 eq), 1-(3-dimethylaminopropyl)-3-ethylcarbodiimide (2 eq), 3H-1,2,3-triazolo[4,5-b]pyridine-3-ol (1.5 eq), and diisopropylamine (5 eq) in tetrahydrofuran was stirred at room temperature for 1 hour. To this was then added ammonium chloride (2 eq) and the resulting mixture was stirred together for 48 hours. Reaction concentrated. Purification on silica gel, 50% acetone in hexanes to yield 4-(2-methoxy-4-(methylamino)-5-nitrophenoxy)pyridine-2-carboxamide as a bright yellow solid. HPLC=3.70 min; MS: MH$^+$=319.

3. Synthesis of 4-(2-methoxy-4-(methylamino)-5-nitrophenoxy)pyridin-2-amine

Liquid bromine (2 eq) was added dropwise to a solution of potassium hydroxide (10 eq) in water at 0° C. 4-(2-methoxy-4-(methylamino)-5-nitrophenoxy)pyridine-2-carboxamide (1 eq) was then added in a small amount of dioxane. Reaction brought to room temperature for 1 hour then heated to 55° C. for 1 hour showing a red homogenous solution. The reaction was brought back to 0° C. and acetic acid (excess) was added. The mixture was heated at 55° C. for 1 hour, cooled to room temperature and sodium carbonate added to neutralize. Reaction was extracted with methylene chloride. Organic layer washed with brine, dried over sodium sulfate and concentrated to yield 4-(2-methoxy-4-(methylamino)-5-nitrophenoxy)pyridin-2-amine as an orange solid. HPLC=3.10 min; MS: MH$^+$=292.

4. Synthesis of N-(4-(2-methoxy-4-(methylamino)-5-nitrophenoxy)pyridin-2-yl)acetamide Under a nitrogen atmosphere, 4-(2-methoxy-4-(methylamino)-5-nitrophenoxy)pyridin-2-amine (1 eq) and disopropylethylamine (4 eq) in methylene chloride was brought to 0° C. Acetyl chloride (1.1 eq) was added dropwise and mixture stirred for 5 minutes. Reaction brought to room temperature and water added. Organic layer washed with brine, dried over sodium sulfate and concentrated to yield N-(4-(2-methoxy-4-(methylamino)-5-nitrophenoxy)pyridin-2-yl)acetamide. HPLC=3.21 min; MS: MH$^+$=333.

5. Synthesis of N-(4-(5-amino-2-methoxy-4-(methylamino)phenoxy)pyridin-2-yl)acetamide The mixture containing N-(4-(2-methoxy-4-(methylamino)-5-nitrophenoxy)pyridin-2-yl)acetamide in methanol with a catalytic amount of 10% Pd/C poisoned with lead was hydrogenated until the disappearance of the yellow color. The reaction was then filtered to remove the catalyst and concentrated to yield N-(4-(5-amino-2-methoxy-4-(methylamino)phenoxy)pyridin-2-yl)acetamide. HPLC=2.25 min; MS: MH$^+$=303.

6. Synthesis of N-{4-[(2-{[2-fluoro-5-(trifluoromethyl)phenyl]amino}-6-methoxy-1-methyl-1H-benzimidazol-5-yl)oxy]pyridin-2-yl}acetamide A solution of N-(4-(5-amino-2-methoxy-4-(methylamino)phenoxy)pyridin-2-yl)acetamide (1 eq) in methanol was treated with 1-fluoro-4-(trifluoromethyl)-2-isothiocyanatobenzene (1 eq) and stirred at room temperature for 16 hours to form the corresponding thiourea. To it was then added iron (III) chloride (1.2 eq) and stirred for another 4 hours. The mixture was then concentrated and partitioned between saturated sodium carbonate and ethyl acetate. The organic layer was separated and washed with water and brine, dried over sodium sulfate and concentrated to give brown crude solid. Purification by HPLC to yield N-{4-[(2-{[2-fluoro-5-(trifluoromethyl)phenyl]amino}-6-methoxy-1-methyl-1H-benzimidazol-5-yl)oxy]pyridin-2-yl}acetamide HPLC=3.02 min; MS: MH$^+$=490.

EXAMPLE 29

Synthesis of N-[4-({2-[(3-isopropylphenyl)amino]-1-methyl-1H-benzimidazol-5-yl}oxy)pyridin-2-yl]-2-piperidin-4-ylacetamide

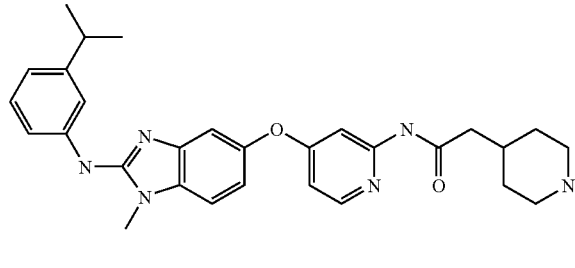 [SMILES: CC(C)c1cccc(Nc2nc3cc(Oc4ccnc(NC(=O)CC5CCNCC5)c4)ccc3n2C)c1]

1. Synthesis of 5-(2-aminopyridin-4-yloxy)-N-(3-isopropylphenyl)-1-methyl-1H-benzo[d]imidazol-2-amine The mixture containing 4-(4-(methylamino)-3-nitrophenoxy)pyridin-2-amine (1 eq) and 1-isopropyl-3-isothiocyanatobenzene (1 eq) in methanol was stirred at room temperature for 16 hours to form the corresponding thiourea. To it was then added iron (III) chloride (1.2 eq) and stirred for another 4 hours. The mixture was then concentrated and partitioned between saturated sodium carbonate and ethyl acetate. The organic layer was separated and washed with water and brine, dried over sodium sulfate and concentrated to give brown crude solid. Purification by trituration with toluene to give 5-(2-aminopyridin-4-yloxy)-N-(3-isopropylphenyl)-1-methyl-1H-benzo[d]imidazol-2-amine as brown solid. HPLC=3.63 min; MS: MH$^+$=374.

2. Synthesis of tert-butyl 4-((4-(2-(3-isopropylphenylamino)-1-methyl-1H-benzo[d]imidazol-5-yloxy)pyridin-2-ylcarbamoyl)methyl)piperidine-1-carboxylate To a mixture of 2-(1-(tert-butoxycarbonyl)piperidin-4-yl)acetic acid (1 eq) in N,N-dimethyl formamide and N,N,diisopropylethylamine (4 eq) was added HATU (2 eq) and the mixture was stirred at ambient temperature until it becomes homogeneous. To it was added 5-(2-aminopyridin-4-yloxy)-N-(3-isopropylphenyl)-1-methyl-1H-benzo[d]imidazol-2-amine (1 eq) and 4-(dimethylamino)pyridine (0.05 eq) and the resulting mixture was stirred at room temperature for 16 h. The reaction mixture was then concentrated and partitioned between ethyl acetate and water. The organic layer was dried over sodium sulfate and the resulting tert-butyl 4-((4-(4-(methylamino)-3-nitrophenoxy)pyridin-2-ylcarbamoyl)methyl)piperidine-1-carboxylate was purified by HPLC. HPLC=4.63 min; MS: MH$^+$=599.

3. Synthesis of N-[4-({2-[(3-isopropylphenyl)amino]-1-methyl-1H-benzimidazol-5-yl}oxy)pyridin-2-yl]-2-piperidin-4-ylacetamide To tert-butyl 4-((4-(4-(methylamino)-3-nitrophenoxy)pyridin-2-ylcarbamoyl)methyl)-piperidine-1-carboxylate (1 eq) in water and acetonitrile was added trifluoroacetic acid (2 eq) and stirred at room temperature for 16 hours. The resulting solution was frozen with liquid nitrogen and the lyophilized sample yielded N-[4-({2-[(3-isopropylphenyl)amino]-1-methyl-1H-benzimidazol-5-yl}oxy)pyridin-2-yl]-2-piperidin-4-ylacetamide. HPLC=3.49 min; MS: MH$^+$=499.

EXAMPLE 30

Synthesis of N-[4-({2-[(3-isopropylphenyl)amino]-1-methyl-1H-benzimidazol-5-yl}oxy)pyridin-2-yl]-2-(1-methylpiperidin-4-yl)acetamide

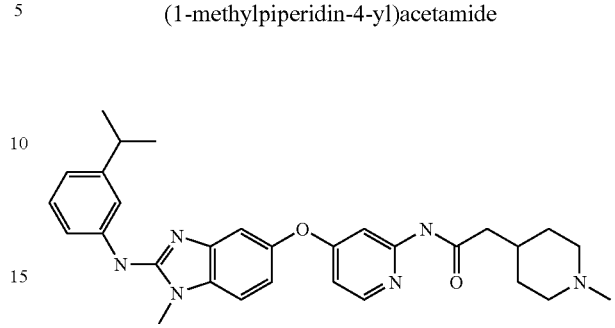

1. Synthesis of 5-(2-aminopyridin-4-yloxy)-N-(3-isopropylphenyl)-1-methyl-1H-benzo[d]imidazol-2-amine The mixture containing 4-(4-(methylamino)-3-nitrophenoxy)pyridin-2-amine (1 eq) and 1-isopropyl-3-isothiocyanatobenzene (1 eq) in methanol was stirred at room temperature for 16 hours to form the corresponding thiourea. To it was then added iron (III) chloride (1.2 eq) and stirred for another 4 hours. The mixture was then concentrated and partitioned between saturated sodium carbonate and ethyl acetate. The organic layer was separated and washed with water and brine, dried over sodium sulfate and concentrated to give brown crude solid. Purification by trituration with toluene to give 5-(2-aminopyridin-4-yloxy)-N-(3-isopropylphenyl)-1-methyl-1H-benzo[d]imidazol-2-amine as brown solid. HPLC=3.63 min; MS: MH$^+$=374.

2. Synthesis of tert-butyl 4-((4-(2-(3-isopropylphenylamino)-1-methyl-1H-benzo[d]imidazol-5-yloxy)pyridin-2-ylcarbamoyl)methyl)piperidine-1-carboxylate To a mixture of 2-(1-(tert-butoxycarbonyl)piperidin-4-yl)acetic acid (1 eq) in N,N-dimethyl formamide and N,N,diisopropylethylamine (4 eq) was added HATU (2 eq) and the mixture was stirred at ambient temperature until it becomes homogeneous. To it was added 5-(2-aminopyridin-4-yloxy)-N-(3-isopropylphenyl)-1-methyl-1H-benzo[d]imidazol-2-amine (1 eq) and 4-(dimethylamino)pyridine (0.05 eq) and the resulting mixture was stirred at room temperature for 16 h. The reaction mixture was then concentrated and partitioned between ethyl acetate and water. The organic layer was dried over sodium sulfate and the resulting tert-butyl 4-((4-(4-(methylamino)-3-nitrophenoxy)pyridin-2-ylcarbamoyl)methyl)piperidine-1-carboxylate was purified by HPLC. HPLC=4.63 min; MS: MH$^+$=599.

3. Synthesis of N-(4-(2-(3-isopropylphenylamino)-1-methyl-1H-benzo[d]imidazol-5-yloxy)pyridin-2-yl)-2-(piperidin-4-yl)acetamide To tert-butyl 4-((4-(4-(methylamino)-3-nitrophenoxy)pyridin-2-ylcarbamoyl)methyl)-piperidine-1-carboxylate (1 eq) in water and acetonitrile was added trifluoroacetic acid (2 eq) and stirred at room temperature for 16 hours. The resulting solution was frozen with liquid nitrogen and the lyophilized sample yielded N-(4-(2-(3-isopropylphenylamino)-

1-methyl-1H-benzo[d]imidazol-5-yloxy)pyridin-2-yl)-2-(piperidin-4-yl)acetamide. HPLC=3.49 min; MS: MH+=499.

4. Synthesis of N-[4-({2-[(3-isopropylphenyl)amino]-1-methyl-1H-benzimidazol-5-yl}oxy)pyridin-2-yl]-2-(1-methylpiperidin-4-yl)acetamide To the mixture containing N-(4-(2-(3-isopropylphenylamino)-1-methyl-1H-benzo[d]imidazol-5-yloxy)pyridin-2-yl)-2-(piperidin-4-yl)acetamide (1 eq), glacial acetic acid (2 eq), and formaline (7.5 eq) in tetrahydrofuran:methanol (1:1) was added sodium cyanoborohydride (2 eq) and stirred at room temperature for one hour. Reaction neutralized with saturated sodium carbonate solution and extracted with ethyl acetate. The organic layer was washed with brine, dried over sodium sulfate and concentrated to give crude product. Purification by HPLC to yield N-[4-({2-[(3-isopropylphenyl)amino]-1-methyl-1H-benzimidazol-5-yl}oxy)pyridin-2-yl]-2-(1-methylpiperidin-4-yl)acetamide.

HPLC=3.51 min; MS: MH+=513.

EXAMPLE 31

Synthesis of N-{4-[(2-{[2-fluoro-5-(trifluoromethyl)phenyl]amino}-1-methyl-1H-benzimidazol-5-yl)oxy]pyridin-2-yl}-2-[(2S)-2-(hydroxymethyl)pyrrolidin-1-yl]acetamide

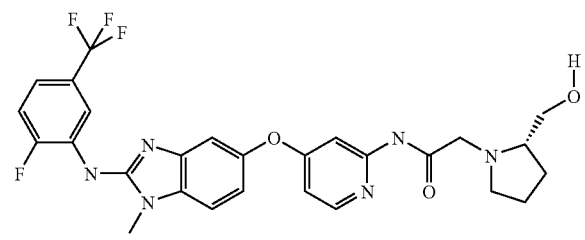 [SMILES: Cn1c(Nc2cc(C(F)(F)F)ccc2F)nc2cc(Oc3ccnc(NC(=O)CN4CCC[C@H]4CO)c3)ccc21]

Step 1:

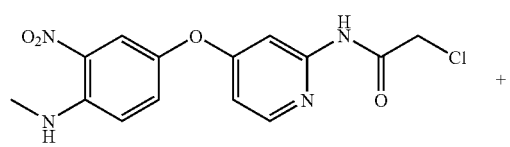

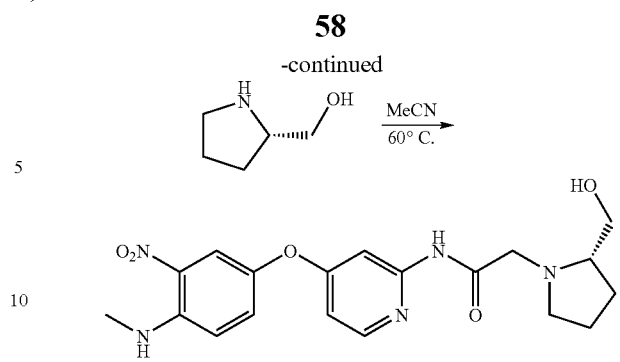

L-Prolinol (3.0 eq) was added to a mixture of 2-chloro-N-{4-[4-(methylamino)-2-nitrophenoxy](2-pyridyl)}acetamide (1 eq) in acetonitrile. The resulting mixture was brought to 60° C. LC/MS showed quantitative conversion after stirring for 1 hour. The reaction was concentrated to about half the volume of solvent and then partitioned between water and ethyl acetate. The aqueous layer was extracted 2× with ethyl acetate. The organic layers were combined and washed with water followed by saturated sodium chloride, dried over magnesium sulfate and concentrate to yield pure product. MS: MH+=402.2.

Step 2:

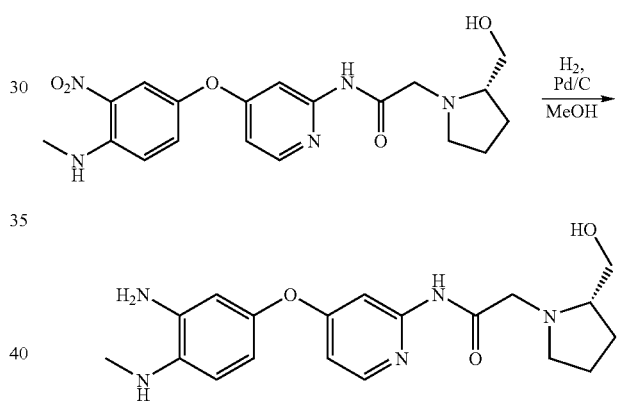

2-(2-Hydroxymethyl-pyrrolidin-1-yl)-N-[4-(4-methylamino-3-nitro-phenoxy)-pyridin-2-yl]-acetamide was hydrogenated in methanol in the presence of Pd C for 4 hours. The catalyst was removed via filtration through Celite and filtrate was concentrated to give N-[4-(3-Amino-4-methylamino-phenoxy)-pyridin-2-yl]-2-(2-hydroxymethyl-pyrrolidin-1-yl)-acetamide. MS: MH+=372.4.

Step 3:

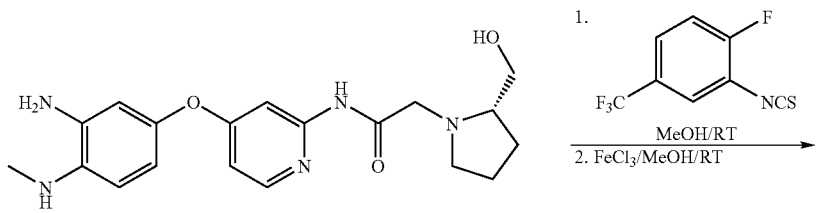

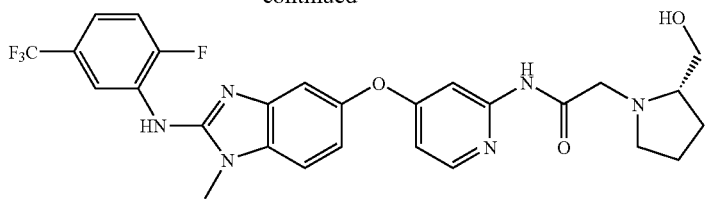

2-Fluoro-5-(trifluoromethyl)phenyl isothiocyanate was added to a solution of N-[4-(3-Amino-4-methylamino-phenoxy)-pyridin-2-yl]-2-(2-hydroxymethyl-pyrrolidin-1-yl)-acetamide in methanol. Reaction was stirred at room temperature for 15 hours. Thiourea formation was confirmed by LC/MS. Ferric chloride was added and the resulting mixture was stirred at room temperature for 4 hours. After cyclization was complete by LC/MS the reaction mixture was concentrated and aqueous sodium carbonate was added until basic pH. The reaction mixture was partitioned between ethyl acetate and water. The organic layer was washed with water then brine, and dried over magnesium sulfate and concentrated. The crude product was purified by reverse phase HPLC. MS: MH+=559.3.

EXAMPLE 32

Synthesis of (2S)-N-{4-[(2-{[2-fluoro-5-(trifluoromethyl)phenyl]amino}-1-methyl-1H-benzimidazol-5-yl)oxy]pyridin-2-yl}piperidine-2-carboxamide Step 1:

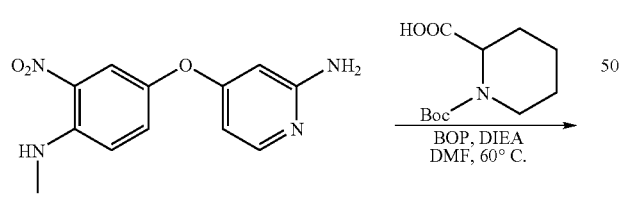

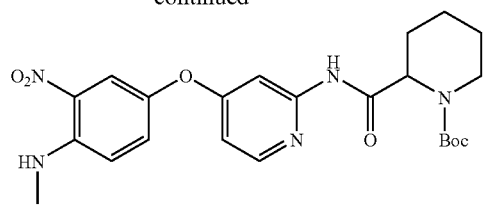

N-Boc homoproline (1.0 eq) was added to a solution of the amino pyridine (1.0 eq), BOP (2.0 eq) and disopropylethylamine (3.0 eq) in DMF. The solution is heated overnight at 60° C. The solution is concentrated on a rotovap to about one fourth its original volume, then poured into water and EtOAc. The layers are separated and the organic is washed with water and then brine, dried over MgSO4, filtered, silica added, and the solution is concentrated. The product is then purified by column chromatography (gradient of 2% MeOH:DCM->10% MeOH:DCM) to yield the desired product MH+=472.5.

Step 2:

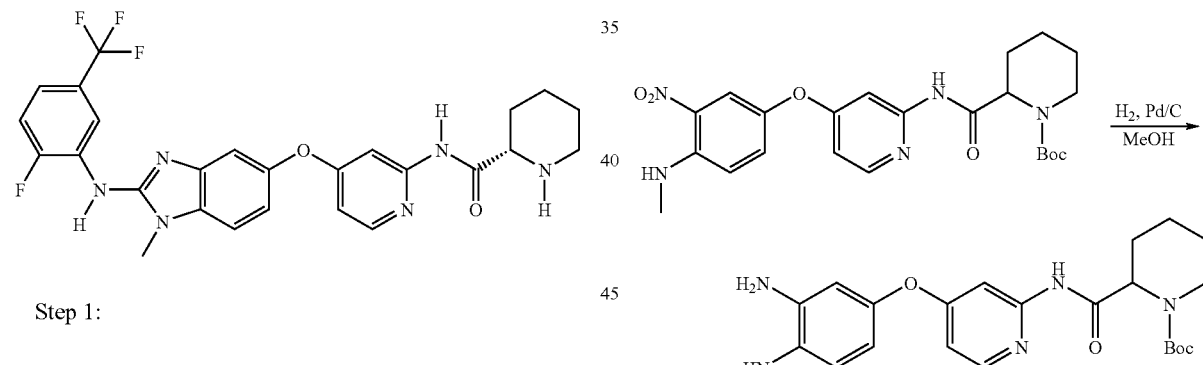

The nitroaniline was hydrogenated in methanol in the presence of Pd/C for 4 hours. The catalyst was removed via filtration through Celite and filtrate was concentrated to give phenylenediamine. MS: MH+=442.4.

Step 3:

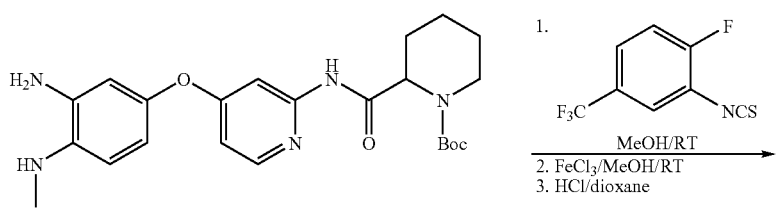

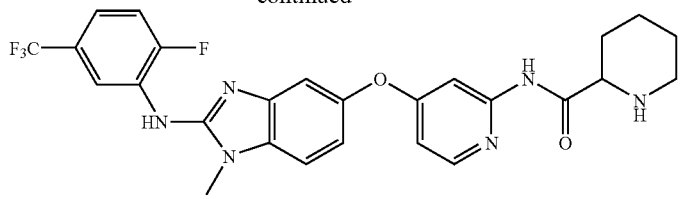

2-Fluoro-5-(trifluoromethyl)phenyl isothiocyanate was added to a solution of phenylenediamine in methanol. Reaction was stirred at room temperature for 15 hours. Thiourea formation was confirmed by LC/MS. Ferric chloride was added and the resulting mixture was stirred at room temperature for 4 hours. After cyclization was complete by LC/MS the reaction mixture was concentrated and aqueous sodium carbonate was added until basic pH. The reaction mixture was partitioned between ethyl acetate and water. The organic layer was washed with water then brine, and dried over sodium sulfate and concentrated. The protecting group is removed by treating the crude product with HCl in dioxane for 30 minutes at room temperature whereupon the solvent is removed. The crude product was purified by reverse phase HPLC. MS: $MH^+=529.5$.

EXAMPLE 33

Synthesis of N-[4-({2-[(2-fluoro-5-pyridin-4-ylphenyl)amino]-1-methyl-1H-benzimidazol-5-yl}oxy)pyridin-2-yl]acetamide

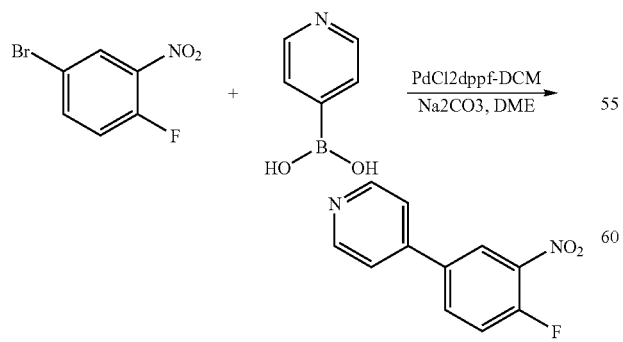

Step 1:

5-Bromo-2-fluoronitrobenzene (1.0 eq), 4-pyridylboronic acid (2.0 eq), and [1,1'-bis(diphenylphosphino)ferocene] dichloro palladium (II) complex with DCM are mixed in ethyleneglycol dimethylether and 2M aqueous sodium carbonate (4.0 eq). The solution is purged with argon for 20 minutes and then heated overnight at 10° C. At this time the reaction mixture is cooled and then poured into water and EtOAc. The layers are separated and the organic is washed with water and then brine, dried over $MgSO_4$, filtered, silica added, and the solution is concentrated. The product is then purified by column chromatography (gradient of 1% MeOH:DCM->10% MeOH:DCM) to yield the desired product. MS: $MH^+=219.2$.

Step 2:

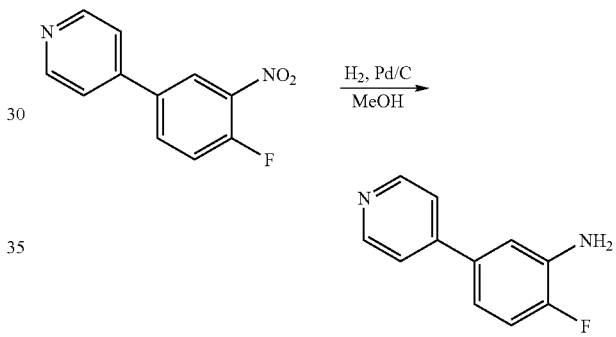

The nitrophenyl compound was hydrogenated in methanol in the presence of Pd/C for 4 hours. The catalyst was removed via filtration through Celite and filtrate was concentrated to give the desired aniline. MS: $MH^+=189.2$.

Step 3:

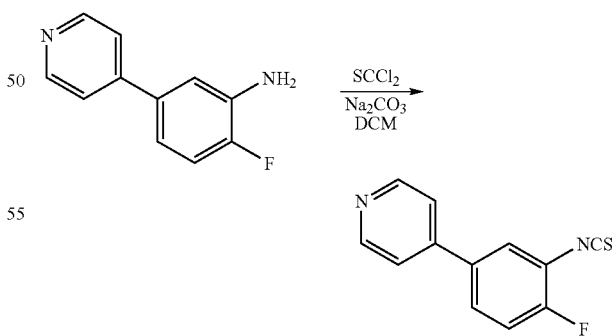

The aniline (1.0 eq) was cooled in a biphasic mixture of dichloromethane and sodium carbonate (4.0 eq) to 0° C. At this time thiophosgene (1.0 eq) was added. The solution was allowed to stir for 30 minutes at which time the phases were separated and the organic phase was dried over magnesium sulfate.

Step 4:

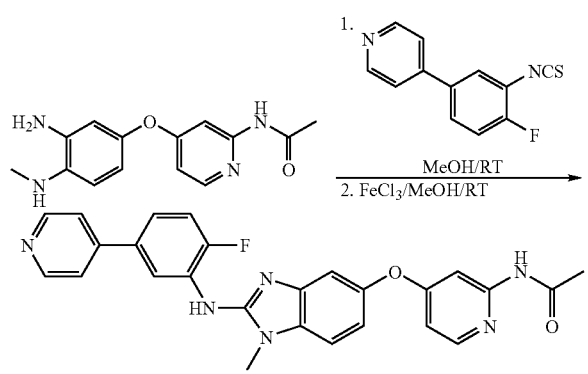

2-fluoro-5-(4-pyridyl)phenyl isothiocyanate was added as a solution in dcm to a solution of phenylenediamine in methanol. Reaction was stirred at room temperature for 15 hours. Thiourea formation was confirmed by lc/ms. Ferric chloride was added and the resulting mixture was stirred at room temperature for 4 hours. After cyclization was complete by lc/ms the reaction mixture was concentrated and aqueous sodium carbonate was added until basic ph. The reaction mixture was partitioned between ethyl acetate and water. The organic layer was washed with water then brine, and dried over magnesium sulfate and concentrated. The crude product was purified by reverse phase HPLC. MS: MH$^+$=469.5.

EXAMPLE 34

Synthesis of N-[4-({2-[(3-tert-butylphenyl)amino]-1-methyl-1H-benzimidazol-5-yl}oxy)pyridin-2-yl]-2-(4-methylpiperidin-1-yl)acetamide

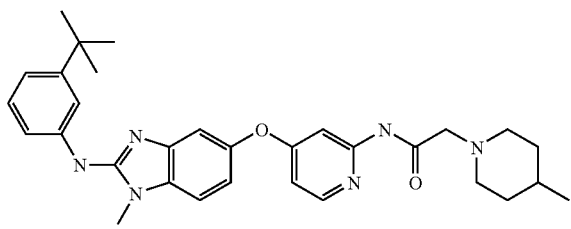 [SMILES: CC1CCN(CC(=O)Nc2cc(Oc3ccc4c(c3)nc(Nc3cccc(C(C)(C)C)c3)n4C)ccn2)CC1]

Step 1:

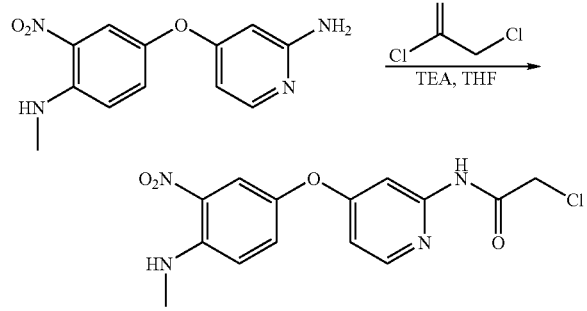

Chloroacetyl chloride (1.4 eq) was added dropwise over 15 minutes to a stirring solution of the amino pyridine (1.0 eql) and triethylamine (2.7 eq) in THF (1.2 L) at room temperature. After 2 hours LC shows 80% conversion to the desired product with a small amount of starting material and some bis acylated product (<10%) as well. The solution is concentrated on a rotovap to about one fourth its original volume, then poured into water and EtOAc. The layers are separated and the organic is washed with water and then brine, dried over MgSO$_4$, filtered, silica added, and the solution is concentrated. The product is then purified by column chromatography (gradient of 30% EtOAc:hexanes->60% EtOAc hexanes) to yield the desired product (39% yield).

Step 2:

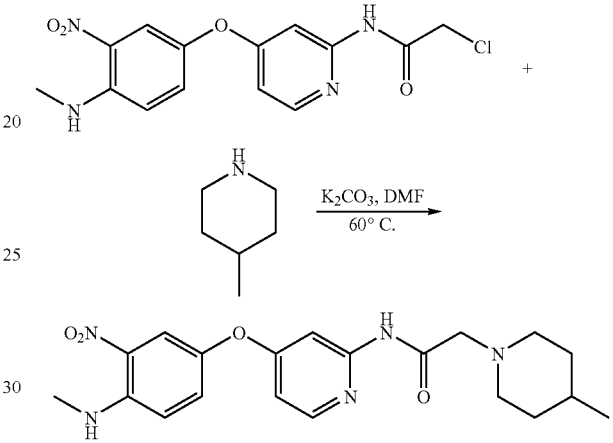

4-Methylpiperidine (2.8 eq) was added to a mixture of 2-chloro-N-{4-[4-(methylamino)-2-nitrophenoxy](2-pyridyl)}acetamide (1 eq), and potassium carbonate (3.3 eq) in dimethylformamide. The resulting mixture was brought to 60° C. LC/MS showed quantitative conversion after stirring for 1 hour. The reaction was partitioned between water and ethyl acetate. The aqueous layer was extracted 2× with ethyl acetate. The organic layers were combined and washed with water followed by saturated sodium chloride, dried over sodium sulfate and concentrated. The crude product was passed through a plug of silica and eluted with 10% methanol/methylene chloride. MS: MH$^+$=400.2.

Step 3:

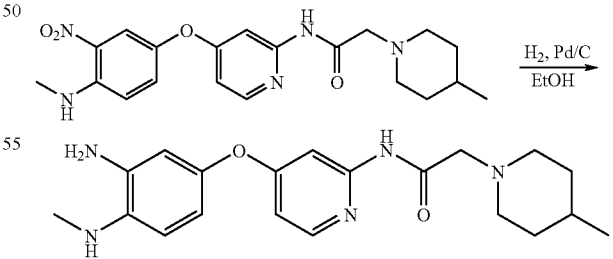

N-{4-[4-(methylamino)-3-nitrophenoxy] (2-pyridyl)}-2-(4-methylpiperidyl)acetamide was hydrogenated in the presence of Pd C for 4 hours. The catalyst was removed via filtration and filtrate was concentrated to give N-{4-[3-amino-4-(methylamino)phenoxy](2-pyridyl)}-2-(4-methylpiperidyl)acetamide. MS: MH$^+$=370.2.

Step 4:

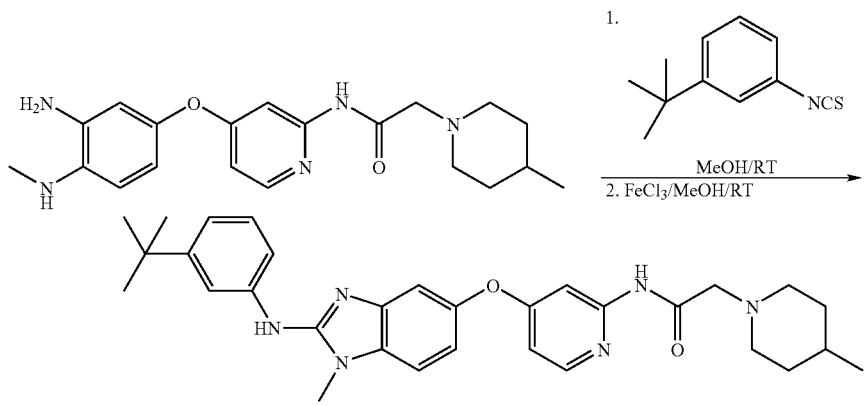

3-(tert-Butyl)benzenisothiocyanate was added to a solution of N-{4-[3-amino-4-(methylamino)phenoxy](2-pyridyl)}-2-(4-methylpiperidyl)acetamide in methanol. Reaction was stirred at room temperature for 15 hours. Thiourea formation was confirmed by LC/MS. Ferric chloride was added and the resulting mixture was stirred at room temperature for 4 hours. After cyclization was complete by LC/MS the reaction mixture was concentrated and aqueous sodium carbonate was added until basic pH. The reaction mixture was partitioned between ethyl acetate and water. The organic layer was washed with water then brine, and dried over sodium sulfate and concentrated. The crude product was purified by reverse phase HPLC. MS: MH+=527.2.

EXAMPLES 35-68

The glycinamides in Examples 35-68 were synthesized in a manner similar to that described above using the indicated starting materials and reagents.

EXAMPLE 35

Synthesis of N-[4-({2-[(2-fluoro-5-isopropylphenyl)amino]-1-methyl-1H-benzimidazol-5-yl}oxy)pyridin-2-yl]-2-(4-methylpiperidin-1-yl)acetamide

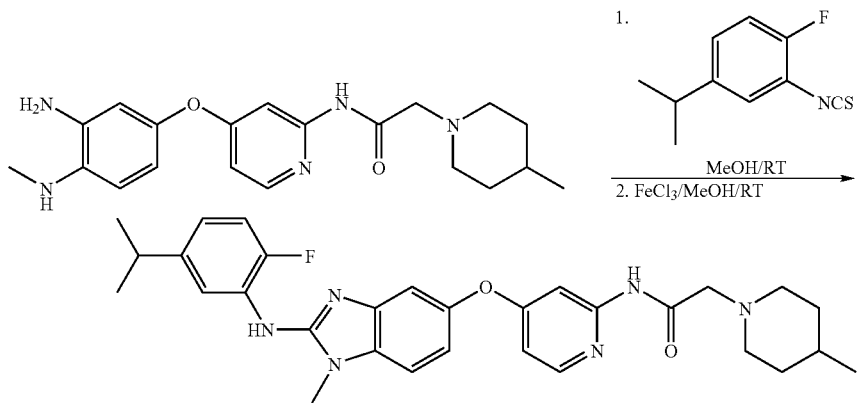

MS: MH+=531.1.

EXAMPLE 36

Synthesis of 2-(4-methylpiperidin-1-yl)-N-{4-[(1-methyl-2-{[4-(trifluoromethyl)phenyl]amino}-1H-benzimidazol-5-yl)oxy]pyridin-2-yl}acetamide

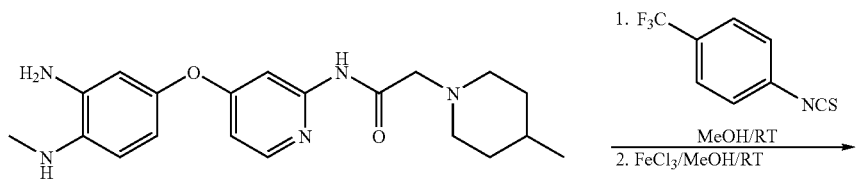

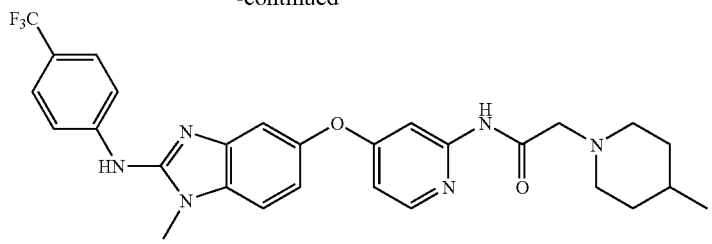
MS: MH⁺=539.1.
EXAMPLE 37
Synthesis of N-[4-({2-[(4-fluoro-3-isopropylphenyl)amino]-1-methyl-1H-benzimidazol-5-yl}oxy)pyridin-2-yl]-2-(4-methylpiperidin-1-yl)acetamide
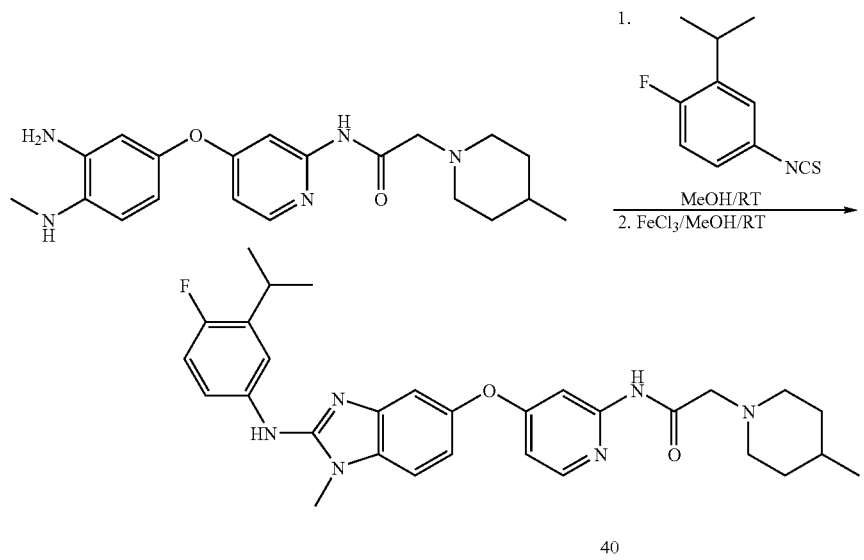
MS: MH⁺=531.1.
EXAMPLE 38
Synthesis of N-{4-[(2-{[2-fluoro-5-(trifluoromethyl)phenyl]amino}-1-methyl-1H-benzimidazol-5-yl)oxy]pyridin-2-yl}-2-(4-methylpiperidin-1-yl)acetamide
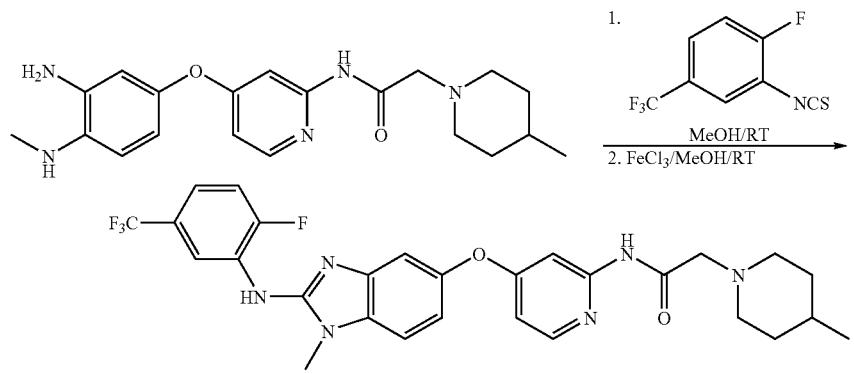
MS: MH⁺=557.1.

EXAMPLE 39
Synthesis of N-{4-[(2-{[2,4-difluoro-5-(trifluoromethyl)phenyl]amino}-1-methyl-1H-benzimidazol-5-yl)oxy]pyridin-2-yl}-2-(4-methylpiperidin-1-yl)acetamide
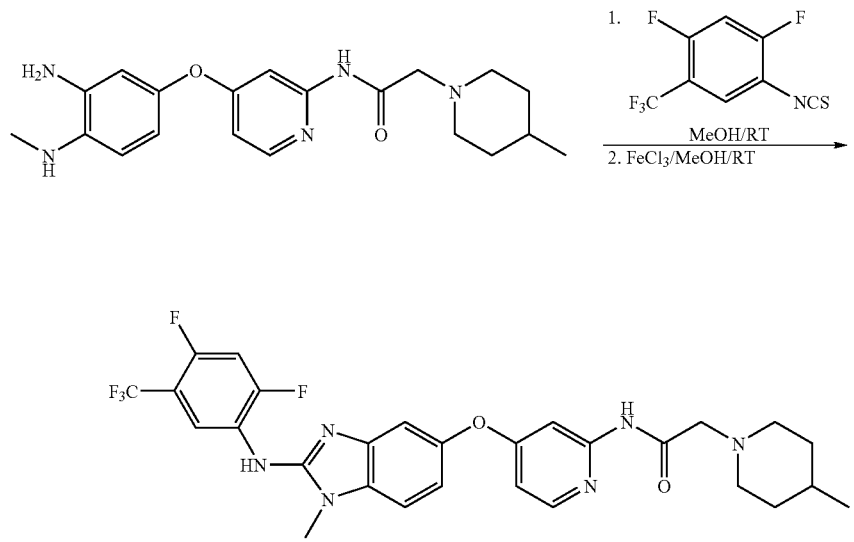
MS: MH$^+$=575.0.
EXAMPLE 40
Synthesis of N-[4-({2-[(2,4-difluoro-5-isopropylphenyl)amino]-1-methyl-1H-benzimidazol-5-yl}oxy)pyridin-2-yl]-2-(4-methylpiperidin-1-yl)acetamide
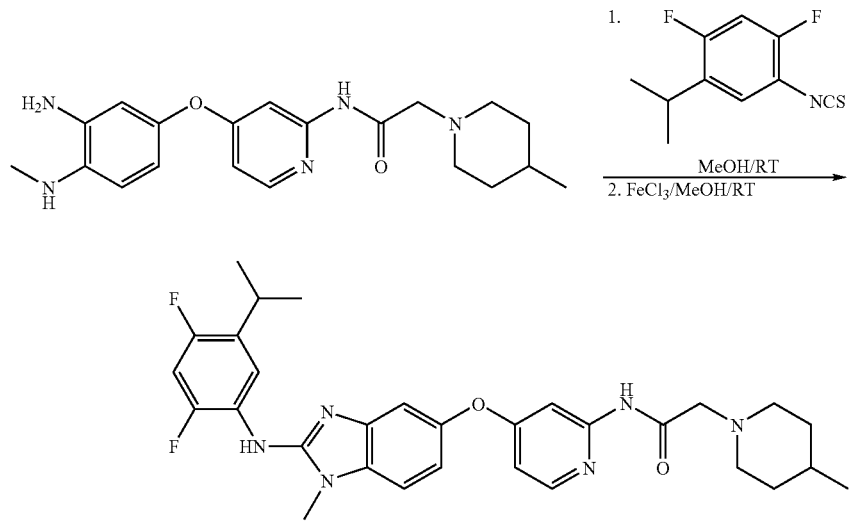
MS: MH$^+$=549.1.

EXAMPLE 41
Synthesis of N-[4-({2-[(5-tert-butyl-2-fluorophenyl)amino]-1-methyl-1H-benzimidazol-5-yl}oxy)pyridin-2-yl]-2-(4-methylpiperidin-1-yl)acetamide
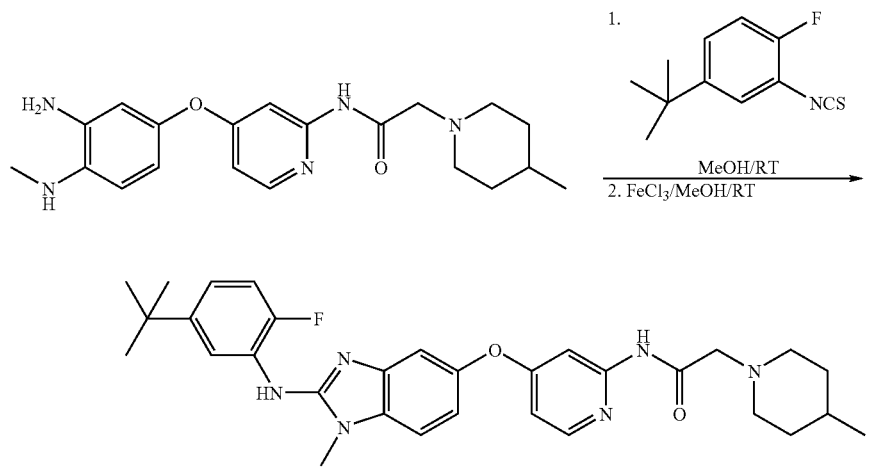
MS: MH$^+$=545.1.
EXAMPLE 42
Synthesis of N~1~-[4-({2-[(3-tert-butylphenyl)amino]-1-methyl-1H-benzimidazol-5-yl}oxy)pyridin-2-yl]-N~2~,N~2~-diethylglycinamide
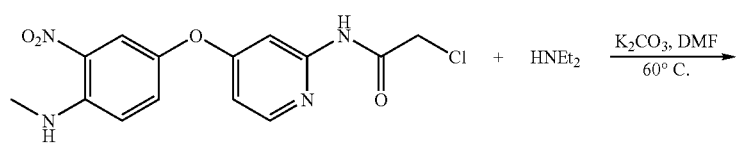
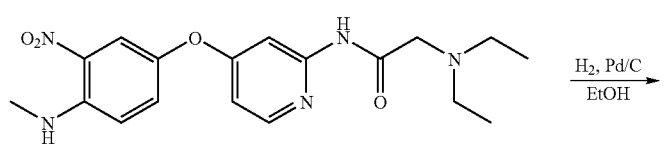
MS: MH+ = 374.2
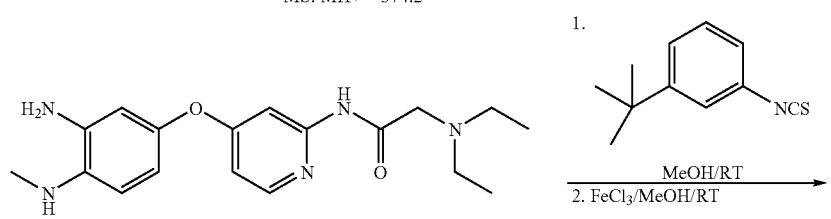
MS: MH+ = 344.1
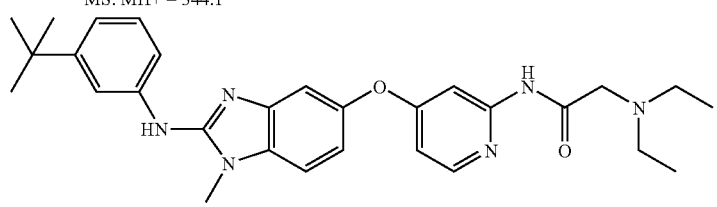
MS: MH+ = 501.1

EXAMPLE 43

Synthesis of N~2~,N~2~-diethyl-N~1~-[4-({2-[(2-fluoro-5-isopropylphenyl)amino]-1-methyl-1H-benzimidazol-5-yl}oxy)pyridin-2-yl]glycinamide

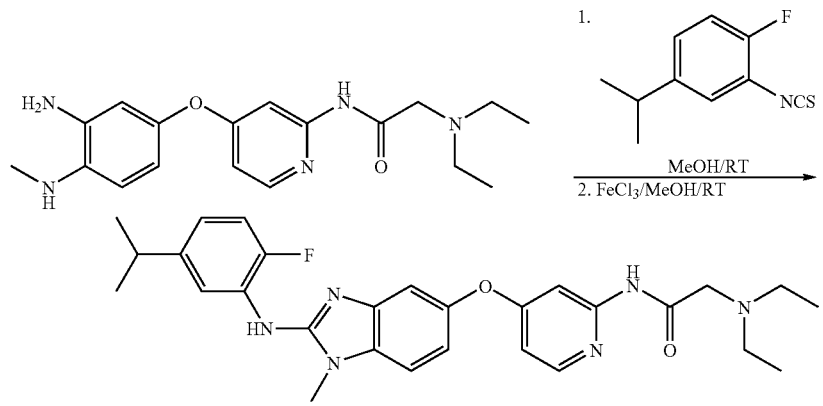

MS: MH+=505.1.

EXAMPLE 44

Synthesis of N~2~,N~2~-diethyl-N~1~-{4-[(1-methyl-2-{[4-(trifluoromethyl)phenyl]amino}-1H-benzimidazol-5-yl)oxy]pyridin-2-yl}glycinamide

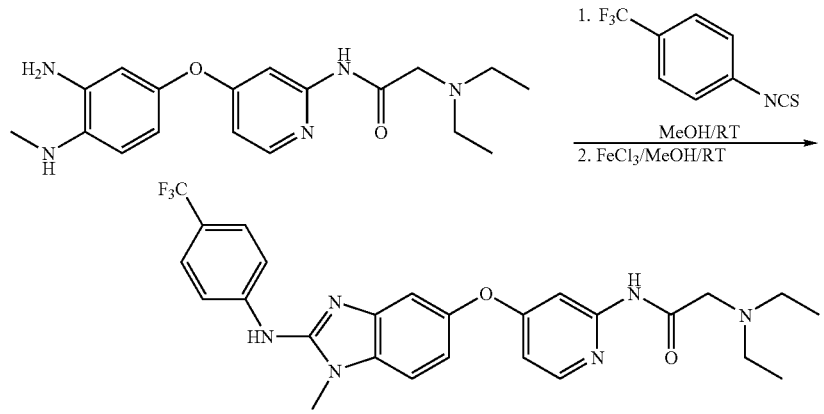

MS: MH+=513.0.

EXAMPLE 45

Synthesis of N~2~,N~2~-diethyl-N~1~-[4-({2-[(4-fluoro-3-isopropylphenyl)amino]-1-methyl-1H-benzimidazol-5-yl}oxy)pyridin-2-yl]glycinamide

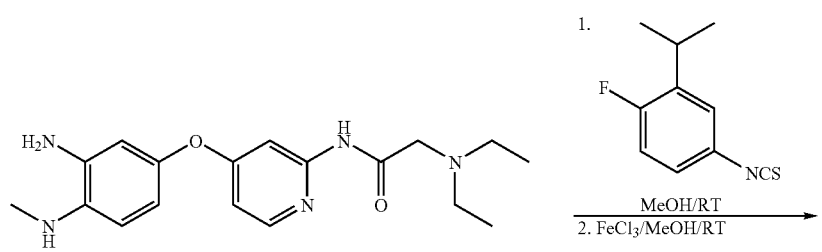

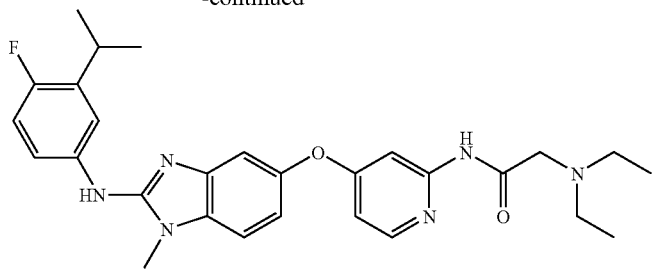
MS: MH⁺=505.1.
EXAMPLE 46
Synthesis of N~2~,N~2~-diethyl-N~1~-{4-[(2-{[2-fluoro-5-(trifluoromethyl)phenyl]amino}-1-methyl-1H-benzimidazol-5-yl)oxy]pyridin-2-yl}glycinamide
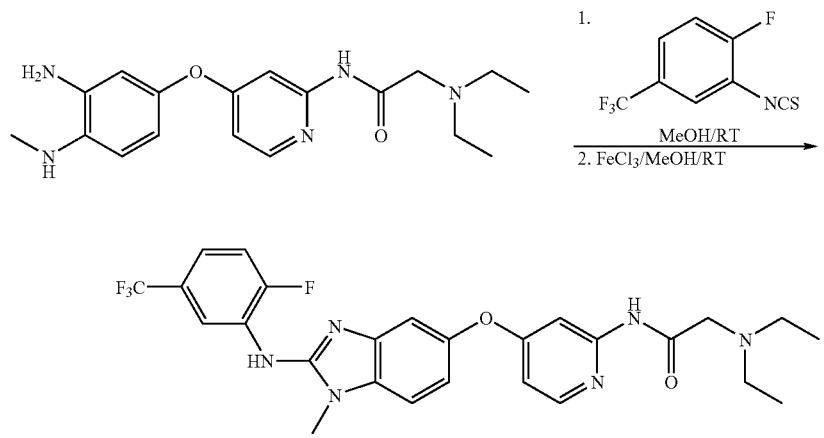
MS: MH⁺=531.1.
EXAMPLE 47
Synthesis of N~1~-[4-({2-[(3-tert-butylphenyl)amino]-1-methyl-1H-benzimidazol-5-yl}oxy)pyridin-2-yl]-N~2~-ethyl-N~2~-propylglycinamide
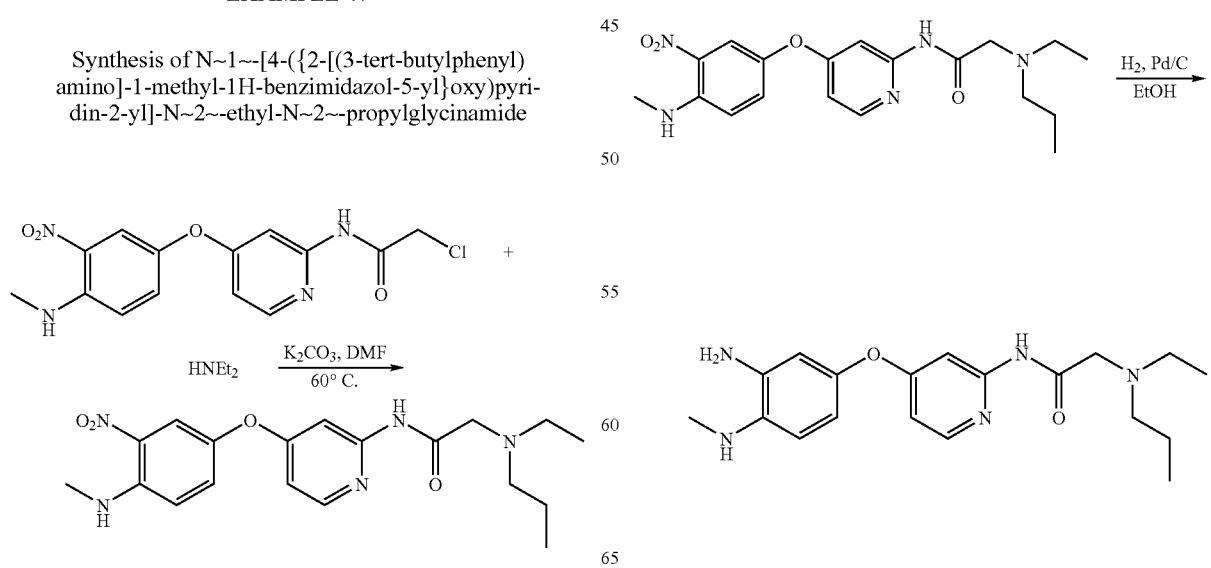
MS: MH⁺=388.3.
MS: MH⁺=358.2.

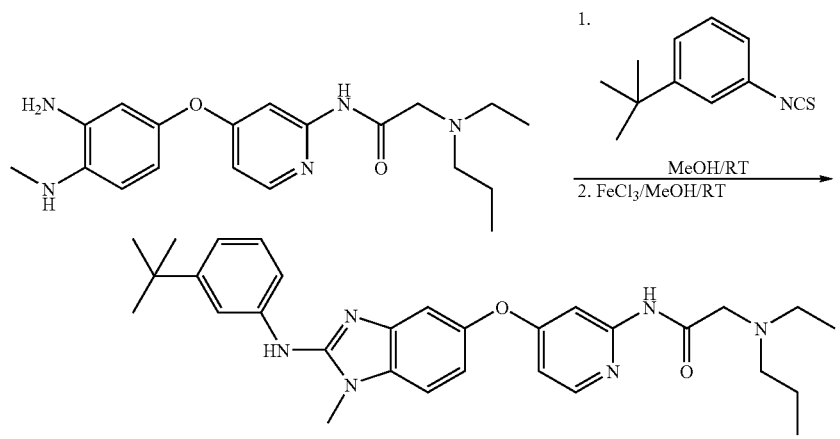
MS: MH⁺=515.1.
EXAMPLE 48
Synthesis of N~2~-ethyl-N~1~-[4-({2-[(2-fluoro-5-isopropylphenyl)amino]-1-methyl-1H-benzimidazol-5-yl}oxy)pyridin-2-yl]-N~2~-propylglycinamide
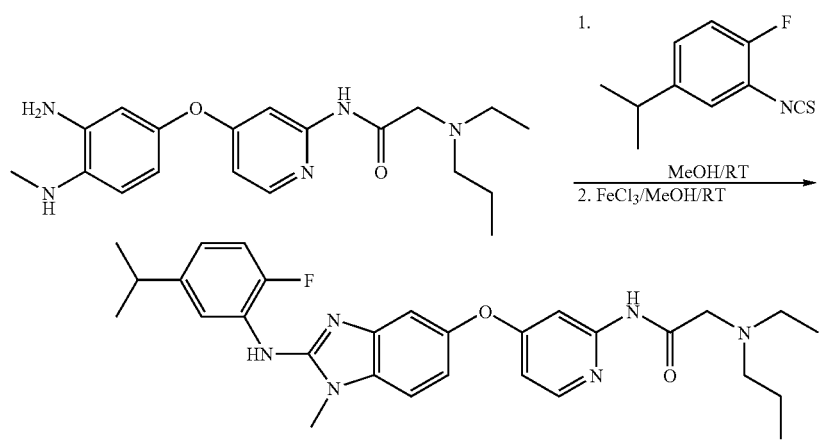
MS: MH⁺=519.1.
EXAMPLE 49
Synthesis of N~2~-ethyl-N~1~-{4-[(1-methyl-2-{[4-(trifluoromethyl)phenyl]amino}-1H-benzimidazol-5-yl)oxy]pyridin-2-yl}-N~2~-propylglycinamide
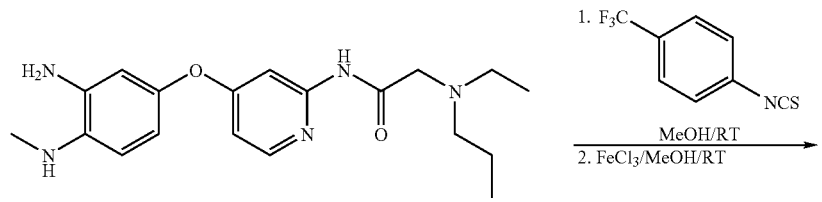

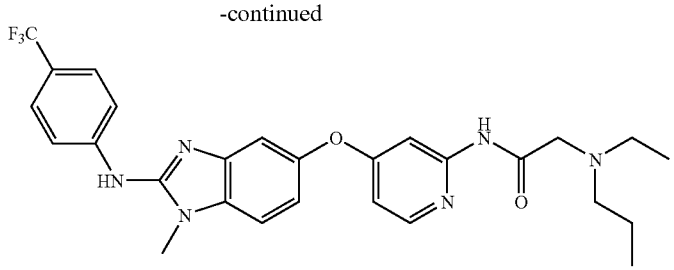
MS: MH+=527.1.
EXAMPLE 50
Synthesis of N~2~-ethyl-N~1~-[4-({2-[(4-fluoro-3-isopropylphenyl)amino]-1-methyl-1H-benzimidazol-5-yl}oxy)pyridin-2-yl]-N~2~-propylglycinamide
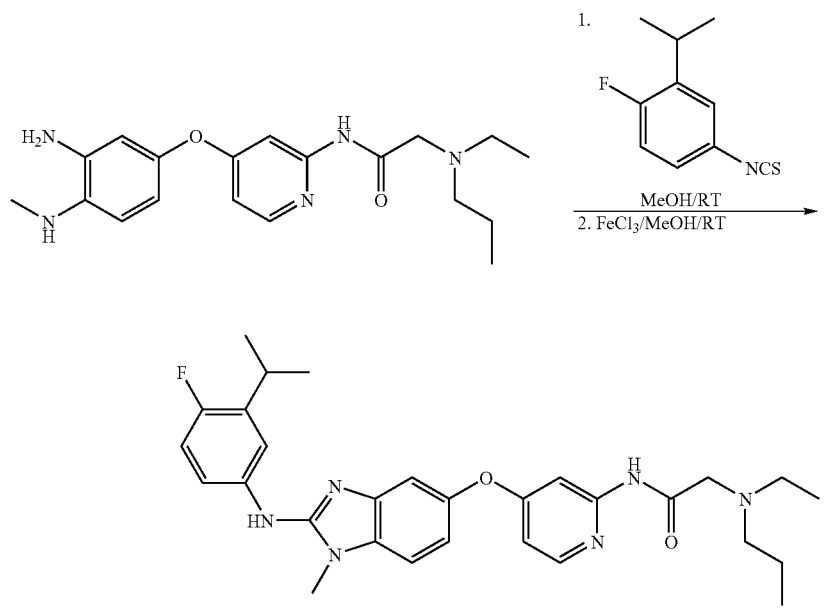
MS: MH+=519.1.
EXAMPLE 51
Synthesis of N~2~-ethyl-N~1~-{4-[(2-{[2-fluoro-5-(trifluoromethyl)phenyl]amino}-1-methyl-1H-benzimidazol-5-yl)oxy]pyridin-2-yl}-N~2~-propylglycinamide
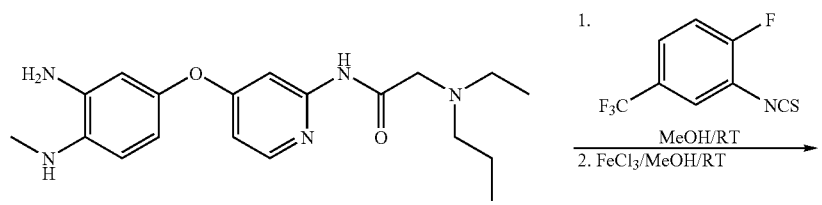

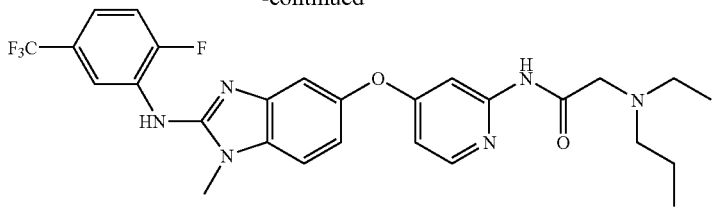
MS: MH⁺=545.1.
EXAMPLE 52
Synthesis of N~1~-{4-[(2-{[2,4-difluoro-5-(trifluoromethyl)phenyl]amino}-1-methyl-1H-benzimidazol-5-yl)oxy]pyridin-2-yl}-N~2~-ethyl-N~2~-propylglycinamide
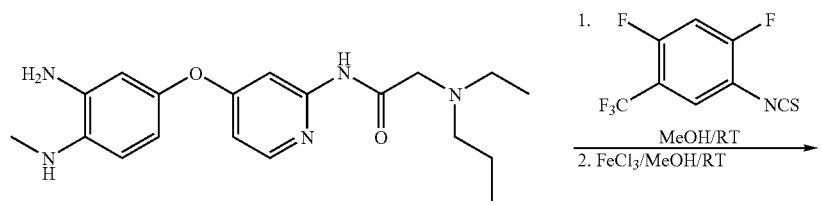
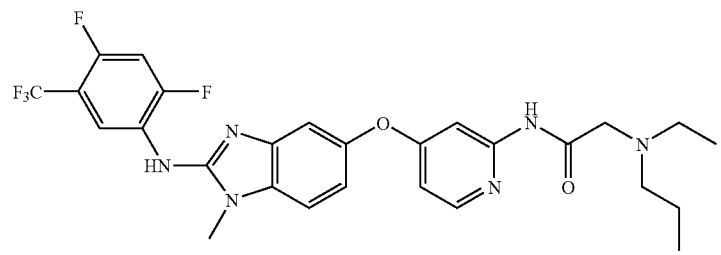
MS: MH⁺=563.0.
EXAMPLE 53
Synthesis of N~1~-[4-({2-[(2,4-difluoro-5-isopropylphenyl)amino]-1-methyl-1H-benzimidazol-5-yl}oxy)pyridin-2-yl]-N~2~-ethyl-N~2~-propylglycinamide
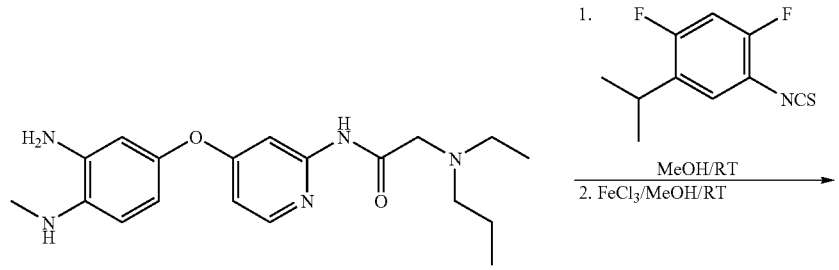

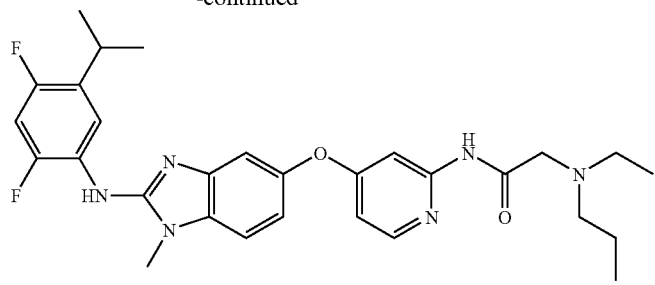
MS: MH⁺=537.1.
EXAMPLE 54
Synthesis of N~1~-[4-({2-[(5-tert-butyl-2-fluorophenyl)amino]-1-methyl-1H-benzimidazol-5-yl}oxy)pyridin-2-yl]-N~2~-ethyl-N~2~-propylglycinamide
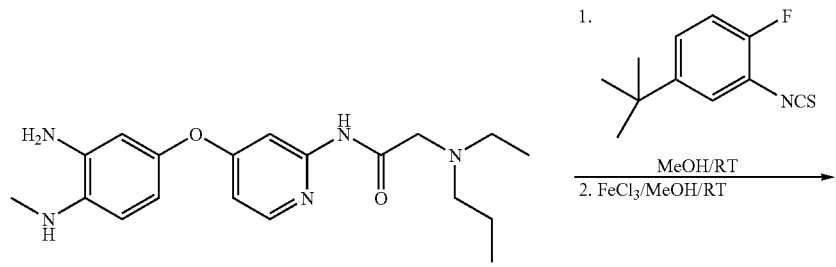
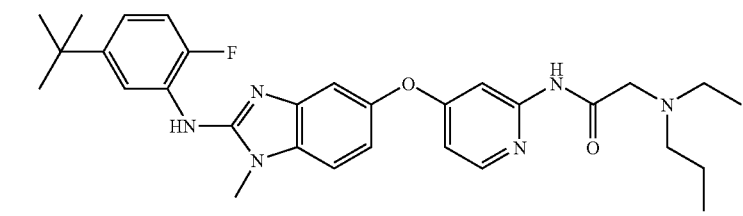
MS: MH⁺=533.1.
EXAMPLE 55
Synthesis of N-[4-({2-[(5-tert-butyl-2-fluorophenyl)amino]-1-methyl-1H-benzimidazol-5-yl}oxy)pyridin-2-yl]-2-piperidin-1-ylacetamide
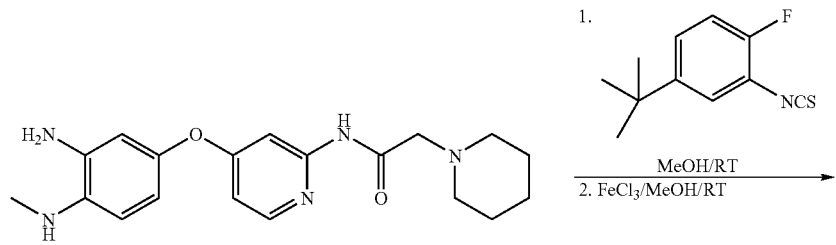

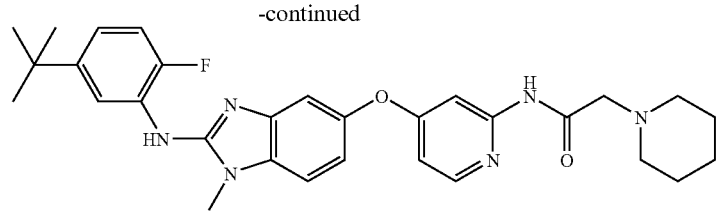
MS: MH⁺=531.2.
EXAMPLE 56
Synthesis of N-[4-({2-[(2-fluoro-5-pyridin-4-ylphenyl)amino]-1-methyl-1H-benzimidazol-5-yl}oxy)pyridin-2-yl]-2-piperidin-1-ylacetamide
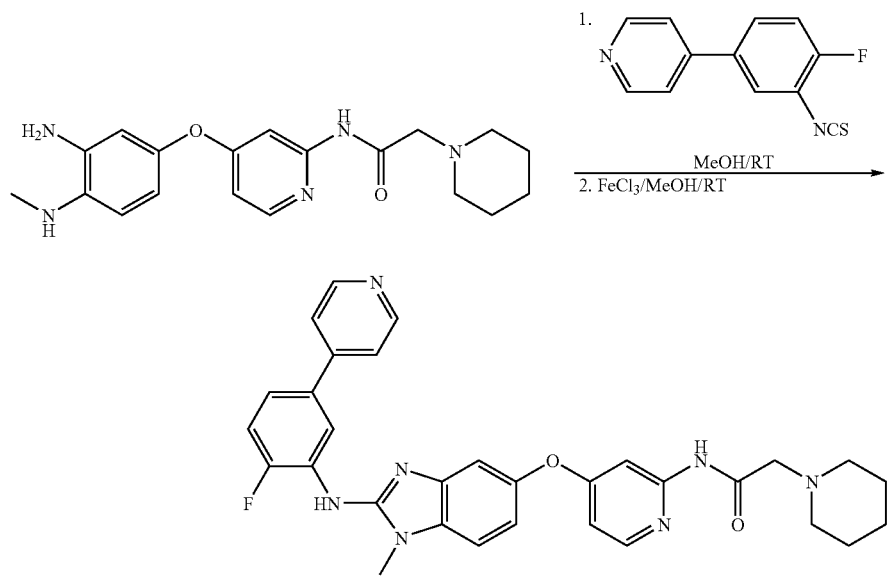
MS: MH⁺=552.1.
EXAMPLE 57
Synthesis of N-[4-({2-[(5-tert-butyl-2-fluorophenyl)amino]-1-methyl-1H-benzimidazol-5-yl}oxy)pyridin-2-yl]-2-(3,5-dimethylpiperidin-1-yl)acetamide
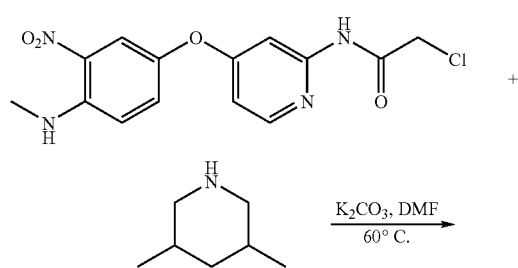
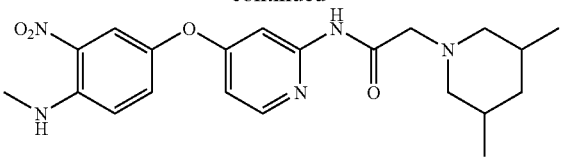
MS: MH⁺=414.1.
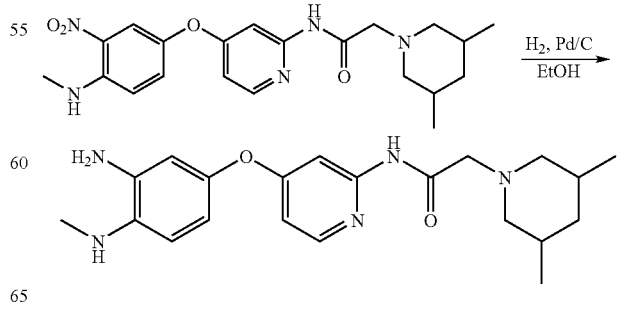
MS: MH⁺=384.2

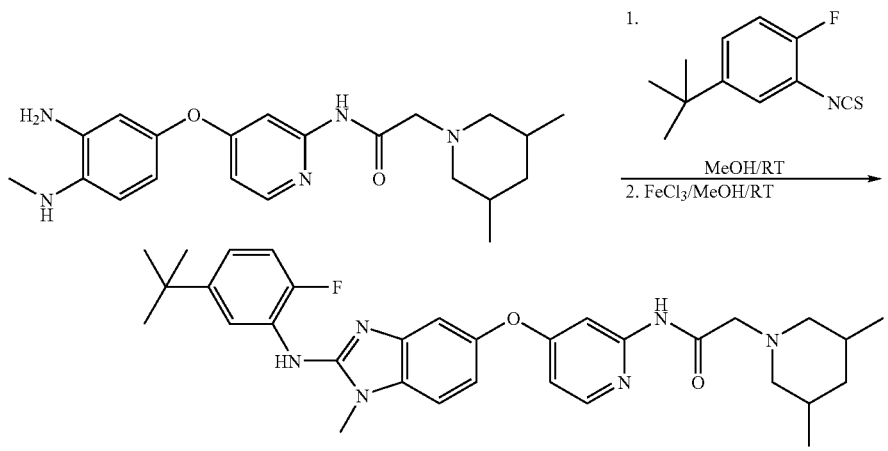
MS: MH+=559.2.
EXAMPLE 58
Synthesis of 2-(3,5-dimethylpiperidin-1-yl)-N-{4-[(2-{[2-fluoro-5-(trifluoromethyl)phenyl]amino}-1-methyl-1H-benzimidazol-5-yl)oxy]pyridin-2-yl}acetamide
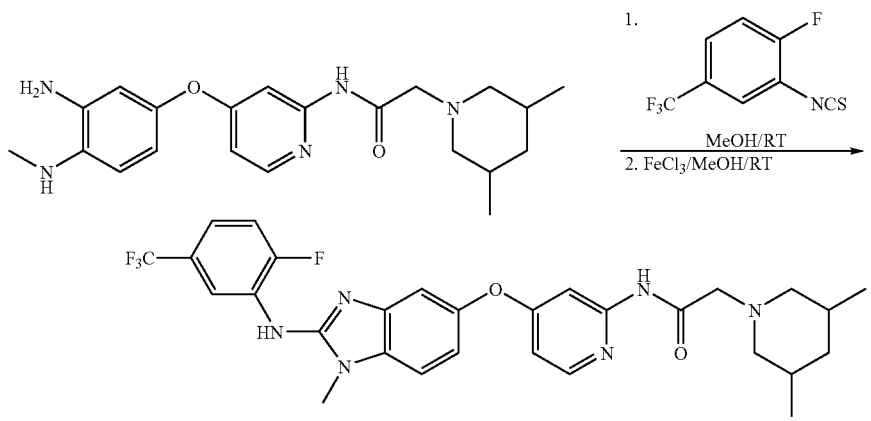
MS: MH+=571.1
EXAMPLE 59
Synthesis of 2-(3,5-dimethylpiperidin-1-yl)-N-[4-({2-[(4-fluoro-3-isopropylphenyl)amino]-1-methyl-1H-benzimidazol-5-yl}oxy)pyridin-2-yl]acetamide
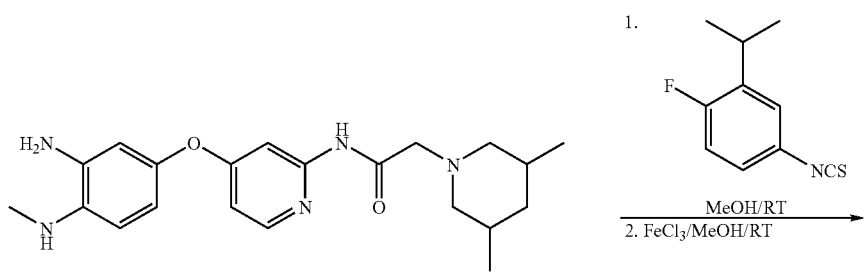

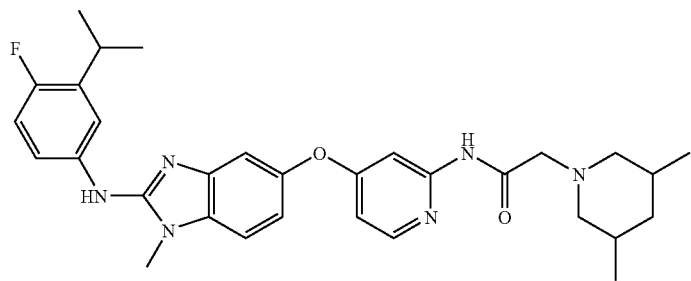
MS: MH⁺=545.2.
EXAMPLE 60
Synthesis of 2-azetidin-1-yl-N-[4-({2-[(5-tert-butyl-2-fluorophenyl)amino]-1-methyl-1H-benzimidazol-5-yl}oxy)pyridin-2-yl]acetamide
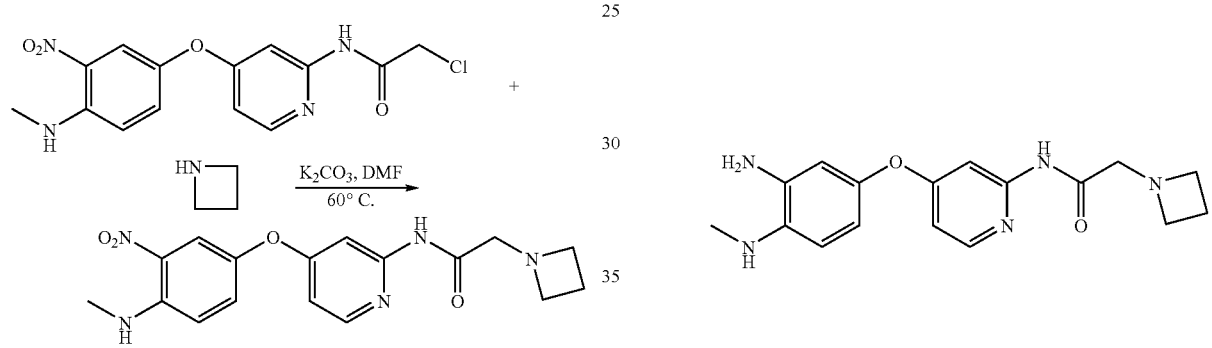
MS: MH⁺=358.1.   MS: MH⁺=328.1.
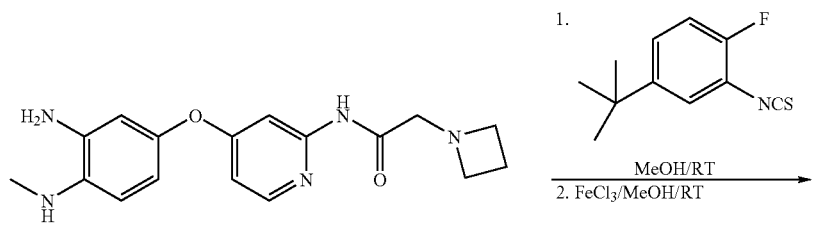
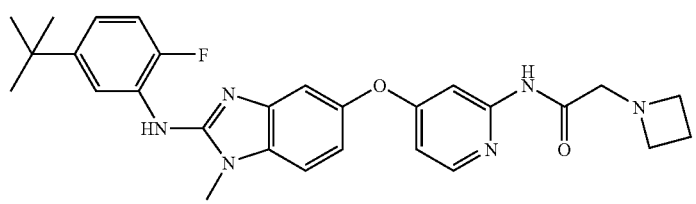
MS: MH⁺=503.1.

EXAMPLE 61
Synthesis of 2-azetidin-1-yl-N-{4-[(2-{[3-fluoro-4-(trifluoromethyl)phenyl]amino}-1-methyl-1H-benzimidazol-5-yl)oxy]pyridin-2-yl}acetamide
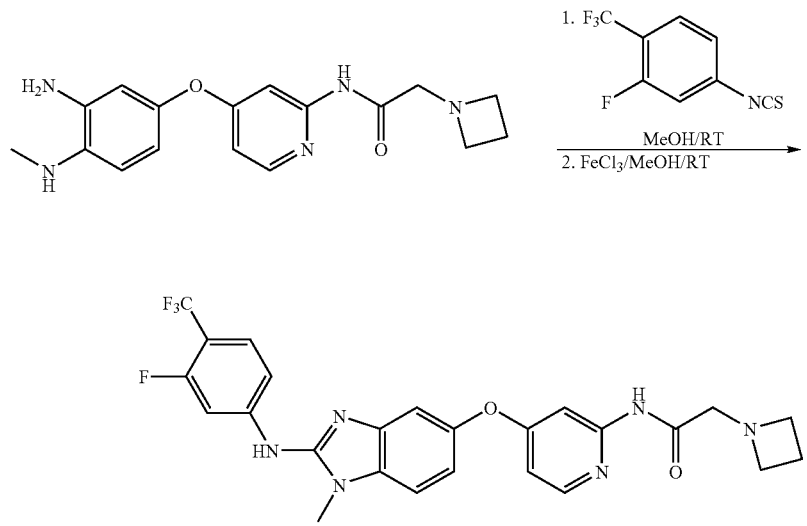
MS: MH$^+$=515.0.
EXAMPLE 62
Synthesis of 2-azetidin-1-yl-N-[4-({2-[(2-fluoro-5-pyridin-4-ylphenyl)amino]-1-methyl-1H-benzimidazol-5-yl}oxy)pyridin-2-yl]acetamide
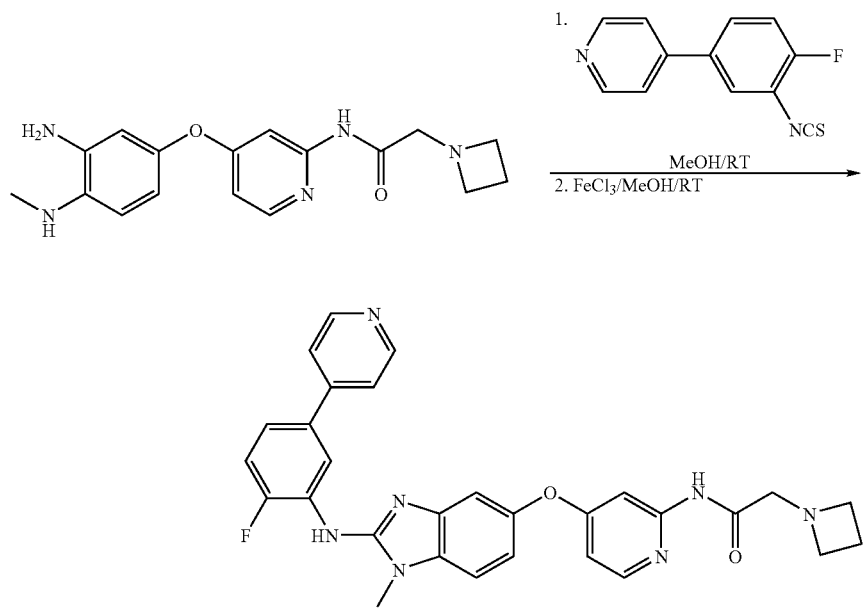
MS: MH$^+$=524.1.

EXAMPLE 63
Synthesis of 2-[4-(dimethylamino)piperidin-1-yl]-N-{4-[(2-{[2-fluoro-5-(trifluoromethyl)phenyl]amino}-1-methyl-1H-benzimidazol-5-yl)oxy]pyridin-2-yl}acetamide
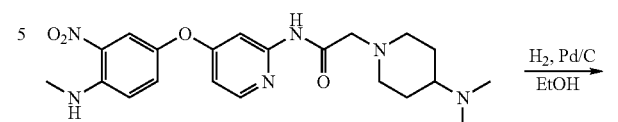
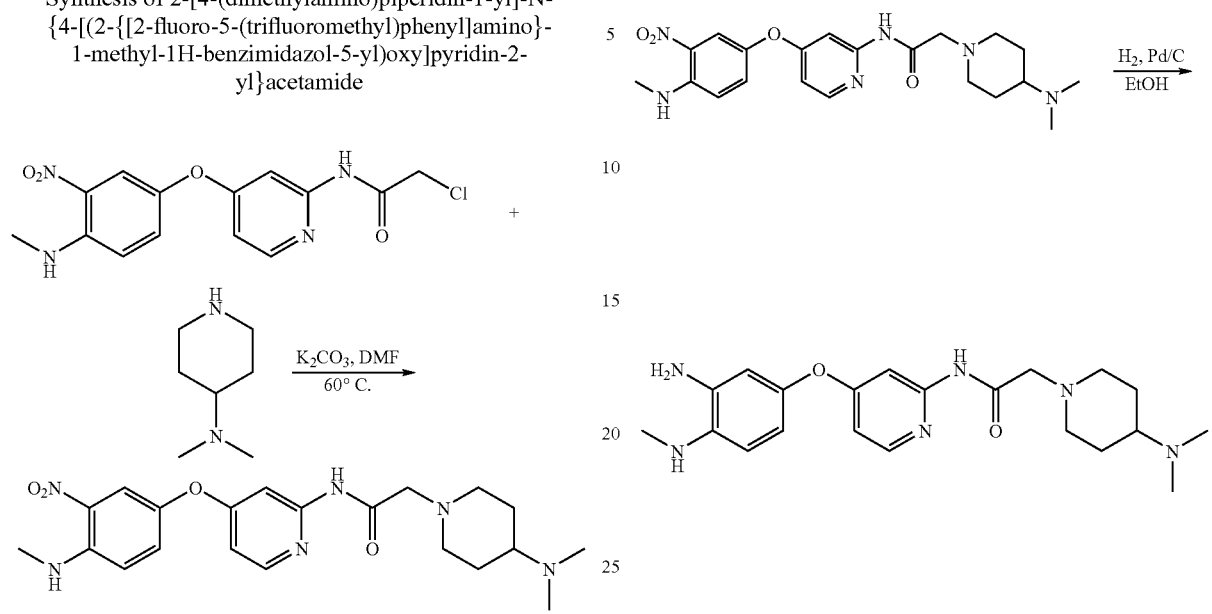
MS: MH+=429.1.
MS: MH+=399.2.
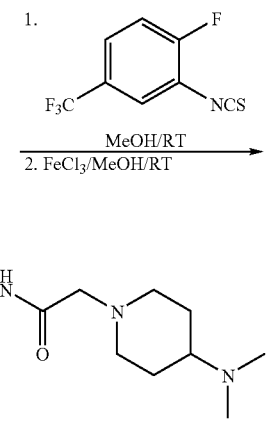
MS: MH+=586.1.
EXAMPLE 64
Synthesis of 2-[4-(dimethylamino)piperidin-1-yl]-N-[4-({2-[(2-fluoro-5-pyridin-4-ylphenyl)amino]-1-methyl-1H-benzimidazol-5-yl}oxy)pyridin-2-yl]acetamide
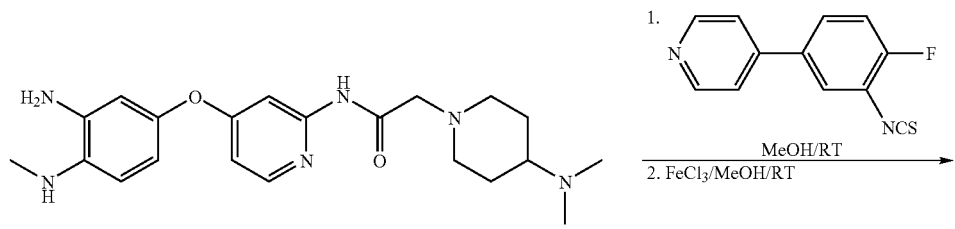

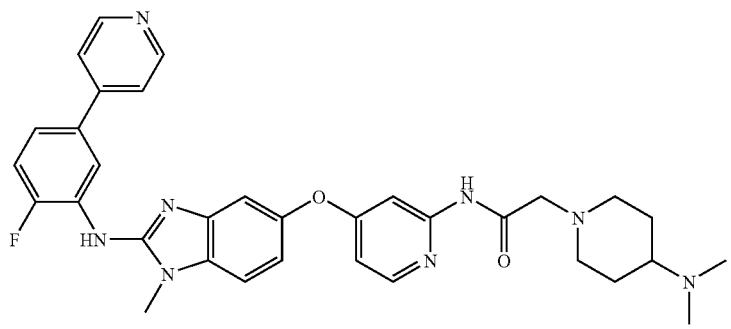

MS: MH+=595.2.

EXAMPLE 65

Synthesis of N-{4-[(2-{[2-fluoro-5-(trifluoromethyl)phenyl]amino}-1-methyl-1H-benzimidazol-5-yl)oxy]pyridin-2-yl}-2-(4-methoxypiperidin-1-yl)acetamide

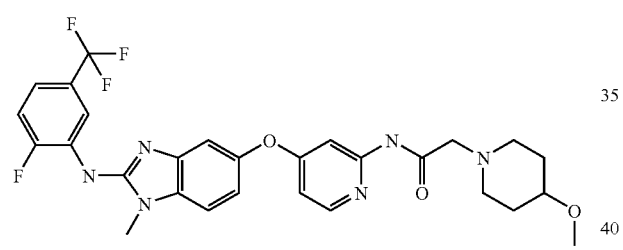

Step 1:

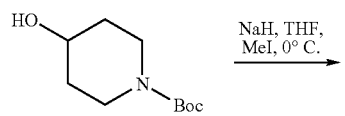

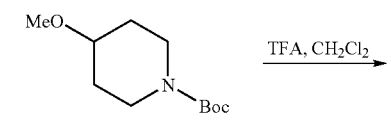

1-N-Boc-4-hydroxypiperidine (1.0 eq; O. Takuna, H. Yoshitaka, Y. Kaoru, O. Yoshitaka, M. Hideaki. WO2003018019. Preparation of Substituted 2-(1,1-Dioxaperhydro-1,4-thiazepin-7-yl)acetamides for Treating Inflammatory Respiratory Disease) in THF (10 mL) was added to NaH (2.7 eq) in THF (20 mL) at 0° C. After 20 min MeI (1.1 eq) was added dropwise. This mixture stirred for 2 h and was then quenched with H₂O and extracted twice with EtOAc. The organic layer was dried over sodium sulfate and concentrated. MS: MH+=216.1 (MH+-t-Bu). The material was dissolved in CH₂Cl₂ and TFA (3:1) and stirred overnight. The solvent was then removed by rotory evaporation to give a clear oil. MS: MH+=116.0.

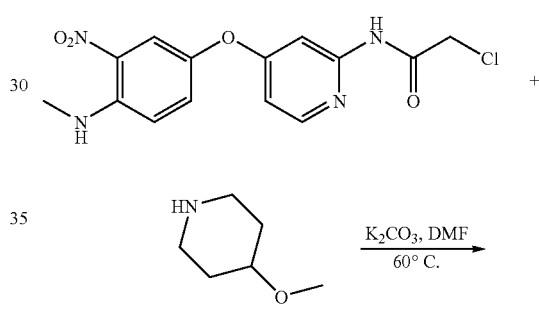

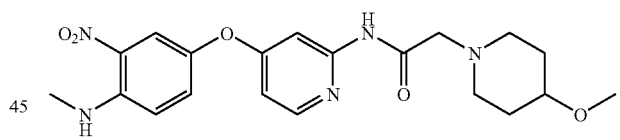

MS: MH+=416.1.

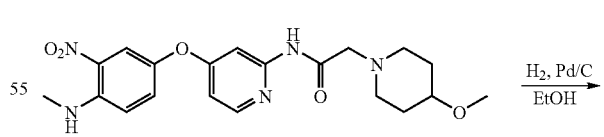

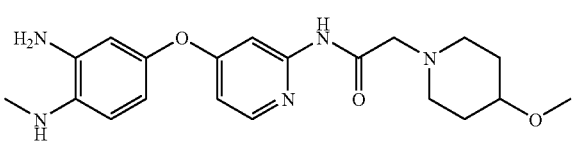

MS: MH+=386.2.

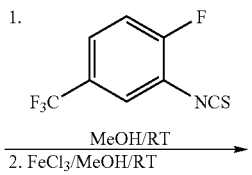

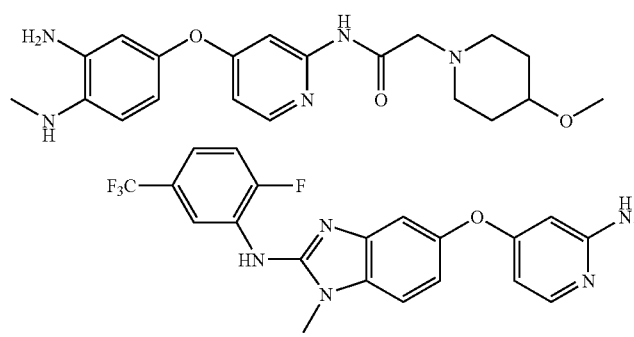

MS: MH⁺=573.1.

EXAMPLE 66

Synthesis of N-{4-[(2-{[2-chloro-5-(trifluoromethyl)phenyl]amino}-1-methyl-1H-benzimidazol-5-yl)oxy]pyridin-2-yl}-2-(4-methoxypiperidin-1-yl)acetamide

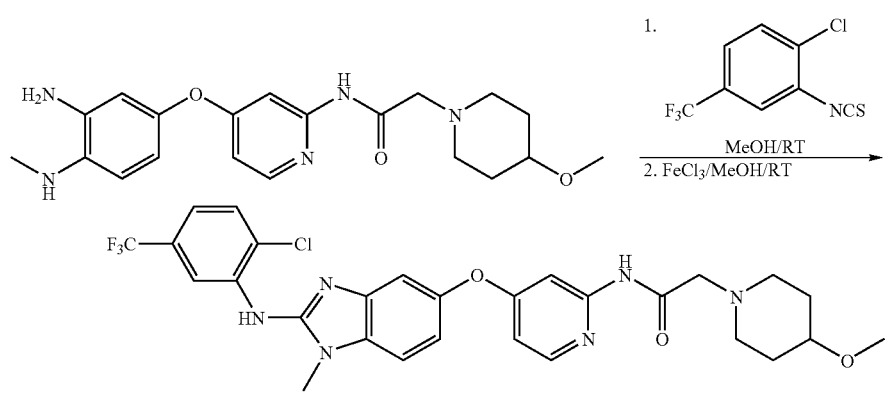

MS: MH⁺=589.1.

EXAMPLE 67

Synthesis of N-{4-[(2-{[2-fluoro-5-(trifluoromethyl)phenyl]amino}-1-methyl-1H-benzimidazol-5-yl)oxy]pyridin-2-yl}-2-(3-methoxyazetidin-1-yl)acetamide -continued

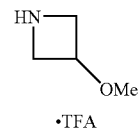

1-N-Boc-3-hydroxyazetidine (1.0 eq) in THF (10 mL) was added to NaH (2.6 eq) in THF (20 mL) at 0° C. After 20 min, MeI (1.1 eq) was added dropwise. This mixture stirred for 2 h and was then quenched with H₂O and extracted twice with EtOAc. The organic layer was dried over sodium sulfate and concentrated. MS: MH⁺=132.1 (MH⁺-t-Bu). The material was dissolved in CH₂Cl₂ and TFA (3:1) and stirred overnight. The solvent was then removed by rotary evaporation to give a clear oil. MS: MH⁺=87.9.

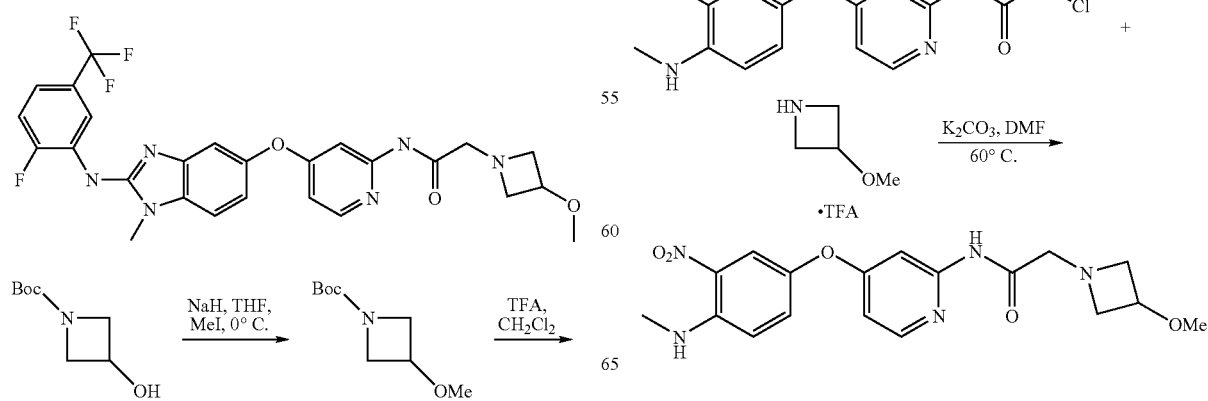

MS: MH⁺=388.1.

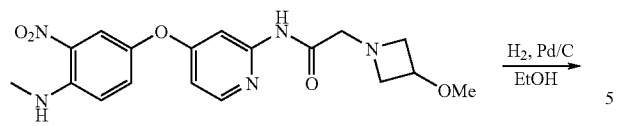
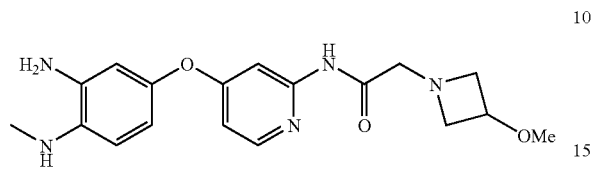
MS: MH+=358.2.
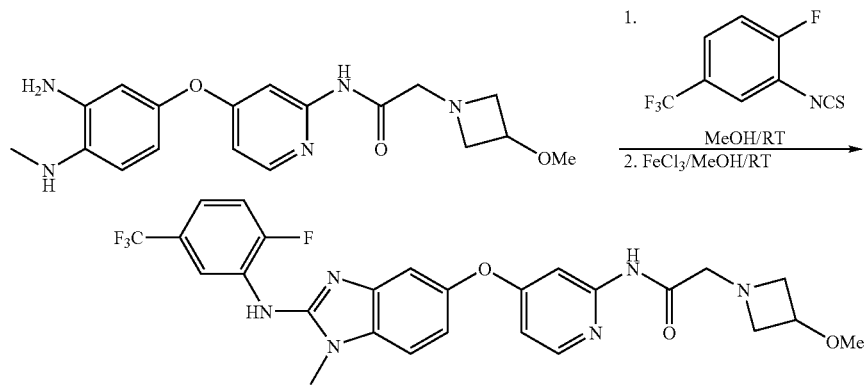
MS: MH+=545.1.
EXAMPLE 68
Synthesis of N-{4-[(2-{[2-chloro-5-(trifluoromethyl) phenyl]amino}-1-methyl-1H-benzimidazol-5-yl) oxy]pyridin-2-yl}-2-(3-methoxyazetidin-1-yl)acetamide
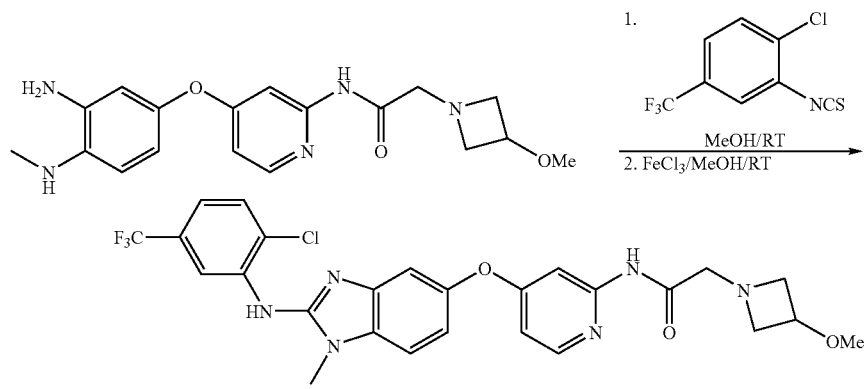
MS: MH+=561.1.

EXAMPLE 69

Synthesis of N-{4-[(1-methyl-2-{[4-(trifluoromethyl)phenyl]amino}-1H-benzimidazol-5-yl)oxy]pyridin-2-yl}propanamide

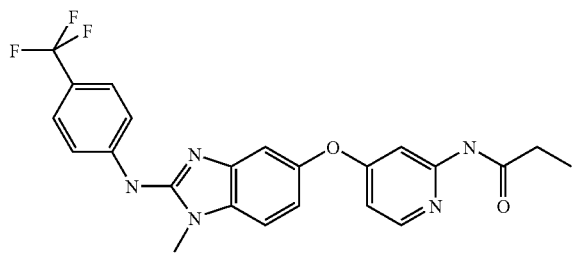 [SMILES: CCC(=O)Nc1cc(Oc2ccc3c(c2)nc(Nc2ccc(C(F)(F)F)cc2)n3C)ccn1]

was extracted with EtOAc (3×). The combined organic portions were washed with brine, dried (MgSO$_4$), concentrated, and the resulting residue was adsorbed onto SiO$_2$. Purification by flash chromatography (0.5:99.5, 0.75:99.25, 1:99, 2:98, methanol-CH$_2$Cl$_2$) gave 310 mg of a bright orange solid as 71b: $^1$H NMR (300 MHz, CDCl$_3$) ☐ 8.35 (br s, 1 H), 8.13 (d, J=5.77 Hz, 1 H), 7.91 (d, J=2.74 Hz, 1 H), 7.68 (d, J=2.2 Hz, 1 H), 7.38 (dd, J=2.74, 2.75 Hz 1H), 7.11 (d, J=9.61 Hz, 1 H), 6.68 (dd, J=2.47, 2.47 Hz, 1 H), 3.065 (d, J=3.85 Hz, 3 H), 2.40 (m, 2 H), 1.141 (m, 3 H).

2. Synthesis of N-{4-[(1-methyl-2-{[4-(trifluoromethyl)phenyl]amino}-1H-benzimidazol-5-yl)oxy]pyridin-2-yl}propanamide

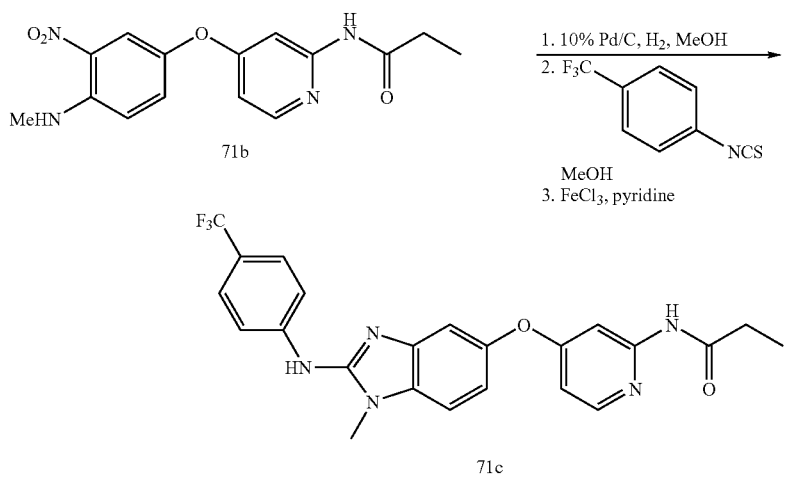

1. Synthesis of N-[4-(4-Methylamino-3-nitro-phenoxy)-pyridin-2-yl]-propionamide

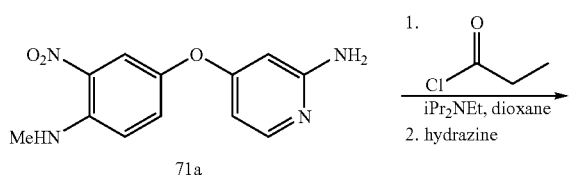

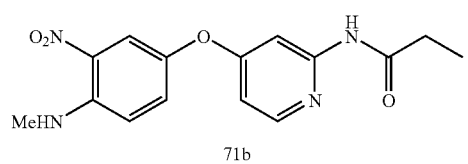

To a stirring suspension of 71a (1 eq) and iPr$_2$NEt (1.5 eq) in dioxane (4 mL) was added propionyl chloride (2 eq) and maintained at rt overnight. Hydrazine (1 eq) was added and stirred for 2 hours. Crude product was concentrated down, and was then partitioned between EtOAc and saturated aqueous Na$_2$CO$_3$. The layers were separated and the aqueous layer A suspension of propionamide 71b (1 eq) and 10% Pd/C (10 mol %) in methanol (4 mL) was charged with H$_2$ and the resulting reaction mixture was maintained under a H$_2$ atmosphere for 1 h at rt. The mixture was filtered and the remaining solids washed thoroughly with EtOAc and methanol. The combined organic portions were evaporated to afford 272 mg of a brown residue as the phenylene diamine, which was carried forward without further purification.

The above diamine (1 eq) was dissolved in methanol (2 mL) and 4-trifluoromethyl phenylthioisocyanate (1 eq) was added. The reaction was maintained for 16 h. Pyridine (3 eq) was added to the reaction, followed by ferric chloride (11.1 eq). The resulting dark reaction mixture was maintained at rt for 16 h, then suspended in saturated aqueous Na$_2$CO$_3$ solution, and filtered with Celite. The remaining solids were washed with EtOAc and the combined filtrate was partitioned and separated. The aqueous portion was extracted with EtOAc (3×) and the combined organic portions were washed with brine, dried (MgSO$_4$), and evaporated. Purification by semi-prep HPLC gave 71c as the TFA salt. LCMS m/z 456.2 (MH$^+$), t$_R$=3.21 min.

EXAMPLE 70

Synthesis of N-(4-{[1-methyl-2-({4-[(trifluoromethyl)thio]phenyl}amino)-1H-benzimidazol-5-yl]oxy}pyridin-2-yl)propanamide

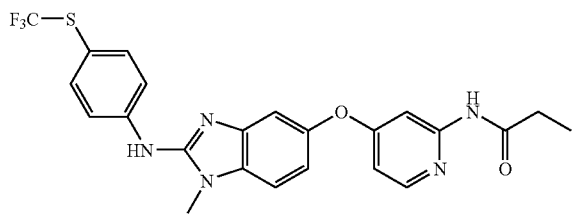 [SMILES: CCC(=O)Nc1cc(Oc2ccc3c(c2)nc(Nc2ccc(SC(F)(F)F)cc2)n3C)ccn1]

Synthesized as described above in Example 69 using 4-trifluoromethylphenyl isothiocyanate. LCMS m/z 488.2 (MH+), R$_t$ 3.72 min.

EXAMPLE 71

Synthesis of N-[4-({2-[(3-tert-butylphenyl)amino]-1-methyl-1H-benzimidazol-5-yl}oxy)pyridin-2-yl]propanamide

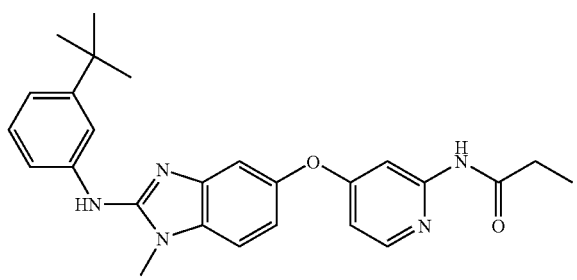 [SMILES: CCC(=O)Nc1cc(Oc2ccc3c(c2)nc(Nc2cccc(C(C)(C)C)c2)n3C)ccn1]

Synthesized as described above in Example 69 using 3-tert-butylphenyl isothiocyanate. LCMS m/z 44.3 (MH+), R$_t$ 3.47 min.

EXAMPLE 72

Synthesis of N-[4-({2-[(4-tert-butylphenyl)amino]-1-methyl-1H-benzimidazol-5-yl}oxy)pyridin-2-yl]propanamide

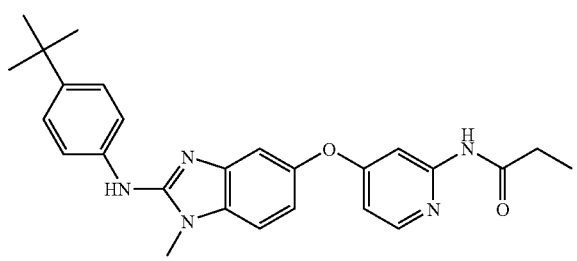 [SMILES: CCC(=O)Nc1cc(Oc2ccc3c(c2)nc(Nc2ccc(C(C)(C)C)cc2)n3C)ccn1]

Synthesized as described above in Example 69 using 4-tert-butylphenyl isothiocyanate. LCMS m/z 44.3 (MH+), R$_t$ 3.52 min.

EXAMPLE 73

Synthesis of N-[4-({2-[(4-fluoro-3-tetrahydrofuran-3-ylphenyl)amino]-1-methyl-1H-benzimidazol-5-yl}oxy)pyridin-2-yl]propanamide

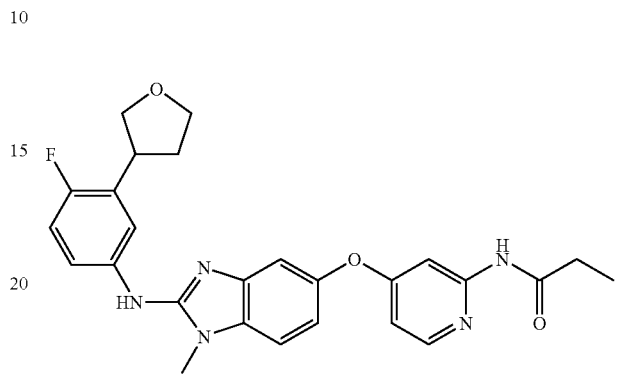

Synthesized as described above in Example 69 using 3-(2-fluoro-5-isothiocyanato-phenyl)-tetrahydro-furan. LCMS m/z 476.3 (MH+), R$_t$ 2.73 min.

EXAMPLE 74

Synthesis of 2-methoxy-N-{4-[(1-methyl-2-{[4-(trifluoromethyl)phenyl]amino}-1H-benzimidazol-5-yl)oxy]pyridin-2-yl}acetamide

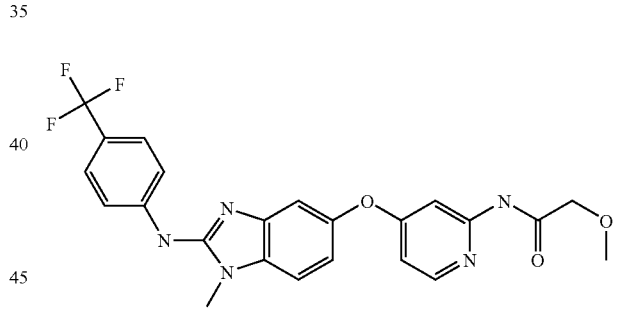

1. Synthesis of 2-Methoxy-N-[4-(4-methylamino-3-nitro-phenoxy)-pyridin-2-yl]-acetamide

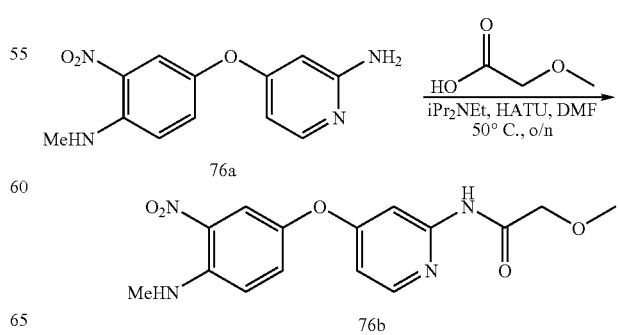

To a solution of iPr₂NEt (6 eq) and cry DMF (8 mL) was added methoxyacetic acid (2 eq). The resulting solution maintained at rt for 30 min, at which time HATU (2.2 eq) was added, and continued stirring at rt for 1 hour. 76a (1 eq) was added, the flask was sealed and the resulting solution was heated to 50° C. overnight. Crude product was partitioned between EtOAc and water, the layers were separated and the aqueous layer was extracted with EtOAc (3×). The combined organic portions were washed with brine, dried (MgSO4), concentrated, and the resulting residue was adsorbed onto SiO₂. Purification by flash chromatography (0.5:99.5, 0.75:99.25, 1:99, 2:98, methanol-CH₂Cl₂) gave 640 mg of a bright orange solid as 76b: ¹H NMR (300 MHz, CDCl₃) ☐ 8.67 (br s, 1 H), 8.15 (d, J=5.76 Hz, 1 H), 8.04 (br s, 1H), 7.965 (d, J=2.75 Hz, 1 H), 7.807 (d, J=2.2 Hz 1 H), 7.30 (dd, J=2.75, 2.75 Hz, 1H), 6.916 (d, J=9.34 Hz, 1 H), 6.63 (dd, J=2.47, 2.48 Hz, 1 H), 3.98 (s, 2 H), 3.48 (s, 3 H), 3.06 (d, J=5.22 Hz, 3 H).

2. Synthesis of 2-methoxy-N-{4-[(1-methyl-2-{[4-(trifluoromethyl)phenyl]amino}-1H-benzimidazol-5-yl)oxy]pyridin-2-yl}acetamide

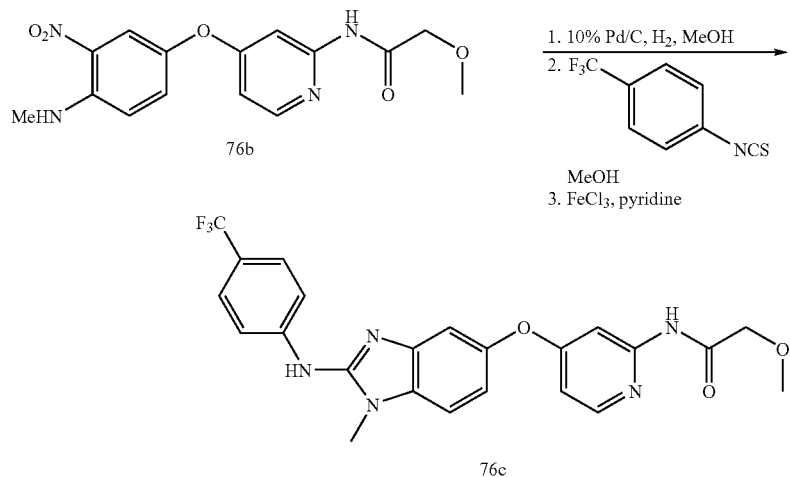

A suspension of methoxyacetamide 76b (1 eq) and 10% Pd/C (10 mol %) in methanol (4 mL) was charged with H₂ and the resulting reaction mixture was maintained under a H₂ atmosphere for 1 h at rt. The mixture was filtered and the remaining solids washed thoroughly with EtOAc and methanol. The combined organic portions were evaporated to afford 272 mg of a brown residue as the phenylene diamine, which was carried forward without further purification.

The above diamine (1 eq) was dissolved in methanol (2 mL) and 4-trifluoromethyl phenylthioisocyanate (1 eq) was added. The reaction was maintained for 16 h. Pyridine (3 eq) was added to the reaction, followed by ferric chloride (1.1 eq). The resulting dark reaction mixture was maintained at rt for 16 h, then suspended in saturated aqueous Na₂CO₃ solution, and filtered with Celite. The remaining solids were washed with EtOAc and the combined filtrate was partitioned and separated. The aqueous portion was extracted with EtOAc (3×) and the combined organic portions were washed with brine, dried (MgSO₄), and evaporated. Purification by semi-prep HPLC gave 76c as the TFA salt. LCMS m/z 474.2 (MH⁺), $t_R$=2.24 min.

EXAMPLE 75

Synthesis of N~2~-isopropyl-N~1~-{4-[(1-methyl-2-{[4-(trifluoromethyl)phenyl]amino}-1H-benzimidazol-5-yl)oxy]pyridin-2-yl}glycinamide

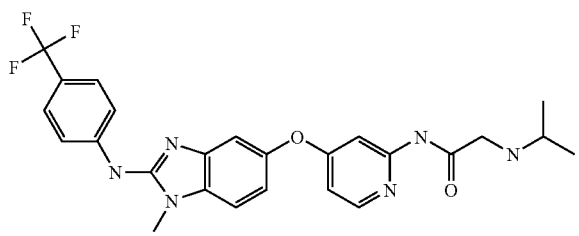 [SMILES: CC(C)NCC(=O)Nc1cc(Oc2ccc3c(c2)nc(Nc2ccc(C(F)(F)F)cc2)n3C)ccn1]

1. Synthesis of {[4-(4-Methylamino-3-nitro-phenoxy)-pyridin-2-ylcarbamoyl]-methyl}-carbamic acid tert-butyl ester

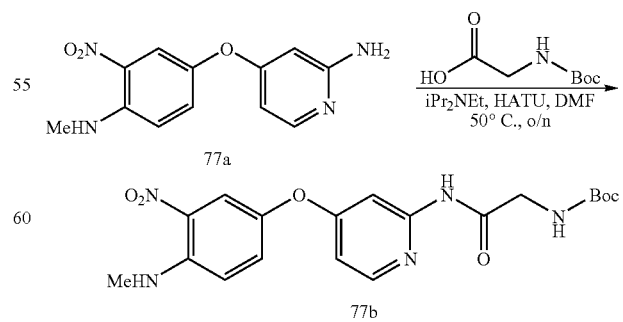

To a solution of iPr₂NEt (4.5 eq) and dry DMF (75 mL) was added tert-Butoxycarbonylamino-acetic acid (1.5 eq). The resulting solution maintained at rt for 30 min, at which time HATU (2 eq) was added, and continued stirring at rt for 1 hour. 77a (1 eq) was added, the flask was sealed and the resulting solution was heated to 50° C. overnight. Crude product was partitioned between EtOAc and water, the layers were separated and the aqueous layer was extracted with EtOAc (3×). The combined organic portions were washed with brine, dried (MgSO4), concentrated, and the resulting residue was adsorbed onto $SiO_2$. Purification by flash chromatography (0.5:99.5, 0.75:99.25, 1:99, 2:98, methanol-$CH_2Cl_2$) gave 4.11 g of a bright orange solid as 77b.

2. Synthesis of 2-Amino-N-{4-[1-methyl-2-(4-trifluoromethyl-phenylamino)-1H-benzoimidazol-5-yloxy]-pyridin-2-yl}-acetamide

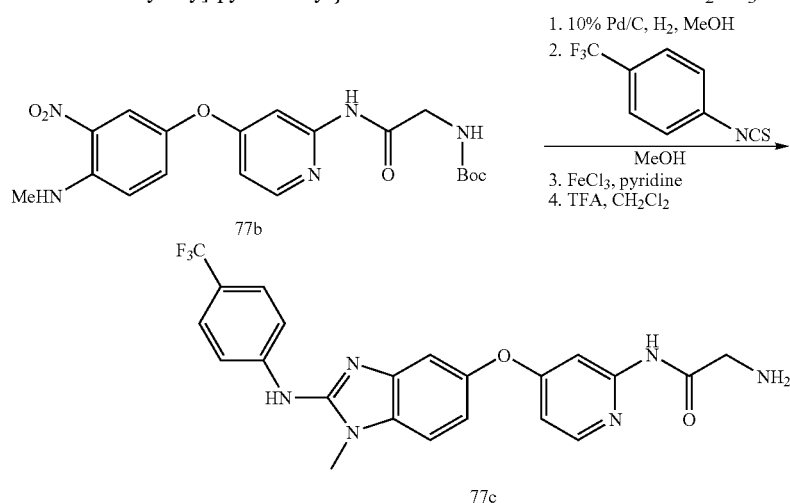

A suspension of 77b (1 eq) and 10% Pd/C (10 mol %) in methanol (4 mL) was charged with $H_2$ and the resulting reaction mixture was maintained under a $H_2$ atmosphere for 1 h at rt. The mixture was filtered and the remaining solids washed thoroughly with EtOAc and methanol. The combined organic portions were evaporated to afford 380 mg of a brown residue as the phenylene diamine, which was carried forward without further purification.

The above diamine (1 eq) was dissolved in methanol (2 mL) and 4-trifluoromethyl phenylthioisocyanate (1 eq) was added. The reaction was maintained for 16 h. Pyridine (3 eq) was added to the reaction, followed by ferric chloride (11.1 eq). The resulting dark reaction mixture was maintained at rt for 16 h, then suspended in saturated aqueous $Na_2CO_3$ solution, and filtered with Celite. The remaining solids were washed with EtOAc and the combined filtrate was partitioned and separated. The aqueous portion was extracted with EtOAc (3×) and the combined organic portions were washed with brine, dried (MgSO$_4$), and evaporated.

The above glycine-amide (1 eq was dissolved in $CH_2Cl_2$ (1 mL) and trifluoroacetic acid (10 eq) was added. The resulting solution was maintained at rt for 16 h. Crude product was concentrated down, and then neutralized with saturated aqueous $Na_2CO_3$ solution. The aqueous portion was extracted with EtOAc (3×) and the combined organic portions were washed with brine, dried (MgSO$_4$), and evaporated to give 20 mg of 77c as a brownish semi-solid.

3. Synthesis of N~2~-isopropyl-N~1~-{4-[(1-methyl-2-{[4-(trifluoromethyl)phenyl]-amino}-1H-benzimidazol-5-yl)oxy]pyridin-2-yl}glycinamide

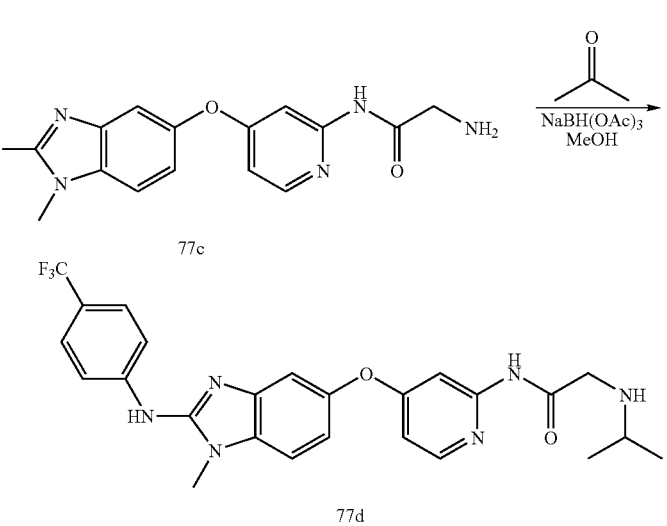

A solution of 77c (1 eq) and acetone (2 eq) in MeOH (100 uL) was maintained at rt for 30 min. NaBH(OAc)$_3$ (3 eq) was added and resulting suspension continued stirring for 30 min. Crude product was concentrated down, then partitioned between EtOAc and water, the layers were separated and the aqueous layer was extracted with EtOAc (3×). The combined organic portions were washed with brine, dried (MgSO4), concentrated. Resulting residue was dissolved in DSMO and purified on semi-prep HPLC to give 77d as the TFA salt. LCMS m/z 499.1 (MH$^{30}$), $t_R$=2.00 min.

EXAMPLE 76

Synthesis of N~1~-[4-({2-[(4-fluoro-3-tetrahydrofuran-3-ylphenyl)amino]-1-methyl-1H-benzimidazol-5-yl}oxy)pyridin-2-yl]-N~2~-isopropylglycinamide

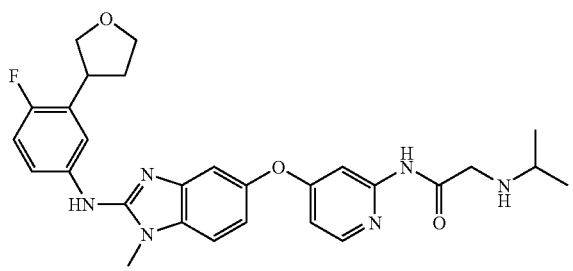 [SMILES: CC(C)NCC(=O)Nc1cc(Oc2ccc3c(c2)nc(Nc2ccc(F)c(C4CCOC4)c2)n3C)ccn1]

Synthesized as described above in Example 75 using 3-(2-fluoro-5-isothiocyanato-phenyl)-tetrahydro-furan. LCMS m/z 519.2 (MH$^+$), R$_t$ 1.80 min.

EXAMPLE 77

Synthesis of N~1~-{4-[(2-{[2-fluoro-5-(trifluoromethyl)phenyl]amino}-1-methyl-1H-benzimidazol-5-yl)oxy]pyridin-2-yl}-N~2~-isopropylglycinamide

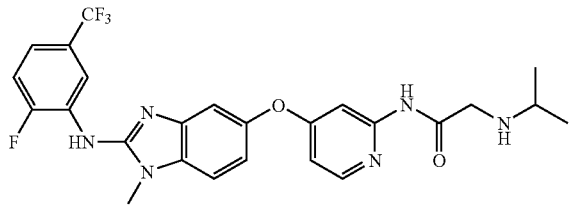 [SMILES: CC(C)NCC(=O)Nc1cc(Oc2ccc3c(c2)nc(Nc2cc(C(F)(F)F)ccc2F)n3C)ccn1]

Synthesized as described above in Example 75 using 2-fluoro-5-trifluoromethylphenyl isothiocyanate. LCMS m/z 517.3 (MH$^+$), R$_t$ 2.02 min.

EXAMPLE 78

Synthesis of N~1~-[4-({2-[(4-fluoro-3-isopropylphenyl)amino]-1-methyl-1H-benzimidazol-5-yl}oxy)pyridin-2-yl]-N~2~-isopropylglycinamide

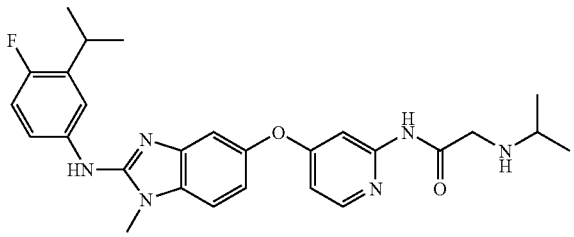 [SMILES: CC(C)NCC(=O)Nc1cc(Oc2ccc3c(c2)nc(Nc2ccc(F)c(C(C)C)c2)n3C)ccn1]

Synthesized as described above in Example 75 using 4-fluoro-3-isopropylphenyl isothiocyanate. LCMS m/z 491.2 (MH$^+$), R$_t$ 2.05 min.

EXAMPLE 79

Synthesis of N~1~-[4-({2-[(2-fluoro-5-isopropylphenyl)amino]-1-methyl-1H-benzimidazol-5-yl}oxy)pyridin-2-yl]-N~2~-isopropylglycinamide

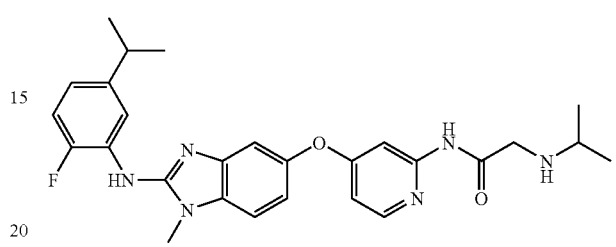

Synthesized as described above in Example 75 using 2-Fluoro-5-isopropylphenyl isothiocyanate. LCMS m/z 491.2 (MH$^+$), R$_t$ 2.09 min.

EXAMPLE 80

Synthesis of N~2~-cyclopentyl-N~1~-[4-({2-[(4-fluoro-3-tetrahydrofuran-3-ylphenyl)amino]-1-methyl-1H-benzimidazol-5-yl}oxy)pyridin-2-yl]glycinamide

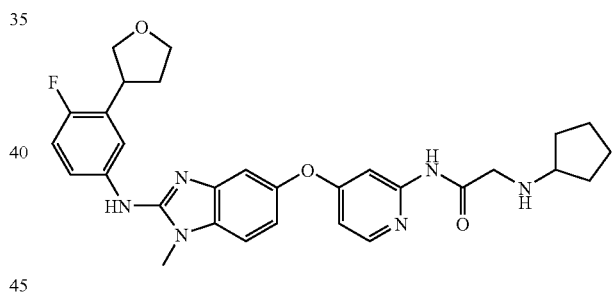

Synthesized as described above in Example 75 using cyclopropanone and 3-(2-fluoro-5-isothiocyanato-phenyl)-tetrahydro-furan. LCMS m/z 545.1 (MH$^+$), R$_t$ 2.86 min.

EXAMPLE 81

Synthesis of 1-isopropylazetidin-3-yl 4-[(1-methyl-2-{[4-(trifluoromethyl)phenyl]amino}-1H-benzimidazol-5-yl)oxy]pyridin-2-ylcarbamate

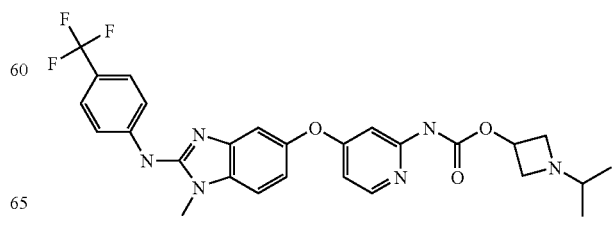

Step 1: Synthesis of 3-[4-(4-Methylamino-3-nitrophenoxy)-pyridin-2-ylcarbamoyloxy]-azetidine-1-carboxylic acid tert-butyl ester

To a suspension of acid 1 (1 eq.) in dry THF (10 mL) at 0° C. was added triethylamine (3.0 eq.) and the resulting reaction was maintained at 0° C. for 45 min to afford a homogenous solution. Diphenylphosphoryl azide (DPPA, 1.1 eq) was added and the reaction was maintained o/n allowing the cooling bath to expire. The reaction was concentrated and the resulting residue dissolved in $CH_2Cl_2$. The organic portion was washed with saturated $NaHCO_3$ (3×) and the combined aqueous phases were extracted with $CH_2Cl_2$. The combined organic portions were dried ($MgSO_4$), filtered, and concentrated. The remaining residue was suspended in toluene. To this suspension was added N—BOC azetidin-2-ol (1 eq) and the reaction mixture was heated to and maintained at 100° C. for 1 h. The reaction was then allowed to cool to rt and concentrated. The residue was dissolved in $CH_2Cl_2$ and washed with saturated $Na_2CO_3$ (3×). The combined aqueous phases were extracted with $CH_2Cl_2$ and the combined organic layers were washed with $Na_2CO_3$ and brine, dried ($MgSO_4$), and evaporated. The crude residue was adsorbed onto $SiO_2$ and purified by flash chromatography (9:1, 4:1, 2:1, 1:1 hexanes-EtOAc) to furnish 625 mg (70%) of a light orange solid as 2: $^1$H NMR (300 MHz, $CDCl_3$) δ 9.32 (br, s, 1 H), 8.17 (d, J=6.0 Hz, 1 H), 8.06 (br dd, J=5.0, 10.2 Hz, 1 H), 7.96 (d, J=2.8 Hz, 1 H), 7.52 (d, J=2.5 Hz, 1 H), 7.30 (dd, J=2.8, 9.2 Hz, 1 H), 6.93 (d, J=9.2 Hz, 1 H), 6.57 (dd, J=2.5, 6.0 Hz, 1 H), 5.18 (dddd, J=4.4, 4.4, 6.9, 6.9 Hz, 1 H), 4.25 (ddd, J=0.8, 6.9, 10.1 Hz, 2 H), 3.94 (ddd, J=0.8, 4.4, 10.1 Hz, 2 H), 3.07 (d, J=5.2 Hz, 3 H), 1.43 (br s, 9 H).

Step 2: Synthesis of 3-[4-(3-Amino-4-methylamino-phenoxy)-pyridin-2-ylcarbamoyloxy]-azetidine-1-carboxylic acid tert-butyl ester

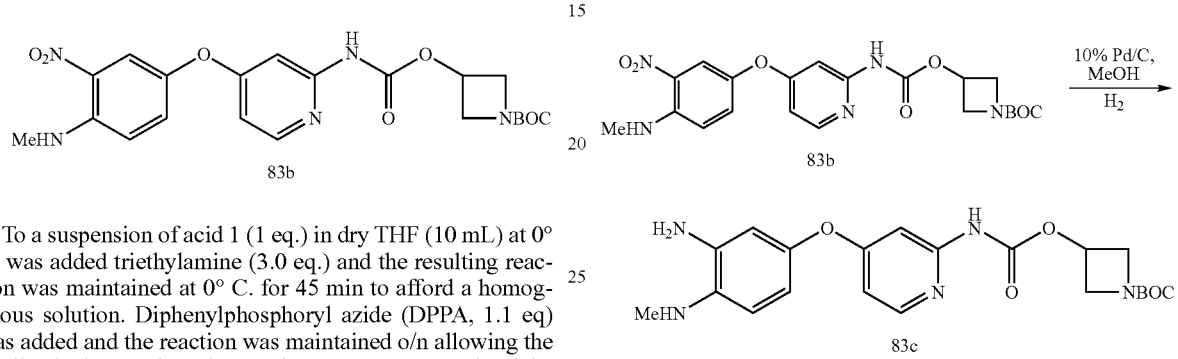

A suspension of nitroaniline 83b (1 eq.) in dry MeOH (8 mL) was sparged with argon over 20 min. 10% Pd C (0.1 eq) was added in one portion and the reaction vessel sealed with a three-way stopcock fitted with a balloon filled with hydrogen. The reaction mixture was purged with hydrogen and the reaction maintained at rt over 3 h. The reaction was filtered through Celite and the filtrate was concentrated to give 474 mg (94%) of a brown residue as 83c. The material was carried forward without further purification: LCMS m/z 430.3 (MH$^+$), $t_R$=2.07 min.

Step 3: 1-isopropyl azetidin-3-yl 4-[(1-methyl-2-{[4-(trifluoromethyl)phenyl]amino}-1H-benzimidazol-5-yl)oxy]pyridin-2-ylcarbamate

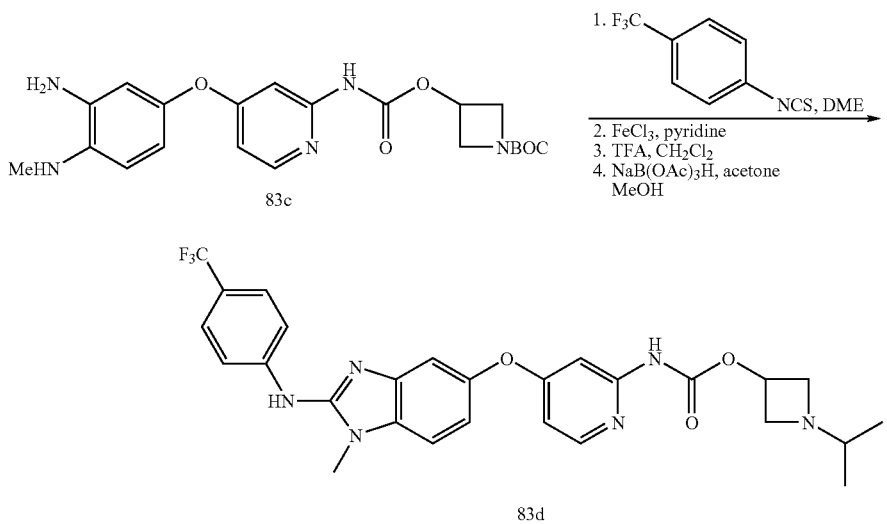

4-Trifluoromethyl phenylthioisocyanate (1.3 eq.) was added to a solution of diamine 83c (1 eq.) in dry DME (10 mL) and the reaction was maintained at rt for 14 h. Pyridine (3 eq.) was added and the reaction cooled to 0° C. FeCl$_3$ (1.2 eq.) was added in one portion and the resulting reaction was maintained at 0° C. for 5 min, then at rt for 12 h. The reaction was concentrated and partitioned with EtOAc and saturated Na$_2$CO$_3$. The resulting mixture was filtered through Celite and the remaining solids washed with EtOAc. The combined phases were then partitioned and separated. The organic phase was washed with saturated Na$_2$CO$_3$ (3×) and the combined aqueous portions were extracted with EtOAc. The combined organic portions were washed with brine, dried (MgSO$_4$), and concentrated. The crude residue was adsorbed onto SiO$_2$ and purified by flash chromatography (2:1 hexanes-acetone). The resulting material was dissolved in CH$_2$Cl$_2$ (4 mL), treated with TFA (1 mL) and the resulting reaction maintained at rt for 2 h. The reaction was concentrated and partitioned with CH$_2$Cl$_2$ and saturated Na$_2$CO$_3$. The organic phase was washed with saturated Na$_2$CO$_3$ (3×) and the combined aqueous portions were extracted with CH$_2$Cl$_2$ (3×). The combined organic phases were dried (MgSO$_4$) and concentrated. The resulting residue was dissolved in MeOH (2 mL) and treated with an excess of acetone and NaB(OAc)$_3$H. The reaction was maintained at rt for 14 h and then concentrated. The residue was then suspended in EtOAc and washed with aqueous 0.5 N HCl solution (3×). The combined acidic aqueous phases were made basic (pH=8) by addition of 1 N NaOH solution. The resulting cloudy aqueous phase was extracted with EtOAc (3×) and the combined organic portions were dried (MgSO$_4$) and concentrated. The resulting residue was further purified by preparative HPLC and reconstituted as the mono mesylate salt to afford 72 mg of 2 as a white solid: $^1$H NMR (300 MHz, CD$_3$OD) δ 8.10 (d, J=5.9 Hz, 1 H), 7.73 (d, J=8.9 Hz, 2 H), 7.69 (d, J=8.9 Hz, 2 H), 7.49 (d, J=8.7 Hz, 1 H), 7.38 (d, J=2.2 Hz, 1 H), 7.19 (d, J=2.2 Hz, 1 H), 7.03 (dd, J=2.2 8.7 Hz, 1 H), 6.65 (dd, J=2.2, 5.9 Hz, 1 H), 5.19 (m, 1 H), 4.50 (app dd, J=6.8, 11.7 Hz, 2 H), 4.24 (app dd, J=4.9, 11.7 Hz, 2H), 3.49 (dddd, J=6.6, 6.6, 6.6, 6.6 Hz, 1 H), 2.69 (s, 3 H), 1.24 (d, J=6.6 Hz, 6 H); LCMS m/z 541.1 (MH$^+$), t$_R$=2.03 min.

EXAMPLE 82

Synthesis of Various Intermediates for Use in the Benzimidazole Ring Formation are Described in this Example EXAMPLE 82a 4-fluoro-3-cyclopentyl-1-nitrobenzene

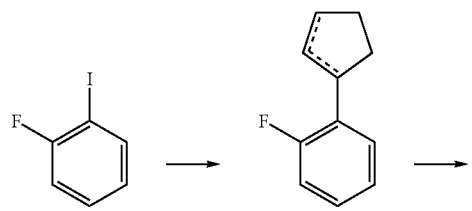

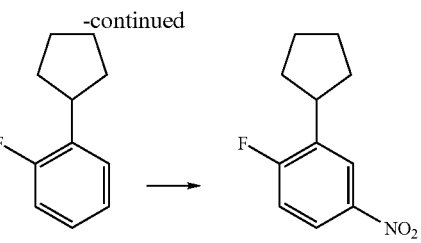

In a steel pressure vessel with stirbar, sodium acetate (4 eq), tetrabutylammonium bromide (1 eq) and Pd(dppf)Cl$_2$—CH$_2$Cl$_2$ (0.03 eq) were suspended in DMA (dimethylacetamide, 0.2M). Nitrogen was bubbled through 10 minutes, then 2-fluoro-1-iodobenzene (1 eq) and cyclopentene (5 eq) were added. The vessel was sealed and heated at 140° C., 14 hrs. The vessel was then cooled to RT, the contents were diluted (ethyl acetate), washed successively with water (2×), aq. NaHCO$_3$, NaCl, then dried over anhydrous K$_2$CO$_3$, filtered and stripped to an oil. Chromatography (3% ethyl acetate in hexanes on silica gel) provides a pale green oil as a mixture of olefin isomers (83%).

Hydrogenation over palladium on carbon (0.5 gm 10% w/w) in methanol (60 mL) at 80 psig and RT converts both to a single, volatile alkane 2'fluorophenylcyclopentane.

A solution of 2'fluorophenylcyclopentane in acetic anhydride (0.2M) was cooled to −10° C. Sulfuric acid (to make 1% v/v) was added. Followed by nitric acid (1.15 eq), dropwise. After addition was complete, the reaction was allowed to warm to RT. After 30 min at RT, TLC showed complete reaction. The mixture was poured onto ice, extracted into ethyl acetate 2×. The combined extracts were washed successively with water, aq. NaHCO$_3$, NaCl, then dried over anhydrous K$_2$CO$_3$, filtered and stripped to an oil. Flash chromatography (3% ethyl acetate in hexanes on silica gel) provides 4-fluoro-3-cyclopentyl-1-nitrobenzene (48% yield)

EXAMPLE 82b

Synthesis of 1-tert-butyl-4-fluorobenzene

In a steel bomb were combined 4-tert-butyl aniline (1 eq) and 70% hydrogen fluoride-pyridine (25 g/gm aniline). Sodium nitrite (1.5 eq) was then added portion wise over 5 minutes. The resulting solution was allowed to stir for 1 h at room temperature and then the bomb was sealed and heated at 85° C. for 1 h. Solution was then quenched with water/ice and extracted with ethyl ether. Organics washed with brine and dried with sodium sulfate and concentrated to afford 1-tert-butyl-4-fluorobenzene.

$^1$H NMR (DMSO, δ ppm): 1.22 (9H, s), 7.07 (2H, t), 7.38 (2H, dd)

EXAMPLE 82c

Synthesis of 4-tert-butyl-1-fluoro-2-nitrobenzene 1-tert-butyl-4-fluorobenzene (1 eq) was dissolved in concentrated sulfuric acid (1.65M) and cooled to 0° C. in an ice/water bath. Potassium nitrate (1 eq) was then added in small portions as to allow the temperature of the reaction not to exceed 7° C. After complete addition the mixture was allowed to stir for an additional 30 minutes, then poured onto ice/water and extracted with ethyl acetate. Organics were washed with a saturated solution of sodium bicarbonate, brine and dried with sodium sulfate and concentrated. Crude mixture was purified by flash chromatography on silica. (85% Hex:15% EtOAc) to afford 4-tert-butyl-1-fluoro-2-nitrobenzene.

$^1$H NMR (CDCl$_3$, δ ppm): 1.3 (9H, s), 7.2 (1H, dd), 7.62 (1H, ddd), 8.03 (1H, dd)

EXAMPLE 82d

Synthesis of 5-tert-butyl-2-fluorobenzenamine

To 4-tert-butyl-1-fluoro-2-nitrobenzene in methanol was added a catalytic amount of palladium on carbon (10%). The mixture was allowed to stir for 1 h at room temperature under an atmosphere of hydrogen. Mixture was filtered though celite and concentrated to afford 5-tert-butyl-2-fluorobenzenamine.
MS: MH$^+$=168

EXAMPLE 82e

Synthesis of 1-(2-fluoro-5-nitrophenyl)ethanone

In a 3-neck flask equipped with an internal thermometer was added sulfuric acid and cooled to 10° C. in an ice/salt/water batch. 2'-fluoroacetophenone (1 eq) in sulfuric acid was added dropwise over 10 minutes via addition funnel to produce a solution of 0.2M. Nitric acid (1.15 eq) in sulfuric acid was then added dropwise at a rate not to exceed 5° C. After complete addition resulting solution was allowed to stir at for 30 minutes. Solution was poured onto ice and extracted with ethyl acetate. Organics were washed with a saturated solution of sodium bicarbonate, brine, dried with sodium sulfate and concentrated. Crude product was purified using flash chromatography (85% Hex:15% EtoAc) on silica to afford 1-(2-fluoro-5-nitrophenyl)ethanone.

$^1$H NMR (CDCl$_3$, δ ppm): 2.7 (3H, s), 7.28 (1H, t), 8.4 (1H, m), 8.8 (1H, dd)

EXAMPLE 82f

Synthesis of 1-fluoro-4-nitro-2-(prop-1-en-2-yl)benzene

KHMDS (1 eq) in toluene is added dropwise over 5 minutes to a stirred suspension of triphenylphosphinemethyl bromide (1.2 eq) in THF at −78° C. under nitrogen. After complete addition solution is allowed to warm to room temperature for 5 minutes then cooled a second time to 78° C. 1-(2-fluoro-5-nitrophenyl)ethanone (1 eq) in THF is then added via cannulla into the cold suspension over 10 minutes. Resulting mixture is then allowed to warm to room temperature and stirred for 1 h. Solvent is then removed under reduced pressure, cyclohexane is then added and mixture heated briefly to reflux, cooled to room temperature, filtered and filtrate concentrated. Crude product is purified using flash chromatography (85% Hex:15% EtOAc) on silica to afford 1-fluoro-4-nitro-2-(prop-1-en-2-yl)benzene.

$^1$H NMR (CDCl$_3$, δ ppm): 2.15 (3H, s), 5.25 (2H, d), 7.19 (1H, t), 8.1 (1H, m), 8.2 (1H, dd)

EXAMPLE 82g

Synthesis 2-(2-fluoro-5-nitrophenyl)-2-methyloxirane 1-fluoro-4-nitro-2-(prop-1-en-2-yl)benzene (1 eq) was dissolved in dichloromethane and cooled to 10° C. using and ice/salt/water bath under nitrogen. MCPBA (1.5 eq) in dichloromethane was then added dropwise and resulting solution allowed to warm to room temperature and allowed to stir 48 h. Solution was quenched with 10% sodium sulfite, neutralized with saturated solution of sodium bicarbonate, extracted with dichloromethane. Organics were washed with brine, dried with sodium sulfate and concentrated. Crude product was purified with flash chromatography (85% Hex: 15% EtoAc) to afford 2-(2-fluoro-5-nitrophenyl)-2-methyloxirane.

$^1$H NMR (CDCl$_3$, δ ppm): 1.7 (3H, s), 2.8 (1H, d), 3.05 (1H, d), 7.2 (1H, t), 8.2 (1H, m), 8.35 (1H, dd)

EXAMPLE 82h

Synthesis of 2-(2-fluoro-5-nitrophenyl) propanal 2-(2-fluoro-5-nitrophenyl)-2-methyloxirane (1 eq) was dissolved in ethyl ether (1 mL) under nitrogen. BF$_3$-etherate (0.87 eq) was added dropwise at room temperature and after complete addition solution was allowed to stir for 1 h. Solution was then quenched with water, extracted with ethyl ether. Organics washed with brine, dried with sodium sulfate and concentrated. Crude product was purified using flash chromatography (85% Hex:15% EtOAc) on silica to afford 2-(2-fluoro-5-nitrophenyl) propanal.

$^1$H NMR (CDCl$_3$, δ ppm): 1.5 (3H, d), 3.9 (1H, c), 7.2 (1H, t), 8.15 (1H, dd), 8.21 (1H, m), 9.7 (1H, s)

EXAMPLE 82i

Synthesis of 2-(2-fluoro-5-nitrophenyl)-2-methylpent-4-enal

To a solution of palladium acetate (0.1 eq), triphenylphosphine (0.2 eq), lithium chloride (1.0 eq) in THF were sequentially added 2-(2-fluoro-5-nitrophenyl) propanal (1.1 eq) in THF, allyl alcohol (1.0 eq), triethylamine (1.2 eq) and triethylborane (2.4 eq) under nitrogen at room temperature. Solution was allowed to stir for 2 h. Mixture was diluted with saturated solution of sodium bicarbonate, extracted with ethyl acetate. Organics were washed with brine, dried with sodium sulfate and concentrated. Crude product was purified using flash chromatography (85% Hex:15% EtoAc) on silica to afford 2-(2-fluoro-5-nitrophenyl)-2-methylpent-4-enal.

$^1$H NMR (CDCl$_3$, B ppm): 1.5 (3H, s), 2.6-2.85 (2H, m), 5.1 (2H, m), 5.5 (1H, m), 7.2 (1H, t), 8.2 (2H, m), 9.7 (1H, d)

EXAMPLE 82j

Synthesis of 2-(2-fluoro-5-nitrophenyl)-2-methylbutane-1,4-diol 2-(2-fluoro-5-nitrophenyl)-2-methylpent-4-enal (1 eq) was dissolved in dichloromethane:methanol (3:1) and cooled to −78° C. Ozone was then bubbled through the solution until a blue color was noticed. Air was then passed through the solution followed by the addition of sodium borohydride (5 eq). Resulting solution was allowed to warm to room temperature and diluted with brine, extracted with dichloromethane. Organics were dried with sodium sulfate and concentrated to afford 2-(2-fluoro-5-nitrophenyl)-2-methylbutane-1,4-diol. The product was used in the next step with no further characterization.

EXAMPLE 82k

Synthesis of 3-(2-fluoro-5-nitrophenyl)-tetrahydro-3-methylfuran

To a solution of triphenylphosphine (2 eq) in dichloromethane at 0° C. under nitrogen was added dropwise triflic anhydride (1 eq). After 15 minutes 2-(2-fluoro-5-nitrophenyl)-2-methylbutane-1,4-diol (1 eq) was added in dichloromethane followed by potassium carbonated (1 eq). The resulting mixture was allowed to warm to room temperature for 5 h. To the mixture was added water and extracted with dichloromethane. The organic layer was washed with brine and dried with sodium sulfate and concentrated. Crude product was purified using flash chromatography (85% Hex:15% EtoAc) on silica to afford 3-(2-fluoro-5-nitrophenyl)-tetrahydro-3-methylfuran.

$^1$H NMR (CDCl$_3$, δ ppm): 1.45 (3H, s), 2.2-2.4 (2H, m), 3.85 (1H, d), 3.9-4.05 (3H, m), 7.2 (1H, t), 8.15 (2H, m)

EXAMPLE 82l

Synthesis of 4-fluoro-3-(tetrahydro-3-methylfuran-3-yl)benzenamine

To 3-(2-fluoro-5-nitrophenyl)-tetrahydro-3-methylfuran in methanol was added a catalytic amount of palladium on carbon (10%). The mixture was allowed to stir for 1 h at room temperature under hydrogen atmosphere. Mixture was filtered though celite and concentrated to afford 4-fluoro-3-(tetrahydro-3-methylfuran-3-yl)benzenamine.

MS: MH$^+$=196

EXAMPLE 82m

Preparation of [4-(4-methylamino-3-nitro-phenoxy)-pyridin-2-yl]-carbamic acid ethyl ester

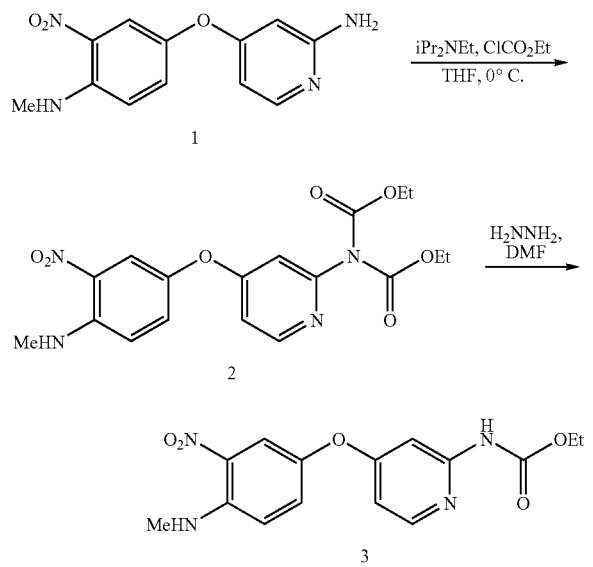

Ethyl chloroformate (2 eq.) was added to a stirring solution of aniline 1 (1 eq.) and iPr$_2$NEt (2 eq.) in dry THF (14 mL) at 0° C. The reaction was allowed to warm to rt over 2 h. The reaction concentrated and the resulting residue dissolved in EtOAc. The organic phase was washed with saturated aqueous NaHCO$_3$ (3×) and the combined aqueous portions were extracted with EtOAc. The combined organic portions were concentrated to give an orange residue as 2. The residue was dissolved in DMF (20 mL), hydrazine monohydrate (1 eq.) added and the resulting reaction maintained at rt for 14 h. The reaction volume was reduced and the remaining solution was partitioned between EtOAc and water. The layers were separated and the aqueous phase extracted with EtOAc (3×). The combined organic layers were concentrated to give an orange solid as 3 which was carried forward without further purification: LCMS m/z 333.3 (MH$^+$), t$_R$=2.29 min.

EXAMPLE 82n

Synthesis of 4-(3-aminophenyl)-1-(2,2,2-trifluoroethyl)piperidin-4-ol (3)

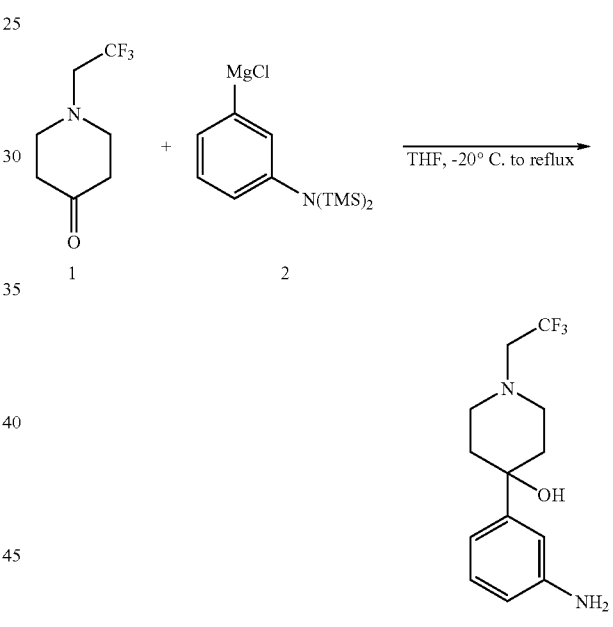

1 equivalent of known compound 1 (WO 9521452) as a 1M solution in dry THF was cooled to −20° C. under argon. 1.1 Equivalents of grignard compound 2 (Aldrich) as a 2M solution in THF was then added dropwise via syringe. Reaction stirred at −20° C. for 20 mins, allowed to warm to room temperature, then briefly refluxed.

Solution was then cooled in an ice bath and an excess of dilute aqueous HCl was carefully added. An aqueous solution of sodium bicarbonate was added to bring the pH>7 and the product was extracted with ethyl acetate. Removal of organic solvent in vacuo gave a residue that was purified via silica gel column chromatography (30% ethyl acetate in hexane). Compound 3 was then further purified by recrystallizing from a hexane/ethyl acetate solution to give a clear oil in a 75% yield. LCMS m/z 275.3 (MH$^+$)

EXAMPLE 82o

Synthesis of 3-[4-Methoxy-1-(2,2,2-trifluoro-ethyl)-piperidin-4-yl]-phenylamine

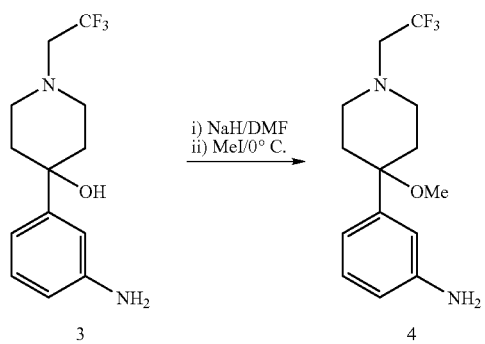

To Compound 3 (1 eq) in cry DIM as a 1M solution was added 1.1 eq of sodium hydride at room temperature. This solution was allowed to react for 30 mins. The solution was then cool to 0° C. and 1.1 eq of methyl iodine added. Reaction was then slowly warmed to room temperature where water was added. The product was extracted with ethyl acetate, washed with water, dried over magnesium sulfate, and the solvent removed to give Compound 4 in sufficient purity. LCMS m/z 289.3 (MH$^+$).

EXAMPLE 82p

Synthesis of 3-[1-(2,2,2-Trifluoro-ethyl)-piperidin-4-yl]-phenylamine

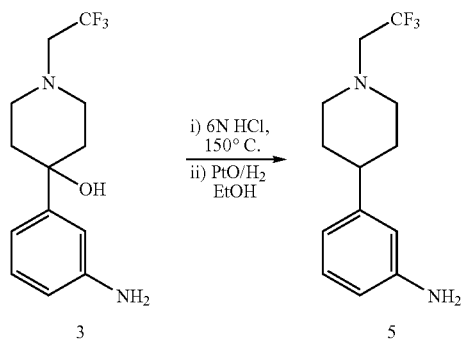

Compound 3 was heated to 150° C. in a 6N HCl solution via a microwave reactor for 5 mins. Solution was neutralized and extracted with ethyl acetate. After removal of solvent, the intermediate was dissolved in ethanol and reduced over PtO in a hydrogen gas atmosphere. The catalyst was removed by filtering through celite and the ethanol evaporated to give Compound 5.

EXAMPLE 82q

Synthesis of 1-(2,2,2-Trifluoro-ethyl)-piperidine-4-carboxylic acid [4-(4-methylamino-3-nitro-phenoxy)-pyridin-2-yl]-amide

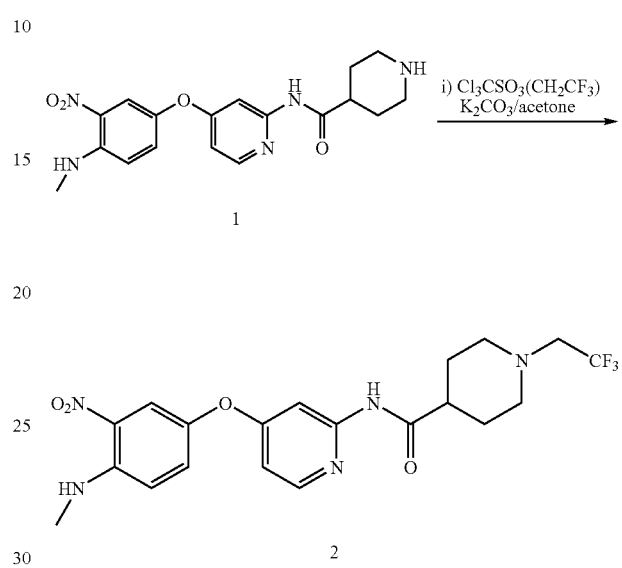

To 1 eq. of Compound 1 in acetone as a 1M solution and 4 eq. Of potassium carbonate was added 1 eq of 2,2,2-trifluoromethyl trichloromethansulfonate. Solution briefly refluxed, cooled, solvent removed and residue partitioned between water and ethyl acetate. Organic separated, dried over magnesium sulfate, solvent evaporated to provide 2.

EXAMPLE 83

Synthesis of N-(4-{[2-({3-[4-fluoro-1-(2,2,2-trifluoroethyl)piperidin-4-yl]phenyl}amino)-1-methyl-1H-benzimidazol-5-yl]oxy}pyridin-2-yl)acetamide

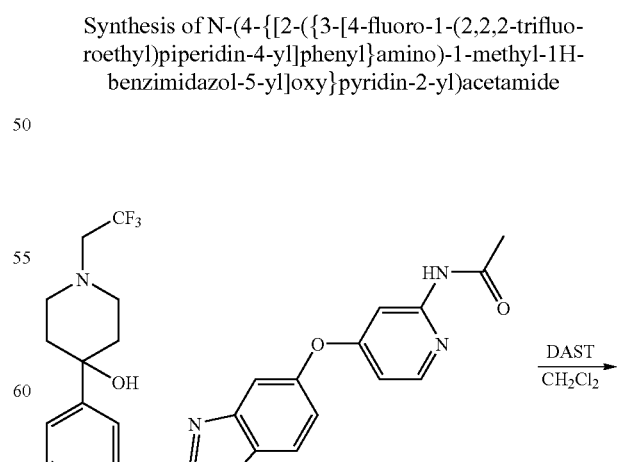

-continued

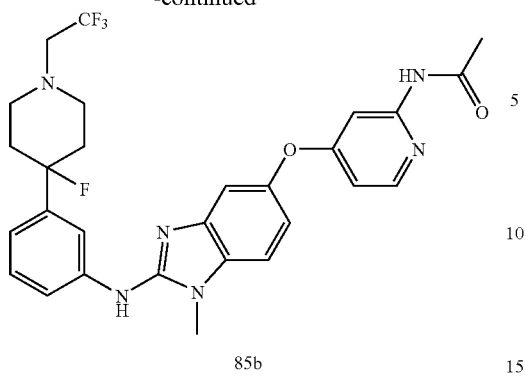

85b

Compound 85a (1 eq) was dissolved in dichloromethane to a 1M solution under argon. DAST (Aldrich), 1 eq., was then added and solution allowed to react for 1 hr.

Water was added, the phases separated, and the organic solvent removed in vacuo. The residue was purified via silica gel column chromatography (5% MeOH/DCM) to give Compound 85b in nearly quantitative yield. LCMS m/z 557.5 (MH$^+$), R$_t$ 1.61 min.

EXAMPLES 84-515

The compounds in the following Table 1 (Examples 84-515) were similarly synthesized according to the procedures described in Examples 1-83.

TABLE 1

| Ex. | Structure | Name | MH+ |
|---|---|---|---|
| 84 | 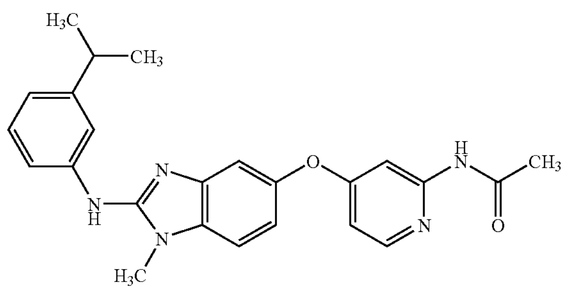 [SMILES: CC(=O)Nc1cc(Oc2ccc3c(c2)nc(Nc2cccc(C(C)C)c2)n3C)ccn1] | N-[4-({2-[(3-isopropylphenyl)-amino]-1-methyl-1H-benzimidazol-5-yl}oxy)pyridin-2-yl]acetamide | 416.5 |
| 85 | 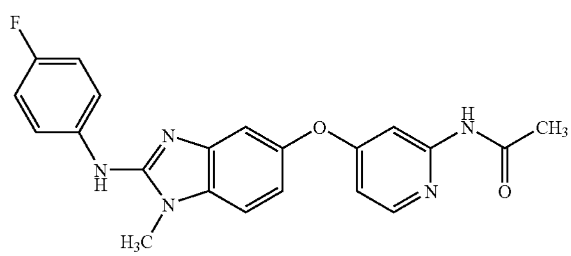 [SMILES: CC(=O)Nc1cc(Oc2ccc3c(c2)nc(Nc2ccc(F)cc2)n3C)ccn1] | N-[4-({2-[(4-fluorophenyl)amino]-1-methyl-1H-benzimidazol-5-yl}oxy)pyridin-2-yl]acetamide | 392.4 |
| 86 | 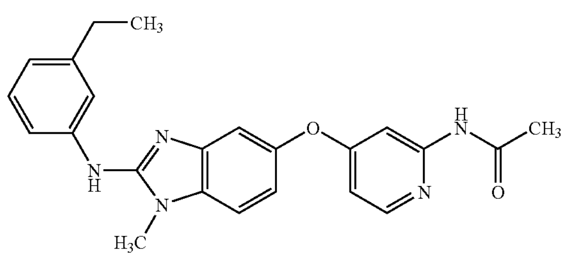 [SMILES: CCc1cccc(Nc2nc3cc(Oc4ccnc(NC(C)=O)c4)ccc3n2C)c1] | N-[4-({2-[(3-ethylphenyl)amino]-1-methyl-1H-benzimidazol-5-yl}oxy)pyridin-2-yl]acetamide | 402.5 |
| 87 | 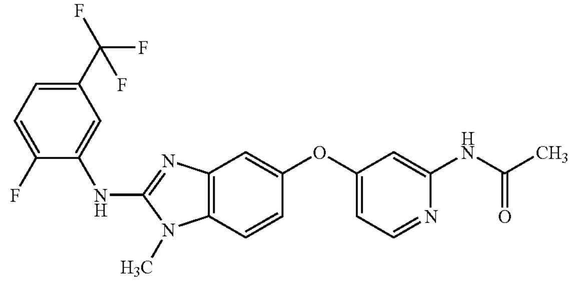 [SMILES: CC(=O)Nc1cc(Oc2ccc3c(c2)nc(Nc2cc(C(F)(F)F)ccc2F)n3C)ccn1] | N-{4-[(2-{[2-fluoro-5-(trifluoromethyl)phenyl]amino}-1-methyl-1H-benzimidazol-5-yl)oxy]pyridin-2-yl}acetamide | 460.4 |

TABLE 1-continued

| Ex. | Structure | Name | MH+ |
|---|---|---|---|
| 88 | 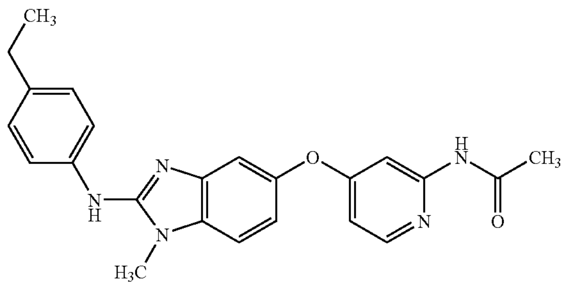 [SMILES: CCc1ccc(Nc2nc3cc(Oc4ccnc(NC(C)=O)c4)ccc3n2C)cc1] | N-[4-({2-[(4-ethylphenyl)amino]-1-methyl-1H-benzimidazol-5-yl}oxy)pyridin-2-yl]acetamide | 402.5 |
| 89 | 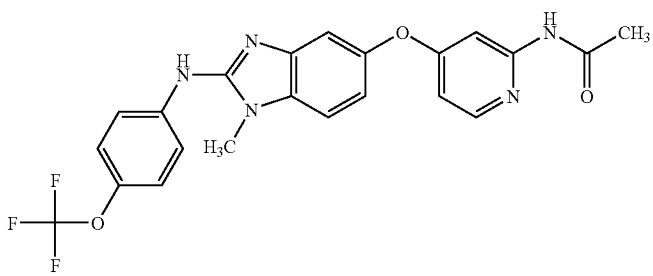 [SMILES: CC(=O)Nc1cc(Oc2ccc3c(c2)nc(Nc2ccc(OC(F)(F)F)cc2)n3C)ccn1] | N-{4-[(1-methyl-2-{[4-(trifluoromethoxy)phenyl]amino}-1H-benzimidazol-5-yl)oxy]pyridin-2-yl}acetamide | 458.4 |
| 90 | 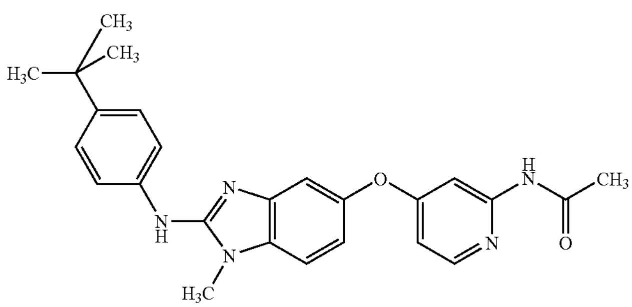 [SMILES: CC(=O)Nc1cc(Oc2ccc3c(c2)nc(Nc2ccc(C(C)(C)C)cc2)n3C)ccn1] | N-[4-({2-[(4-tert-butylphenyl)amino]-1-methyl-1H-benzimidazol-5-yl}oxy)pyridin-2-yl]acetamide | 430.5 |
| 91 | 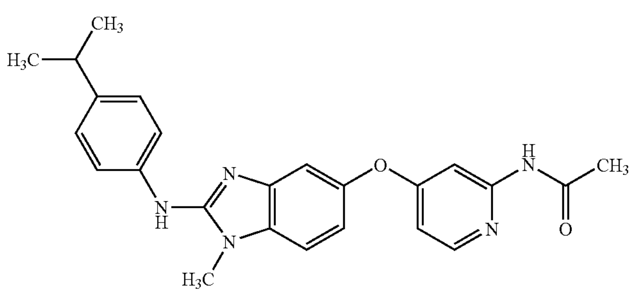 [SMILES: CC(=O)Nc1cc(Oc2ccc3c(c2)nc(Nc2ccc(C(C)C)cc2)n3C)ccn1] | N-[4-({2-[(4-isopropylphenyl)amino]-1-methyl-1H-benzimidazol-5-yl}oxy)pyridin-2-yl]acetamide | 416.5 |
| 92 | 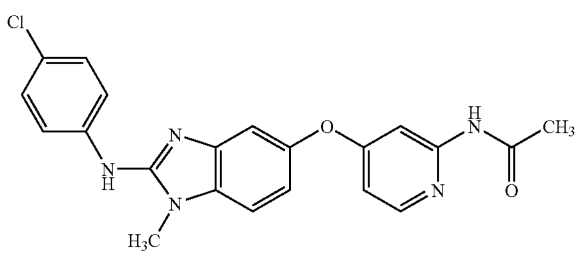 [SMILES: CC(=O)Nc1cc(Oc2ccc3c(c2)nc(Nc2ccc(Cl)cc2)n3C)ccn1] | N-[4-({2-[(4-chlorophenyl)amino]-1-methyl-1H-benzimidazol-5-yl}oxy)pyridin-2-yl]acetamide | 408.9 |

TABLE 1-continued

| Ex. | Structure | Name | MH+ |
|---|---|---|---|
| 93 | 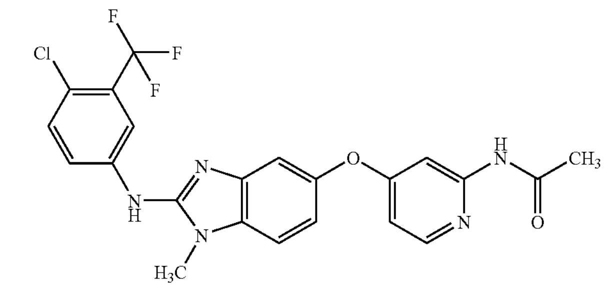 [SMILES: CC(=O)Nc1cc(Oc2ccc3c(c2)nc(Nc2ccc(Cl)c(C(F)(F)F)c2)n3C)ccn1] | N-{4-[(2-{[4-chloro-3-(trifluoromethyl)phenyl]amino}-1-methyl-1H-benzimidazol-5-yl)oxy]pyridin-2-yl}acetamide | 476.9 |
| 94 | 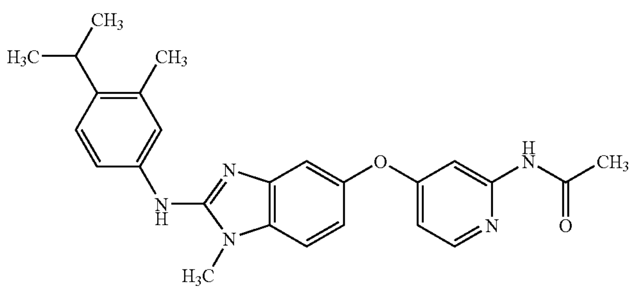 [SMILES: CC(=O)Nc1cc(Oc2ccc3c(c2)nc(Nc2ccc(C(C)C)c(C)c2)n3C)ccn1] | N-[4-({2-[(4-isopropyl-3-methyl-phenyl)amino]-1-methyl-1H-benzimidazol-5-yl}oxy)pyridin-2-yl]acetamide | 430.5 |
| 95 | 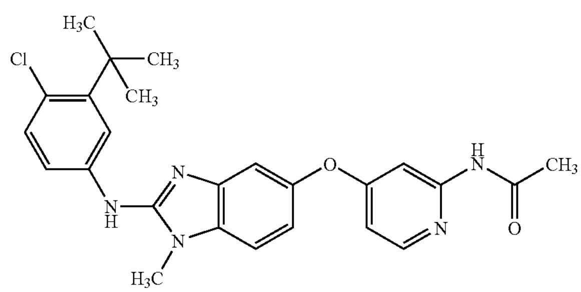 [SMILES: CC(=O)Nc1cc(Oc2ccc3c(c2)nc(Nc2ccc(Cl)c(C(C)(C)C)c2)n3C)ccn1] | N-[4-({2-[(3-tert-butyl-4-chloro-phenyl)amino]-1-methyl-1H-benzimidazol-5-yl}oxy)pyridin-2-yl]acetamide | 465 |
| 96 | 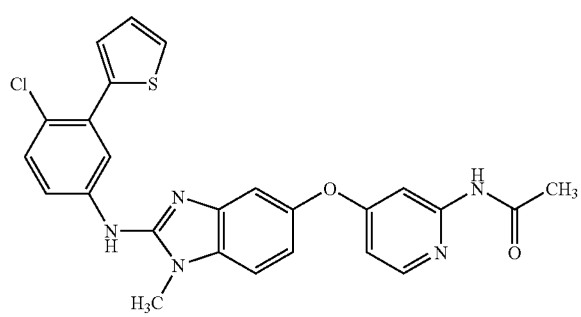 [SMILES: CC(=O)Nc1cc(Oc2ccc3c(c2)nc(Nc2ccc(Cl)c(-c4cccs4)c2)n3C)ccn1] | N-[4-({2-[(4-chloro-3-thien-2-ylphenyl)amino]-1-methyl-1H-benzimidazol-5-yl}oxy)pyridin-2-yl]acetamide | 491 |
| 97 | 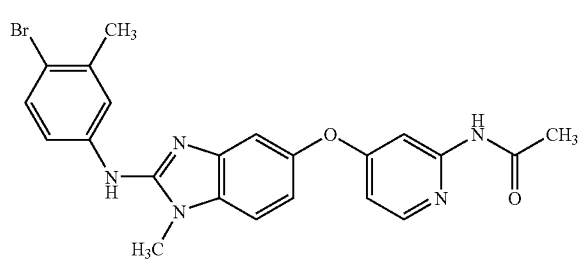 [SMILES: CC(=O)Nc1cc(Oc2ccc3c(c2)nc(Nc2ccc(Br)c(C)c2)n3C)ccn1] | N-[4-({2-[(4-bromo-3-methyl-phenyl)amino]-1-methyl-1H-benzimidazol-5-yl}oxy)pyridin-2-yl]acetamide | 467.3 |

TABLE 1-continued

| Ex. | Structure | Name | MH+ |
|---|---|---|---|
| 98 | 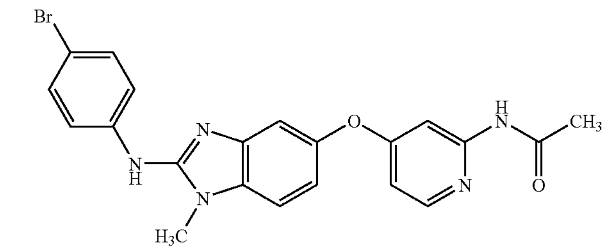 | N-[4-({2-[(4-bromophenyl)amino]-1-methyl-1H-benzimidazol-5-yl}oxy)pyridin-2-yl]acetamide | 453.3 |
| 99 | 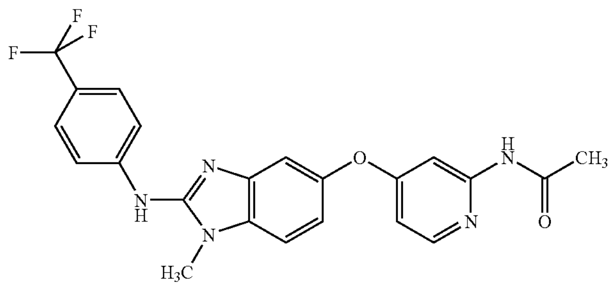 [SMILES: CC(=O)Nc1cc(Oc2ccc3c(c2)nc(Nc2ccc(C(F)(F)F)cc2)n3C)ccn1] | N-{4-[(1-methyl-2-{[4-(trifluoromethyl)phenyl]amino}-1H-benzimidazol-5-yl)oxy]pyridin-2-yl}acetamide | 442.4 |
| 100 | 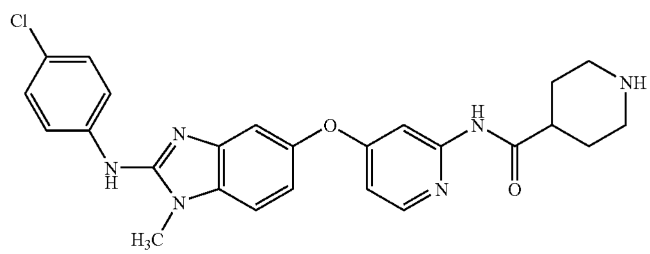 [SMILES: Cn1c(Nc2ccc(Cl)cc2)nc2cc(Oc3ccnc(NC(=O)C4CCNCC4)c3)ccc21] | N-[4-({2-[(4-chlorophenyl)amino]-1-methyl-1H-benzimidazol-5-yl}oxy)pyridin-2-yl]piperidine-4-carboxamide | 478 |
| 101 | 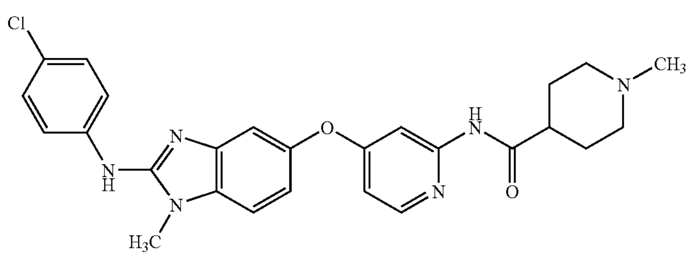 [SMILES: CN1CCC(C(=O)Nc2cc(Oc3ccc4c(c3)nc(Nc3ccc(Cl)cc3)n4C)ccn2)CC1] | N-[4-({2-[(4-chlorophenyl)amino]-1-methyl-1H-benzimidazol-5-yl}oxy)pyridin-2-yl]-1-methylpiperidine-4-carboxamide | 492 |
| 102 | 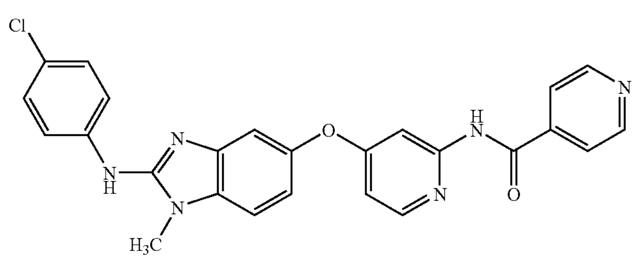 [SMILES: Cn1c(Nc2ccc(Cl)cc2)nc2cc(Oc3ccnc(NC(=O)c4ccncc4)c3)ccc21] | N-[4-({2-[(4-chlorophenyl)amino]-1-methyl-1H-benzimidazol-5-yl}oxy)pyridin-2-yl]isonicotinamide | 471.9 |
| 103 | 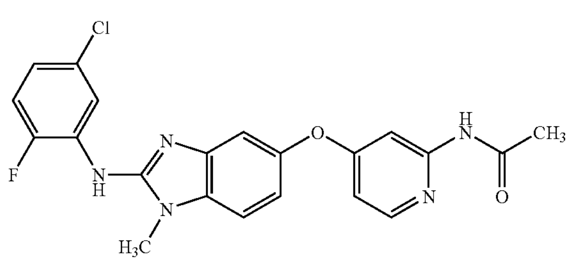 [SMILES: CC(=O)Nc1cc(Oc2ccc3c(c2)nc(Nc2cc(Cl)ccc2F)n3C)ccn1] | N-[4-({2-[(5-chloro-2-fluorophenyl)amino]-1-methyl-1H-benzimidazol-5-yl}oxy)pyridin-2-yl]acetamide | 426.8 |

TABLE 1-continued

| Ex. | Structure | Name | MH+ |
|---|---|---|---|
| 104 | 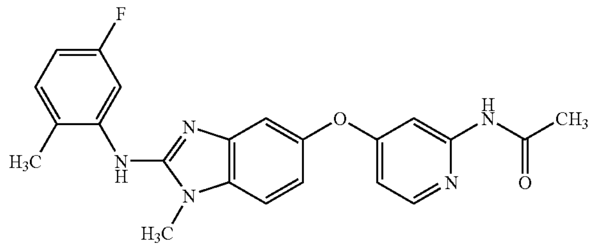 [SMILES: CC(=O)Nc1cc(Oc2ccc3c(c2)nc(Nc2cc(F)ccc2C)n3C)ccn1] | N-[4-({2-[(5-fluoro-2-methyl-phenyl)amino]-1-methyl-1H-benzimidazol-5-yl}oxy)pyridin-2-yl]acetamide | 406.4 |
| 105 | 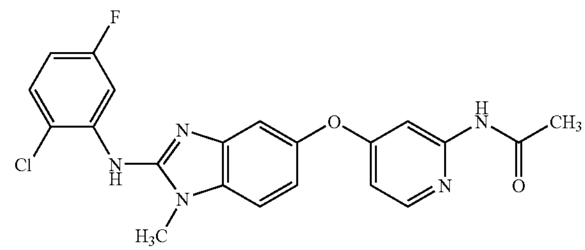 | N-[4-({2-[(2-chloro-5-fluoro-phenyl)amino]-1-methyl-1H-benzimidazol-5-yl}oxy)pyridin-2-yl]acetamide | 426.8 |
| 106 | 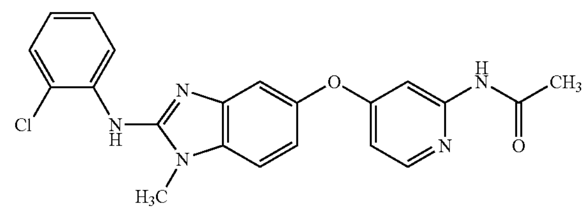 [SMILES: CC(=O)Nc1cc(Oc2ccc3c(c2)nc(Nc2ccccc2Cl)n3C)ccn1] | N-[4-({2-[(2-chlorophenyl)amino]-1-methyl-1H-benzimidazol-5-yl}-oxy)pyridin-2-yl]acetamide | 408.9 |
| 107 | 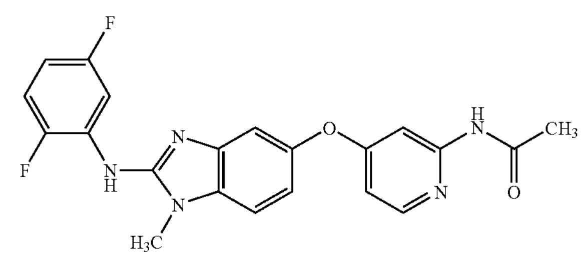 | N-[4-({2-[(2,5-difluorophenyl)-amino]-1-methyl-1H-benzimidazol-5-yl}oxy)pyridin-2-yl]acetamide | 410.4 |
| 108 | 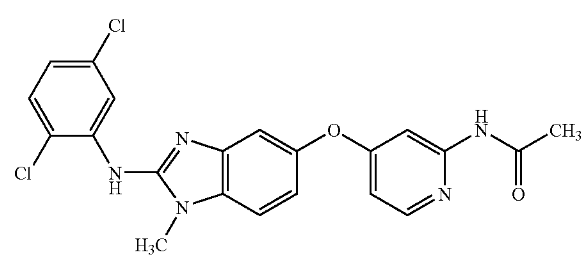 [SMILES: CC(=O)Nc1cc(Oc2ccc3c(c2)nc(Nc2cc(Cl)ccc2Cl)n3C)ccn1] | N-[4-({2-[(2,5-dichlorophenyl)amino]-1-methyl-1H-benzimidazol-5-yl}oxy)pyridin-2-yl]acetamide | 443.3 |
| 109 | 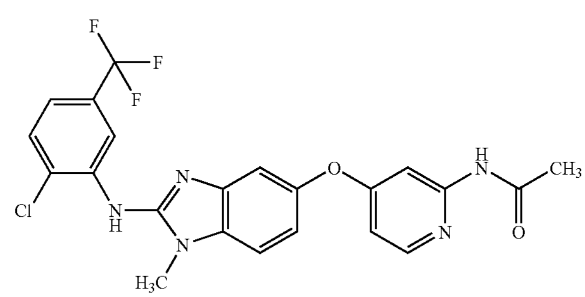 [SMILES: CC(=O)Nc1cc(Oc2ccc3c(c2)nc(Nc2cc(C(F)(F)F)ccc2Cl)n3C)ccn1] | N-{4-[(2-{[2-chloro-5-(trifluoro-methyl)phenyl]amino}-1-methyl-1H-benzimidazol-5-yl)oxy]pyridin-2-yl}acetamide | 476.9 |

TABLE 1-continued

| Ex. | Structure | Name | MH+ |
|---|---|---|---|
| 110 | 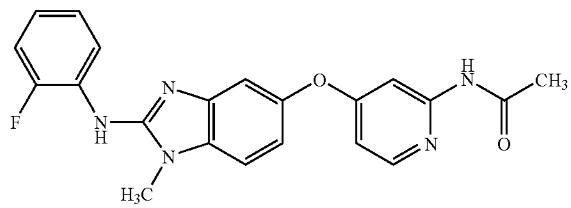 [SMILES: CC(=O)Nc1cc(Oc2ccc3c(c2)nc(Nc2ccccc2F)n3C)ccn1] | N-[4-({2-[(2-fluorophenyl)amino]-1-methyl-1H-benzimidazol-5-yl}oxy)pyridin-2-yl]acetamide | 392.4 |
| 111 | 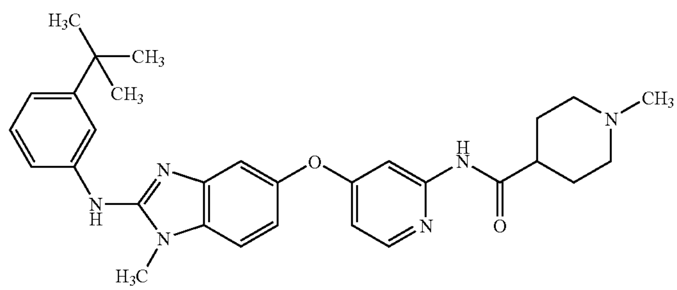 [SMILES: CN1CCC(C(=O)Nc2cc(Oc3ccc4c(c3)nc(Nc3cccc(C(C)(C)C)c3)n4C)ccn2)CC1] | N-[4-({2-[(3-tert-butylphenyl)amino]-1-methyl-1H-benzimidazol-5-yl}oxy)pyridin-2-yl]-1-methyl-piperidine-4-carboxamide | 513.7 |
| 112 | 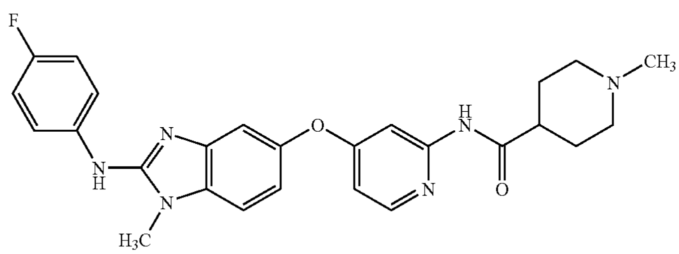 [SMILES: CN1CCC(C(=O)Nc2cc(Oc3ccc4c(c3)nc(Nc3ccc(F)cc3)n4C)ccn2)CC1] | N-[4-({2-[(4-fluorophenyl)amino]-1-methyl-1H-benzimidazol-5-yl}oxy)-pyridin-2-yl]-1-methylpiperidine-4-carboxamide | 475.5 |
| 113 | 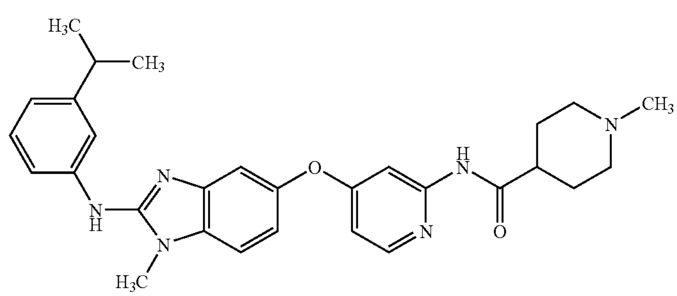 [SMILES: CC(C)c1cccc(Nc2nc3cc(Oc4ccnc(NC(=O)C5CCN(C)CC5)c4)ccc3n2C)c1] | N-[4-({2-[(3-isopropylphenyl)-amino]-1-methyl-1H-benzimidazol-5-yl}oxy)pyridin-2-yl]-1-methylpiperidine-4-carboxamide | 499.6 |
| 114 | 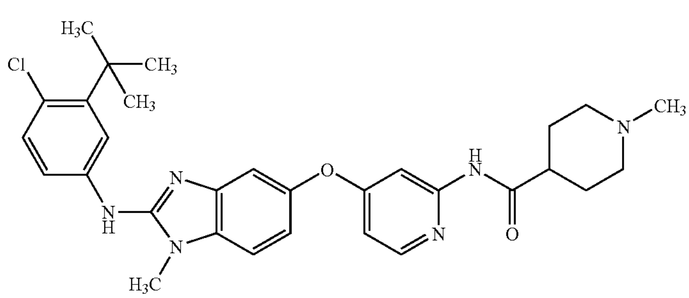 [SMILES: CN1CCC(C(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-1-methylpiperidine-4-carboxamide | 548.1 |

TABLE 1-continued

| Ex. | Structure | Name | MH+ |
| --- | --- | --- | --- |
| 115 | 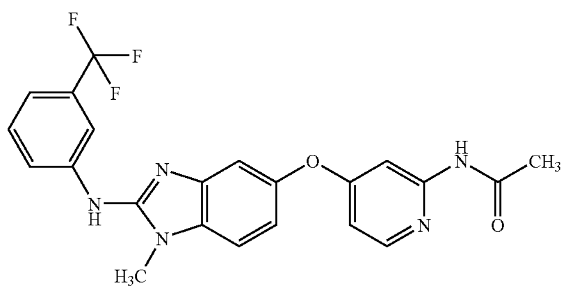 [SMILES: CC(=O)Nc1cc(Oc2ccc3c(c2)nc(Nc2cccc(C(F)(F)F)c2)n3C)ccn1] | N-{4-[(1-methyl-2-{[3-(trifluoro-methyl)phenyl]amino}-1H-benzimidazol-5-yl)oxy]pyridin-2-yl}acetamide | 442.4 |
| 116 | 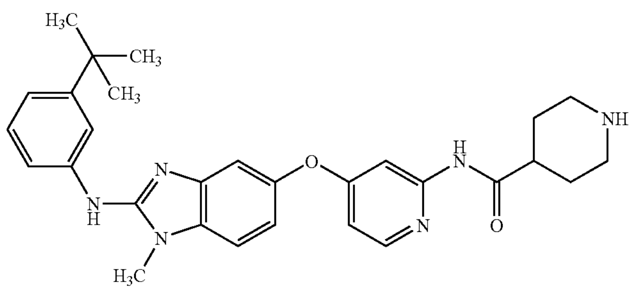 [SMILES: Cn1c(Nc2cccc(C(C)(C)C)c2)nc2cc(Oc3ccnc(NC(=O)C4CCNCC4)c3)ccc21] | N-[4-({2-[(3-tert-butylphenyl)amino]-1-methyl-1H-benzimidazol-5-yl}-oxy)pyridin-2-yl]piperidine-4-carboxamide | 499.6 |
| 117 | 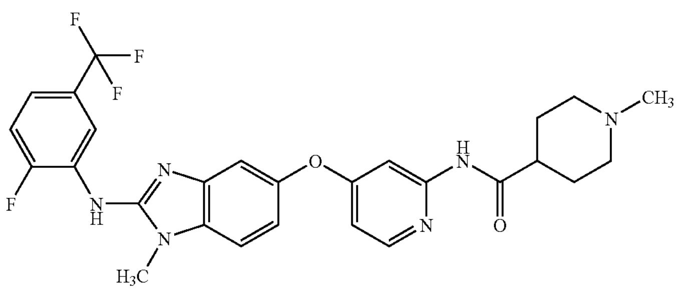 [SMILES: CN1CCC(C(=O)Nc2cc(Oc3ccc4c(c3)nc(Nc3cc(C(F)(F)F)ccc3F)n4C)ccn2)CC1] | N-{4-[(2-{[2-fluoro-5-(trifluoro-methyl)phenyl]amino}-1-methyl-1H-benzimidazol-5-yl)oxy]pyridin-2-yl]-1-methylpiperidine-4-carboxamide | 543.5 |
| 118 | 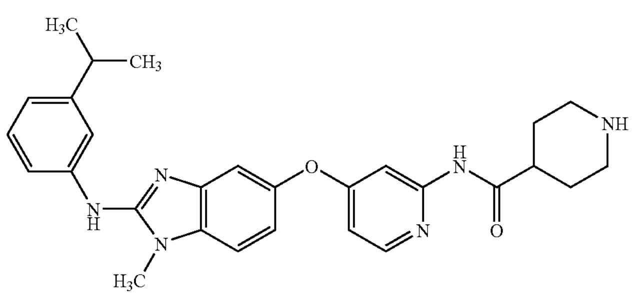 [SMILES: CC(C)c1cccc(Nc2nc3cc(Oc4ccnc(NC(=O)C5CCNCC5)c4)ccc3n2C)c1] | N-[4-({2-[(3-isopropylphenyl)-amino]-1-methyl-1H-benzimidazol-5-yl}oxy)pyridin-2-yl]piperidine-4-carboxamide | 485.6 |
| 119 | 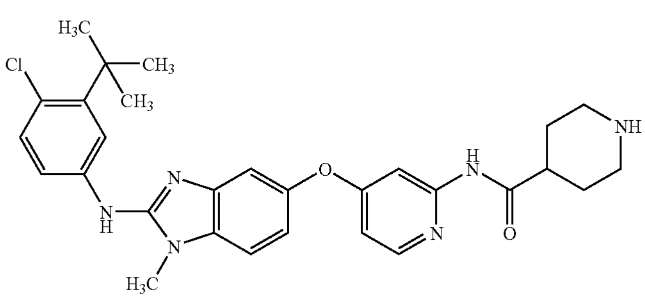 [SMILES: Cn1c(Nc2ccc(Cl)c(C(C)(C)C)c2)nc2cc(Oc3ccnc(NC(=O)C4CCNCC4)c3)ccc21] | N-[4-({2-[(3-tert-butyl-4-chloro-phenyl)amino]-1-methyl-1H-benzimidazol-5-yl}oxy)pyridin-2-yl]piperidine-4-carboxamide | 534.1 |

TABLE 1-continued

| Ex. | Structure | Name | MH+ |
|---|---|---|---|
| 120 | 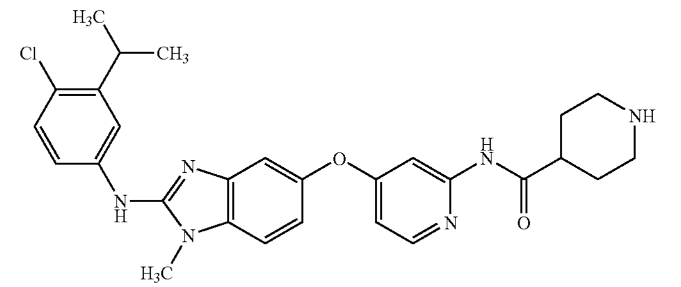 [SMILES: CC(C)c1cc(Nc2nc3cc(Oc4ccnc(NC(=O)C5CCNCC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]piperidine-4-carboxamide | 520 |
| 121 | 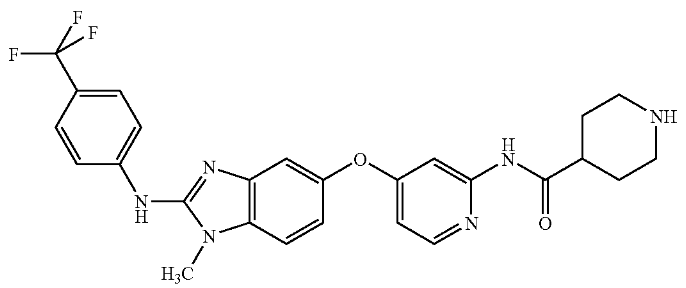 [SMILES: Cn1c(Nc2ccc(C(F)(F)F)cc2)nc2cc(Oc3ccnc(NC(=O)C4CCNCC4)c3)ccc21] | N-{4-[(1-methyl-2-{[4-(trifluoro-methyl)phenyl]amino}-1H-benzimidazol-5-yl)oxy]pyridin-2-yl}piperidine-4-carboxamide | 511.5 |
| 122 | 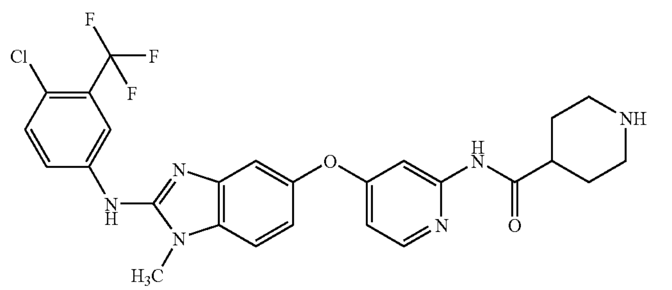 [SMILES: Cn1c(Nc2ccc(Cl)c(C(F)(F)F)c2)nc2cc(Oc3ccnc(NC(=O)C4CCNCC4)c3)ccc21] | N-{4-[(2-{[4-chloro-3-(trifluoro-methyl)phenyl]amino}-1-methyl-1H-benzimidazol-5-yl)oxy]pyridin-2-yl}piperidine-4-carboxamide | 546 |
| 123 | 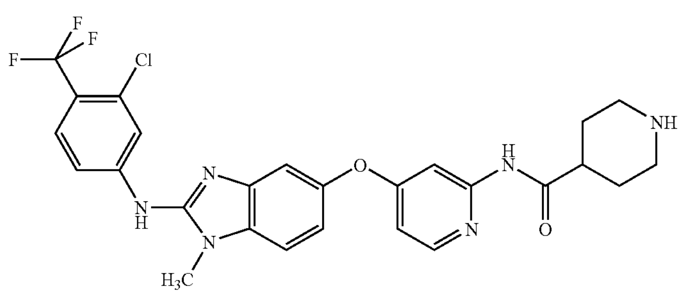 [SMILES: Cn1c(Nc2ccc(C(F)(F)F)c(Cl)c2)nc2cc(Oc3ccnc(NC(=O)C4CCNCC4)c3)ccc21] | N-{4-[(2-{[3-chloro-4-(trifluoro-methyl)phenyl]amino}-1-methyl-1H-benzimidazol-5-yl)oxy]pyridin-2-yl}piperidine-4-carboxamide. 546 | |
| 124 | 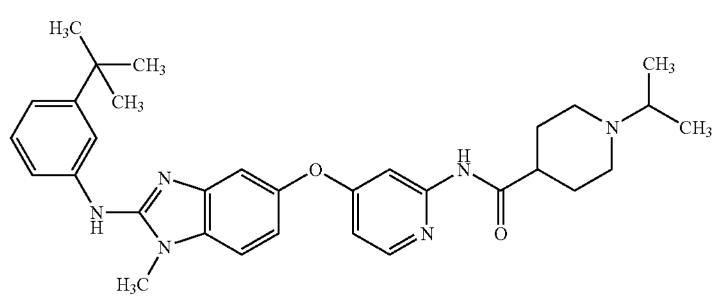 [SMILES: CC(C)N1CCC(C(=O)Nc2cc(Oc3ccc4c(c3)nc(Nc3cccc(C(C)(C)C)c3)n4C)ccn2)CC1] | N-[4-({2-[(3-tert-butylphenyl)amino]-1-methyl-1H-benzimidazol-5-yl}-oxy)pyridin-2-yl]-1-isopropyl-piperidine-4-carboxamide | 541.7 |

TABLE 1-continued

| Ex. | Structure | Name | MH+ |
|---|---|---|---|
| 125 | 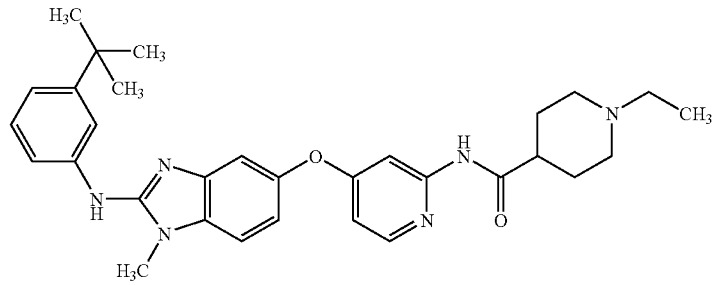 [SMILES: CCN1CCC(C(=O)Nc2cc(Oc3ccc4c(c3)nc(Nc3cccc(C(C)(C)C)c3)n4C)ccn2)CC1] | N-[4-({2-[(3-tert-butylphenyl)amino]-1-methyl-1H-benzimidazol-5-yl}oxy)pyridin-2-yl]-1-ethyl-piperidine-4-carboxamide | 527.7 |
| 126 | 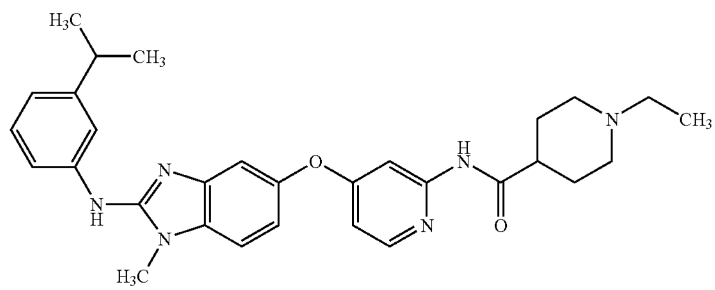 [SMILES: CCN1CCC(C(=O)Nc2cc(Oc3ccc4c(c3)nc(Nc3cccc(C(C)C)c3)n4C)ccn2)CC1] | 1-ethyl-N-[4-({2-[(3-isopropyl-phenyl)amino]-1-methyl-1H-benzimidazol-5-yl}oxy)pyridin-2-yl]piperidine-4-carboxamide | 513.7 |
| 127 | 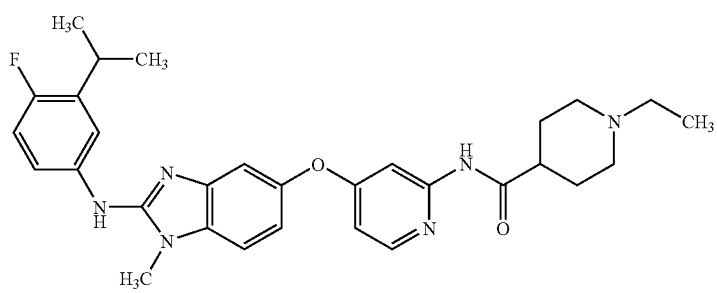 [SMILES: CCN1CCC(C(=O)Nc2cc(Oc3ccc4c(c3)nc(Nc3ccc(F)c(C(C)C)c3)n4C)ccn2)CC1] | 1-ethyl-N-[4-({2-[(4-fluoro-3-isopropylphenyl)amino]-1-methyl-1H-benzimidazol-5-yl}oxy)pyridin-2-yl]piperidine-4-carboxamide | 531.6 |
| 128 | 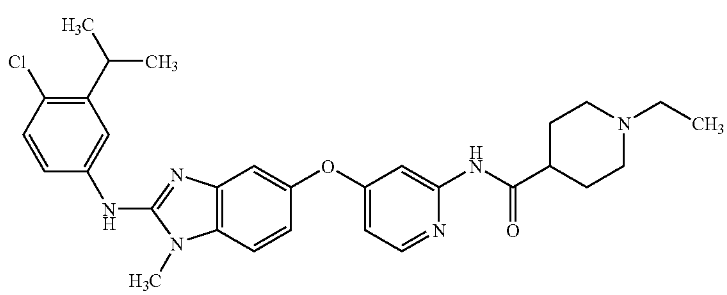 [SMILES: CCN1CCC(C(=O)Nc2cc(Oc3ccc4c(c3)nc(Nc3ccc(Cl)c(C(C)C)c3)n4C)ccn2)CC1] | N-[4-({2-[(4-chloro-3-isopropyl-phenyl)amino]-1-methyl-1H-benzimidazol-5-yl}oxy)pyridin-2-yl]-1-ethylpiperidine-4-carboxamide | 548.1 |
| 129 | 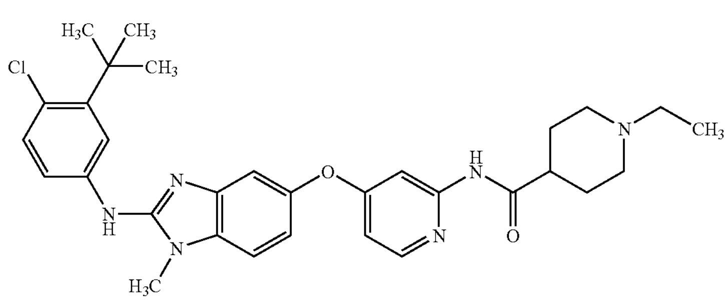 [SMILES: CCN1CCC(C(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-1-ethylpiperidine-4-carboxamide | 562.1 |

| Ex. | Structure | Name | MH+ |
|---|---|---|---|
| 130 | 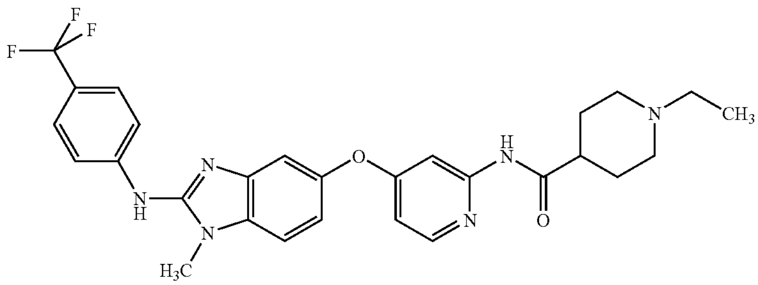 [SMILES: CCN1CCC(C(=O)Nc2cc(Oc3ccc4c(c3)nc(Nc3ccc(C(F)(F)F)cc3)n4C)ccn2)CC1] | 1-ethyl-N-{4-[(1-methyl-2-{[4-(trifluoromethyl)phenyl]amino}-1H-benzimidazol-5-yl)oxy]pyridin-2-yl}piperidine-4-carboxamide | 539.6 |
| 131 | 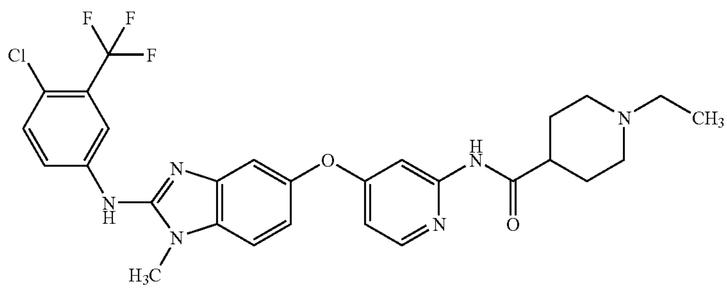 [SMILES: CCN1CCC(C(=O)Nc2cc(Oc3ccc4c(c3)nc(Nc3ccc(Cl)c(C(F)(F)F)c3)n4C)ccn2)CC1] | N-{4-[(2-{[4-chloro-3-(trifluoromethyl)phenyl]amino}-1-methyl-1H-benzimidazol-5-yl)oxy]pyridin-2-yl}-1-ethylpiperidine-4-carboxamide | 574 |
| 132 | 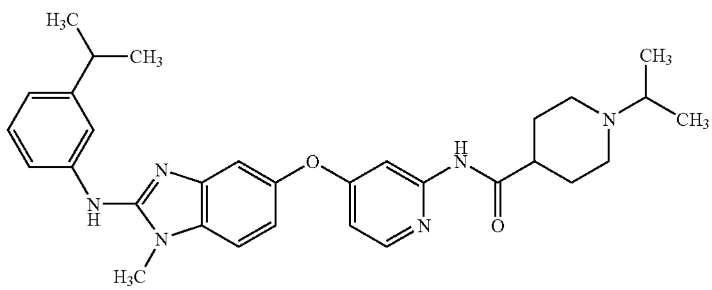 [SMILES: CC(C)c1cccc(Nc2nc3cc(Oc4ccnc(NC(=O)C5CCN(C(C)C)CC5)c4)ccc3n2C)c1] | 1-isopropyl-N-[4-({2-[(3-isopropylphenyl)amino]-1-methyl-1H-benzimidazol-5-yl}oxy)pyridin-2-yl]piperidine-4-carboxamide | 527.7 |
| 133 | 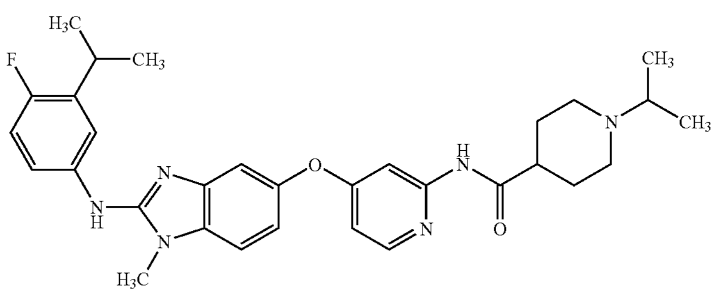 [SMILES: CC(C)c1cc(Nc2nc3cc(Oc4ccnc(NC(=O)C5CCN(C(C)C)CC5)c4)ccc3n2C)ccc1F] | N-[4-({2-[(4-fluoro-3-isopropylphenyl)amino]-1-methyl-1H-benzimidazol-5-yl}oxy)pyridin-2-yl]-1-isopropylpiperidine-4-carboxamide | 545.7 |
| 134 | 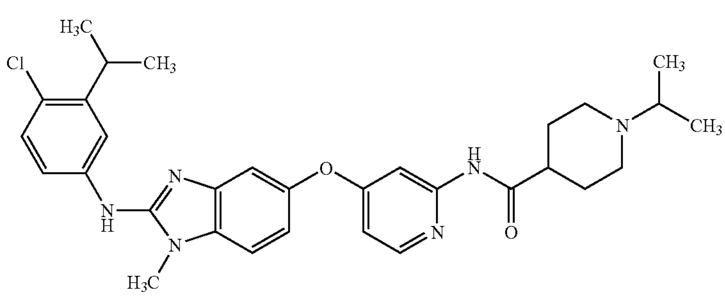 [SMILES: CC(C)c1cc(Nc2nc3cc(Oc4ccnc(NC(=O)C5CCN(C(C)C)CC5)c4)ccc3n2C)ccc1Cl] | N-[4-({2-[(4-chloro-3-isopropylphenyl)amino]-1-methyl-1H-benzimidazol-5-yl}oxy)pyridin-2-yl]-1-isopropylpiperidine-4-carboxamide | 562.1 |

TABLE 1-continued

| Ex. | Structure | Name | MH+ |
|---|---|---|---|
| 135 | 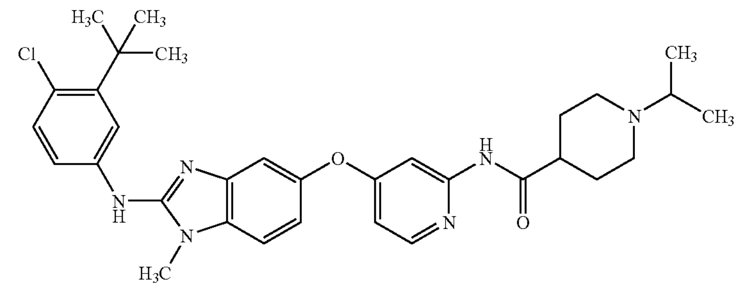 [SMILES: CC(C)N1CCC(C(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-1-isopropylpiperidine-4-carboxamide | 576.2 |
| 136 | 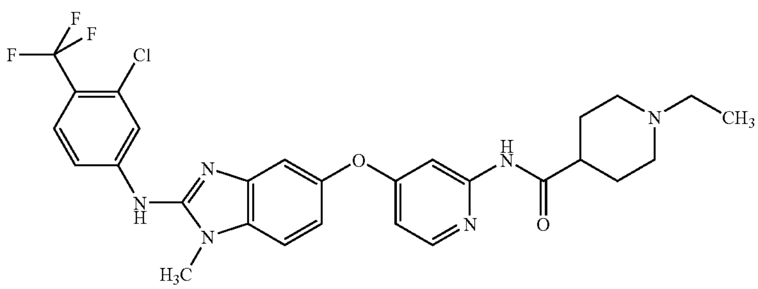 [SMILES: CCN1CCC(C(=O)Nc2cc(Oc3ccc4c(c3)nc(Nc3ccc(C(F)(F)F)c(Cl)c3)n4C)ccn2)CC1] | N-{4-[(2-{[3-chloro-4-(trifluoro-methyl)phenyl]amino}-1-methyl-1H-benzimidazol-5-yl)oxy]pyridin-2-yl}-1-ethylpiperidine-4-carboxamide | 574 |
| 137 | 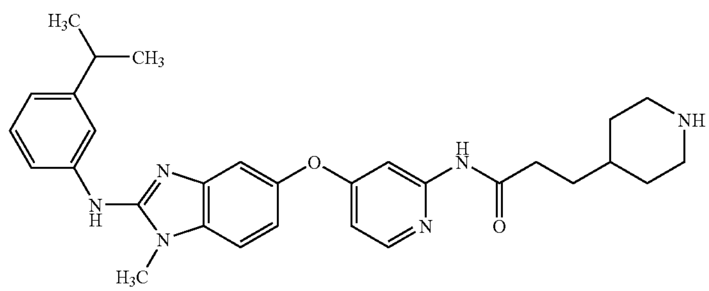 [SMILES: CC(C)c1cccc(Nc2nc3cc(Oc4ccnc(NC(=O)CCC5CCNCC5)c4)ccc3n2C)c1] | N-[4-({2-[(3-isopropylphenyl)-amino]-1-methyl-1H-benzimidazol-5-yl}oxy)pyridin-2-yl]-3-piperidin-4-ylpropanamide | 513.7 |
| 138 | 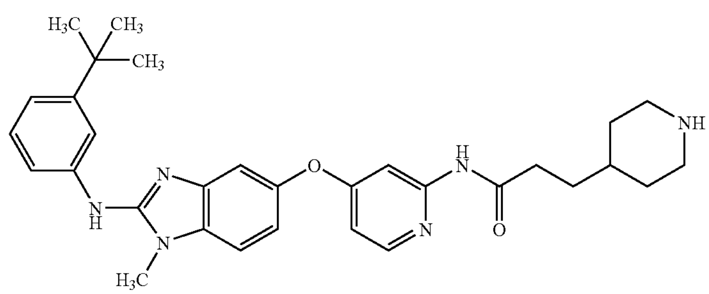 [SMILES: Cn1c(Nc2cccc(C(C)(C)C)c2)nc2cc(Oc3ccnc(NC(=O)CCC4CCNCC4)c3)ccc21] | N-[4-({2-[(3-tert-butylphenyl)amino]-1-methyl-1H-benzimidazol-5-yl}oxy)pyridin-2-yl]-3-piperidin-4-ylpropanamide | 527.7 |
| 139 | 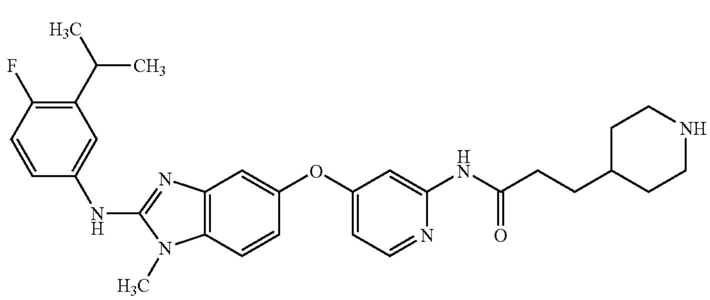 [SMILES: CC(C)c1cc(Nc2nc3cc(Oc4ccnc(NC(=O)CCC5CCNCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-3-piperidin-4-ylpropanamide | 531.6 |

TABLE 1-continued

| Ex. | Structure | Name | MH+ |
|---|---|---|---|
| 140 | 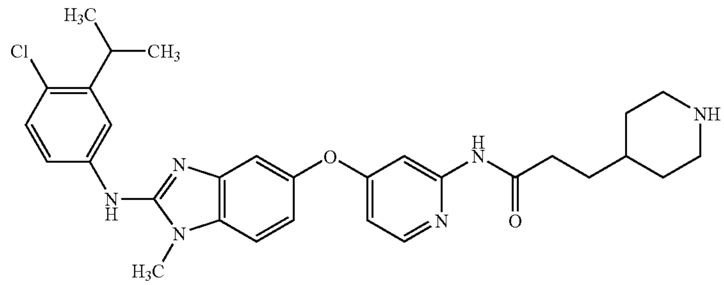 [SMILES: CC(C)c1cc(Nc2nc3cc(Oc4ccnc(NC(=O)CCC5CCNCC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-3-piperidin-4-ylpropanamide | 548.1 |
| 141 | 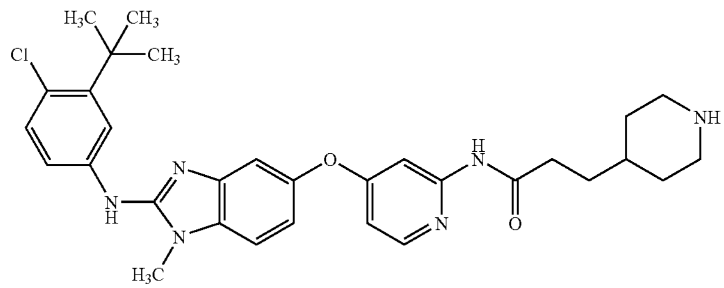 [SMILES: Cn1c(Nc2ccc(Cl)c(C(C)(C)C)c2)nc2cc(Oc3ccnc(NC(=O)CCC4CCNCC4)c3)ccc21] | N-[4-(2-[(3-tert-butyl-4-chloro-phenyl)amino]-1-methyl-1H-benzimidazol-5-yl}oxy)pyridin-2-yl]-3-piperidin-4-ylpropanamide | 562.1 |
| 142 | 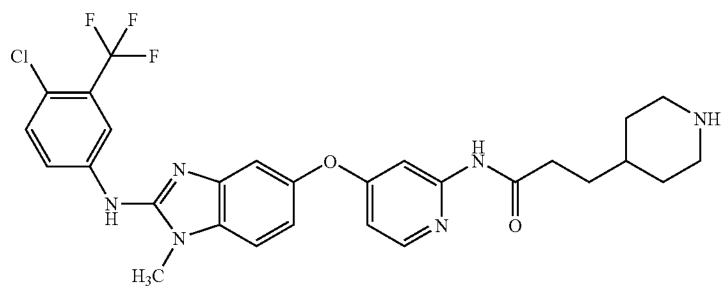 [SMILES: Cn1c(Nc2ccc(Cl)c(C(F)(F)F)c2)nc2cc(Oc3ccnc(NC(=O)CCC4CCNCC4)c3)ccc21] | N-{4-[(2-{[4-chloro-3-(trifluoro-methyl)phenyl]amino}-1-methyl-1H-benzimidazol-5-yl)oxy]pyridin-2-yl}-3-piperidin-4-ylpropanamide | 574 |
| 143 | 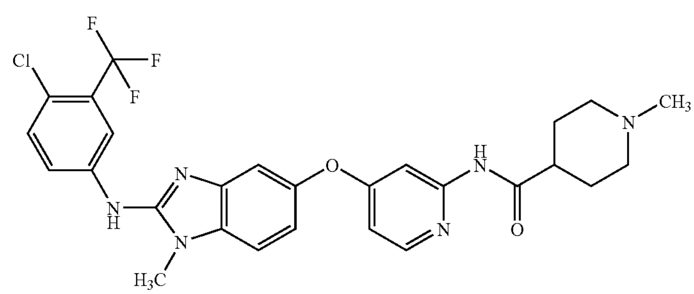 [SMILES: CN1CCC(C(=O)Nc2cc(Oc3ccc4c(c3)nc(Nc3ccc(Cl)c(C(F)(F)F)c3)n4C)ccn2)CC1] | N-{4-[(2-{[4-chloro-3-(trifluoro-methyl)phenyl]amino}-1-methyl-1H-benzimidazol-5-yl)oxy]pyridin-2-yl}-1-methylpiperidine-4-carboxamide | 560 |
| 144 | 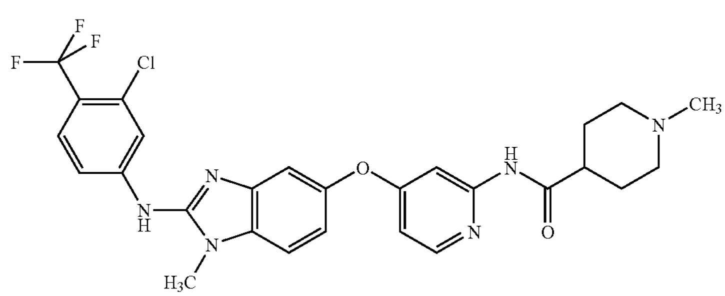 [SMILES: CN1CCC(C(=O)Nc2cc(Oc3ccc4c(c3)nc(Nc3ccc(C(F)(F)F)c(Cl)c3)n4C)ccn2)CC1] | N-{4-[(2-{[3-chloro-4-(trifluoro-methyl)phenyl]amino}-1-methyl-1H-benzimidazol-5-yl)oxy]pyridin-2-yl}-1-methylpiperidine-4-carboxamide | 560 |

TABLE 1-continued

| Ex. | Name | MH+ |
|---|---|---|
| 145 | N-[4-({2-[(4-ethylphenyl)amino]-1-methyl-1H-benzimidazol-5-yl}oxy)-pyridin-2-yl]-1-methylpiperidine-4-carboxamide | 485.6 |
| 146 | N-{4-[(2-{[4-fluoro-3-(trifluoro-methyl)phenyl]amino}-1-methyl-1H-benzimidazol-5-yl)oxy]pyridin-2-yl}-1-methylpiperidine-4-carboxamide | 543.5 |
| 147 | N-[4-({2-[(3-tert-butylphenyl)amino]-1-methyl-1H-benzimidazol-5-yl}oxy)pyridin-2-yl]-3-(1-methyl-piperidin-4-yl)propanamide | 541.7 |
| 148 | N-[4-({2-[(3-isopropylphenyl)-amino]-1-methyl-1H-benzimidazol-5-yl}oxy)pyridin-2-yl]-3-(1-methyl-piperidin-4-yl)propanamide | 527.7 |
| 149 | N-[4-({2-[(4-fluoro-3-isopropyl-phenyl)amino]-1-methyl-1H-benzimidazol-5-yl}oxy)pyridin-2-yl]-3-(1-methylpiperidin-4-yl)propanamide | 545.7 |

TABLE 1-continued

| Ex. | Structure | Name | MH+ |
|---|---|---|---|
| 150 | 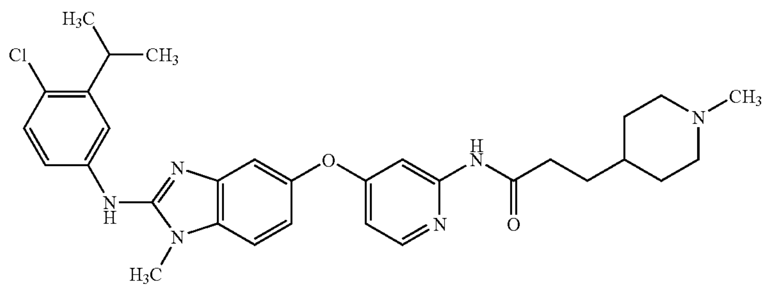 [SMILES: CC(C)c1cc(Nc2nc3cc(Oc4ccnc(NC(=O)CCC5CCN(C)CC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-3-(1-methylpiperidin-4-yl)-propanamide | 562.1 |
| 151 | 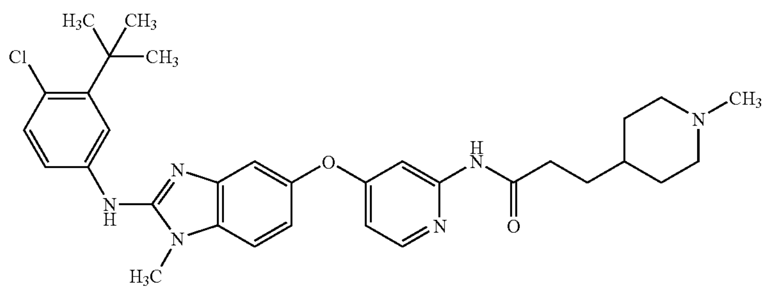 [SMILES: CN1CCC(CCC(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-3-(1-methylpiperidin-4-yl)-propanamide | 576.2 |
| 152 | 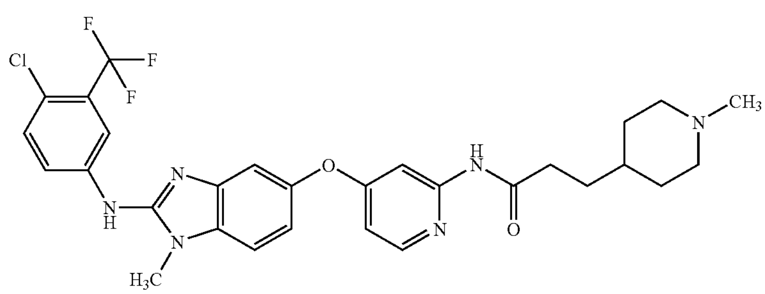 [SMILES: CN1CCC(CCC(=O)Nc2cc(Oc3ccc4c(c3)nc(Nc3ccc(Cl)c(C(F)(F)F)c3)n4C)ccn2)CC1] | N-{4-[(2-{[4-chloro-3-(trifluoro-methyl)phenyl]amino}-1-methyl-1H-benzimidazol-5-yl)oxy]pyridin-2-yl}-3-(1-methylpiperidin-4-yl)-propanamide | 588 |
| 153 | 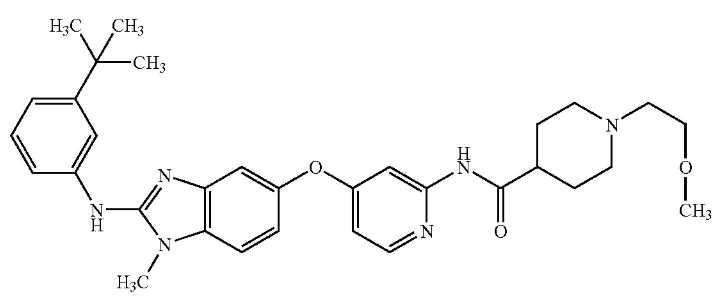 [SMILES: COCCN1CCC(C(=O)Nc2cc(Oc3ccc4c(c3)nc(Nc3cccc(C(C)(C)C)c3)n4C)ccn2)CC1] | N-[4-({2-[(3-tert-butylphenyl)amino]-1-methyl-1H-benzimidazol-5-yl}-oxy)pyridin-2-yl]-1-(2-methoxy-ethyl)piperidine-4-carboxamide | 557.7 |
| 154 | 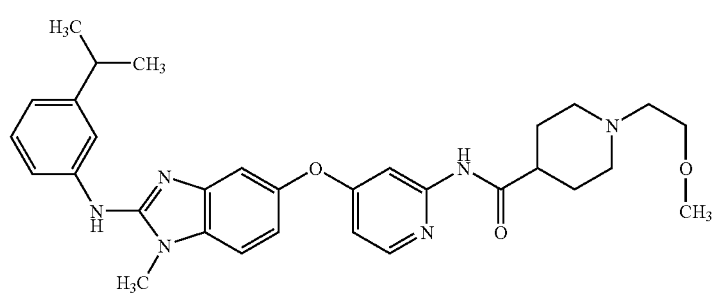 [SMILES: COCCN1CCC(C(=O)Nc2cc(Oc3ccc4c(c3)nc(Nc3cccc(C(C)C)c3)n4C)ccn2)CC1] | N-[4-({2-[(3-isopropylphenyl)-amino]-1-methyl-1H-benzimidazol-5-yl}oxy)pyridin-2-yl]-1-(2-methoxy-ethyl)piperidine-4-carboxamide | 543.7 |

TABLE 1-continued

| Ex. | Structure | Name | MH+ |
| --- | --- | --- | --- |
| 155 | 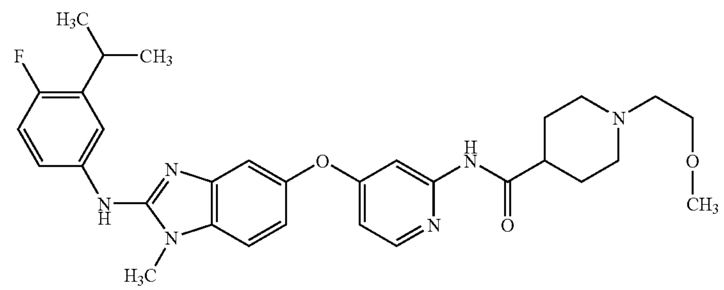 [SMILES: COCCN1CCC(C(=O)Nc2cc(Oc3ccc4c(c3)nc(Nc3ccc(F)c(C(C)C)c3)n4C)ccn2)CC1] | N-[4-({2-[(4-fluoro-3-isopropyl-phenyl)amino]-1-methyl-1H-benzimidazol-5-yl}oxy)pyridin-2-yl]-1-(2-methoxyethyl)piperidine-4-carboxamide | 561.7 |
| 156 | 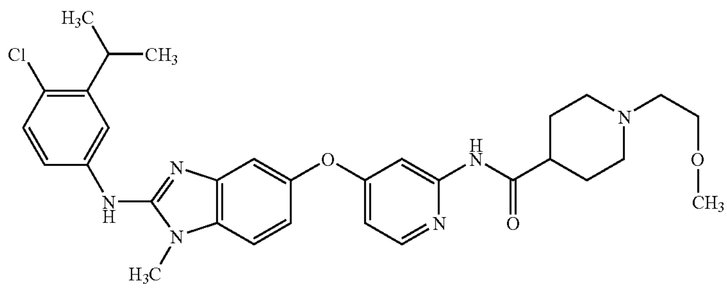 [SMILES: COCCN1CCC(C(=O)Nc2cc(Oc3ccc4c(c3)nc(Nc3ccc(Cl)c(C(C)C)c3)n4C)ccn2)CC1] | N-[4-({2-[(4-chloro-3-isopropyl-phenyl)amino]-1-methyl-1H-benzimidazol-5-yl}oxy)pyridin-2-yl]-1-(2-methoxyethyl)piperidine-4-carboxamide | 578.1 |
| 157 | 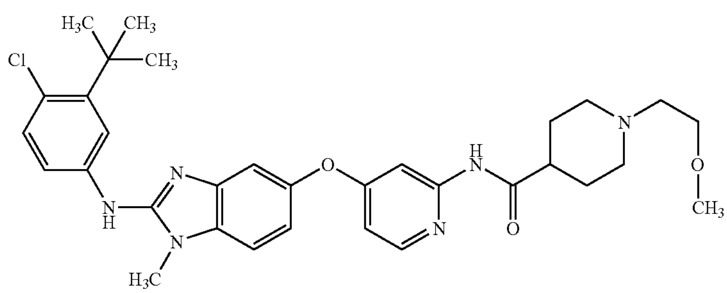 [SMILES: COCCN1CCC(C(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-1-(2-methoxyethyl)piperidine-4-carboxamide | 592.2 |
| 158 | 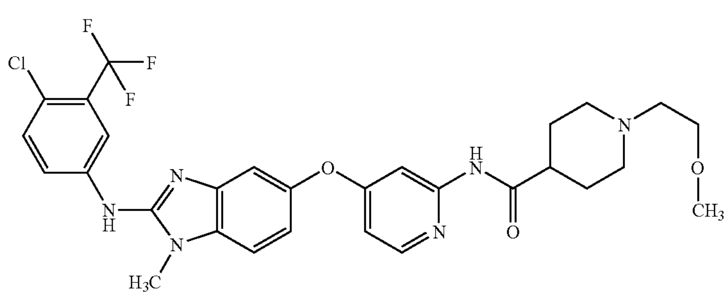 [SMILES: COCCN1CCC(C(=O)Nc2cc(Oc3ccc4c(c3)nc(Nc3ccc(Cl)c(C(F)(F)F)c3)n4C)ccn2)CC1] | N-{4-[(2-{[4-chloro-3-(trifluoro-methyl)phenyl]amino}-1-methyl-1H-benzimidazol-5-yl)oxy]pyridin-2-yl}-1-(2-methoxyethyl)piperidine-4-carboxamide | 604 |
| 159 | 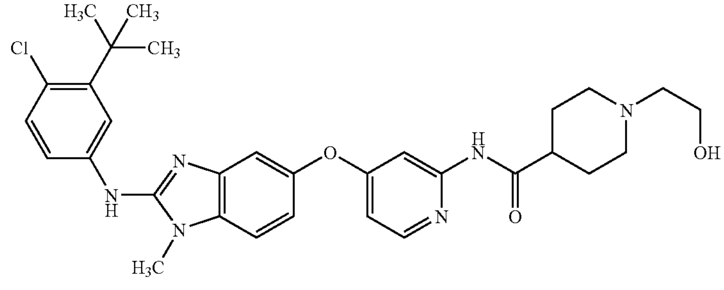 [SMILES: Cn1c(Nc2ccc(Cl)c(C(C)(C)C)c2)nc2cc(Oc3ccnc(NC(=O)C4CCN(CCO)CC4)c3)ccc21] | N-[4-({2-[(3-tert-butyl-4-chloro-phenyl)amino]-1-methyl-1H-benzimidazol-5-yl}oxy)pyridin-2-yl]-1-(2-hydroxyethyl)piperidine-4-carboxamide | 578.1 |

TABLE 1-continued

| Ex. | Structure | Name | MH+ |
|---|---|---|---|
| 160 | 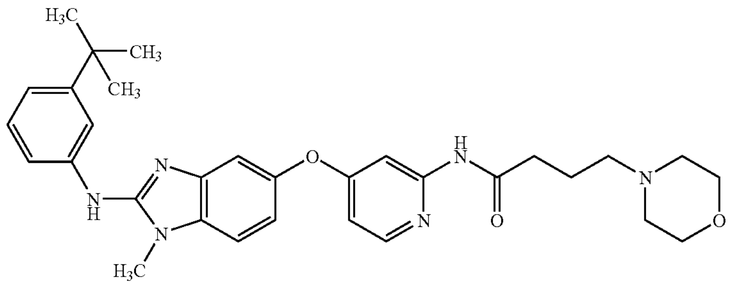 [SMILES: Cn1c(Nc2cccc(C(C)(C)C)c2)nc2cc(Oc3ccnc(NC(=O)CCCN4CCOCC4)c3)ccc21] | N-[4-({2-[(3-tert-butylphenyl)amino]-1-methyl-1H-benzimidazol-5-yl}-oxy)pyridin-2-yl]-4-morpholin-4-ylbutanamide | 543.7 |
| 161 | 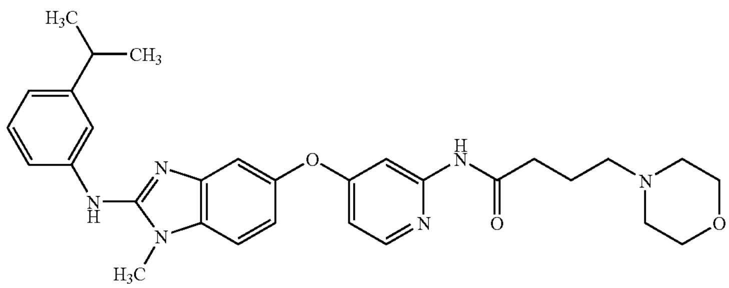 [SMILES: CC(C)c1cccc(Nc2nc3cc(Oc4ccnc(NC(=O)CCCN5CCOCC5)c4)ccc3n2C)c1] | N-[4-({2-[(3-isopropylphenyl)-amino]-1-methyl-1H-benzimidazol-5-yl}oxy)pyridin-2-yl]-4-morpholin-4-ylbutanamide | 529.7 |
| 162 | 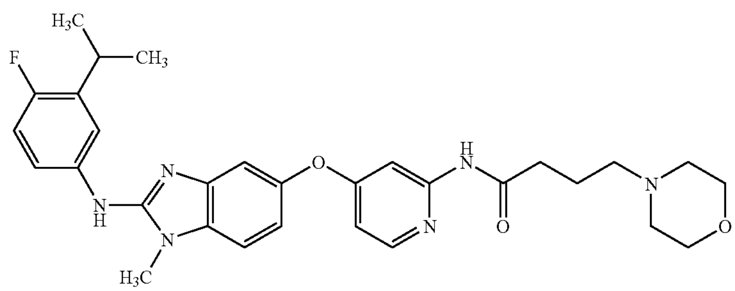 [SMILES: CC(C)c1cc(Nc2nc3cc(Oc4ccnc(NC(=O)CCCN5CCOCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-4-morpholin-4-ylbutanamide | 547.6 |
| 163 | 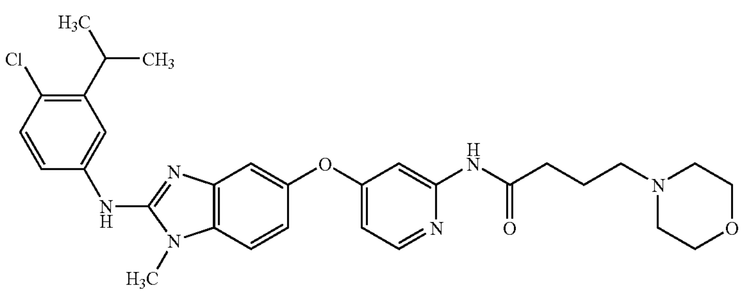 [SMILES: CC(C)c1cc(Nc2nc3cc(Oc4ccnc(NC(=O)CCCN5CCOCC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-4-morpholin-4-ylbutanamide | 564.1 |
| 164 | 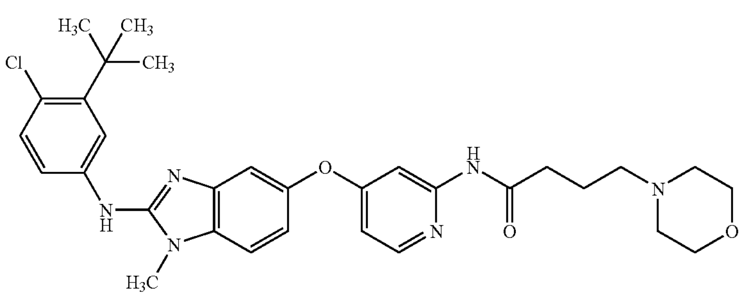 [SMILES: Cn1c(Nc2ccc(Cl)c(C(C)(C)C)c2)nc2cc(Oc3ccnc(NC(=O)CCCN4CCOCC4)c3)ccc21] | N-[4-({2-[(3-tert-butyl-4-chloro-phenyl)amino]-1-methyl-1H-benzimidazol-5-yl}oxy)pyridin-2-yl]-4-morpholin-4-ylbutanamide | 578.1 |

TABLE 1-continued

| Ex. | Structure | Name | MH+ |
|---|---|---|---|
| 165 | 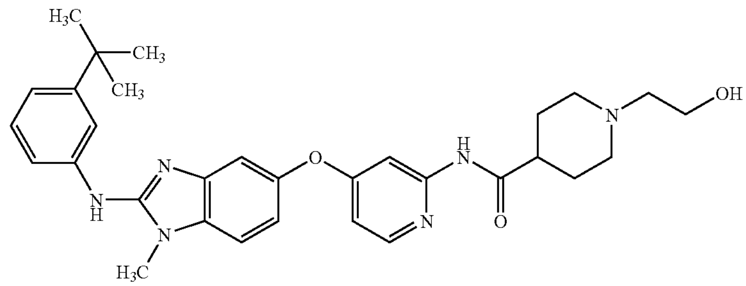 [SMILES: Cn1c(Nc2cccc(C(C)(C)C)c2)nc2cc(Oc3ccnc(NC(=O)C4CCN(CCO)CC4)c3)ccc21] | N-[4-({2-[(3-tert-butylphenyl)amino]-1-methyl-1H-benzimidazol-5-yl}oxy)pyridin-2-yl]-1-(2-hydroxyethyl)piperidine-4-carboxamide | 543.7 |
| 166 | 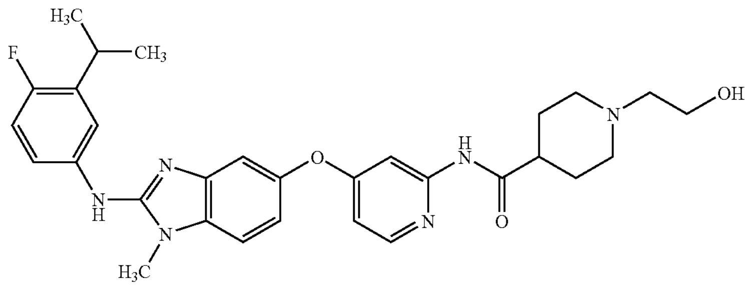 [SMILES: CC(C)c1cc(Nc2nc3cc(Oc4ccnc(NC(=O)C5CCN(CCO)CC5)c4)ccc3n2C)ccc1F] | N-[4-({2-[(4-fluoro-3-isopropylphenyl)amino]-1-methyl-1H-benzimidazol-5-yl}oxy)pyridin-2-yl]-carboxamide | 547.6 |
| 167 | 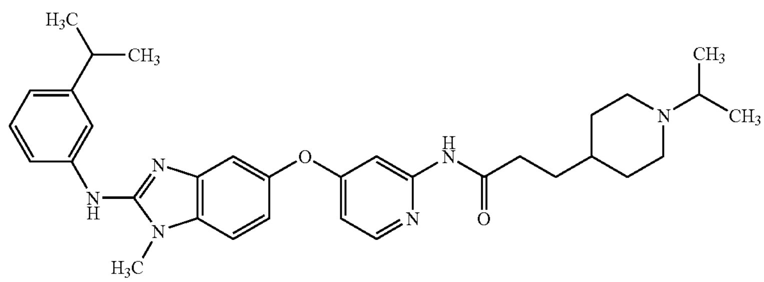 [SMILES: CC(C)c1cccc(Nc2nc3cc(Oc4ccnc(NC(=O)CCC5CCN(C(C)C)CC5)c4)ccc3n2C)c1] | N-[4-({2-[(3-isopropylphenyl)amino]-1-methyl-1H-benzimidazol-5-yl}oxy)pyridin-2-yl]-3-(1-isopropylpiperidin-4-yl)propanamide | 555.7 |
| 168 | 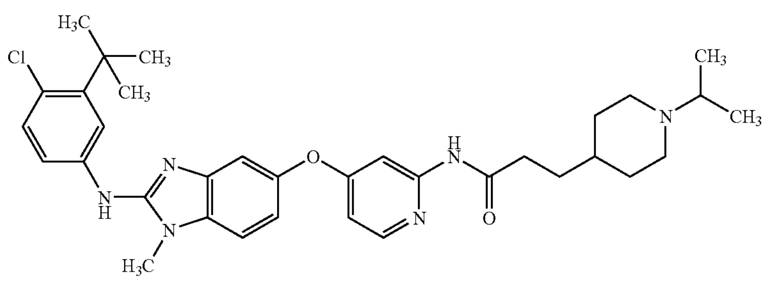 [SMILES: CC(C)N1CCC(CCC(=O)Nc2cc(Oc3ccc4c(c3)nc(Nc3ccc(Cl)c(C(C)(C)C)c3)n4C)ccn2)CC1] | N-[4-({2-[(3-tert-butyl-4-chlorophenyl)amino]-1-methyl-1H-benzimidazol-5-yl}oxy)pyridin-2-yl]-3-(1-isopropylpiperidin-4-yl)propanamide | 604.2 |
| 169 | 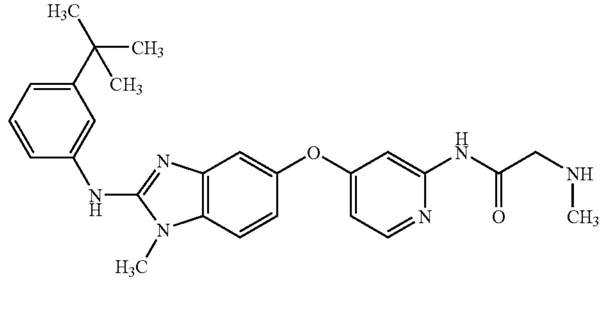 [SMILES: CNCC(=O)Nc1cc(Oc2ccc3c(c2)nc(Nc2cccc(C(C)(C)C)c2)n3C)ccn1] | N~1~-[4-({2-[(3-tert-butylphenyl)amino]-1-methyl-1H-benzimidazol-5-yl}oxy)pyridin-2-yl]-N~2~-methylglycinamide | 459.6 |

TABLE 1-continued

| Ex. | Structure | Name | MH+ |
|---|---|---|---|
| 170 | 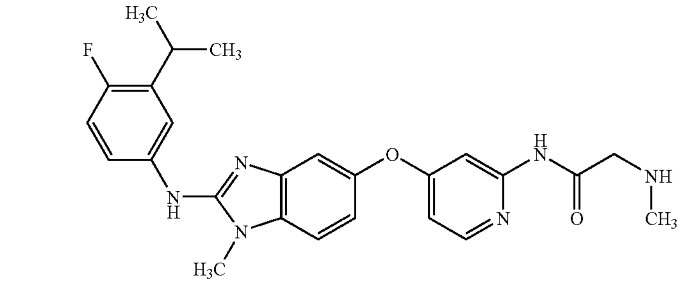 [SMILES: CNCC(=O)Nc1cc(Oc2ccc3c(c2)nc(Nc2ccc(F)c(C(C)C)c2)n3C)ccn1] | N~1~-[4-({2-[(4-fluoro-3-isopropyl-phenyl)amino]-1-methyl-1H-benzimidazol-5-yl}oxy)pyridin-2-yl]-N~2~-methylglycinamide | 463.5 |
| 171 | 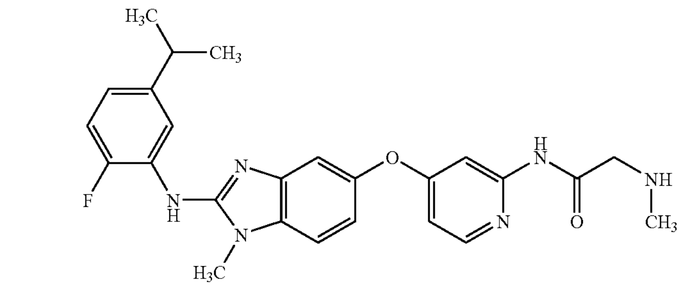 [SMILES: CNCC(=O)Nc1cc(Oc2ccc3c(c2)nc(Nc2cc(C(C)C)ccc2F)n3C)ccn1] | N~1~-[4-({2-[(2-fluoro-5-isopropyl-phenyl)amino]-1-methyl-1H-benzimidazol-5-yl}oxy)pyridin-2-yl]-N~2~-methylglycinamide | 463.5 |
| 172 | 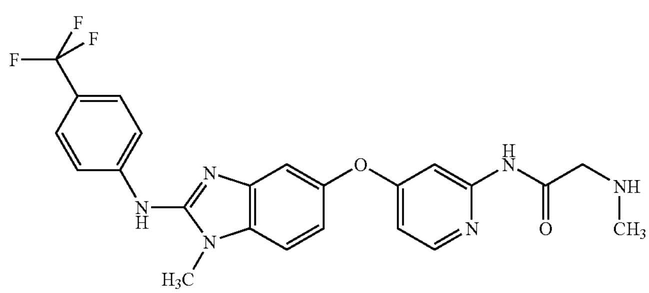 [SMILES: CNCC(=O)Nc1cc(Oc2ccc3c(c2)nc(Nc2ccc(C(F)(F)F)cc2)n3C)ccn1] | N~2~-methyl-N~1~-{4-[(1-methyl-2-{[4-(trifluoromethyl)phenyl]amino}-1H-benzimidazol-5-yl)oxy]pyridin-2-yl}glycinamide | 471.5 |
| 173 | 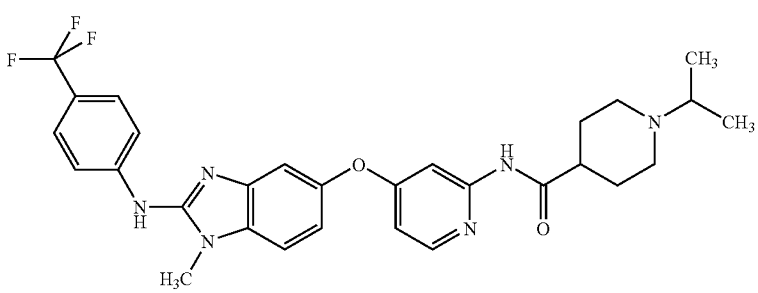 [SMILES: CC(C)N1CCC(C(=O)Nc2cc(Oc3ccc4c(c3)nc(Nc3ccc(C(F)(F)F)cc3)n4C)ccn2)CC1] | 1-isopropyl-N-{4-[(1-methyl-2-{[4-(trifluoromethyl)phenyl]amino}-1H-benzimidazol-5-yl)oxy]pyridin-2-yl}piperidine-4-carboxamide | 553.6 |
| 174 | 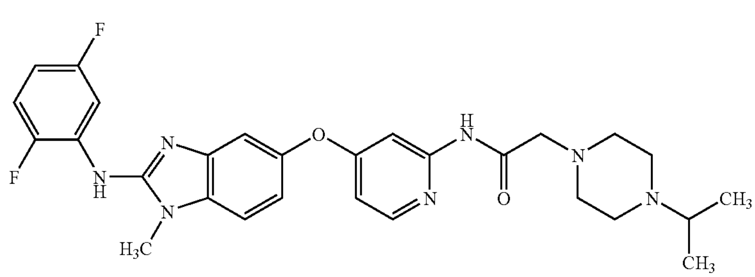 [SMILES: CC(C)N1CCN(CC(=O)Nc2cc(Oc3ccc4c(c3)nc(Nc3cc(F)ccc3F)n4C)ccn2)CC1] | N-[4-({2-[(2,5-difluorophenyl)-amino]-1-methyl-1H-benzimidazol-5-yl}oxy)pyridin-2-yl]-2-(4-isopropyl-piperazin-1-yl)acetamide | 536.6 |

TABLE 1-continued

| Ex. | Structure | Name | MH+ |
|---|---|---|---|
| 175 | 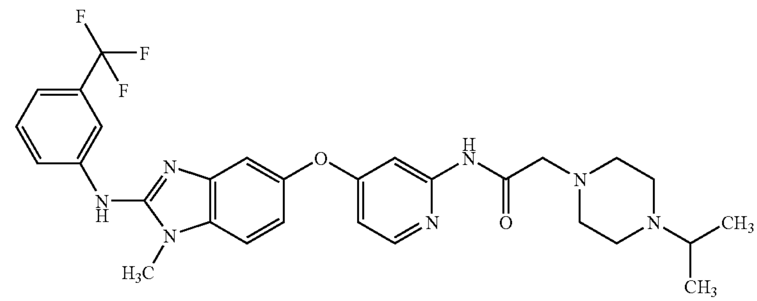 [SMILES: CC(C)N1CCN(CC(=O)Nc2cc(Oc3ccc4c(c3)nc(Nc3cccc(C(F)(F)F)c3)n4C)ccn2)CC1] | 2-(4-isopropylpiperazin-1-yl)-N-{4-[(1-methyl-2-{[3-(trifluoromethyl)-phenyl]amino}-1H-benzimidazol-5-yl)oxy]pyridin-2-yl}acetamide | 568.6 |
| 176 | 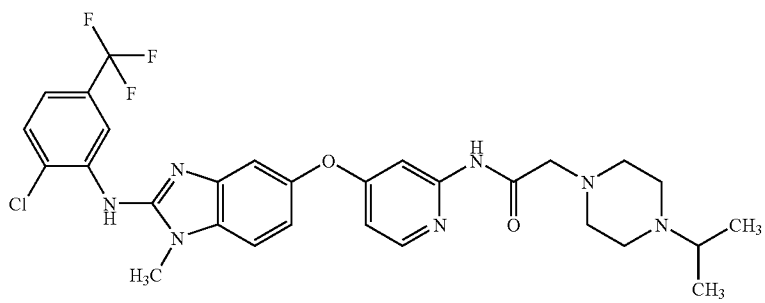 [SMILES: CC(C)N1CCN(CC(=O)Nc2cc(Oc3ccc4c(c3)nc(Nc3cc(C(F)(F)F)ccc3Cl)n4C)ccn2)CC1] | N-{4-[(2-{[2-chloro-5-(trifluoro-methyl)phenyl]amino}-1-methyl-1H-benzimidazol-5-yl)oxy]pyridin-2-yl}-(2-(4-isopropylpiperazin-1-yl)acetamide | 603.1 |
| 177 | 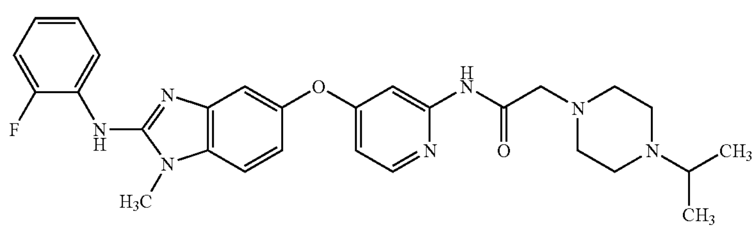 [SMILES: CC(C)N1CCN(CC(=O)Nc2cc(Oc3ccc4c(c3)nc(Nc3ccccc3F)n4C)ccn2)CC1] | N-[4-({2-[(2-fluorophenyl)amino]-1-methyl-1H-benzimidazol-5-yl}oxy)-pyridin-2-yl]-2-(4-isopropyl-piperazin-1-yl)acetamide | 518.6 |
| 178 | 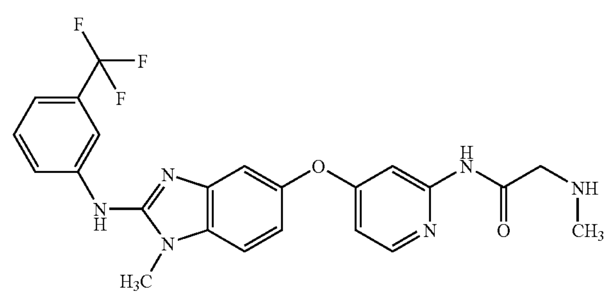 [SMILES: CNCC(=O)Nc1cc(Oc2ccc3c(c2)nc(Nc2cccc(C(F)(F)F)c2)n3C)ccn1] | N~2~-methyl-N~1~-{(4-[(1-methyl-2-{[3-(trifluoromethyl)phenyl]-amino}-1H-benzimidazol-5-yl)oxy]-pyridin-2-yl}glycinamide | 471.5 |
| 179 | 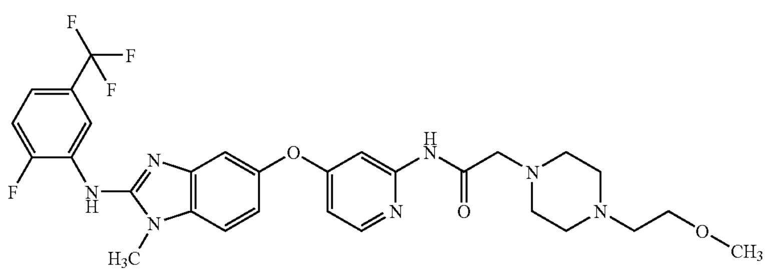 [SMILES: COCCN1CCN(CC(=O)Nc2cc(Oc3ccc4c(c3)nc(Nc3cc(C(F)(F)F)ccc3F)n4C)ccn2)CC1] | N-{4-[(2-{[2-fluoro-5-(trifluoro-methyl)phenyl]amino}-1-methyl-1H-benzimidazol-5-yl)oxy]pyridin-2-yl}-2-[4-(2-methoxyethyl)piperazin-1-yl]acetamide | 602.6 |

TABLE 1-continued

| Ex. | Structure | Name | MH+ |
|---|---|---|---|
| 180 | 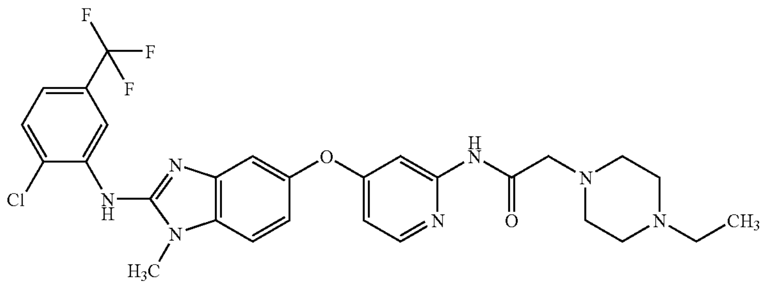 [SMILES: CCN1CCN(CC(=O)Nc2cc(Oc3ccc4c(c3)nc(Nc3cc(C(F)(F)F)ccc3Cl)n4C)ccn2)CC1] | N-{4-[(2-{[2-chloro-5-(trifluoromethyl)phenyl]amino}-1-methyl-1H-benzimidazol-5-yl)oxy]pyridin-2-yl}-2-(4-ethylpiperazin-1-yl)acetamide | 589 |
| 181 | 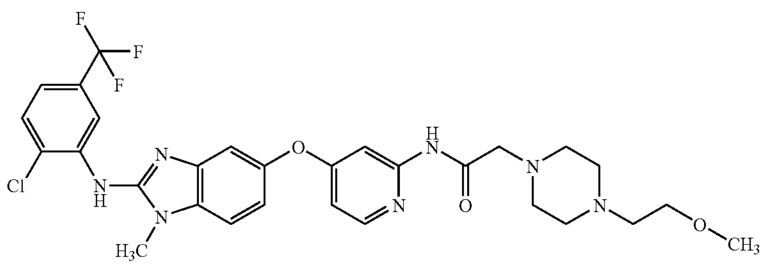 [SMILES: COCCN1CCN(CC(=O)Nc2cc(Oc3ccc4c(c3)nc(Nc3cc(C(F)(F)F)ccc3Cl)n4C)ccn2)CC1] | N-{4-[(2-{[2-chloro-5-(trifluoromethyl)phenyl]amino}-1-methyl-1H-benzimidazol-5-yl)oxy]pyridin-2-yl}-2-[4-(2-methoxyethyl)piperazin-1-yl]acetamide | 619.1 |
| 182 | 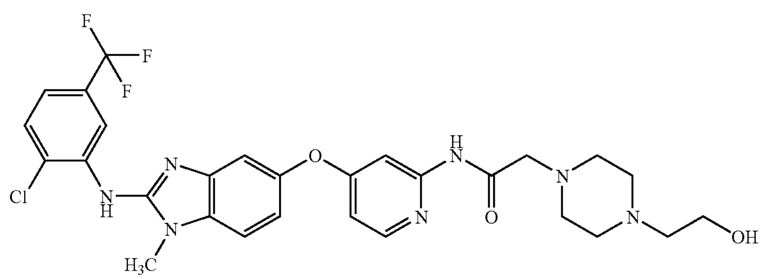 [SMILES: Cn1c(Nc2cc(C(F)(F)F)ccc2Cl)nc2cc(Oc3ccnc(NC(=O)CN4CCN(CCO)CC4)c3)ccc21] | N-{4-[(2-{[2-chloro-5-(trifluoromethyl)phenyl]amino}-1-methyl-1H-benzimidazol-5-yl)oxy]pyridin-2-yl}-2-[4-(2-hydroxyethyl)piperazin-1-yl]acetamide | 605 |
| 183 | 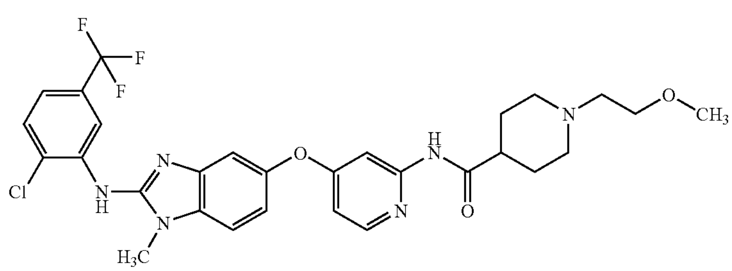 [SMILES: COCCN1CCC(C(=O)Nc2cc(Oc3ccc4c(c3)nc(Nc3cc(C(F)(F)F)ccc3Cl)n4C)ccn2)CC1] | N-{4-[(2-{[2-chloro-5-(trifluoromethyl)phenyl]amino}-1-methyl-1H-benzimidazol-5-yl)oxy]pyridin-2-yl}-1-(2-methoxyethyl)piperidine-4-carboxamide | 604 |
| 184 | 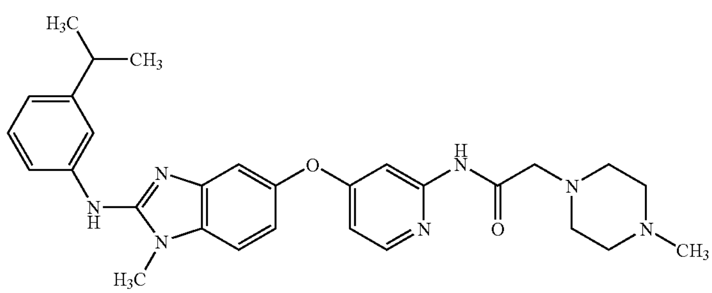 [SMILES: CC(C)c1cccc(Nc2nc3cc(Oc4ccnc(NC(=O)CN5CCN(C)CC5)c4)ccc3n2C)c1] | N-[4-({2-[(3-isopropylphenyl)amino]-1-methyl-1H-benzimidazol-5-yl}oxy)pyridin-2-yl]-2-(4-methylpiperazin-1-yl)acetamide | 514.6 |

TABLE 1-continued

| Ex. | Structure | Name | MH+ |
|---|---|---|---|
| 185 | 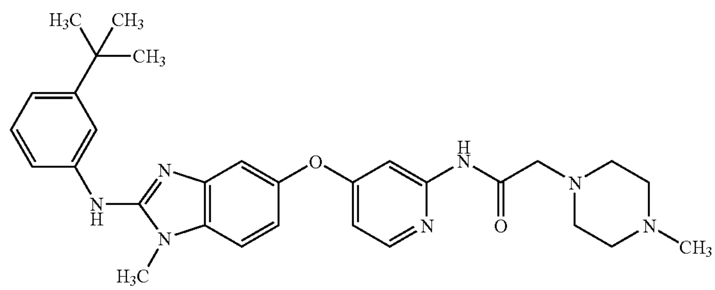 [SMILES: CN1CCN(CC(=O)Nc2cc(Oc3ccc4c(c3)nc(Nc3cccc(C(C)(C)C)c3)n4C)ccn2)CC1] | N-[4-({2-[(3-tert-butylphenyl)amino]-1-methyl-1H-benzimidazol-5-yl}oxy)pyridin-2-yl]-2-(4-methyl-piperazin-1-yl)acetamide | 528.7 |
| 186 | 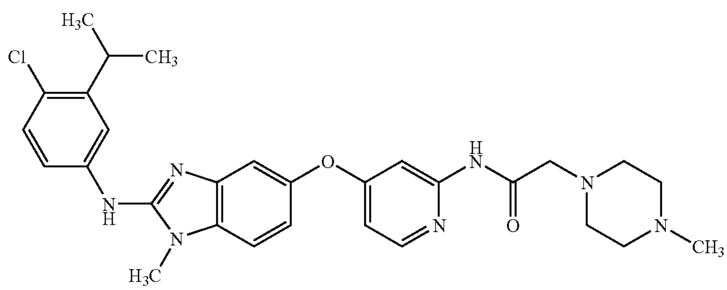 [SMILES: CC(C)c1cc(Nc2nc3cc(Oc4ccnc(NC(=O)CN5CCN(C)CC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-2-(4-methylpiperazin-1-yl)acetamide | 549.1 |
| 187 | 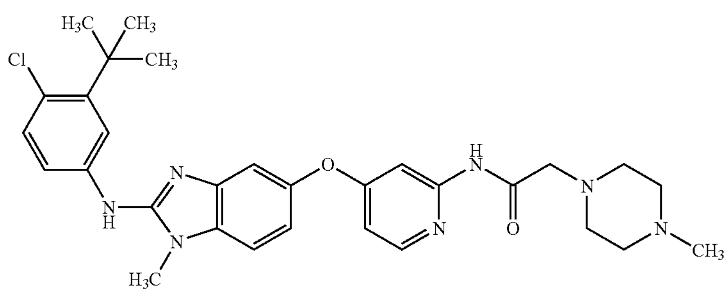 [SMILES: CN1CCN(CC(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-2-(4-methylpiperazin-1-yl)acetamide | 563.1 |
| 188 | 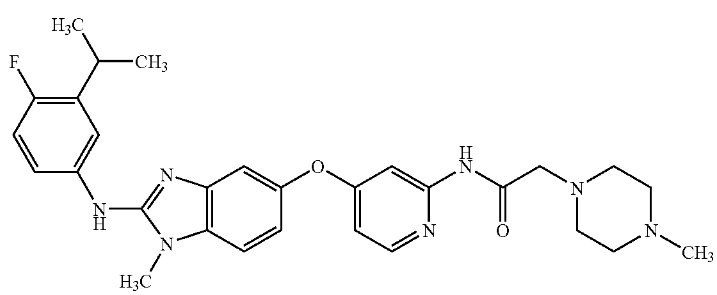 [SMILES: CC(C)c1cc(Nc2nc3cc(Oc4ccnc(NC(=O)CN5CCN(C)CC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-(4-methylpiperazin-1-yl)acetamide | 532.6 |
| 189 | 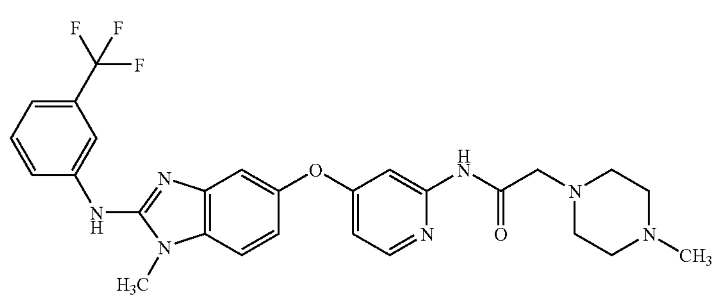 [SMILES: CN1CCN(CC(=O)Nc2cc(Oc3ccc4c(c3)nc(Nc3cccc(C(F)(F)F)c3)n4C)ccn2)CC1] | 2-(4-methylpiperazin-1-yl)-N-{4-[(1-methyl-2-{[3-(trifluoromethyl)-phenyl]amino}-1H-benzimidazol-5-yl)oxy]pyridin-2-yl}acetamide | 540.6 |

TABLE 1-continued

| Ex. | Structure | Name | MH+ |
|---|---|---|---|
| 190 | 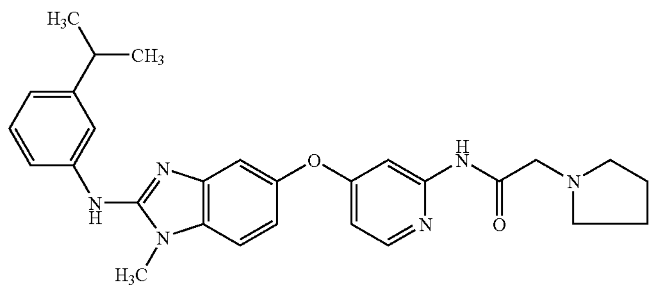 [SMILES: CC(C)c1cccc(Nc2nc3cc(Oc4ccnc(NC(=O)CN5CCCC5)c4)ccc3n2C)c1] | N-[4-({2-[(3-isopropylphenyl)-amino]-1-methyl-1H-benzimidazol-5-yl}oxy)pyridin-2-yl]-2-pyrrolidin-1-ylacetamide | 485.6 |
| 191 | 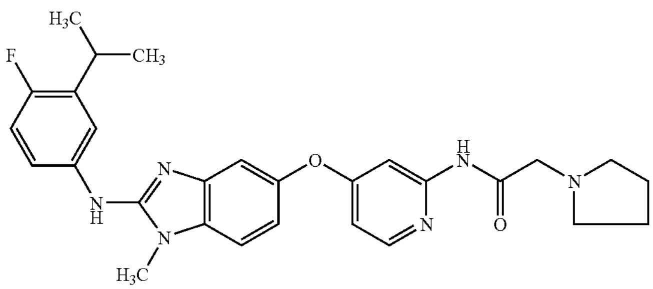 [SMILES: CC(C)c1cc(Nc2nc3cc(Oc4ccnc(NC(=O)CN5CCCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-pyrrolidin-1-ylacetamide | 503.6 |
| 192 | 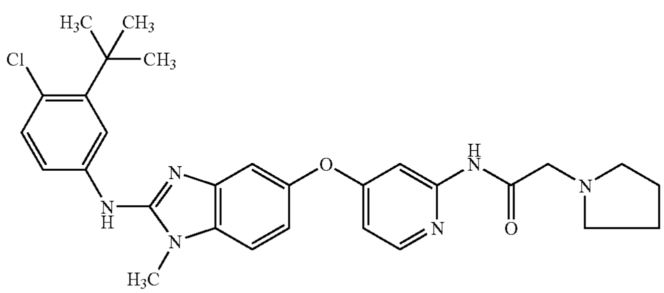 [SMILES: Cn1c(Nc2ccc(Cl)c(C(C)(C)C)c2)nc2cc(Oc3ccnc(NC(=O)CN4CCCC4)c3)ccc21] | N-[4-({2-[(3-tert-butyl-4-chloro-phenyl)amino]-1-methyl-1H-benzimidazol-5-yl}oxy)pyridin-2-yl]-2-pyrrolidin-1-ylacetamide | 534.1 |
| 193 | 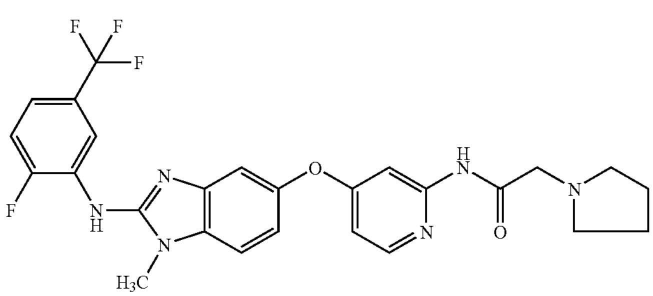 [SMILES: Cn1c(Nc2cc(C(F)(F)F)ccc2F)nc2cc(Oc3ccnc(NC(=O)CN4CCCC4)c3)ccc21] | N-{4-[(2-{[2-fluoro-5-(trifluoro-methyl)phenyl]amino}-1-methyl-1H-benzimidazol-5-yl)oxy]pyridin-2-yl}-2-pyrrolidin-1-ylacetamide | 529.5 |
| 194 | 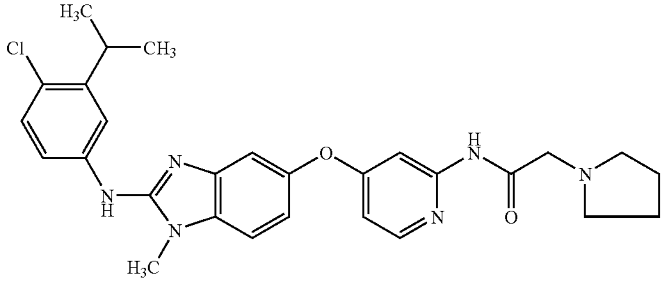 [SMILES: CC(C)c1cc(Nc2nc3cc(Oc4ccnc(NC(=O)CN5CCCC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-2-pyrrolidin-1-ylacetamide | 520 |

TABLE 1-continued

| Ex. | Structure | Name | MH+ |
|---|---|---|---|
| 195 | 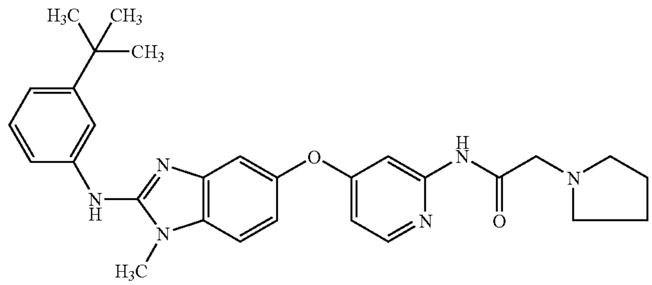 [SMILES: Cn1c(Nc2cccc(C(C)(C)C)c2)nc2cc(Oc3ccnc(NC(=O)CN4CCCC4)c3)ccc21] | N-[4-({2-[(3-tert-butylphenyl)amino]-1-methyl-1H-benzimidazol-5-yl}oxy)pyridin-2-yl]-2-pyrrolidin-1-ylacetamide | 499.6 |
| 196 | 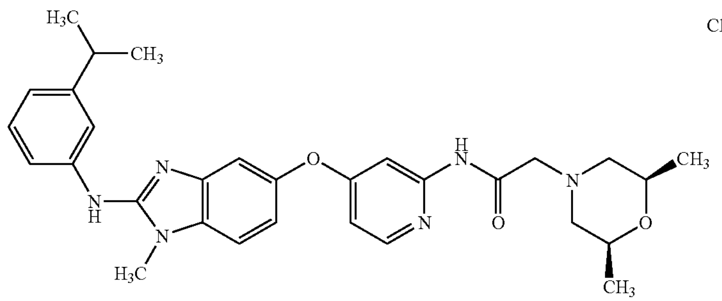 | Chiral 2-[(2R,6S)-2,6-dimethylmorpholin-4-yl]-N-[4-({2-[(3-isopropyl-phenyl)amino]-1-methyl-1H-benzimidazol-5-yl}oxy)pyridin-2-yl]acetamide | 529.7 |
| 197 | 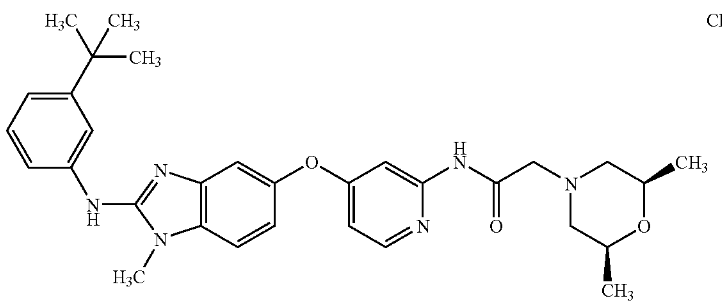 | Chiral N-[4-({2-[(3-tert-butylphenyl)amino]-1-methyl-1H-benzimidazol-5-yl}oxy)pyridin-2-yl]-2-[(2R,6S)-2,6-dimethylmorpholin-4-yl]acetamide | 543.7 |
| 198 | 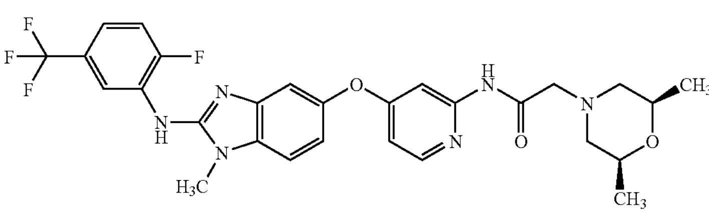 | Chiral 2-[(2R,6S)-2,6-dimethylmorpholin-4-yl]-N-{4-[(2-{[2-fluoro-5-(trifluoromethyl)phenyl]amino}-1-methyl-1H-benzimidazol-5-yl)oxy]pyridin-2-yl}acetamide | 573.6 |
| 199 | 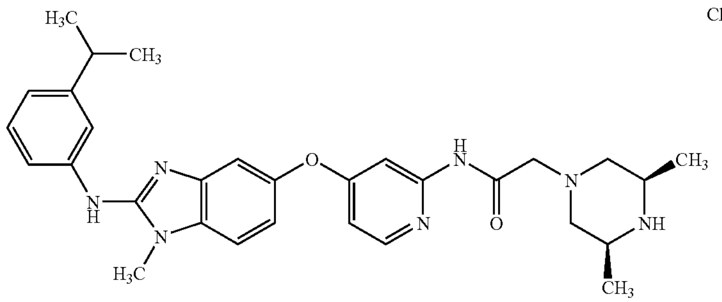 | Chiral 2-[(3R,5S)-3,5-dimethylpiperazin-1-yl]-N-[4-({2-[(3-isopropyl-phenyl)amino]-1-methyl-1H-benzimidazol-5-yl}oxy)pyridin-2-yl]acetamide | 528.7 |

TABLE 1-continued

| Ex. | Structure | Name | MH+ |
|---|---|---|---|
| 200 | 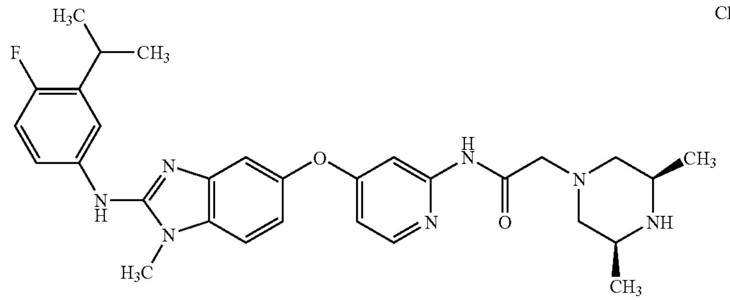 | Chiral 2-[(3R,5S)-3,5-dimethylpiperazin-1-yl]-N-[4-({2-[(4-fluoro-3-isopropyl-phenyl)amino]-1-methyl-1H-benzimidazol-5-yl}oxy)pyridin-2-yl]acetamide | 546.7 |
| 201 | 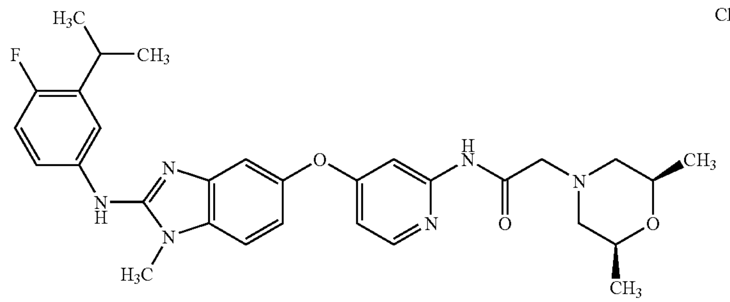 | Chiral 2-[(2R,6S)-2,6-dimethylmorpholin-4-yl]-N-[4-({2-[(4-fluoro-3-isopropyl-phenyl)amino]-1-methyl-1H-benzimidazol-5-yl}oxy)pyridin-2-yl]acetamide | 547.6 |
| 202 | 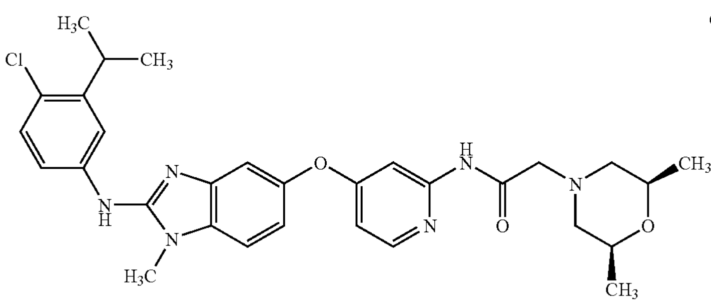 | Chiral N-[4-({2-[(4-chloro-3-isopropyl-phenyl)amino]-1-methyl-1H-benzimidazol-5-yl}oxy)pyridin-2-yl]-2-[(2R,6S)-2,6-dimethylmorpholin-4-yl]acetamide | 564.1 |
| 203 | 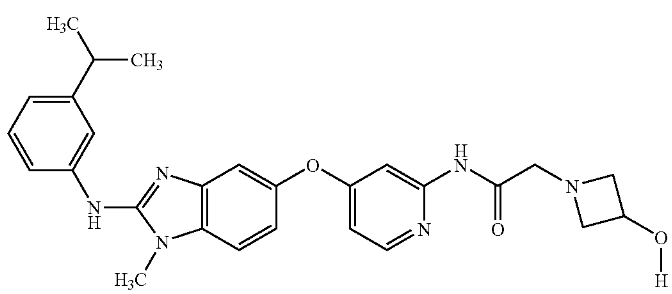 [SMILES: CC(C)c1cccc(Nc2nc3cc(Oc4ccnc(NC(=O)CN5CC(O)C5)c4)ccc3n2C)c1] | 2-(3-hydroxyazetidin-1-yl)-N-[4-({2-[(3-isopropylphenyl)amino]-1-methyl-1H-benzimidazol-5-yl}-oxy)pyridin-2-yl]acetamide | 487.6 |
| 204 | 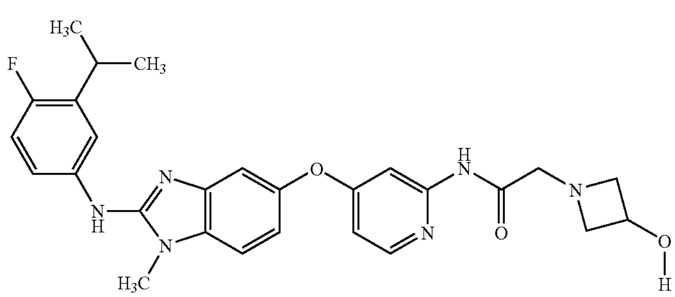 [SMILES: CC(C)c1cc(Nc2nc3cc(Oc4ccnc(NC(=O)CN5CC(O)C5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-(3-hydroxyazetidin-1-yl)-acetamide | 505.6 |

TABLE 1-continued

| Ex. | Structure | Name | MH+ |
|---|---|---|---|
| 205 | 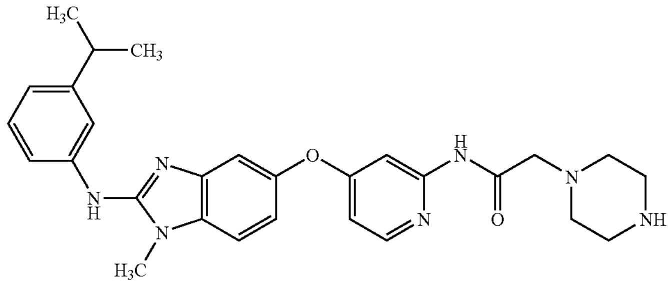 [SMILES: CC(C)c1cccc(Nc2nc3cc(Oc4ccnc(NC(=O)CN5CCNCC5)c4)ccc3n2C)c1] | N-[4-({2-[(3-isopropylphenyl)-amino]-1-methyl-1H-benzimidazol-5-yl}oxy)pyridin-2-yl]-2-piperazin-1-ylacetamide | 500.6 |
| 206 | 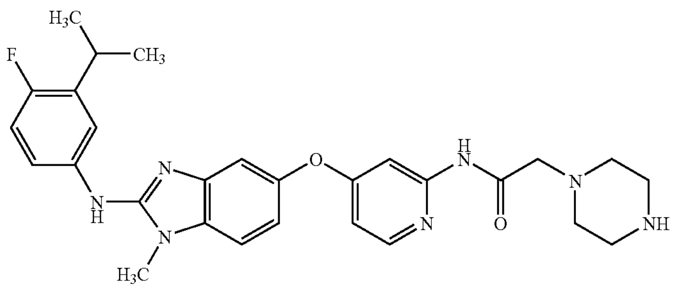 [SMILES: CC(C)c1cc(Nc2nc3cc(Oc4ccnc(NC(=O)CN5CCNCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-piperazin-1-ylacetamide | 518.6 |
| 207 | 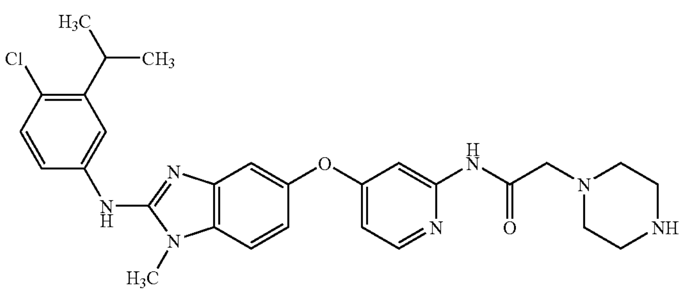 [SMILES: CC(C)c1cc(Nc2nc3cc(Oc4ccnc(NC(=O)CN5CCNCC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-2-piperazin-1-ylacetamide | 535.1 |
| 208 | 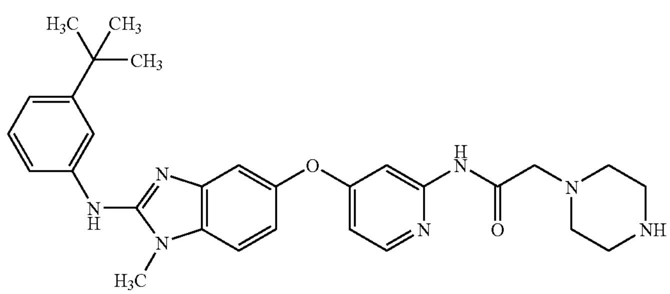 [SMILES: Cn1c(Nc2cccc(C(C)(C)C)c2)nc2cc(Oc3ccnc(NC(=O)CN4CCNCC4)c3)ccc21] | N-[4-({2-[(3-tert-butylphenyl)amino]-1-methyl-1H-benzimidazol-5-yl}-oxy)pyridin-2-yl]-2-piperazin-1-ylacetamide | 514.6 |
| 209 | 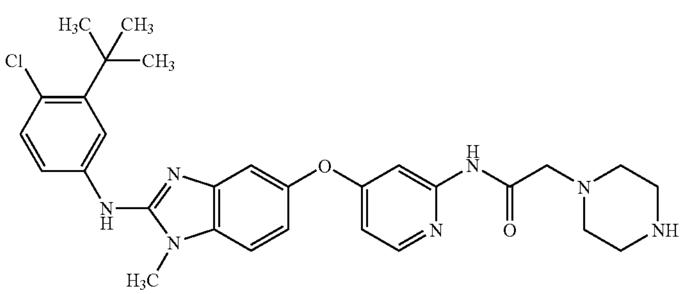 [SMILES: Cn1c(Nc2ccc(Cl)c(C(C)(C)C)c2)nc2cc(Oc3ccnc(NC(=O)CN4CCNCC4)c3)ccc21] | N-[4-(2-[(3-tert-butyl-4-chloro-phenyl)amino]-1-methyl-1H-benzimidazol-5-yl}oxy)pyridin-2-yl]-2-piperazin-1-ylacetamide | 549.1 |

TABLE 1-continued

| Ex. | Structure | Name | MH+ |
|---|---|---|---|
| 210 | 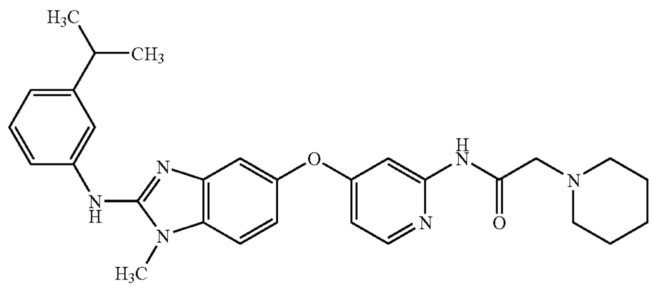 [SMILES: CC(C)c1cccc(Nc2nc3cc(Oc4ccnc(NC(=O)CN5CCCCC5)c4)ccc3n2C)c1] | N-[4-({2-[(3-isopropylphenyl)-amino]-1-methyl-1H-benzimidazol-5-yl}oxy)pyridin-2-yl]-2-piperidin-1-ylacetamide | 499.6 |
| 211 | 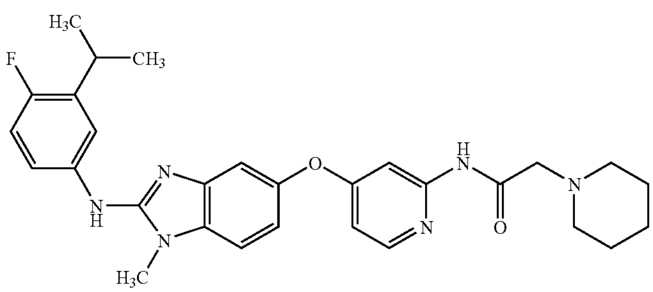 [SMILES: CC(C)c1cc(Nc2nc3cc(Oc4ccnc(NC(=O)CN5CCCCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-piperidin-1-ylacetamide | 517.6 |
| 212 | 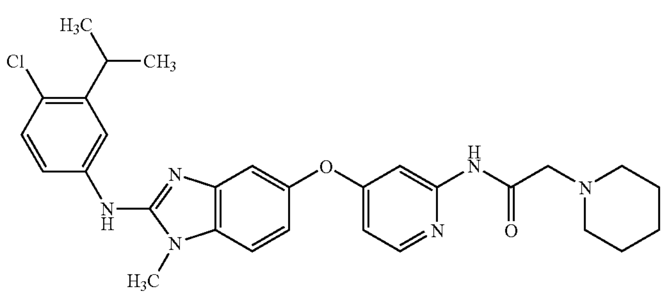 [SMILES: CC(C)c1cc(Nc2nc3cc(Oc4ccnc(NC(=O)CN5CCCCC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-2-piperidin-1-ylacetamide | 534.1 |
| 213 | 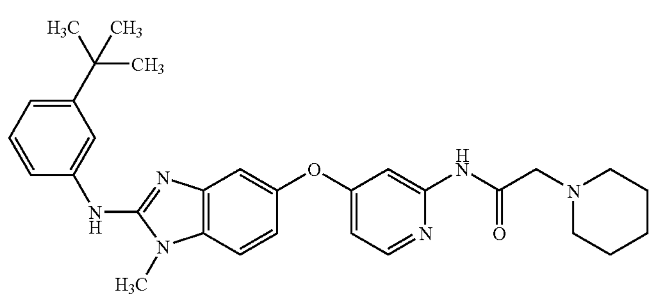 [SMILES: Cn1c(Nc2cccc(C(C)(C)C)c2)nc2cc(Oc3ccnc(NC(=O)CN4CCCCC4)c3)ccc21] | N-[4-({2-[(3-tert-butylphenyl)amino]-1-methyl-1H-benzimidazol-5-yl}-oxy)pyridin-2-yl]-2-piperidin-1-ylacetamide | 513.7 |
| 214 | 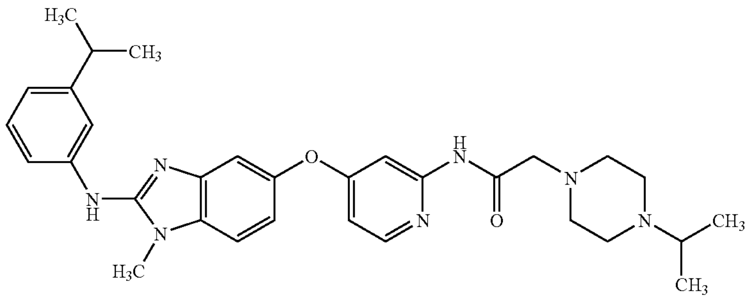 [SMILES: CC(C)c1cccc(Nc2nc3cc(Oc4ccnc(NC(=O)CN5CCN(C(C)C)CC5)c4)ccc3n2C)c1] | N-[4-({2-[(3-isopropylphenyl)-amino]-1-methyl-1H-benzimidazol-5-yl}oxy)pyridin-2-yl]-2-(4-isopropyl-piperazin-1-yl)acetamide | 542.7 |

TABLE 1-continued

| Ex. | Structure | Name | MH+ |
|---|---|---|---|
| 215 | 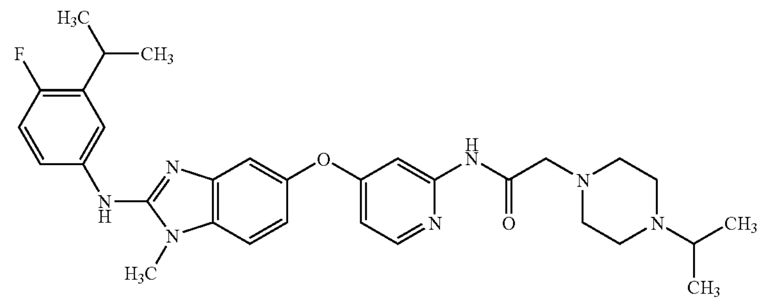 [SMILES: CC(C)c1cc(Nc2nc3cc(Oc4ccnc(NC(=O)CN5CCN(C(C)C)CC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-(4-isopropylpiperazin-1-yl)-acetamide | 560.7 |
| 216 | 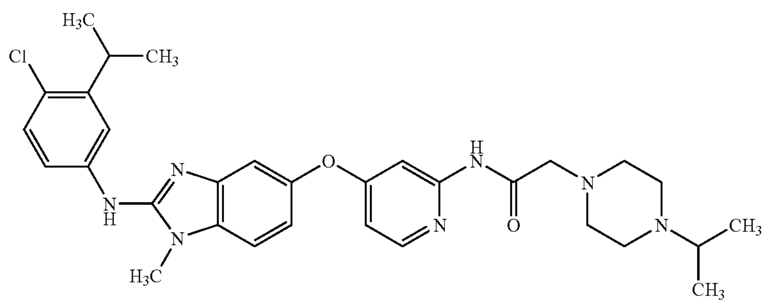 [SMILES: CC(C)c1cc(Nc2nc3cc(Oc4ccnc(NC(=O)CN5CCN(C(C)C)CC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-2-(4-isopropylpiperazin-1-yl)acetamide | 577.1 |
| 217 | 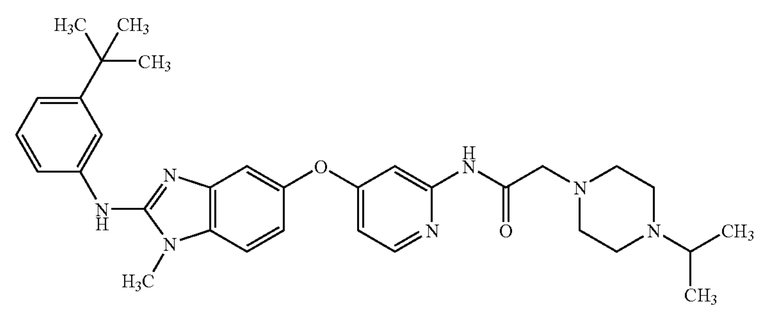 [SMILES: CC(C)N1CCN(CC(=O)Nc2cc(Oc3ccc4c(c3)nc(Nc3cccc(C(C)(C)C)c3)n4C)ccn2)CC1] | N-[4-({2-[(3-tert-butylphenyl)amino]-1-methyl-1H-benzimidazol-5-yl}-oxy)pyridin-2-yl]-2-(4-isopropyl-piperazin-1-yl)acetamide | 556.7 |
| 218 | 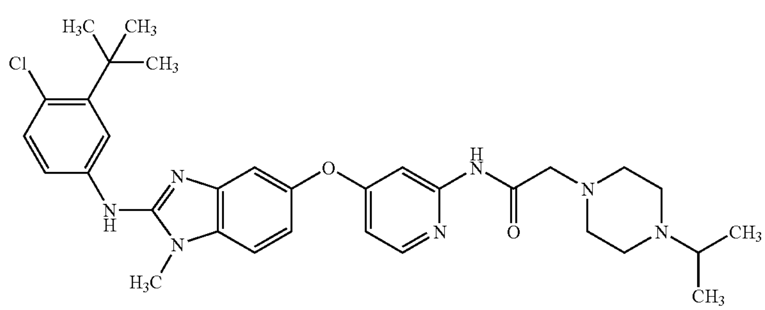 [SMILES: CC(C)N1CCN(CC(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-2-(4-isopropylpiperazin-1-yl)-acetamide | 591.2 |
| 219 | 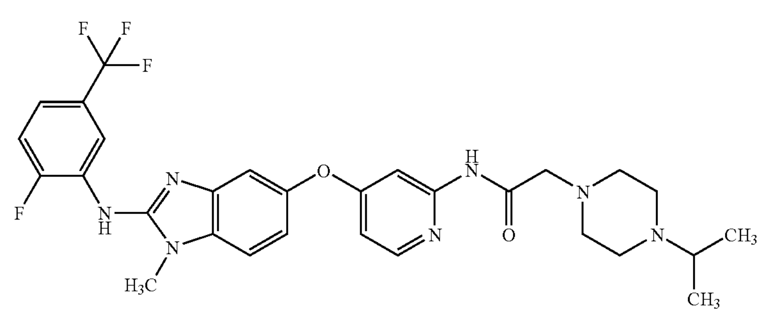 [SMILES: CC(C)N1CCN(CC(=O)Nc2cc(Oc3ccc4c(c3)nc(Nc3cc(C(F)(F)F)ccc3F)n4C)ccn2)CC1] | N-{4-[(2-{[2-fluoro-5-(trifluoro-methyl)phenyl]amino}-1-methyl-1H-benzimidazol-5-yl)oxy]pyridin-2-yl}-2-(4-isopropylpiperazin-1-yl)acetamide | 586.6 |

TABLE 1-continued

| Ex. | Structure | Name | MH+ |
|---|---|---|---|
| 220 | 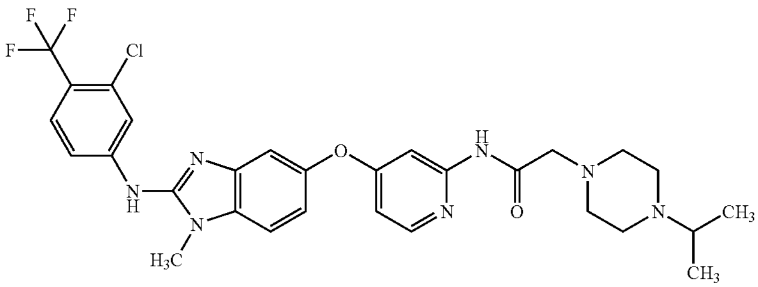 | N-{4-[(2-{[3-chloro-4-(trifluoro-methyl)phenyl]amino}-1-methyl-1H-benzimidazol-5-yl)oxy]pyridin-2-yl}-2-(4-isopropylpiperazin-1-yl)-acetamide | 603.1 |
| 221 | 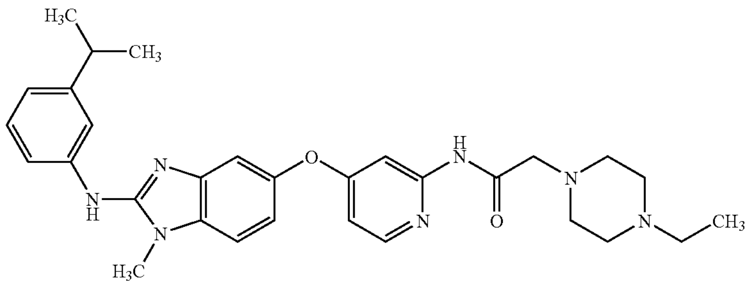 [SMILES: CCN1CCN(CC(=O)Nc2cc(Oc3ccc4c(c3)nc(Nc3cccc(C(C)C)c3)n4C)ccn2)CC1] | 2-(4-ethylpiperazin-1-yl)-N-[4-({2-[(3-isopropylphenyl)amino]-1-methyl-1H-benzimidazol-5-yl}-oxy)pyridin-2-yl]acetamide | 528.7 |
| 222 | 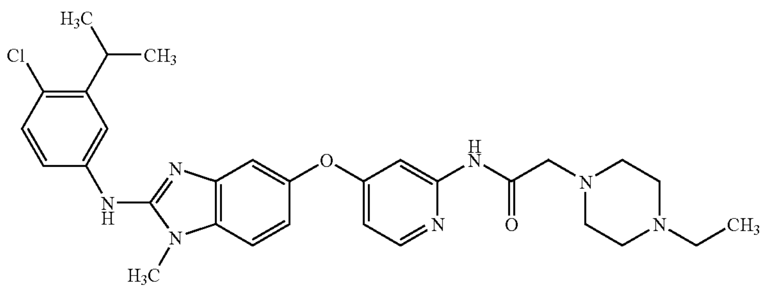 [SMILES: CCN1CCN(CC(=O)Nc2cc(Oc3ccc4c(c3)nc(Nc3ccc(Cl)c(C(C)C)c3)n4C)ccn2)CC1] | N-[4-({2-[(4-chloro-3-isopropyl-phenyl)amino]-1-methyl-1H-benzimidazol-5-yl}oxy)pyridin-2-yl]-2-(4-ethylpiperazin-1-yl)acetamide | 563.1 |
| 223 | 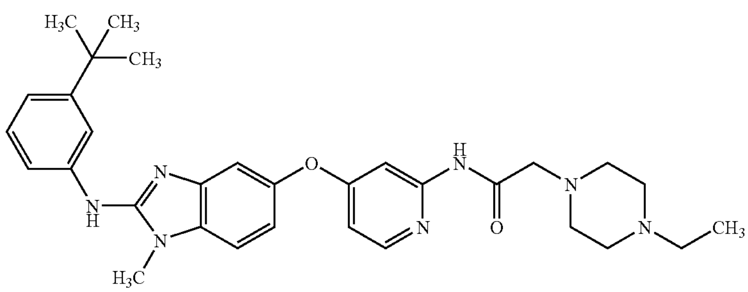 [SMILES: CCN1CCN(CC(=O)Nc2cc(Oc3ccc4c(c3)nc(Nc3cccc(C(C)(C)C)c3)n4C)ccn2)CC1] | N-[4-({2-[(3-tert-butylphenyl)amino]-1-methyl-1H-benzimidazol-5-yl}-oxy)pyridin-2-yl]-2-(4-ethyl-piperazin-1-yl)acetamide | 542.7 |
| 224 | 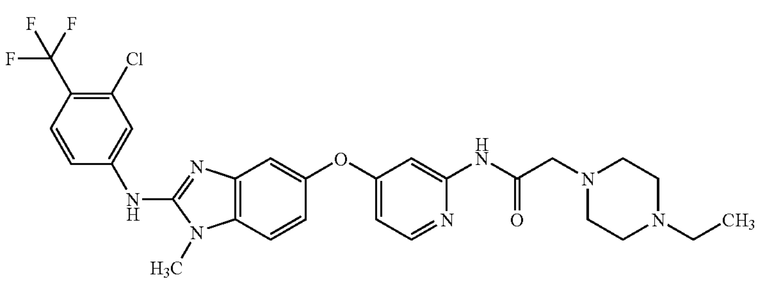 [SMILES: CCN1CCN(CC(=O)Nc2cc(Oc3ccc4c(c3)nc(Nc3ccc(C(F)(F)F)c(Cl)c3)n4C)ccn2)CC1] | N-{4-[(2-{[3-chloro-4-(trifluoro-methyl)phenyl]amino}-1-methyl-1H-benzimidazol-5-yl)oxy]pyridin-2-yl}-2-(4-ethylpiperazin-1-yl)acetamide | 589 |

TABLE 1-continued

| Ex. | Structure | Name | MH+ |
|---|---|---|---|
| 225 | 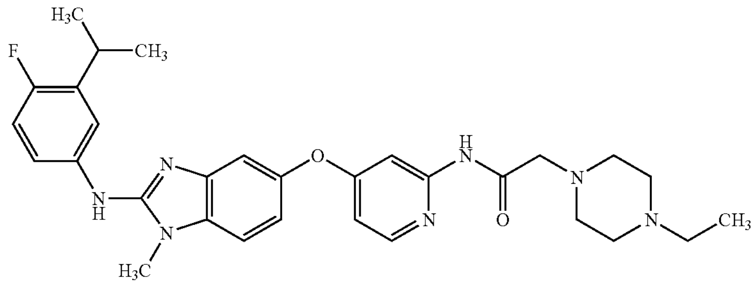 [SMILES: CCN1CCN(CC(=O)Nc2cc(Oc3ccc4c(c3)nc(Nc3ccc(F)c(C(C)C)c3)n4C)ccn2)CC1] | 2-(4-ethylpiperazin-1-yl)-N-[4-({2-[(4-fluoro-3-isopropylphenyl)-amino]-1-methyl-1H-benzimidazol-5-yl}oxy)pyridin-2-yl]acetamide | 546.7 |
| 226 | 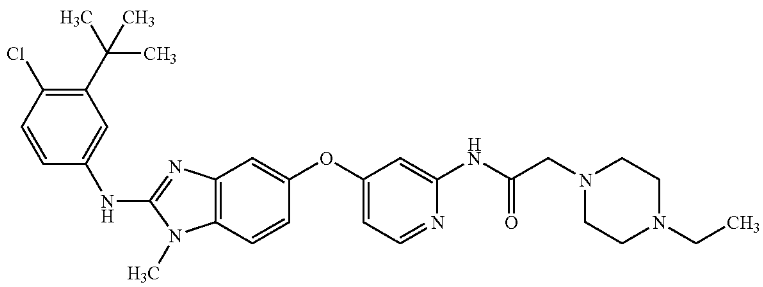 [SMILES: CCN1CCN(CC(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-2-(4-ethylpiperazin-1-yl)acetamide | 577.1 |
| 227 | 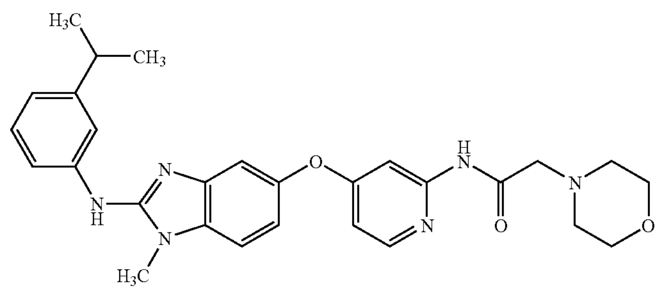 [SMILES: CC(C)c1cccc(Nc2nc3cc(Oc4ccnc(NC(=O)CN5CCOCC5)c4)ccc3n2C)c1] | N-[4-({2-[(3-isopropylphenyl)-amino]-1-methyl-1H-benzimidazol-5-yl}oxy)pyridin-2-yl]-2-morpholin-4-ylacetamide | 501.6 |
| 228 | 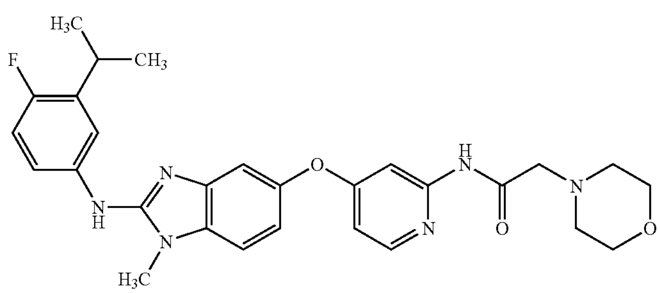 | N-[4-({2-[(4-fluoro-3-isopropyl-phenyl)amino]-1-methyl-1H-benzimidazol-5-yl}oxy)pyridin-2-yl]-2-morpholin-4-ylacetamide | 519.6 |
| 229 | 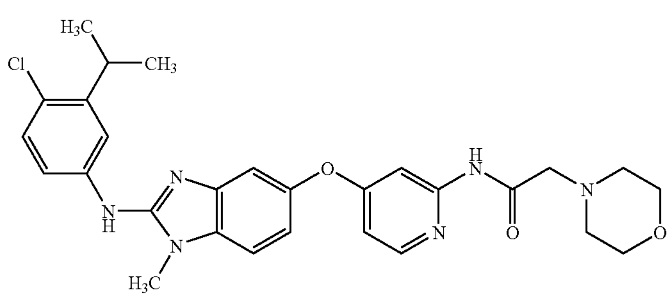 [SMILES: CC(C)c1cc(Nc2nc3cc(Oc4ccnc(NC(=O)CN5CCOCC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-2-morpholin-4-ylacetamide | 536 |

TABLE 1-continued

| Ex. | Structure | Name | MH+ |
|---|---|---|---|
| 230 | 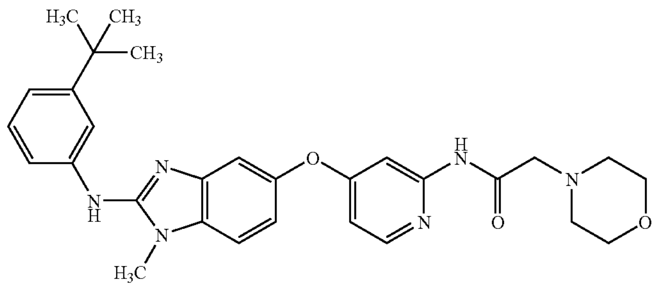 [SMILES: Cn1c(Nc2cccc(C(C)(C)C)c2)nc2cc(Oc3ccnc(NC(=O)CN4CCOCC4)c3)ccc21] | N-[4-({2-[(3-tert-butylphenyl)amino]-1-methyl-1H-benzimidazol-5-yl}-oxy)pyridin-2-yl]-2-morpholin-4-ylacetamide | 515.6 |
| 231 | 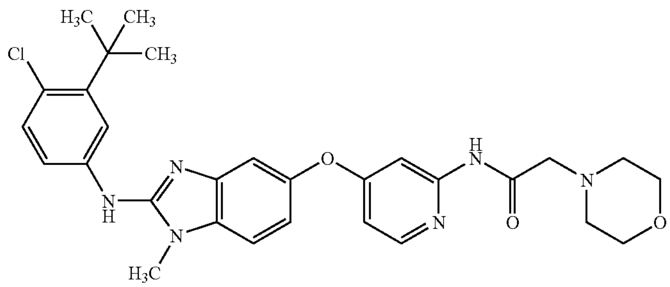 [SMILES: Cn1c(Nc2ccc(Cl)c(C(C)(C)C)c2)nc2cc(Oc3ccnc(NC(=O)CN4CCOCC4)c3)ccc21] | N-[4-({2-[(3-tert-butyl-4-chloro-phenyl)amino]-1-methyl-1H-benzimidazol-5-yl}oxy)pyridin-2-yl]-2-morpholin-4-ylacetamide | 550.1 |
| 232 | 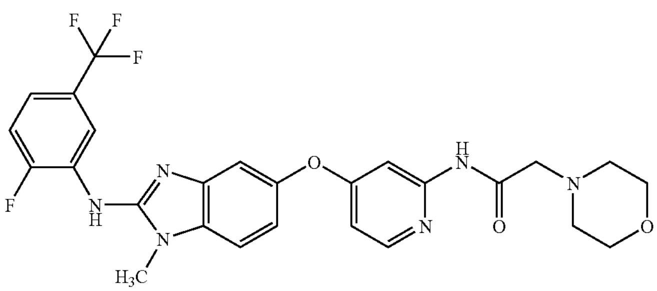 [SMILES: Cn1c(Nc2cc(C(F)(F)F)ccc2F)nc2cc(Oc3ccnc(NC(=O)CN4CCOCC4)c3)ccc21] | N-{4-[(2-{[2-fluoro-5-(trifluoromethyl)phenyl]amino}-1-methyl-1H-benzimidazol-5-yl)oxy]pyridin-2-yl}-2-morpholin-4-ylacetamide | 545.5 |
| 233 | 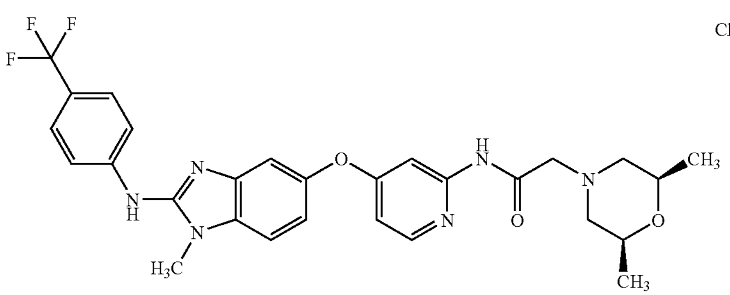 | Chiral 2-[(2R,6S)-2,6-dimethylmorpholin-4-yl]-N-{4-[(1-methyl-2-{[4-(trifluoromethyl)phenyl]amino}-1H-benzimidazol-5-yl)oxy]pyridin-2-yl}acetamide | 555.6 |
| 234 | 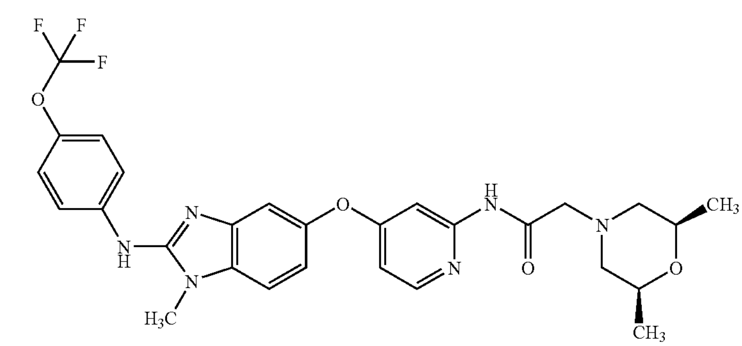 [SMILES: C[C@@H]1CN(CC(=O)Nc2cc(Oc3ccc4c(c3)nc(Nc3ccc(OC(F)(F)F)cc3)n4C)ccn2)C[C@H](C)O1] | 2-[(2R,6S)-2,6-dimethylmorpholin-4-yl]-N-{4-[(1-methyl-2-{[4-(trifluoromethoxy)phenyl]amino}-1H-benzimidazol-5-yl)oxy]pyridin-2-yl}acetamide | 571.6 |

TABLE 1-continued

| Ex. | Structure | Name | MH+ |
|---|---|---|---|
| 235 | 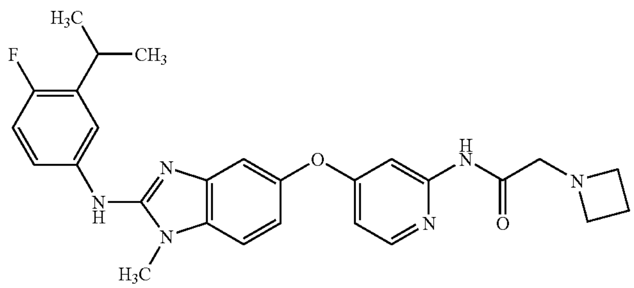 [SMILES: CC(C)c1cc(Nc2nc3cc(Oc4ccnc(NC(=O)CN5CCC5)c4)ccc3n2C)ccc1F] | 2-azetidin-1-yl-N-[4-({2-[(4-fluoro-3-isopropylphenyl)amino]-1-methyl-1H-benzimidazol-5-yl}oxy)pyridin-2-yl]acetamide | 489.6 |
| 236 | 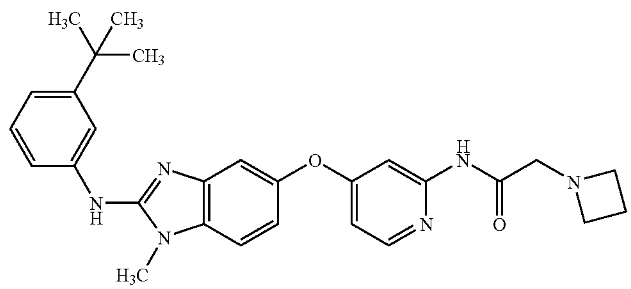 [SMILES: Cn1c(Nc2cccc(C(C)(C)C)c2)nc2cc(Oc3ccnc(NC(=O)CN4CCC4)c3)ccc21] | 2-azetidin-1-yl-N-[4-({2-[(3-tert-butylphenyl)amino]-1-methyl-1H-benzimidazol-5-yl}oxy)pyridin-2-yl]acetamide | 485.6 |
| 237 | 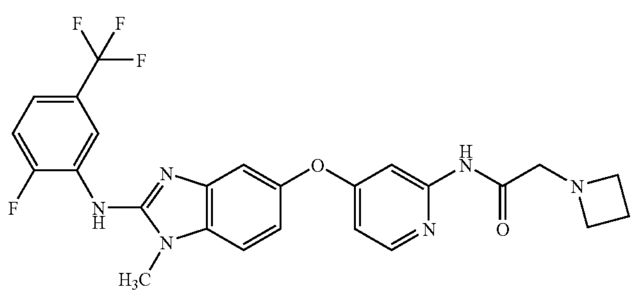 [SMILES: Cn1c(Nc2cc(C(F)(F)F)ccc2F)nc2cc(Oc3ccnc(NC(=O)CN4CCC4)c3)ccc21] | 2-azetidin-1-yl-N-{4-[(2-{[2-fluoro-5-(trifluoromethyl)phenyl]amino}-1-methyl-1H-benzimidazol-5-yl)oxy]pyridin-2-yl}acetamide | 515.5 |
| 238 | 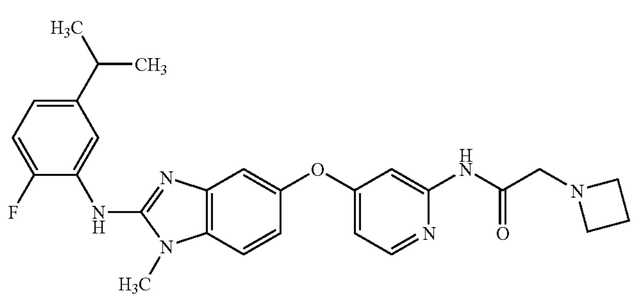 [SMILES: CC(C)c1ccc(F)c(Nc2nc3cc(Oc4ccnc(NC(=O)CN5CCC5)c4)ccc3n2C)c1] | 2-azetidin-1-yl-N-[4-({2-[(2-fluoro-5-isopropylphenyl)amino]-1-methyl-1H-benzimidazol-5-yl}oxy)pyridin-2-yl]acetamide | 489.6 |
| 239 | 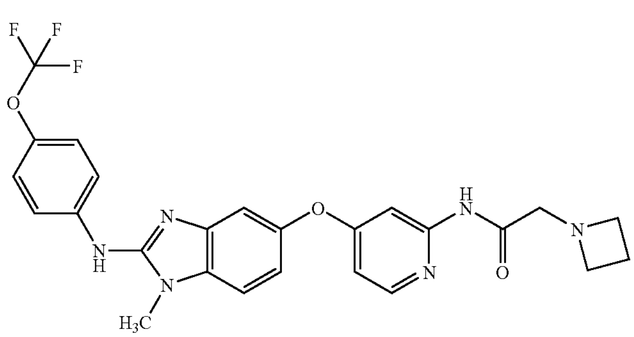 [SMILES: Cn1c(Nc2ccc(OC(F)(F)F)cc2)nc2cc(Oc3ccnc(NC(=O)CN4CCC4)c3)ccc21] | 2-azetidin-1-yl-N-{4-[(1-methyl-2-{[4-(trifluoromethoxy)phenyl]amino}-1H-benzimidazol-5-yl)oxy]pyridin-2-yl}acetamide | 513.5 |

TABLE 1-continued

| Ex. | Structure | Name | MH+ |
|---|---|---|---|
| 240 | 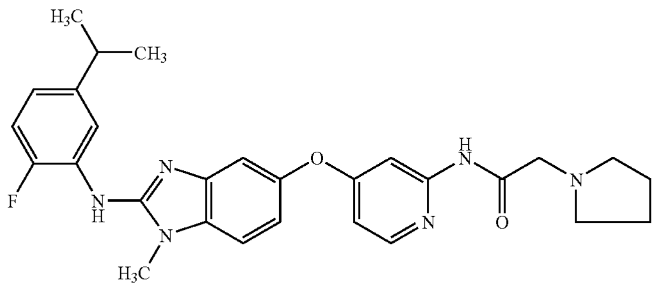 [SMILES: CC(C)c1ccc(F)c(Nc2nc3cc(Oc4ccnc(NC(=O)CN5CCCC5)c4)ccc3n2C)c1] | N-[4-({2-[(2-fluoro-5-isopropyl-phenyl)amino]-1-methyl-1H-benzimidazol-5-yl}oxy)pyridin-2-yl]-2-pyrrolidin-1-ylacetamide | 503.6 |
| 241 | 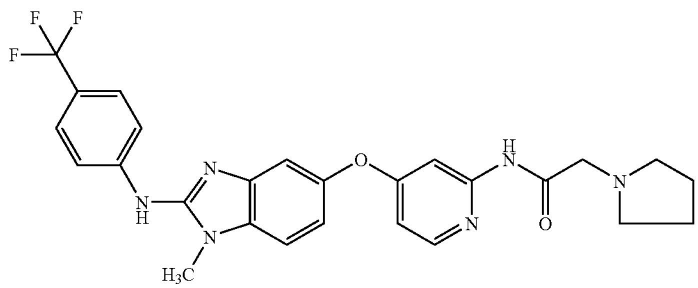 [SMILES: Cn1c(Nc2ccc(C(F)(F)F)cc2)nc2cc(Oc3ccnc(NC(=O)CN4CCCC4)c3)ccc21] | N-{4-[(1-methyl-2-{[4-(trifluoro-methyl)phenyl]amino}-1H-benzimidazol-5-yl)oxy]pyridin-2-yl}-2-pyrrolidin-1-ylacetamide | 511.5 |
| 242 | 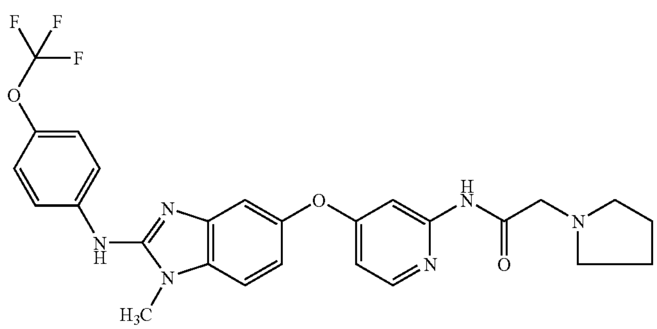 [SMILES: Cn1c(Nc2ccc(OC(F)(F)F)cc2)nc2cc(Oc3ccnc(NC(=O)CN4CCCC4)c3)ccc21] | N-{4-[(1-methyl-2-{[4-(trifluoro-methoxy)phenyl]amino}-1H-benzimidazol-5-yl)oxy]pyridin-2-yl}-2-pyrrolidin-1-ylacetamide | 527.5 |
| 243 | 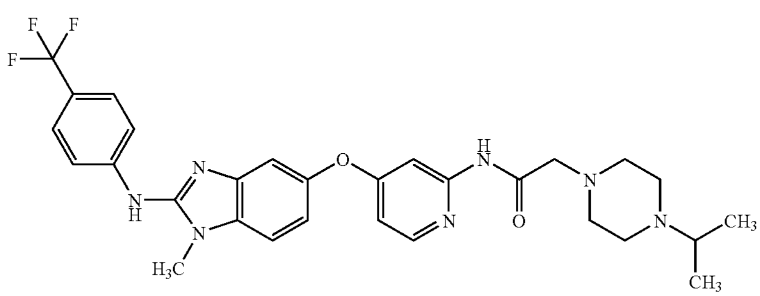 [SMILES: CC(C)N1CCN(CC(=O)Nc2cc(Oc3ccc4c(c3)nc(Nc3ccc(C(F)(F)F)cc3)n4C)ccn2)CC1] | 2-(4-isopropylpiperazin-1-yl)-N-{4-[(1-methyl-2-{[4-(trifluoromethyl)-phenyl]amino}-1H-benzimidazol-5-yl)oxy]pyridin-2-yl}acetamide | 568.6 |
| 244 | 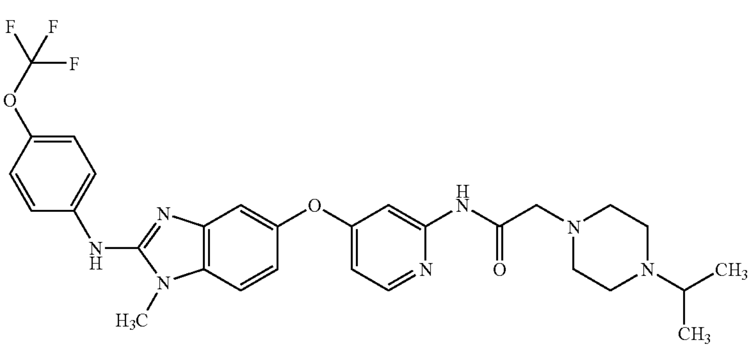 [SMILES: CC(C)N1CCN(CC(=O)Nc2cc(Oc3ccc4c(c3)nc(Nc3ccc(OC(F)(F)F)cc3)n4C)ccn2)CC1] | 2-(4-isopropylpiperazin-1-yl)-N-{4-[(1-methyl-2-{[4-(trifluoromethoxy)-phenyl]amino}-1H-benzimidazol-5-yl)oxy]pyridin-2-yl}acetamide | 584.6 |

TABLE 1-continued

| Ex. | Structure | Name | MH+ |
|---|---|---|---|
| 245 | 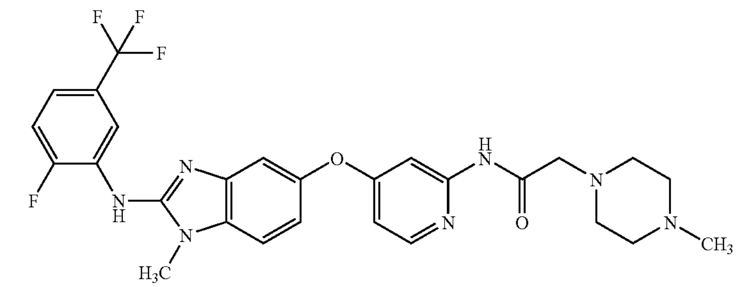 [SMILES: CN1CCN(CC(=O)Nc2cc(Oc3ccc4c(c3)nc(Nc3cc(C(F)(F)F)ccc3F)n4C)ccn2)CC1] | N-{4-[(2-{[2-fluoro-5-(trifluoro-methyl)phenyl]amino}-1-methyl-1H-benzimidazol-5-yl)oxy]pyridin-2-yl}-2-(4-methylpiperazin-1-yl)-acetamide | 558.5 |
| 246 | 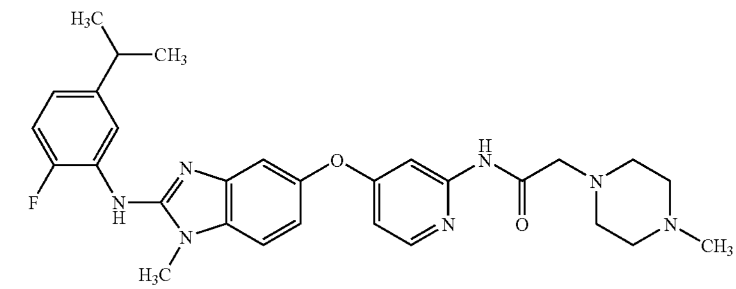 [SMILES: CC(C)c1ccc(F)c(Nc2nc3cc(Oc4ccnc(NC(=O)CN5CCN(C)CC5)c4)ccc3n2C)c1] | N-[4-({2-[(2-fluoro-5-isopropyl-phenyl)amino]-1-methyl-1H-benzimidazol-5-yl}oxy)pyridin-2-yl]-2-(4-methylpiperazin-1-yl)-acetamide | 532.6 |
| 247 | 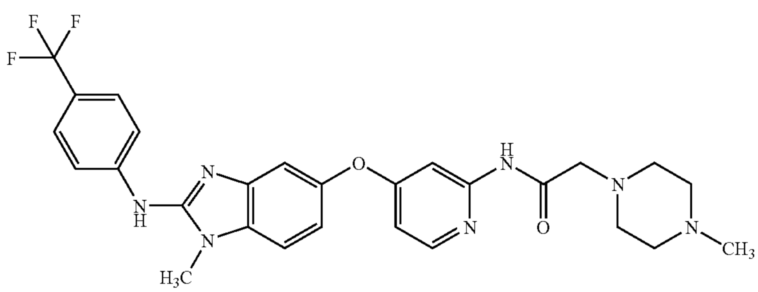 [SMILES: CN1CCN(CC(=O)Nc2cc(Oc3ccc4c(c3)nc(Nc3ccc(C(F)(F)F)cc3)n4C)ccn2)CC1] | 2-(4-methylpiperazin-1-yl)-N-{4-[(1-methyl-2-{[4-(trifluoromethyl)-phenyl]amino}-1H-benzimidazol-5-yl)oxy]pyridin-2-yl}-acetamide | 540.6 |
| 248 | 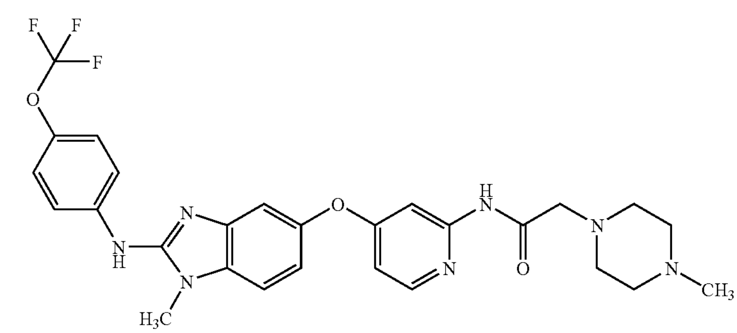 [SMILES: CN1CCN(CC(=O)Nc2cc(Oc3ccc4c(c3)nc(Nc3ccc(OC(F)(F)F)cc3)n4C)ccn2)CC1] | 2-(4-methylpiperazin-1-yl)-N-{4-[(1-methyl-2-{[4-(trifluoromethoxy)-phenyl]amino}-1H-benzimidazol-5-yl)oxy]pyridin-2-yl}acetamide | 556.6 |
| 249 | 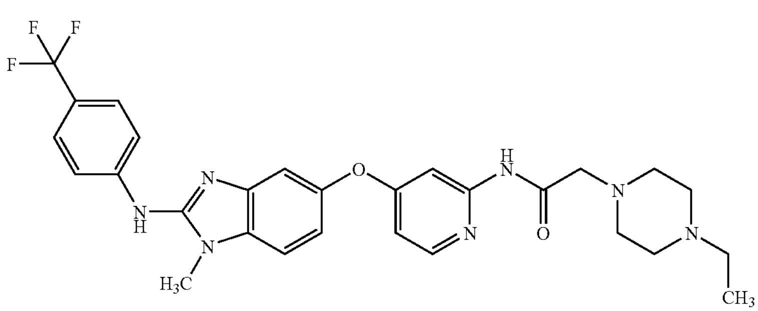 [SMILES: CCN1CCN(CC(=O)Nc2cc(Oc3ccc4c(c3)nc(Nc3ccc(C(F)(F)F)cc3)n4C)ccn2)CC1] | 2-(4-ethylpiperazin-1-yl)-N-{4-[(1-methyl-2-{[4-(trifluoromethyl)-phenyl]amino}-1H-benzimidazol-5-yl)oxy]pyridin-2-yl}acetamide | 554.6 |

TABLE 1-continued

| Ex. | Structure | Name | MH+ |
|---|---|---|---|
| 250 | 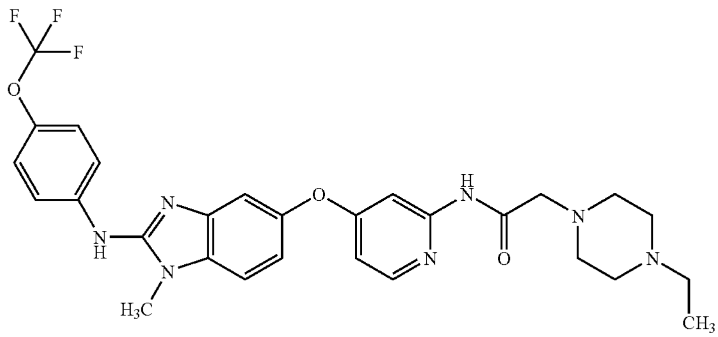 [SMILES: CCN1CCN(CC(=O)Nc2cc(Oc3ccc4c(c3)nc(Nc3ccc(OC(F)(F)F)cc3)n4C)ccn2)CC1] | 2-(4-ethylpiperazin-1-yl)-N-{4-[(1-methyl-2-{[4-(trifluoromethoxy)-phenyl]amino}-1H-benzimidazol-5-yl)oxy]pyridin-2-yl}acetamide | 570.6 |
| 251 | 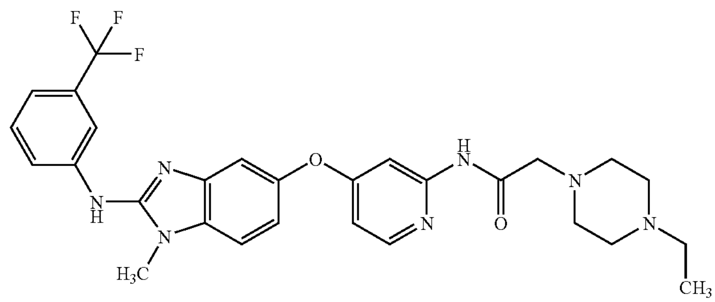 [SMILES: CCN1CCN(CC(=O)Nc2cc(Oc3ccc4c(c3)nc(Nc3cccc(C(F)(F)F)c3)n4C)ccn2)CC1] | 2-(4-ethylpiperazin-1-yl)-N-{4-[(1-methyl-2-{[3-(trifluoromethyl)-phenyl]amino}-1H-benzimidazol-5-yl)oxy]pyridin-2-yl}acetamide | 554.6 |
| 252 | 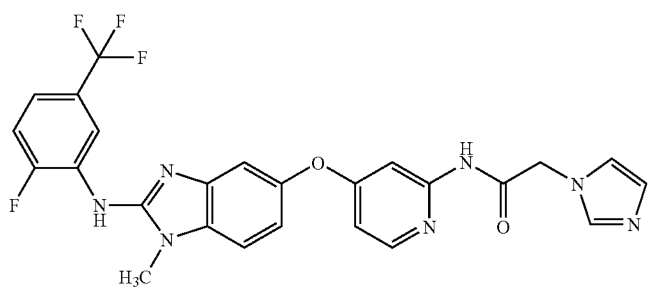 [SMILES: Cn1c(Nc2cc(C(F)(F)F)ccc2F)nc2cc(Oc3ccnc(NC(=O)Cn4ccnc4)c3)ccc21] | N-{4-[(2-{[2-fluoro-5-(trifluoromethyl)phenyl]amino}-1-methyl-1H-benzimidazol-5-yl)oxy]pyridin-2-yl}-2-(1H-imidazol-1-yl)acetamide | 526.5 |
| 253 | 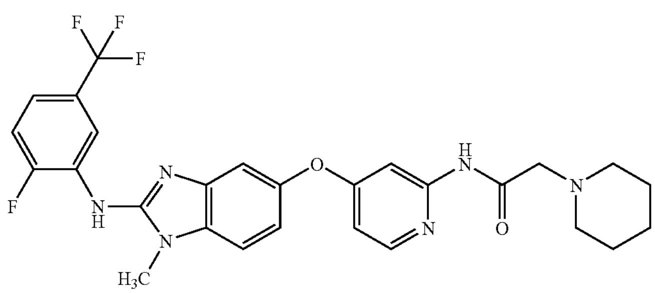 [SMILES: Cn1c(Nc2cc(C(F)(F)F)ccc2F)nc2cc(Oc3ccnc(NC(=O)CN4CCCCC4)c3)ccc21] | N-{4-[(2-{[2-fluoro-5-(trifluoromethyl)phenyl]amino}-1-methyl-1H-benzimidazol-5-yl)oxy]pyridin-2-yl}-2-piperidin-1-ylacetamide | 543.5 |
| 254 | 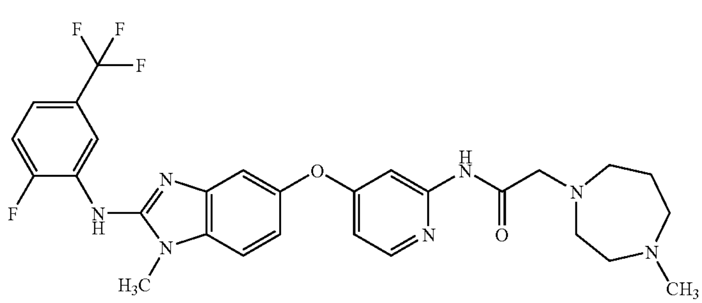 [SMILES: CN1CCCN(CC(=O)Nc2cc(Oc3ccc4c(c3)nc(Nc3cc(C(F)(F)F)ccc3F)n4C)ccn2)CC1] | N-{4-[(2-{[2-fluoro-5-(trifluoromethyl)phenyl]amino}-1-methyl-1H-benzimidazol-5-yl)oxy]pyridin-2-yl}-2-(4-methyl-1,4-diazepan-1-yl)acetamide | 572.6 |

TABLE 1-continued

| Ex. | Structure | Name | MH+ |
|---|---|---|---|
| 255 | 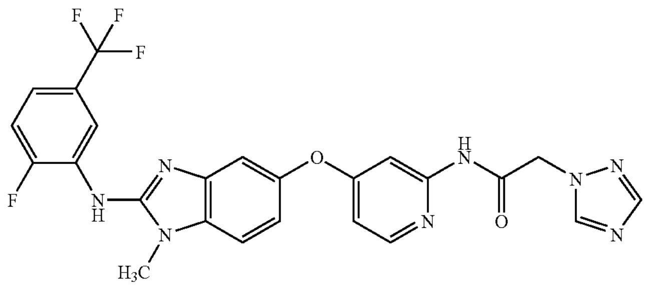 [SMILES: Cn1c(Nc2cc(C(F)(F)F)ccc2F)nc2cc(Oc3ccnc(NC(=O)Cn4cncn4)c3)ccc21] | N-{4-[(2-{[2-fluoro-5-(trifluoromethyl)phenyl]amino}-1-methyl-1H-benzimidazol-5-yl)oxy]pyridin-2-yl}-2-(1H-1,2,4-triazol-1-yl)acetamide | 527.5 |
| 256 | 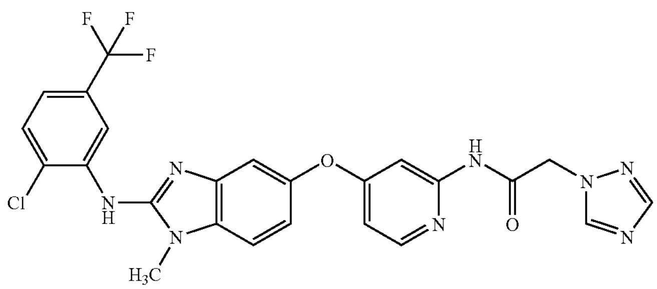 [SMILES: Cn1c(Nc2cc(C(F)(F)F)ccc2Cl)nc2cc(Oc3ccnc(NC(=O)Cn4cncn4)c3)ccc21] | N-{4-[(2-{[2-chloro-5-(trifluoromethyl)phenyl]amino}-1-methyl-1H-benzimidazol-5-yl)oxy]pyridin-2-yl}-2-(1H-1,2,4-triazol-1-yl)acetamide | 543.9 |
| 257 | 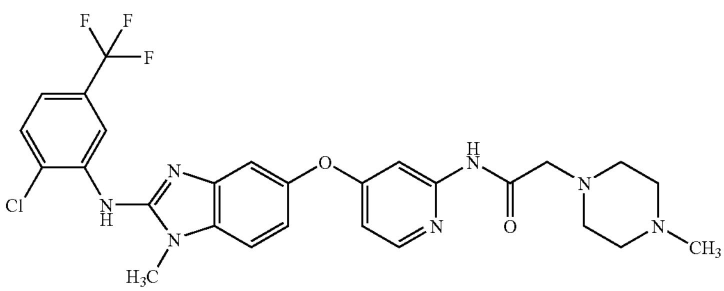 [SMILES: CN1CCN(CC(=O)Nc2cc(Oc3ccc4c(c3)nc(Nc3cc(C(F)(F)F)ccc3Cl)n4C)ccn2)CC1] | N-{4-[(2-{[2-chloro-5-(trifluoromethyl)phenyl]amino}-1-methyl-1H-benzimidazol-5-yl)oxy]pyridin-2-yl}-2-(4-methylpiperazin-1-yl)-acetamide | 575 |
| 258 | 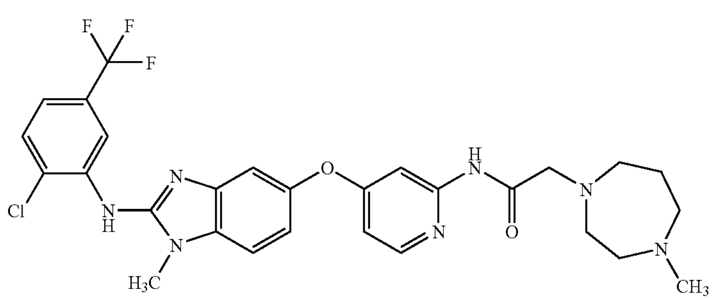 [SMILES: CN1CCCN(CC(=O)Nc2cc(Oc3ccc4c(c3)nc(Nc3cc(C(F)(F)F)ccc3Cl)n4C)ccn2)CC1] | N-{4-[(2-{[2-chloro-5-(trifluoromethyl)phenyl]amino}-1-methyl-1H-benzimidazol-5-yl)oxy]pyridin-2-yl}-2-(4-methyl-1,4-diazepan-1-yl)-acetamide | 589 |
| 259 | 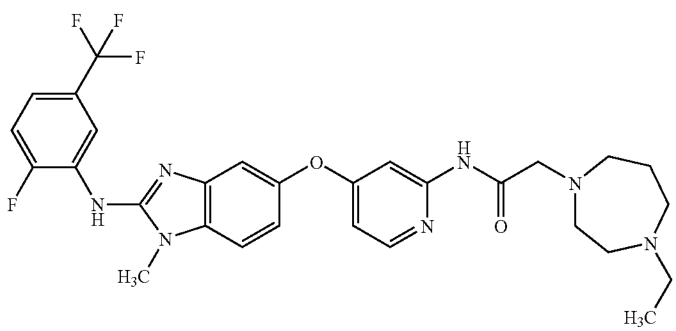 [SMILES: CCN1CCCN(CC(=O)Nc2cc(Oc3ccc4c(c3)nc(Nc3cc(C(F)(F)F)ccc3F)n4C)ccn2)CC1] | 2-(4-ethyl-1,4-diazepan-1-yl)-N-{4-[(2-{[2-fluoro-5-(trifluoromethyl)phenyl]amino}-1-methyl-1H-benzimidazol-5-yl)oxy]pyridin-2-yl}-acetamide | 586.6 |

TABLE 1-continued

| Ex. | Structure | Name | MH+ |
|---|---|---|---|
| 260 | 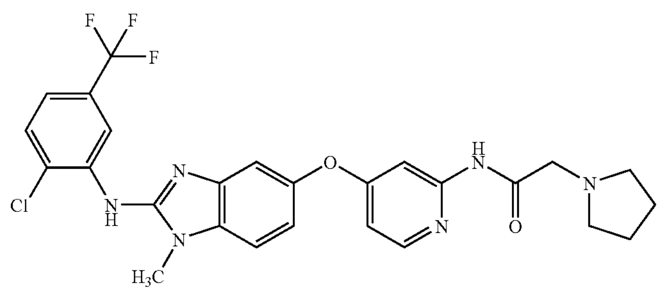 [SMILES: Cn1c(Nc2cc(C(F)(F)F)ccc2Cl)nc2cc(Oc3ccnc(NC(=O)CN4CCCC4)c3)ccc21] | N-{4-[(2-{[2-chloro-5-(trifluoro-methyl)phenyl]amino}-1-methyl-1H-benzimidazol-5-yl)oxy]pyridin-2-yl}-2-pyrrolidin-1-ylacetamide | 546 |
| 261 | 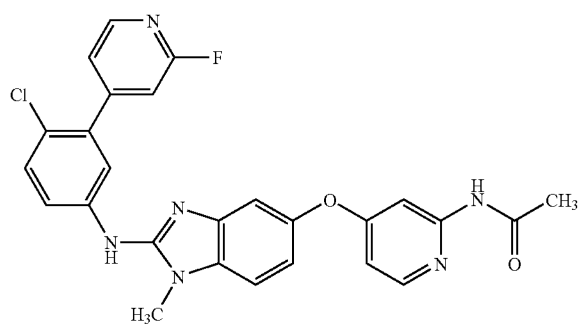 [SMILES: CC(=O)Nc1cc(Oc2ccc3c(c2)nc(Nc2ccc(Cl)c(-c4ccnc(F)c4)c2)n3C)ccn1] | N-{4-[(2-{[4-chloro-3-(2-fluoro-pyridin-4-yl)phenyl]amino}-1-methyl-1H-benzimidazol-5-yl)-oxy]pyridin-2-yl}acetamide | 503.9 |
| 262 | 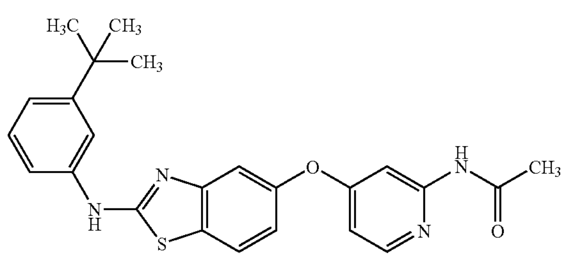 [SMILES: CC(=O)Nc1cc(Oc2ccc3sc(Nc4cccc(C(C)(C)C)c4)nc3c2)ccn1] | N-[4-({2-[(3-tert-butylphenyl)amino]-1,3-benzothiazol-5-yl}oxy)pyridin-2-yl]acetamide | 433.5 |
| 263 | 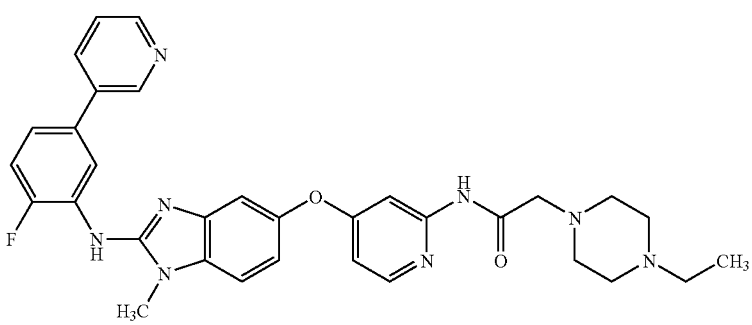 [SMILES: CCN1CCN(CC(=O)Nc2cc(Oc3ccc4c(c3)nc(Nc3cc(-c5cccnc5)ccc3F)n4C)ccn2)CC1] | 2-(4-ethylpiperazin-1-yl)-N-[4-({2-[(2-fluoro-5-pyridin-3-yl-phenyl)amino]-1-methyl-1H-benzimidazol-5-yl}oxy)pyridin-2-yl]acetamide | 581.7 |
| 264 | 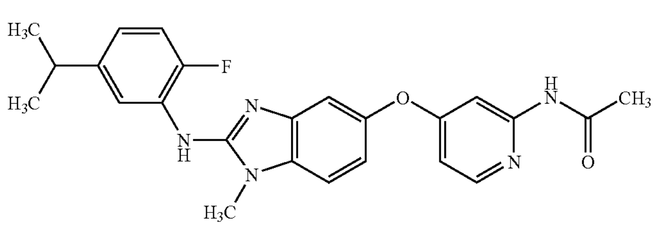 [SMILES: CC(=O)Nc1cc(Oc2ccc3c(c2)nc(Nc2cc(C(C)C)ccc2F)n3C)ccn1] | N-[4-({2-[(2-fluoro-5-isopropyl-phenyl)amino]-1-methyl-1H-benzimidazol-5-yl}oxy)pyridin-2-yl]acetamide | 434.5 |

TABLE 1-continued

| Ex. | Structure | Name | MH+ |
|---|---|---|---|
| 265 | 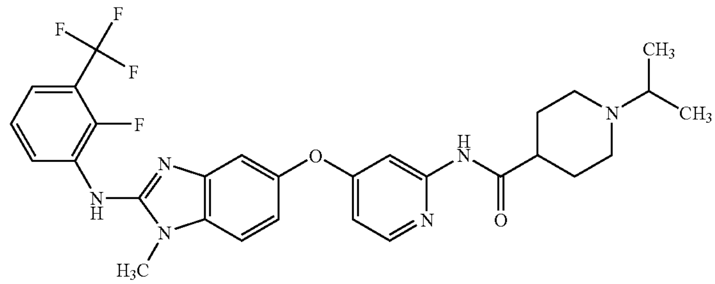 [SMILES: CC(C)N1CCC(C(=O)Nc2cc(Oc3ccc4c(c3)nc(Nc3cccc(C(F)(F)F)c3F)n4C)ccn2)CC1] | N-{4-[(2-{[2-fluoro-3-(trifluoro-methyl)phenyl]amino}-1-methyl-1H-benzimidazol-5-yl)oxy]pyridin-2-yl}-1-isopropylpiperidine-4-carboxamide | 571.6 |
| 266 | 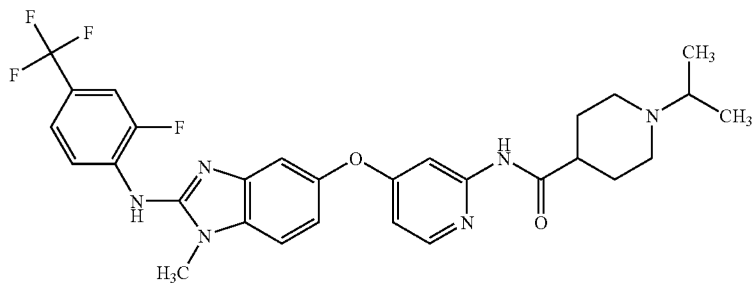 [SMILES: CC(C)N1CCC(C(=O)Nc2cc(Oc3ccc4c(c3)nc(Nc3ccc(C(F)(F)F)cc3F)n4C)ccn2)CC1] | N-{4-[(2-{[2-fluoro-4-(trifluoro-methyl)phenyl]amino}-1-methyl-1H-benzimidazol-5-yl)oxy]pyridin-2-yl}-1-isopropylpiperidine-4-carboxamide | 571.6 |
| 267 | 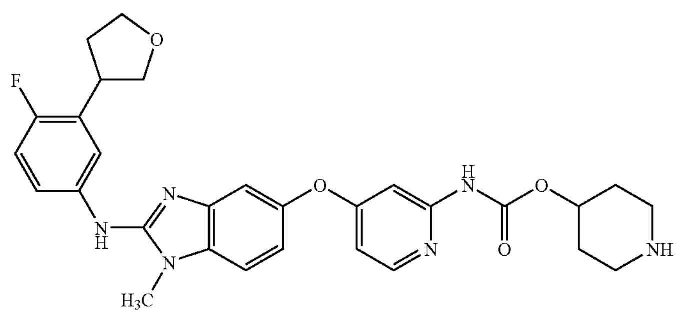 [SMILES: Cn1c(Nc2ccc(F)c(C3CCOC3)c2)nc2cc(Oc3ccnc(NC(=O)OC4CCNCC4)c3)ccc21] | piperidin-4-yl 4-({2-[(4-fluoro-3-tetrahydrofuran-3-ylphenyl)amino]-1-methyl-1H-benzimidazol-5-yl}oxy)pyridin-2-ylcarbamate | 547.6 |
| 268 | 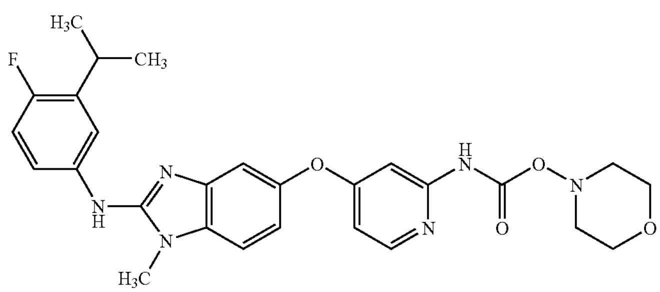 [SMILES: CC(C)c1cc(Nc2nc3cc(Oc4ccnc(NC(=O)ON5CCOCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-morpholin-4-ylacetamide | 519.6 |
| 269 | Chiral | (2S)-N-[4-({2-[(3-tert-butyl-phenyl)amino]-1-methyl-1H-benzimidazol-5-yl}oxy)pyridin-2-yl]piperidine-2-carboxamide | 499.6 |

TABLE 1-continued

| Ex. | Structure | Name | MH+ |
| --- | --- | --- | --- |
| 270 | Chiral | (2S)-N-[4-({2-[(2-fluoro-5-isopropyl-phenyl)amino]-1-methyl-1H-benzimidazol-5-yl}oxy)pyridin-2-yl]piperidine-2-carboxamide | 503.6 |
| 271 | 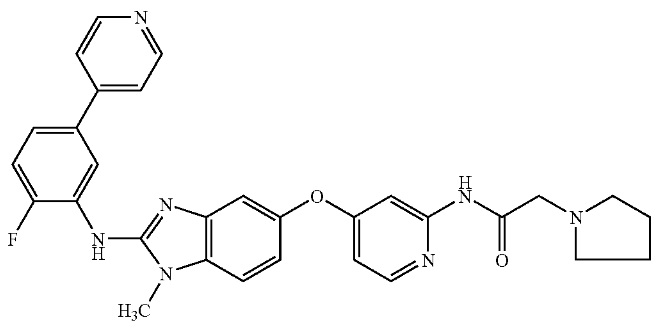 [SMILES: Cn1c(Nc2cc(-c3ccncc3)ccc2F)nc2cc(Oc3ccnc(NC(=O)CN4CCCC4)c3)ccc21] | N-[4-({2-[(2-fluoro-5-pyridin-4-ylphenyl)amino]-1-methyl-1H-benzimidazol-5-yl}oxy)pyridin-2-yl]-2-pyrrolidin-1-ylacetamide | 538.6 |
| 272 | 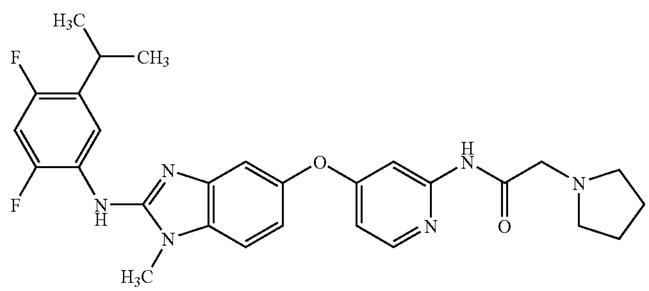 [SMILES: CC(C)c1cc(Nc2nc3cc(Oc4ccnc(NC(=O)CN5CCCC5)c4)ccc3n2C)c(F)cc1F] | N-[4-({2-[(2,4-difluoro-5-isopropyl-phenyl)amino]-1-methyl-1H-benzimidazol-5-yl}oxy)pyridin-2-yl]-2-pyrrolidin-1-ylacetamide | 521.6 |
| 273 | 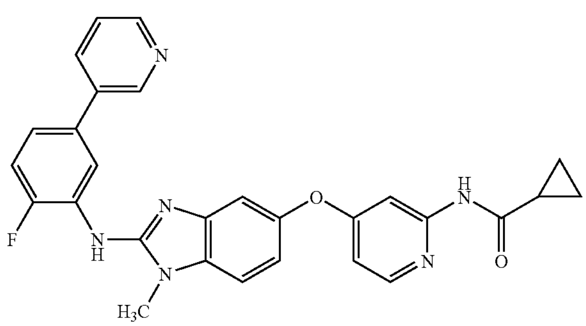 [SMILES: Cn1c(Nc2cc(-c3cccnc3)ccc2F)nc2cc(Oc3ccnc(NC(=O)C4CC4)c3)ccc21] | N-[4-({2-[(2-fluoro-5-pyridin-3-ylphenyl)amino]-1-methyl-1H-benzimidazol-5-yl}oxy)pyridin-2-yl]cyclopropanecarboxamide | 495.5 |
| 274 | 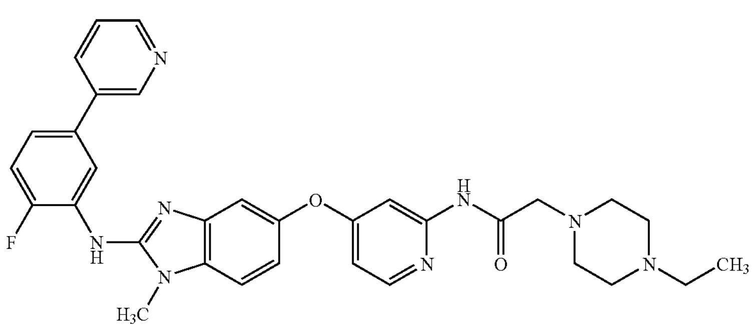 [SMILES: CCN1CCN(CC(=O)Nc2cc(Oc3ccc4c(c3)nc(Nc3cc(-c5cccnc5)ccc3F)n4C)ccn2)CC1] | 2-(4-ethylpiperazin-1-yl)-N-[4-({2-[(2-fluoro-5-pyridin-3-ylphenyl)amino]-1-methyl-1H-benzimidazol-5-yl}oxy)pyridin-2-yl]acetamide | 581.7 |

TABLE 1-continued

| Ex. | Structure | Name | MH+ |
|---|---|---|---|
| 275 | 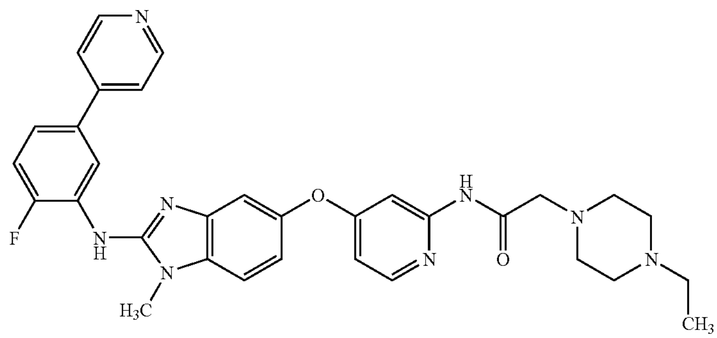 [SMILES: CCN1CCN(CC(=O)Nc2cc(Oc3ccc4c(c3)nc(Nc3cc(-c5ccncc5)ccc3F)n4C)ccn2)CC1] | 2-(4-ethylpiperazin-1-yl)-N-[4-({2-[(2-fluoro-5-pyridin-4-ylphenyl)-amino]-1-methyl-1H-benzimidazol-5-yl}oxy)pyridin-2-yl]acetamide | 581.7 |
| 276 | Chiral | N-[4-({2-[(2-fluoro-5-pyridin-4-ylphenyl)amino]-1-methyl-1H-benzimidazol-5-yl}oxy)pyridin-2-yl]-2-[(2S)-2-(hydroxymethyl)pyrrolidin-1-yl]acetamide | 568.6 |
| 277 | 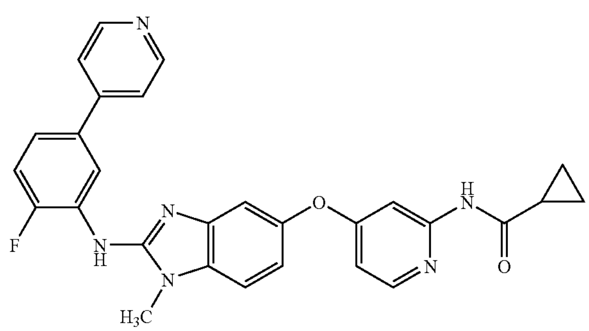 [SMILES: Cn1c(Nc2cc(-c3ccncc3)ccc2F)nc2cc(Oc3ccnc(NC(=O)C4CC4)c3)ccc21] | N-[4-({2-[(2-fluoro-5-pyridin-4-ylphenyl)amino]-1-methyl-1H-benzimidazol-5-yl}oxy)pyridin-2-yl]cyclopropanecarboxamide | 495.5 |
| 278 | 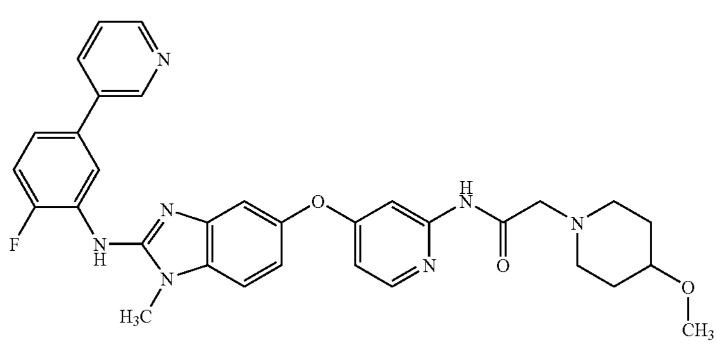 [SMILES: COC1CCN(CC(=O)Nc2cc(Oc3ccc4c(c3)nc(Nc3cc(-c5cccnc5)ccc3F)n4C)ccn2)CC1] | N-[4-({2-[(2-fluoro-5-pyridin-3-ylphenyl)amino]-1-methyl-1H-benzimidazol-5-yl}oxy)pyridin-2-yl]-2-(4-methoxypiperidin-1-yl)acetamide | 582.6 |

TABLE 1-continued

| Ex. | Structure | Name | MH+ |
|---|---|---|---|
| 279 | Chiral | 2-[(2R,4R)-2,4-dimethylazetidin-1-yl]-N-[4-({2-[(2-fluoro-5-pyridin-3-ylphenyl)amino]-1-methyl-1H-benzimidazol-5-yl}oxy)pyridin-2-yl]acetamide | 552.6 |
| 280 | 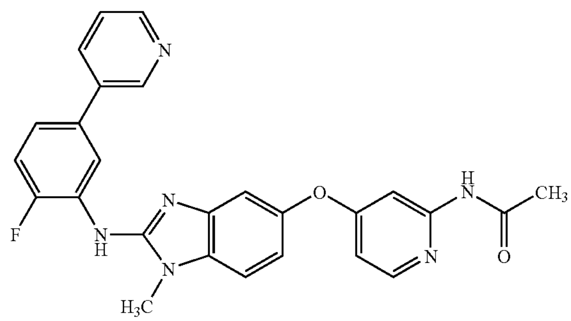 [SMILES: CC(=O)Nc1cc(Oc2ccc3c(c2)nc(Nc2cc(-c4cccnc4)ccc2F)n3C)ccn1] | N-[4-({2-[(2-fluoro-5-pyridin-3-ylphenyl)amino]-1-methyl-1H-benzimidazol-5-yl}oxy)pyridin-2-yl]acetamide | 469.5 |
| 281 | 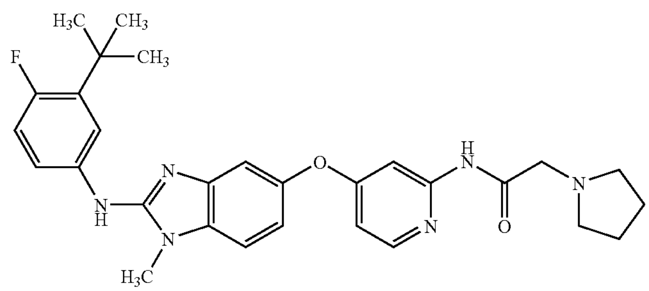 [SMILES: Cn1c(Nc2ccc(F)c(C(C)(C)C)c2)nc2cc(Oc3ccnc(NC(=O)CN4CCCC4)c3)ccc21] | N-[4-({2-[(3-tert-butyl-4-fluorophenyl)amino]-1-methyl-1H-benzimidazol-5-yl}oxy)pyridin-2-yl]-2-pyrrolidin-1-ylacetamide | 517.6 |
| 282 | 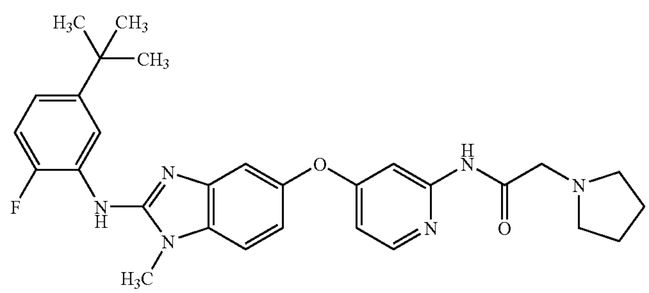 [SMILES: Cn1c(Nc2cc(C(C)(C)C)ccc2F)nc2cc(Oc3ccnc(NC(=O)CN4CCCC4)c3)ccc21] | N-[4-({2-[(5-tert-butyl-2-fluorophenyl)amino]-1-methyl-1H-benzimidazol-5-yl}oxy)pyridin-2-yl]-2-pyrrolidin-1-ylacetamide | 517.6 |
| 283 | Chiral | (2S)-N-[4-({2-[(4-fluoro-3-isopropylphenyl)amino]-1-methyl-1H-benzimidazol-5-yl}oxy)pyridin-2-yl]piperidine-2-carboxamide | 503.6 |

TABLE 1-continued

| Ex. | Structure | Name | MH+ |
|---|---|---|---|
| 284 | 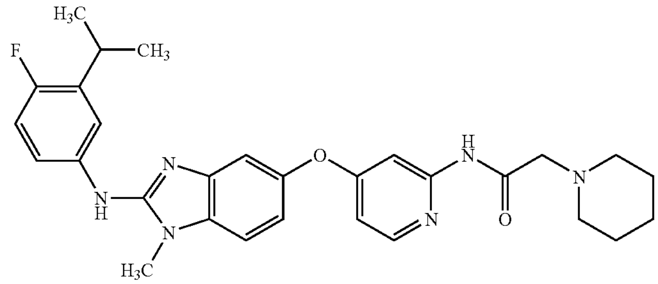 [SMILES: CC(C)c1cc(Nc2nc3cc(Oc4ccnc(NC(=O)CN5CCCCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-2-piperidin-1-ylacetamide | 517.6 |
| 285 | 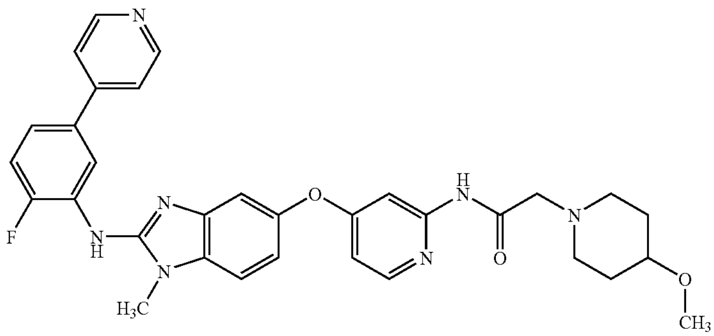 [SMILES: COC1CCN(CC(=O)Nc2cc(Oc3ccc4c(c3)nc(Nc3cc(-c5ccncc5)ccc3F)n4C)ccn2)CC1] | N-[4-({2-[(2-fluoro-5-pyridin-4-ylphenyl)amino]-1-methyl-1H-benzimidazol-5-yl}oxy)pyridin-2-yl]-2-(4-methoxypiperidin-1-yl)-acetamide | 582.6 |
| 286 | 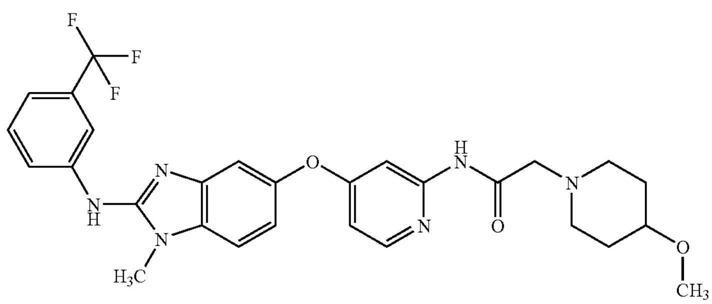 [SMILES: COC1CCN(CC(=O)Nc2cc(Oc3ccc4c(c3)nc(Nc3cccc(C(F)(F)F)c3)n4C)ccn2)CC1] | 2-(4-methoxypiperidin-1-yl)-N-{4-[(1-methyl-2-{[3-(trifluoromethyl)-phenyl]amino}-1H-benzimidazol-5-yl)oxy]pyridin-2-yl}acetamide | 555.6 |
| 287 | 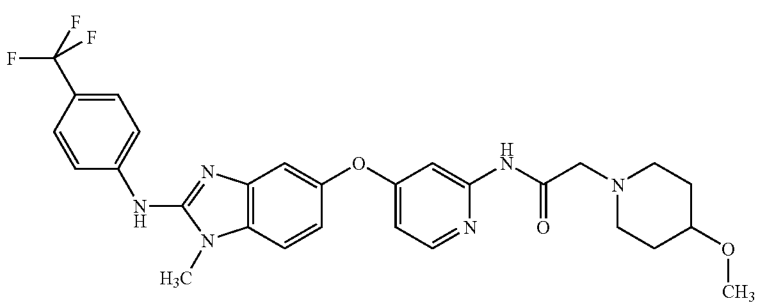 [SMILES: COC1CCN(CC(=O)Nc2cc(Oc3ccc4c(c3)nc(Nc3ccc(C(F)(F)F)cc3)n4C)ccn2)CC1] | 2-(4-methoxypiperidin-1-yl)-N-{4-[(1-methyl-2-{[4-(trifluoromethyl)-phenyl]amino}-1H-benzimidazol-5-yl)oxy]pyridin-2-yl}acetamide | 555.6 |
| 288 | 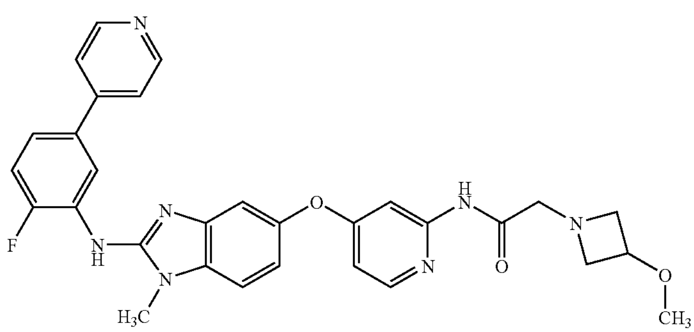 [SMILES: COC1CN(CC(=O)Nc2cc(Oc3ccc4c(c3)nc(Nc3cc(-c5ccncc5)ccc3F)n4C)ccn2)C1] | N-[4-({2-[(2-fluoro-5-pyridin-4-yl-phenyl)amino]-1-methyl-1H-benzimidazol-5-yl}oxy)pyridin-2-yl]-2-(3-methoxyazetidin-1-yl)-acetamide | 554.6 |

TABLE 1-continued

| Ex. | Structure | Name | MH+ |
|---|---|---|---|
| 289 | 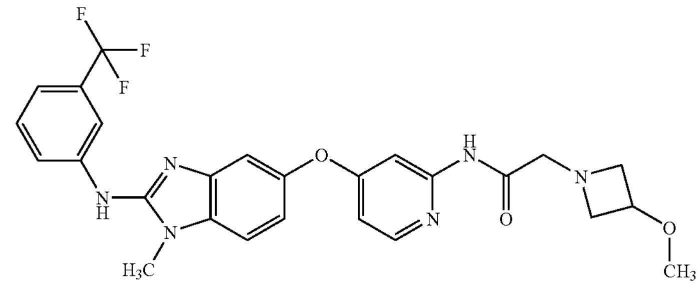 [SMILES: COC1CN(CC(=O)Nc2cc(Oc3ccc4c(c3)nc(Nc3cccc(C(F)(F)F)c3)n4C)ccn2)C1] | 2-(3-methoxyazetidin-1-yl)-N-{4-[(1-methyl-2-{[3-(trifluoromethyl)-phenyl]amino}-1H-benzimidazol-5-yl)oxy]pyridin-2-yl}acetamide | 527.5 |
| 290 | 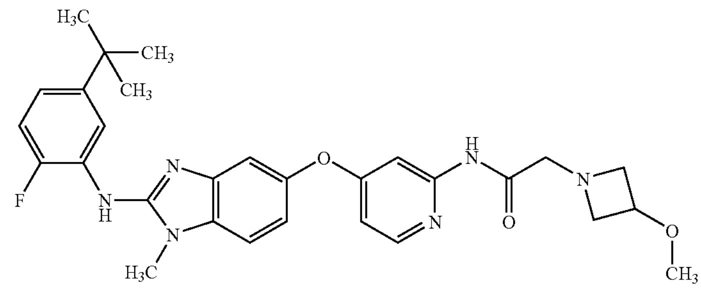 [SMILES: COC1CN(CC(=O)Nc2cc(Oc3ccc4c(c3)nc(Nc3cc(C(C)(C)C)ccc3F)n4C)ccn2)C1] | N-[4-({2-[(5-tert-butyl-2-fluoro-phenyl)amino]-1-methyl-1H-benzimidazol-5-yl}oxy)pyridin-2-yl]-2-(3-methoxyazetidin-1-yl)-acetamide | 533.6 |
| 291 | 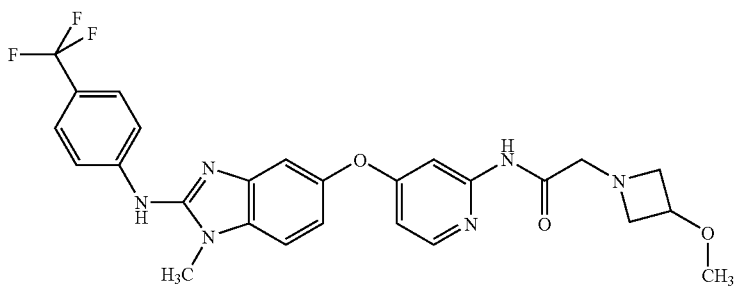 [SMILES: COC1CN(CC(=O)Nc2cc(Oc3ccc4c(c3)nc(Nc3ccc(C(F)(F)F)cc3)n4C)ccn2)C1] | 2-(3-methoxyazetidin-1-yl)-N-{4-[(1-methyl-2-{[4-(trifluoromethyl)-phenyl]amino}-1H-benzimidazol-5-yl)oxy]pyridin-2-yl}acetamide | 527.5 |
| 292 | 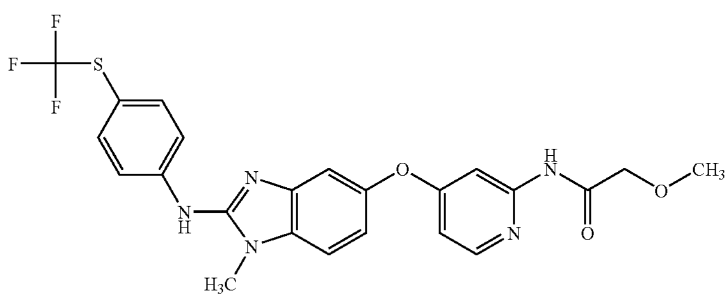 [SMILES: COCC(=O)Nc1cc(Oc2ccc3c(c2)nc(Nc2ccc(SC(F)(F)F)cc2)n3C)ccn1] | 2-methoxy-N-(4-{[1-methyl-2-({4-[(trifluoromethyl)thio]phenyl}amino)-1H-benzimidazol-5-yl]oxy}pyridin-2-yl)acetamide | 504.5 |
| 293 | 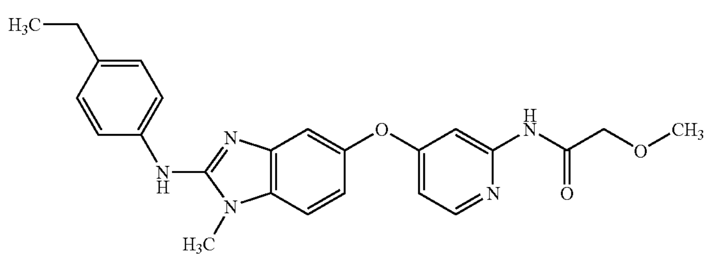 [SMILES: CCc1ccc(Nc2nc3cc(Oc4ccnc(NC(=O)COC)c4)ccc3n2C)cc1] | N-[4-({2-[(4-ethylphenyl)amino]-1-methyl-1H-benzimidazol-5-yl}-oxy)pyridin-2-yl]-2-methoxy-acetamide | 432.5 |

TABLE 1-continued

| Ex. | Structure | Name | MH+ |
|---|---|---|---|
| 294 | 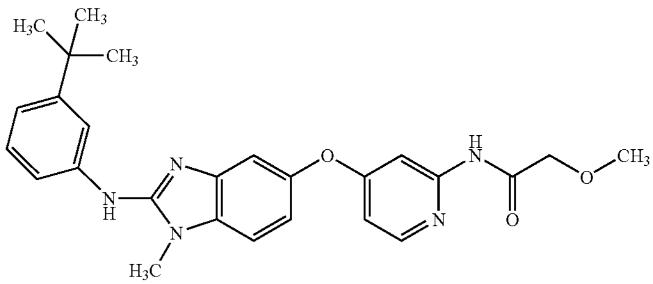 [SMILES: COCC(=O)Nc1cc(Oc2ccc3c(c2)nc(Nc2cccc(C(C)(C)C)c2)n3C)ccn1] | N-[4-({2-[(3-tert-butylphenyl)amino]-1-methyl-1H-benzimidazol-5-yl}-oxy)pyridin-2-yl]-2-methoxy-acetamide | 460.5 |
| 295 | 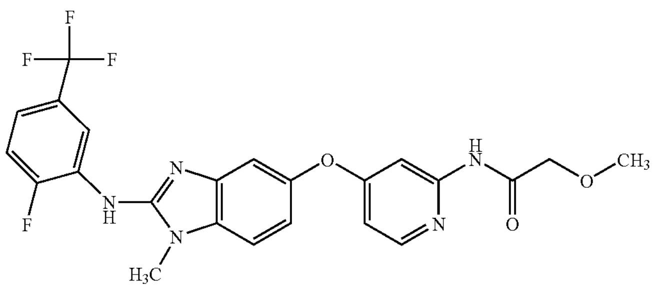 [SMILES: COCC(=O)Nc1cc(Oc2ccc3c(c2)nc(Nc2cc(C(F)(F)F)ccc2F)n3C)ccn1] | N-{4-[(2-{[2-fluoro-5-(trifluoro-methyl)phenyl]amino}-1-methyl-1H-benzimidazol-5-yl)oxy]pyridin-2-yl}-2-methoxyacetamide | 490.4 |
| 296 | 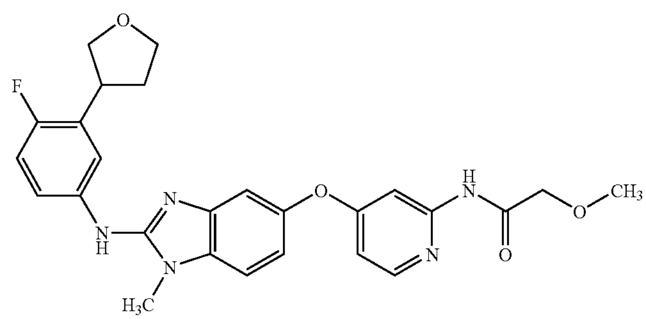 [SMILES: COCC(=O)Nc1cc(Oc2ccc3c(c2)nc(Nc2ccc(F)c(C4CCOC4)c2)n3C)ccn1] | N-[4-({2-[(4-fluoro-3-tetrahydro-furan-3-ylphenyl)amino]-1-methyl-1H-benzimidazol-5-yl}oxy)pyridin-2-yl]-2-methoxyacetamide | 492.5 |
| 297 | 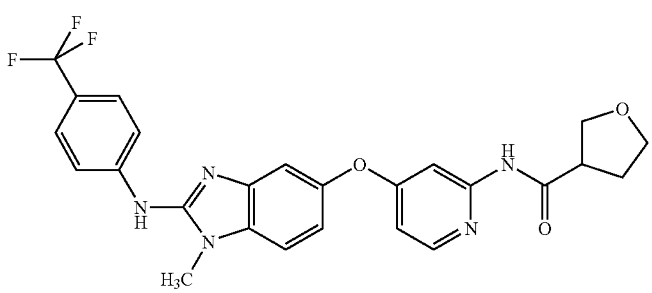 | N-{4-[(1-methyl-2-{[4-(trifluoro-methyl)phenyl]amino}-1H-benzimidazol-5-yl)oxy]pyridin-2-yl}-tetrahydrofuran-3-carboxamide | 498.5 |
| 298 | 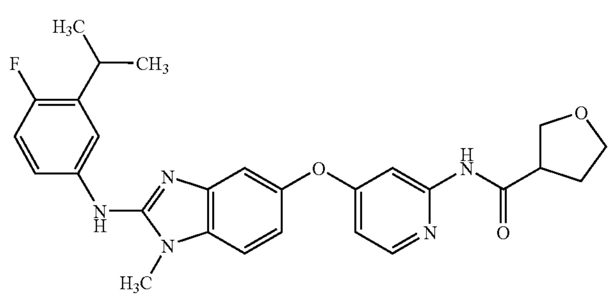 [SMILES: CC(C)c1cc(Nc2nc3cc(Oc4ccnc(NC(=O)C5CCOC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-tetrahydrofuran-3-carboxamide | 490.5 |

TABLE 1-continued

| Ex. | Structure | Name | MH+ |
|---|---|---|---|
| 299 | 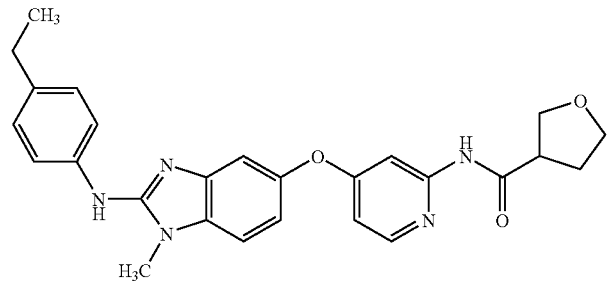 | N-[4-({2-[(4-ethylphenyl)amino]-1-methyl-1H-benzimidazol-5-yl}oxy)-pyridin-2-yl]tetrahydrofuran-3-carboxamide | 458.5 |
| 300 | 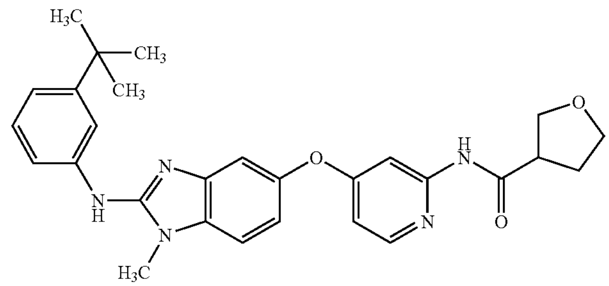 | N-[4-({2-[(3-tert-butylphenyl)amino]-1-methyl-1H-benzimidazol-5-yl}-oxy)pyridin-2-yl]tetrahydrofuran-3-carboxamide | 486.6 |
| 301 | 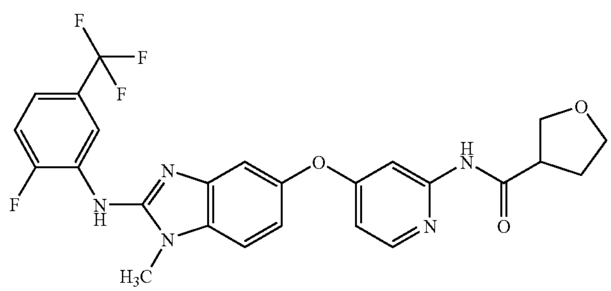 | N-{4-[(2-{[2-fluoro-5-(trifluoro-methyl)phenyl]amino}-1-methyl-1H-benzimidazol-5-yl)oxy]pyridin-2-yl}-tetrahydrofuran-3-carboxamide | 516.5 |
| 302 | 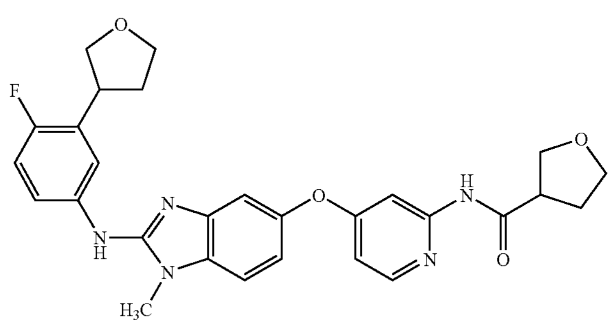 | N-[4-({2-[(4-fluoro-3-tetrahydro-furan-3-ylphenyl)amino]-1-methyl-1H-benzimidazol-5-yl}oxy)pyridin-2-yl]tetrahydrofuran-3-carboxamide | 518.6 |
| 303 | 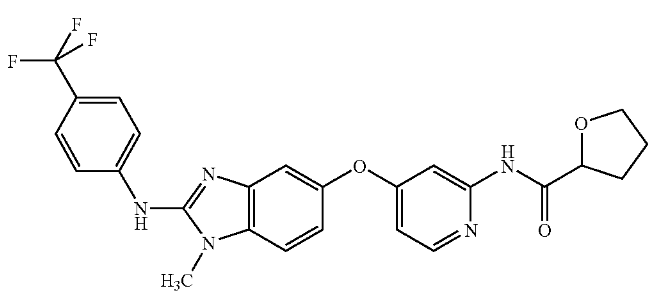 [SMILES: Cn1c(Nc2ccc(C(F)(F)F)cc2)nc2cc(Oc3ccnc(NC(=O)C4CCCO4)c3)ccc21] | N-{4-[(1-methyl-2-{[4-(trifluoro-methyl)phenyl]amino}-1H-benzimidazol-5-yl)oxy]pyridin-2-yl}-tetrahydrofuran-2-carboxamide | 498.5 |

TABLE 1-continued

| Ex. | Structure | Name | MH+ |
|---|---|---|---|
| 304 | 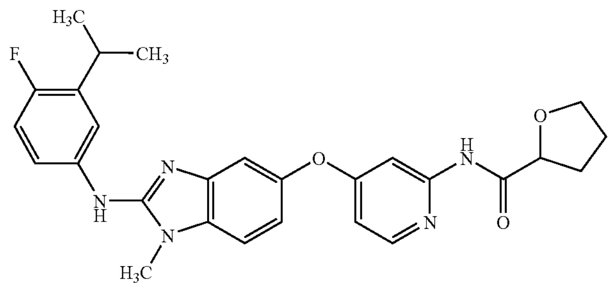 [SMILES: CC(C)c1cc(Nc2nc3cc(Oc4ccnc(NC(=O)C5CCCO5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-tetrahydrofuran-2-carboxamide | 490.5 |
| 305 | 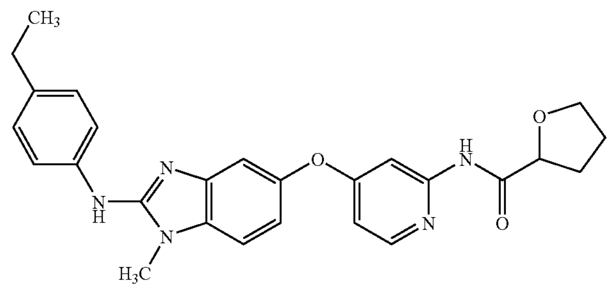 [SMILES: CCc1ccc(Nc2nc3cc(Oc4ccnc(NC(=O)C5CCCO5)c4)ccc3n2C)cc1] | N-[4-({2-[(4-ethylphenyl)amino]-1-methyl-1H-benzimidazol-5-yl}oxy)-pyridin-2-yl]tetrahydrofuran-2-carboxamide | 458.5 |
| 306 | 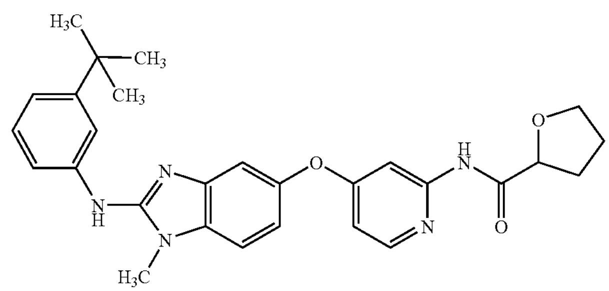 [SMILES: Cn1c(Nc2cccc(C(C)(C)C)c2)nc2cc(Oc3ccnc(NC(=O)C4CCCO4)c3)ccc21] | N-[4-({2-[(3-tert-butylphenyl)amino]-1-methyl-1H-benzimidazol-5-yl}-oxy)pyridin-2-yl]tetrahydrofuran-2-carboxamide | 486.6 |
| 307 | 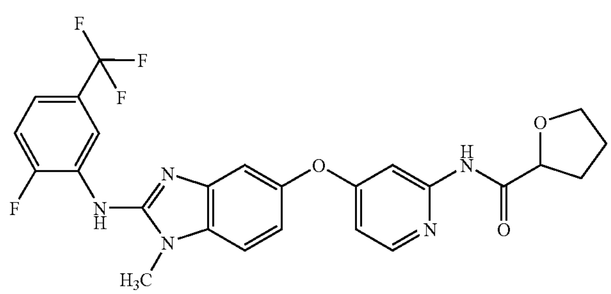 [SMILES: Cn1c(Nc2cc(C(F)(F)F)ccc2F)nc2cc(Oc3ccnc(NC(=O)C4CCCO4)c3)ccc21] | N-{4-[(2-{[2-fluoro-5-(trifluoro-methyl)phenyl]amino}-1-methyl-1H-benzimidazol-5-yl)oxy]pyridin-2-yl}-tetrahydrofuran-2-carboxamide | 516.5 |
| 308 | 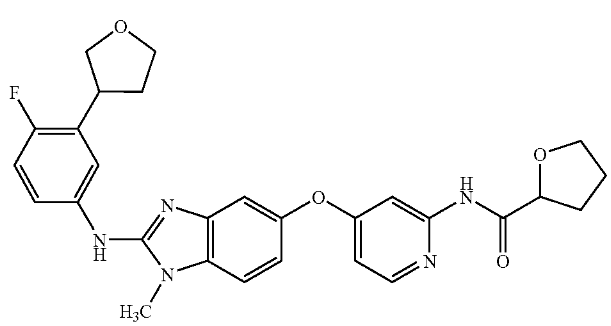 [SMILES: Cn1c(Nc2ccc(F)c(C3CCOC3)c2)nc2cc(Oc3ccnc(NC(=O)C4CCCO4)c3)ccc21] | N-[4-({2-[(4-fluoro-3-tetrahydro-furan-3-ylphenyl)amino]-1-methyl-1H-benzimidazol-5-yl}oxy)pyridin-2-yl]tetrahydrofuran-2-carboxamide | 518.6 |

TABLE 1-continued

| Ex. | Structure | Name | MH+ |
|---|---|---|---|
| 309 | 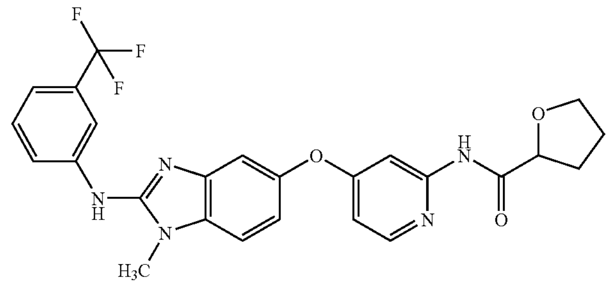 [SMILES: Cn1c(Nc2cccc(C(F)(F)F)c2)nc2cc(Oc3ccnc(NC(=O)C4CCCO4)c3)ccc21] | N-{4-[(1-methyl-2-{[3-(trifluoromethyl)phenyl]amino}-1H-benzimidazol-5-yl)oxy]pyridin-2-yl-tetrahydrofuran-2-carboxamide | 498.5 |
| 310 | 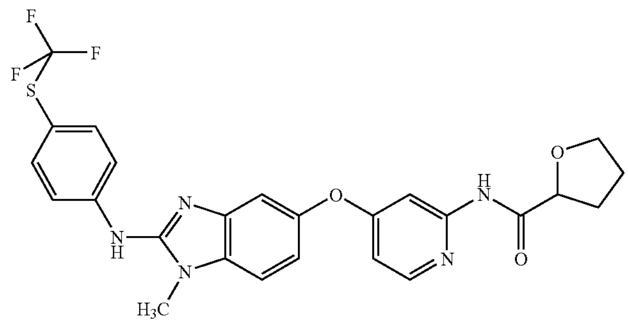 [SMILES: Cn1c(Nc2ccc(SC(F)(F)F)cc2)nc2cc(Oc3ccnc(NC(=O)C4CCCO4)c3)ccc21] | N-(4-{[1-methyl-2-({4-[(trifluoromethyl)thio]phenyl}amino)-1H-benzimidazol-5-yl]oxy}pyridin-2-yl)tetrahydrofuran-2-carboxamide | 530.5 |
| 311 | 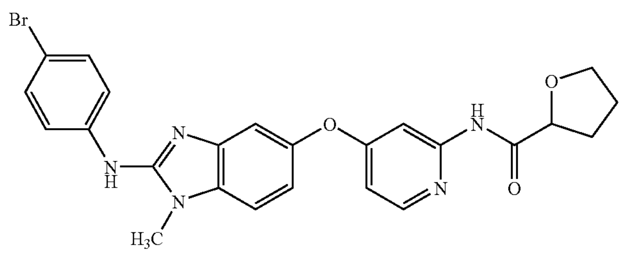 [SMILES: Cn1c(Nc2ccc(Br)cc2)nc2cc(Oc3ccnc(NC(=O)C4CCCO4)c3)ccc21] | N-[4-({2-[(4-bromophenyl)amino]-1-methyl-1H-benzimidazol-5-yl}oxy)-pyridin-2-yl]tetrahydrofuran-2-carboxamide | 509.4 |
| 312 | 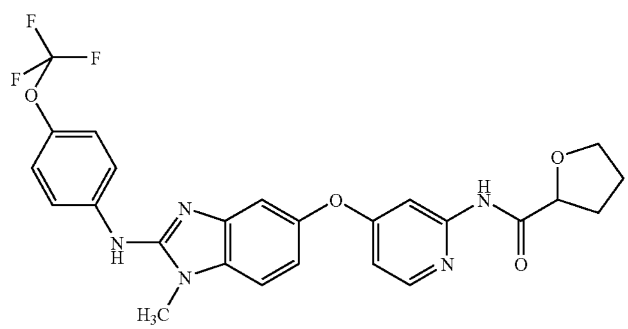 | N-{4-[(1-methyl-2-{[4-(trifluoromethoxy)phenyl]amino}-1H-benzimidazol-5-yl)oxy]pyridin-2-yl}-tetrahydrofuran-2-carboxamide | 514.5 |
| 313 | 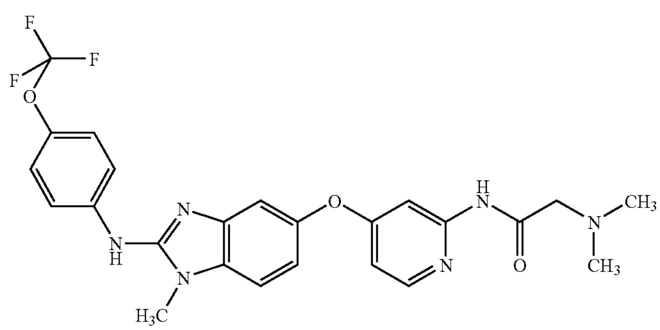 [SMILES: CN(C)CC(=O)Nc1cc(Oc2ccc3c(c2)nc(Nc2ccc(OC(F)(F)F)cc2)n3C)ccn1] | N~2~,N~2~-dimethyl-N~1~-{4-[(1-methyl-2-{[4-(trifluoromethoxy)-phenyl]amino}-1H-benzimidazol-5-yl)oxy]pyridin-2-yl}glycinamide | 501.5 |

TABLE 1-continued

| Ex. | Structure | Name | MH+ |
|---|---|---|---|
| 314 | 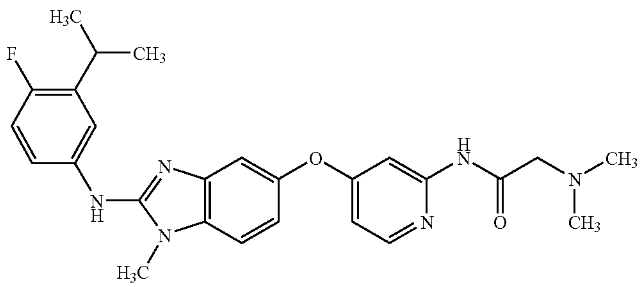 [SMILES: CC(C)c1cc(Nc2nc3cc(Oc4ccnc(NC(=O)CN(C)C)c4)ccc3n2C)ccc1F] | N~1~-[4-({2-[(4-fluoro-3-isopropyl-phenyl)amino]-1-methyl-1H-benzimidazol-5-yl}oxy)pyridin-2-yl]-N~2~,N~2~-dimethylglycinamide | 477.6 |
| 315 | 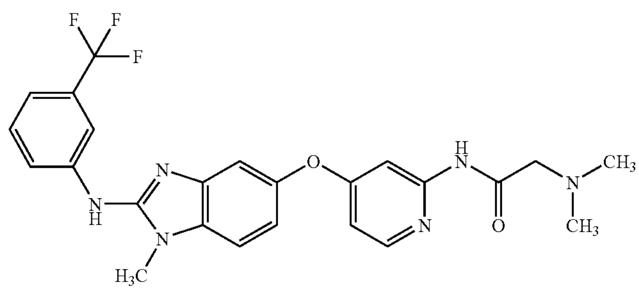 [SMILES: CN(C)CC(=O)Nc1cc(Oc2ccc3c(c2)nc(Nc2cccc(C(F)(F)F)c2)n3C)ccn1] | N~2~,N~2~-dimethyl-N~1~-{4-[(1-methyl-2-{[3-(trifluoromethyl)-phenyl]amino}-1H-benzimidazol-5-yl)oxy]pyridin-2-yl}glycinamide | 485.5 |
| 316 | 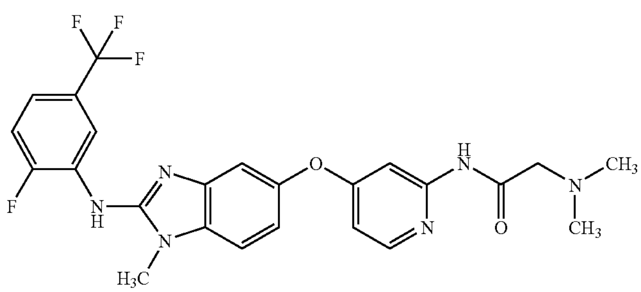 [SMILES: CN(C)CC(=O)Nc1cc(Oc2ccc3c(c2)nc(Nc2cc(C(F)(F)F)ccc2F)n3C)ccn1] | N~1~-{4-[(2-{[2-fluoro-5-(trifluoro-methyl)phenyl]amino}-1-methyl-1H-benzimidazol-5-yl)oxy]pyridin-2-yl]-N~2~,N~2~-dimethylglycinamide | 503.5 |
| 317 | 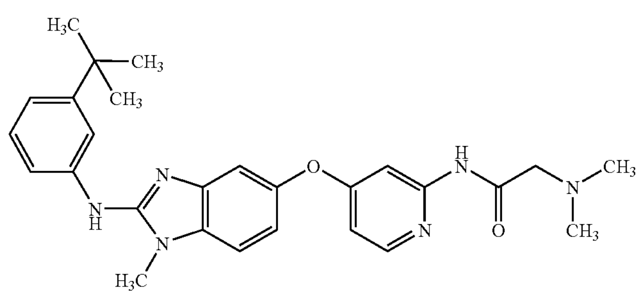 [SMILES: CN(C)CC(=O)Nc1cc(Oc2ccc3c(c2)nc(Nc2cccc(C(C)(C)C)c2)n3C)ccn1] | N~1~-[4-({2-[(3-tert-butylphenyl)-amino]-1-methyl-1H-benzimidazol-5-yl}oxy)pyridin-2-yl]-N~2~,N~2~-dimethylglycinamide | 473.6 |
| 318 | 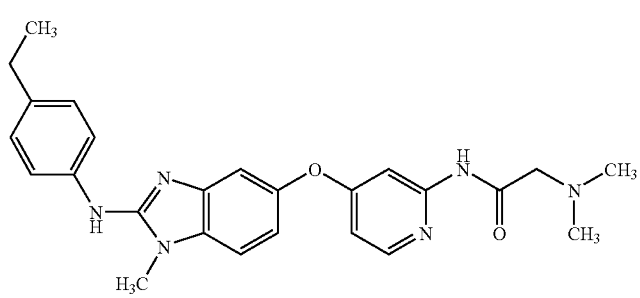 [SMILES: CCc1ccc(Nc2nc3cc(Oc4ccnc(NC(=O)CN(C)C)c4)ccc3n2C)cc1] | N~1~-[4-({2-[(4-ethylphenyl)amino]-1-methyl-1H-benzimidazol-5-yl}oxy)pyridin-2-yl]-N~2~,N~2~-dimethylglycinamide | 445.5 |

TABLE 1-continued

| Ex. | Structure | Name | MH+ |
|---|---|---|---|
| 319 | 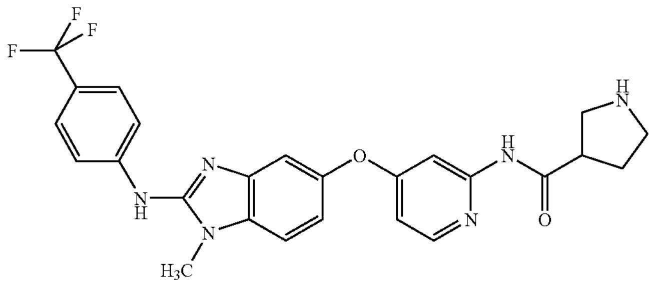 | N-{4-[(1-methyl-2-{[4-(trifluoromethyl)phenyl]amino}-1H-benzimidazol-5-yl)oxy]pyridin-2-yl}-pyrrolidine-3-carboxamide | 497.5 |
| 320 | 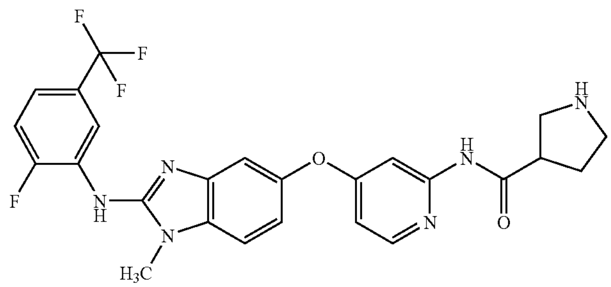 | N-{4-[(2-{[2-fluoro-5-(trifluoromethyl)phenyl]amino}-1-methyl-1H-benzimidazol-5-yl)oxy]pyridin-2-yl}-pyrrolidine-3-carboxamide | 515.5 |
| 321 | 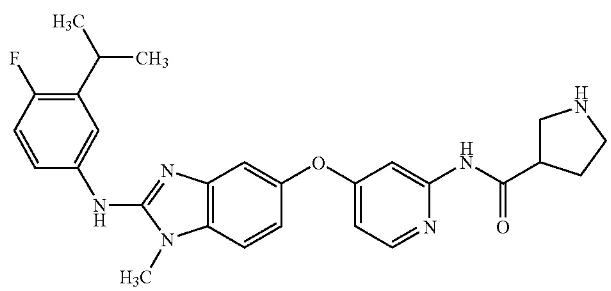 [SMILES: CC(C)c1cc(Nc2nc3cc(Oc4ccnc(NC(=O)C5CCNC5)c4)ccc3n2C)ccc1F] | N-[4-({2-[(4-fluoro-3-isopropylphenyl)amino]-1-methyl-1H-benzimidazol-5-yl}oxy)pyridin-2-yl]-pyrrolidine-3-carboxamide | 489.6 |
| 322 | 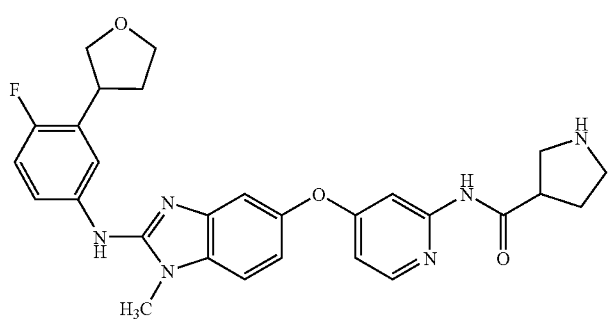 [SMILES: Cn1c(Nc2ccc(F)c(C3CCOC3)c2)nc2cc(Oc3ccnc(NC(=O)C4CCNC4)c3)ccc21] | N-[4-({2-[(4-fluoro-3-tetrahydrofuran-3-ylphenyl)amino]-1-methyl-1H-benzimidazol-5-yl}-oxy)pyridin-2-yl]pyrrolidine-3-carboxamide | 517.6 |
| 323 | 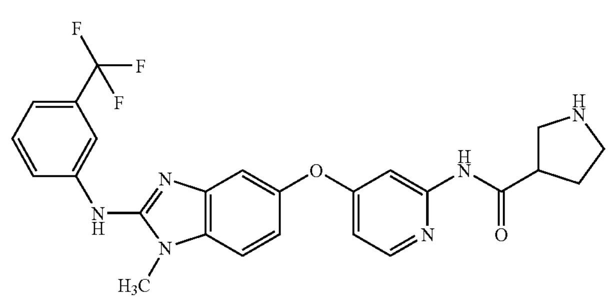 | N-{4-[(1-methyl-2-{[3-(trifluoromethyl)phenyl]amino}-1H-benzimidazol-5-yl)oxy]pyridin-2-yl}-pyrrolidine-3-carboxamide | 497.5 |

TABLE 1-continued

| Ex. | Structure | Name | MH+ |
|---|---|---|---|
| 324 | 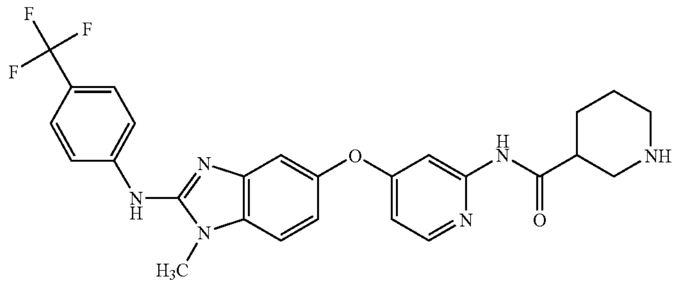 [SMILES: Cn1c(Nc2ccc(C(F)(F)F)cc2)nc2cc(Oc3ccnc(NC(=O)C4CCCNC4)c3)ccc21] | N-{4-[(1-methyl-2-{[4-(trifluoromethyl)phenyl]amino}-1H-benzimidazol-5-yl)oxy]pyridin-2-yl}-piperidine-3-carboxamide | 511.5 |
| 325 | 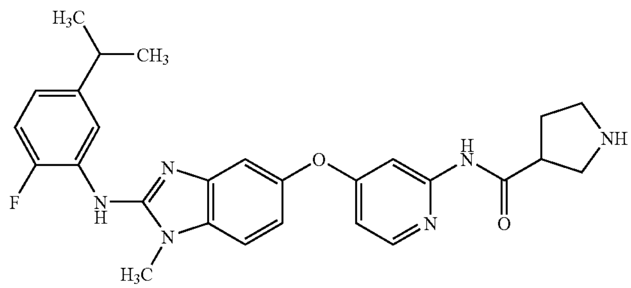 [SMILES: CC(C)c1ccc(F)c(Nc2nc3cc(Oc4ccnc(NC(=O)C5CCNC5)c4)ccc3n2C)c1] | N-[4-({2-[(2-fluoro-5-isopropyl-phenyl)amino]-1-methyl-1H-benzimidazol-5-yl}oxy)pyridin-2-yl]-pyrrolidine-3-carboxamide | 489.6 |
| 326 | 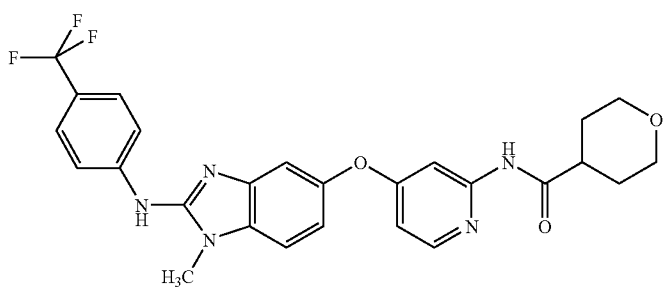 [SMILES: Cn1c(Nc2ccc(C(F)(F)F)cc2)nc2cc(Oc3ccnc(NC(=O)C4CCOCC4)c3)ccc21] | N-{4-[(1-methyl-2-{[4-(trifluoromethyl)phenyl]amino}-1-1H-benzimidazol-5-yl)oxy]pyridin-2-yl}-tetrahydro-2H-pyran-4-carboxamide | 512.5 |
| 327 | 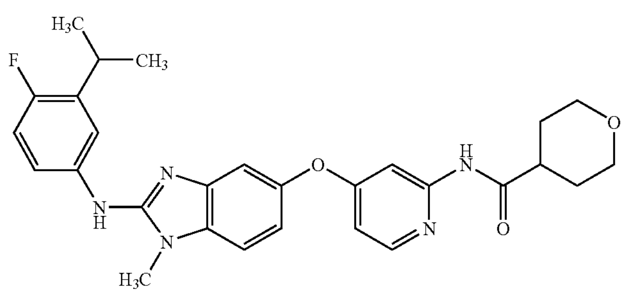 [SMILES: CC(C)c1cc(Nc2nc3cc(Oc4ccnc(NC(=O)C5CCOCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-tetrahydro-2H-pyran-4-carboxamide | 504.6 |
| 328 | 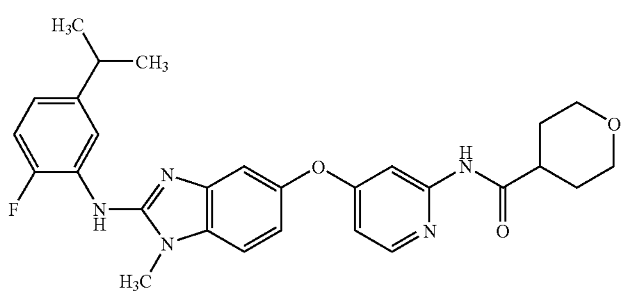 [SMILES: CC(C)c1ccc(F)c(Nc2nc3cc(Oc4ccnc(NC(=O)C5CCOCC5)c4)ccc3n2C)c1] | N-[4-({2-[(2-fluoro-5-isopropyl-phenyl)amino]-1-methyl-1H-benzimidazol-5-yl}oxy)pyridin-2-yl]-tetrahydro-2H-pyran-4-carboxamide | 504.6 |

TABLE 1-continued

| Ex. | Structure | Name | MH+ |
|---|---|---|---|
| 329 | 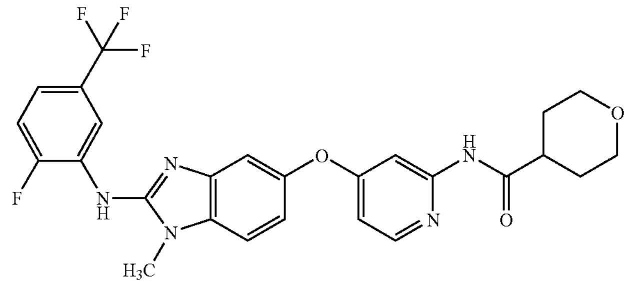 [SMILES: Cn1c(Nc2cc(C(F)(F)F)ccc2F)nc2cc(Oc3ccnc(NC(=O)C4CCOCC4)c3)ccc21] | N-{4-[(2-{[2-fluoro-5-(trifluoro-methyl)phenyl]amino}-1-methyl-1H-benzimidazol-5-yl)oxy]pyridin-2-yl}-tetrahydro-2H-pyran-4-carboxamide | 530.5 |
| 330 | 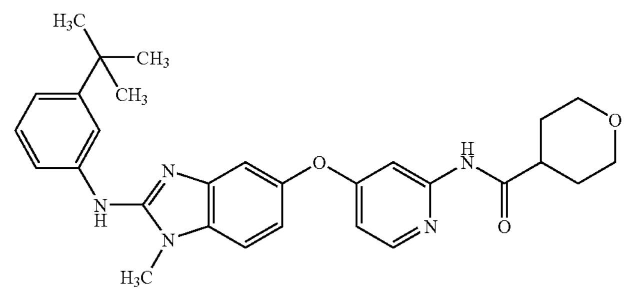 [SMILES: Cn1c(Nc2cccc(C(C)(C)C)c2)nc2cc(Oc3ccnc(NC(=O)C4CCOCC4)c3)ccc21] | N-[4-({2-[(3-tert-butylphenyl)amino]-1-methyl-1H-benzimidazol-5-yl}-oxy)pyridin-2-yl]tetrahydro-2H-pyran-4-carboxamide | 500.6 |
| 331 | 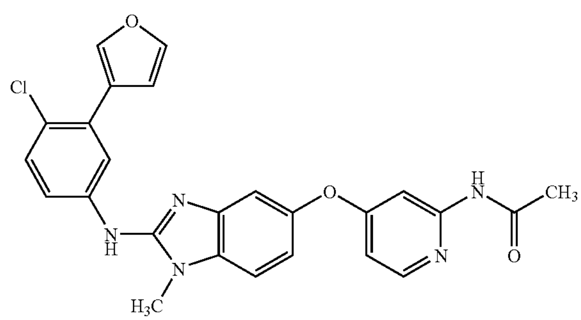 [SMILES: CC(=O)Nc1cc(Oc2ccc3c(c2)nc(Nc2ccc(Cl)c(-c4ccoc4)c2)n3C)ccn1] | N-{4-[(2-{[4-chloro-3-(3-furyl)-phenyl]amino}-1-methyl-1H-benzimidazol-5-yl)oxy]pyridin-2-yl}-acetamide | 474.9 |
| 332 | 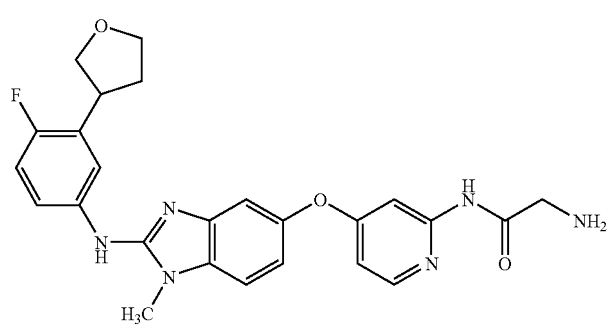 [SMILES: Cn1c(Nc2ccc(F)c(C3CCOC3)c2)nc2cc(Oc3ccnc(NC(=O)CN)c3)ccc21] | N~1~-[4-({2-[(4-fluoro-3-tetrahydro-furan-3-ylphenyl)amino]-1-methyl-1H-benzimidazol-5-yl}oxy)pyridin-2-yl]glycinamide | 477.5 |
| 333 | 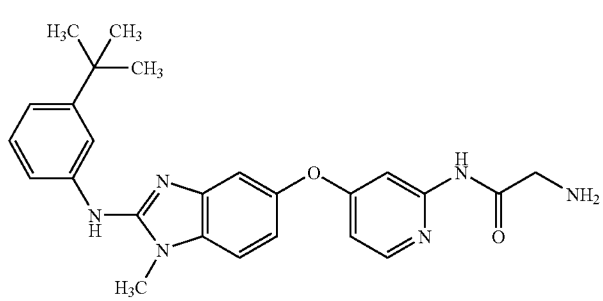 [SMILES: Cn1c(Nc2cccc(C(C)(C)C)c2)nc2cc(Oc3ccnc(NC(=O)CN)c3)ccc21] | N~1~-[4-({2-[(3-tert-butylphenyl)-amino]-1-methyl-1H-benzimidazol-5-yl}oxy)pyridin-2-yl]glycinamide | 445.5 |

TABLE 1-continued

| Ex. | Structure | Name | MH+ |
|---|---|---|---|
| 334 | 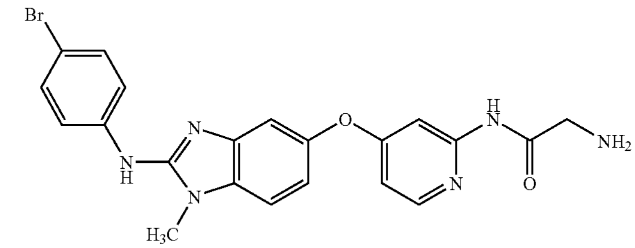 [SMILES: Cn1c(Nc2ccc(Br)cc2)nc2cc(Oc3ccnc(NC(=O)CN)c3)ccc21] | N~1~-[4-({2-[(4-bromophenyl)-amino]-1-methyl-1H-benzimidazol-5-yl}oxy)pyridin-2-yl]glycinamide | 468.3 |
| 335 | 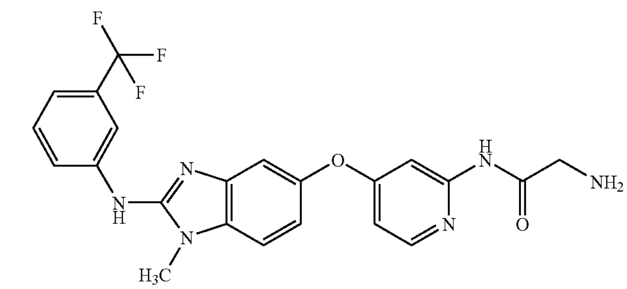 [SMILES: Cn1c(Nc2cccc(C(F)(F)F)c2)nc2cc(Oc3ccnc(NC(=O)CN)c3)ccc21] | N~1~-{4-[(1-methyl-2-{[3-(trifluoromethyl)phenyl]amino}-1H-benzimidazol-5-yl)oxy]pyridin-2-yl}glycinamide | 457.4 |
| 336 | 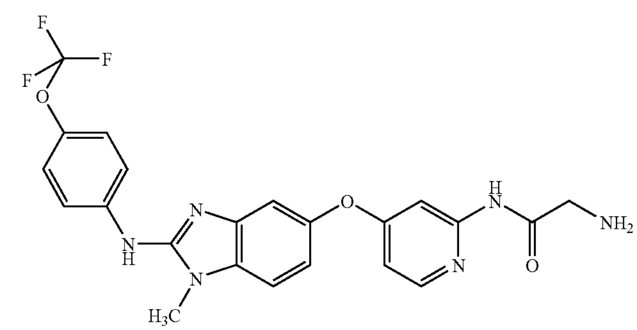 [SMILES: Cn1c(Nc2ccc(OC(F)(F)F)cc2)nc2cc(Oc3ccnc(NC(=O)CN)c3)ccc21] | N~1~-{4-[(1-methyl-2-{[4-(trifluoromethoxy)phenyl]amino}-1H-benzimidazol-5-yl)oxy]pyridin-2-yl}-glycinamide | 473.4 |
| 337 | 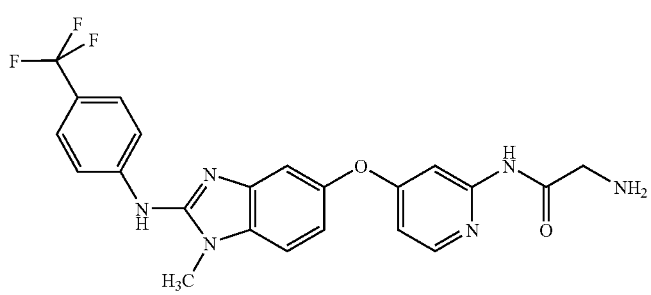 [SMILES: Cn1c(Nc2ccc(C(F)(F)F)cc2)nc2cc(Oc3ccnc(NC(=O)CN)c3)ccc21] | N~1~-{4-[(1-methyl-2-{[4-(trifluoromethyl)phenyl]amino}-1H-benzimidazol-5-yl)oxy]pyridin-2-yl}-glycinamide | 457.4 |
| 338 | 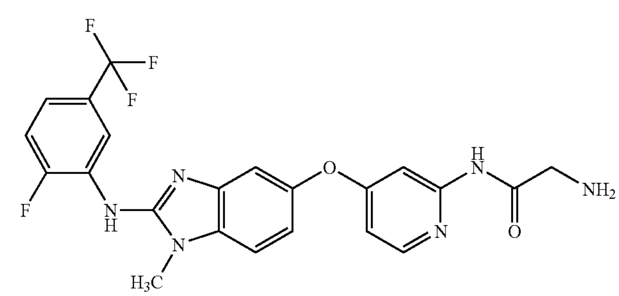 [SMILES: Cn1c(Nc2cc(C(F)(F)F)ccc2F)nc2cc(Oc3ccnc(NC(=O)CN)c3)ccc21] | N~1~-{4-[(2-{[2-fluoro-5-(trifluoromethyl)phenyl]amino}-1-methyl-1H-benzimidazol-5-yl)oxy]pyridin-2-yl}-glycinamide | 475.4 |

TABLE 1-continued

| Ex. | Structure | Name | MH+ |
| --- | --- | --- | --- |
| 339 | 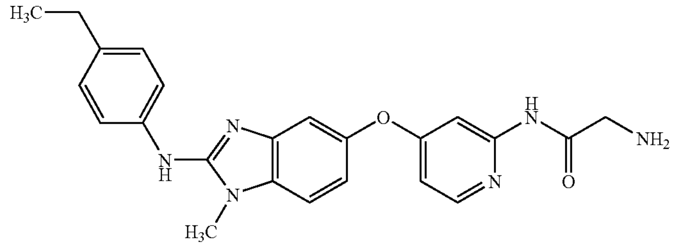 [SMILES: CCc1ccc(Nc2nc3cc(Oc4ccnc(NC(=O)CN)c4)ccc3n2C)cc1] | N~1~-[4-({2-[(4-ethylphenyl)amino]-1-methyl-1H-benzimidazol-5-yl}-oxy)pyridin-2-yl]glycinamide | 417.5 |
| 340 | 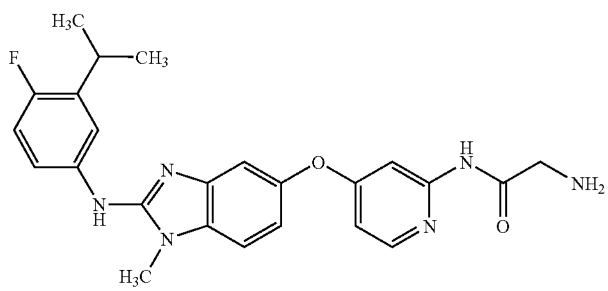 [SMILES: CC(C)c1cc(Nc2nc3cc(Oc4ccnc(NC(=O)CN)c4)ccc3n2C)ccc1F] | N~1~-[4-({2-[(4-fluoro-3-isopropyl-phenyl)amino]-1-methyl-1H-benzimidazol-5-yl}oxy)pyridin-2-yl]-glycinamide | 449.5 |
| 341 | 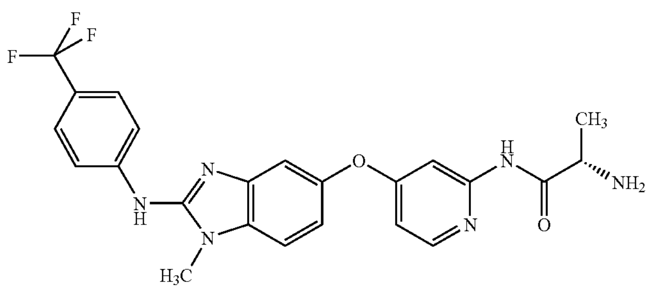 | N~1~-{4-[(1-methyl-2-{[4-(trifluoro-methyl)phenyl]amino}-1H-benzimidazol-5-yl)oxy]pyridin-2-yl}-L-alaninamide | 471.5 |
| 342 | 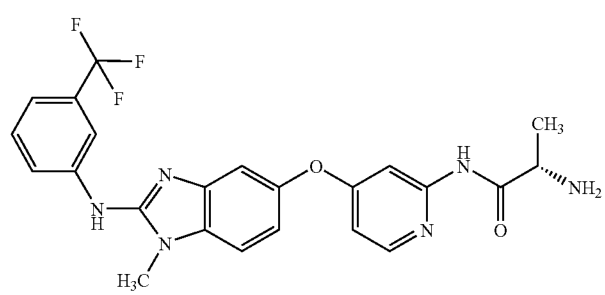 [SMILES: C[C@H](N)C(=O)Nc1cc(Oc2ccc3c(c2)nc(Nc2cccc(C(F)(F)F)c2)n3C)ccn1] | N~1~-{4-[(1-methyl-2-{[3-(trifluoro-methyl)phenyl]amino}-1H-benzimidazol-5-yl)oxy]pyridin-2-yl}-L-alaninamide | 471.5 |
| 343 | Chiral | N~1~-{4-[(2-{[2-fluoro-5-(trifluoro-methyl)phenyl]amino}-1-methyl-1H-benzimidazol-5-yl)oxy]pyridin-2-yl}-L-alaninamide | 489.4 |

TABLE 1-continued

| Ex. | Structure | | Name | MH+ |
|---|---|---|---|---|
| 344 | 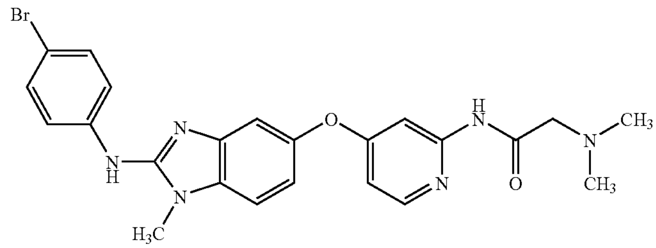 [SMILES: CN(C)CC(=O)Nc1cc(Oc2ccc3c(c2)nc(Nc2ccc(Br)cc2)n3C)ccn1] | | N~1~-[4-({2-[(4-bromophenyl)-amino]-1-methyl-1H-benzimidazol-5-yl}oxy)pyridin-2-yl]-N~2~,N~2~-dimethylglycinamide | 496.4 |
| 345 | 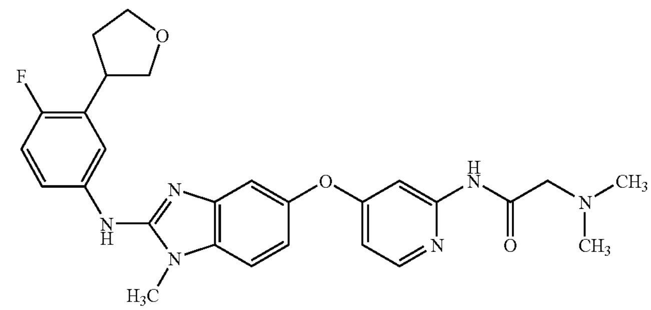 [SMILES: CN(C)CC(=O)Nc1cc(Oc2ccc3c(c2)nc(Nc2ccc(F)c(C4CCOC4)c2)n3C)ccn1] | | N~1~-[4-({2-[(4-fluoro-3-tetrahydro-furan-3-ylphenyl)amino]-1-methyl-1H-benzimidazol-5-yl}oxy)pyridin-2-yl]-N~2~,N~2~-dimethyl-glycinamide | 505.6 |
| 346 | 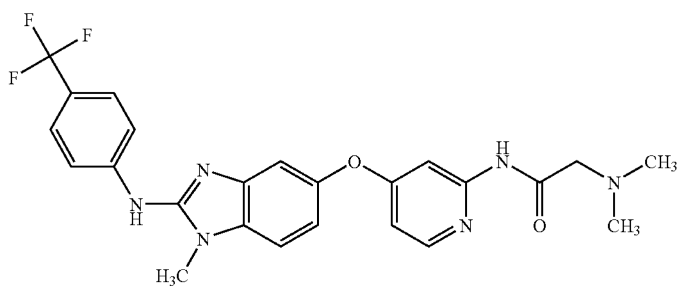 [SMILES: CN(C)CC(=O)Nc1cc(Oc2ccc3c(c2)nc(Nc2ccc(C(F)(F)F)cc2)n3C)ccn1] | | N~2~,N~2~-dimethyl-N~1~-{4-[(1-methyl-2-{[4-(trifluoromethyl)-phenyl]amino}-1H-benzimidazol-5-yl)oxy]pyridin-2-yl}glycinamide | 485.5 |
| 347 | 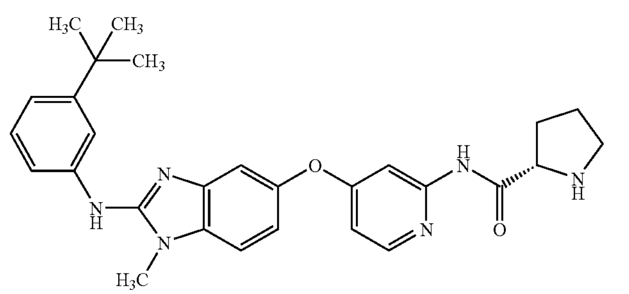 | Chiral | N-[4-({2-[(3-tert-butylphenyl)amino]-1-methyl-1H-benzimidazol-5-yl}oxy)pyridin-2-yl]-L-prolinamide | 485.6 |
| 348 | 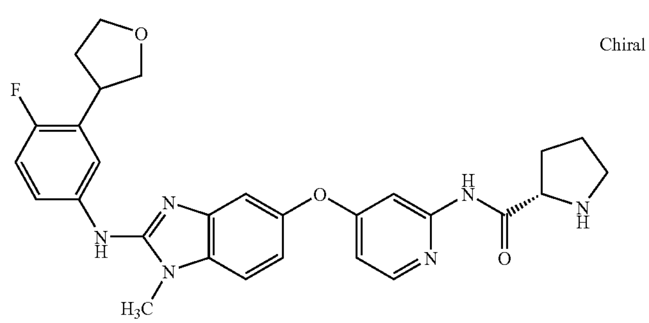 [SMILES: Cn1c(Nc2ccc(F)c(C3CCOC3)c2)nc2cc(Oc3ccnc(NC(=O)[C@@H]4CCCN4)c3)ccc21] | Chiral | N-[4-({2-[(4-fluoro-3-tetrahydro-furan-3-ylphenyl)amino]-1-methyl-1H-benzimidazol-5-yl}oxy)pyridin-2-yl]-L-prolinamide | 517.6 |

TABLE 1-continued

| Ex. | Structure | Name | MH+ |
|---|---|---|---|
| 349 | 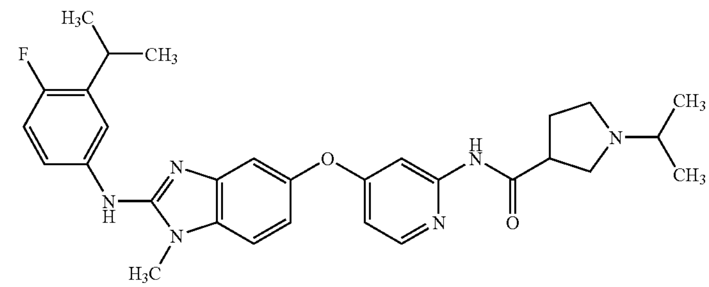 [SMILES: CC(C)c1cc(Nc2nc3cc(Oc4ccnc(NC(=O)C5CCN(C(C)C)C5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-1-isopropylpyrrolidine-3-carboxamide | 531.6 |
| 350 | 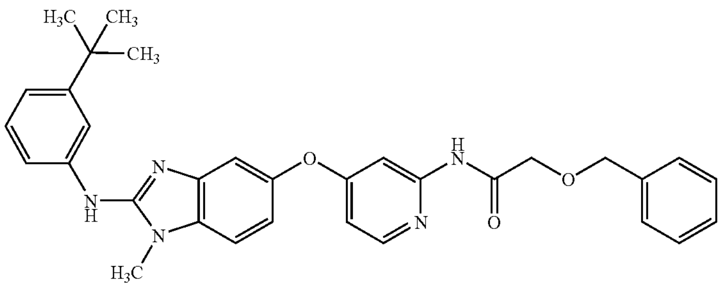 [SMILES: Cn1c(Nc2cccc(C(C)(C)C)c2)nc2cc(Oc3ccnc(NC(=O)COCc4ccccc4)c3)ccc21] | 2-(benzyloxy)-N-[4-({2-[(3-tert-butylphenyl)amino]-1-methyl-1H-benzimidazol-5-yl}oxy)pyridin-2-yl]acetamide | 536.6 |
| 351 | 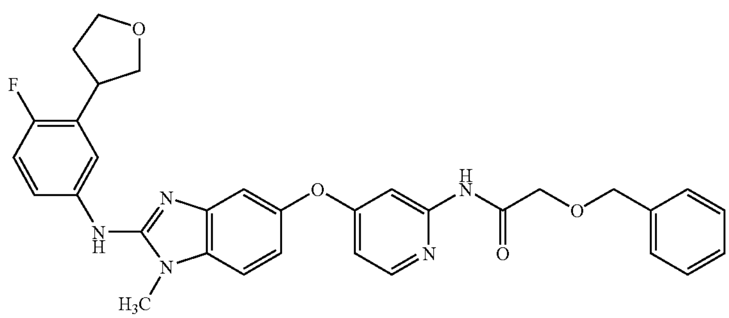 [SMILES: Cn1c(Nc2ccc(F)c(C3CCOC3)c2)nc2cc(Oc3ccnc(NC(=O)COCc4ccccc4)c3)ccc21] | 2-(benzyloxy)-N-[4-({2-[(4-fluoro-3-tetrahydrofuran-3-ylphenyl)amino]-1-methyl-1H-benzimidazol-5-yl}oxy)pyridin-2-yl]acetamide | 568.6 |
| 352 | 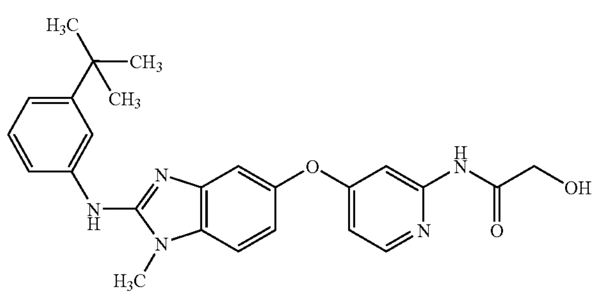 [SMILES: Cn1c(Nc2cccc(C(C)(C)C)c2)nc2cc(Oc3ccnc(NC(=O)CO)c3)ccc21] | N-[4-({2-[(3-tert-butylphenyl)amino]-1-methyl-1H-benzimidazol-5-yl}-oxy)pyridin-2-yl]-2-hydroxyacetamide | 446.5 |
| 353 | 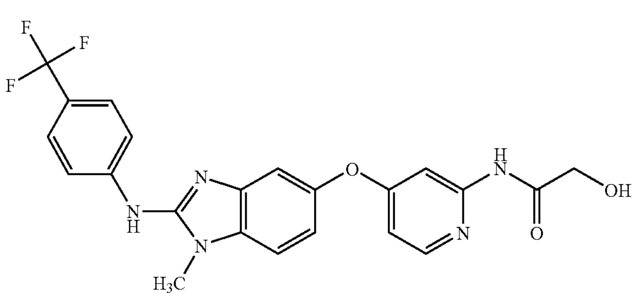 [SMILES: Cn1c(Nc2ccc(C(F)(F)F)cc2)nc2cc(Oc3ccnc(NC(=O)CO)c3)ccc21] | 2-hydroxy-N-{4-[(1-methyl-2-{[4-(trifluoromethyl)phenyl]amino}-1H-benzimidazol-5-yl)oxy]pyridin-2-yl}-acetamide | 458.4 |

TABLE 1-continued

| Ex. | Structure | Name | MH+ |
|---|---|---|---|
| 354 | 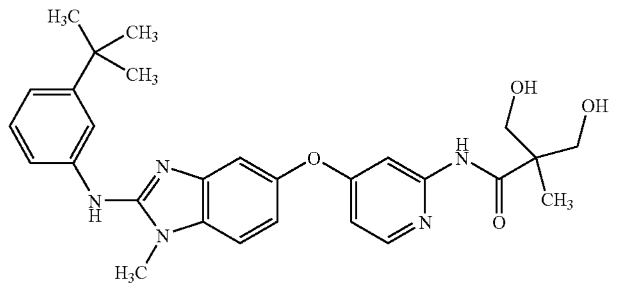 [SMILES: Cn1c(Nc2cccc(C(C)(C)C)c2)nc2cc(Oc3ccnc(NC(=O)C(C)(CO)CO)c3)ccc21] | N-[4-({2-[(3-tert-butylphenyl)amino]-1-methyl-1H-benzimidazol-5-yl}oxy)pyridin-2-yl]-3-hydroxy-2-(hydroxymethyl)-2-methyl-propanamide | 504.6 |
| 355 | 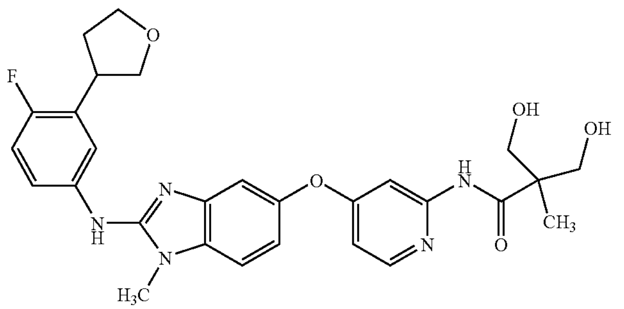 [SMILES: Cn1c(Nc2ccc(F)c(C3CCOC3)c2)nc2cc(Oc3ccnc(NC(=O)C(C)(CO)CO)c3)ccc21] | N-[4-({2-[(4-fluoro-3-tetrahydrofuran-3-ylphenyl)amino]-1-methyl-1H-benzimidazol-5-yl}-oxy)pyridin-2-yl]-3-hydroxy-2-(hydroxymethyl)-2-methyl-propanamide | 536.6 |
| 356 | 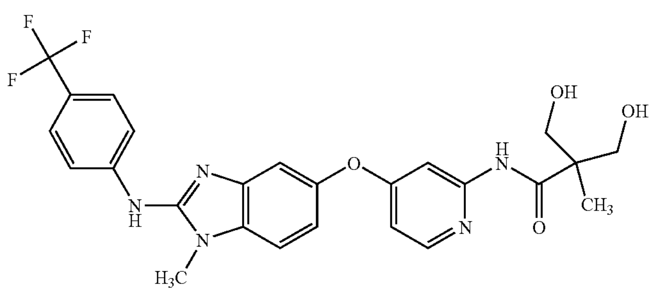 [SMILES: Cn1c(Nc2ccc(C(F)(F)F)cc2)nc2cc(Oc3ccnc(NC(=O)C(C)(CO)CO)c3)ccc21] | 3-hydroxy-2-(hydroxymethyl)-2-methyl-N-{4-[(1-methyl-2-{[4-(trifluoromethyl)phenyl]amino}-1H-benzimidazol-5-yl)oxy]pyridin-2-yl}-propanamide | 516.5 |
| 357 | 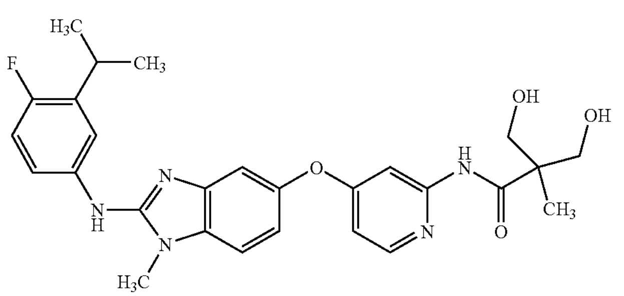 [SMILES: CC(C)c1cc(Nc2nc3cc(Oc4ccnc(NC(=O)C(C)(CO)CO)c4)ccc3n2C)ccc1F] | N-[4-({2-[(4-fluoro-3-isopropyl-phenyl)amino]-1-methyl-1H-benzimidazol-5-yl}oxy)pyridin-2-yl]-3-hydroxy-2-(hydroxymethyl)-2-methylpropanamide | 508.6 |
| 358 | 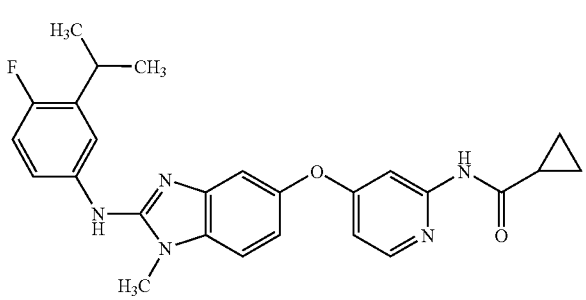 [SMILES: CC(C)c1cc(Nc2nc3cc(Oc4ccnc(NC(=O)C5CC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-cyclopropanecarboxamide | 460.5 |

TABLE 1-continued

| Ex. | Name | MH+ |
|---|---|---|
| 359 | N-[4-({2-[(2-fluoro-5-isopropyl-phenyl)amino]-1-methyl-1H-benzimidazol-5-yl}oxy)pyridin-2-yl]-cyclopropanecarboxamide | 460.5 |
| 360 | N-{4-[(1-methyl-2-{[4-(trifluoromethyl)phenyl]amino}-1H-benzimidazol-5-yl)oxy]pyridin-2-yl}-cyclopropanecarboxamide | 468.4 |
| 361 | N-[4-({2-[(3-tert-butylphenyl)amino]-1-methyl-1H-benzimidazol-5-yl}oxy)pyridin-2-yl]cyclopropane-carboxamide | 456.6 |
| 362 | 1-isopropyl-N-{4-[(1-methyl-2-{[4-(trifluoromethyl)phenyl]amino}-1H-benzimidazol-5-yl)oxy]pyridin-2-yl}piperidine-3-carboxamide | 553.6 |
| 363 | 1-isopropyl-N-{4-[(1-methyl-2-{[4-(trifluoromethyl)phenyl]amino}-1H-benzimidazol-5-yl)oxy]pyridin-2-yl}pyrrolidine-3-carboxamide | 539.6 |

TABLE 1-continued

| Ex. | Structure | Name | MH+ |
|---|---|---|---|
| 364 | 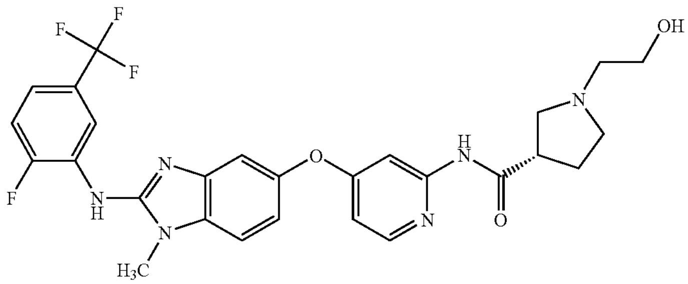 | (3S)-N-{4-[(2-{[2-fluoro-5-(trifluoromethyl)phenyl]amino}-1-methyl-1H-benzimidazol-5-yl)oxy]pyridin-2-yl}-1-(2-hydroxyethyl)pyrrolidine-3-carboxamide  Chiral | 559.5 |
| 365 | 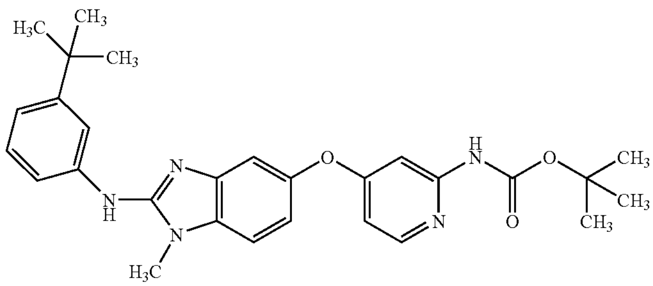 [SMILES: Cn1c(Nc2cccc(C(C)(C)C)c2)nc2cc(Oc3ccnc(NC(=O)OC(C)(C)C)c3)ccc21] | tert-butyl 4-({2-[(3-tert-butylphenyl)amino]-1-methyl-1H-benzimidazol-5-yl}oxy)pyridin-2-ylcarbamate | 488.6 |
| 366 | 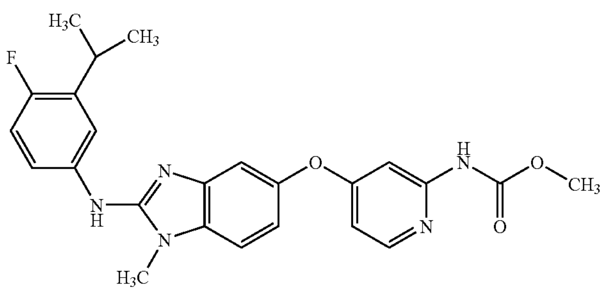 [SMILES: COC(=O)Nc1cc(Oc2ccc3c(c2)nc(Nc2ccc(F)c(C(C)C)c2)n3C)ccn1] | methyl 4-({2-[(4-fluoro-3-isopropylphenyl)amino]-1-methyl-1H-benzimidazol-5-yl}oxy)pyridin-2-ylcarbamate | 450.5 |
| 367 | 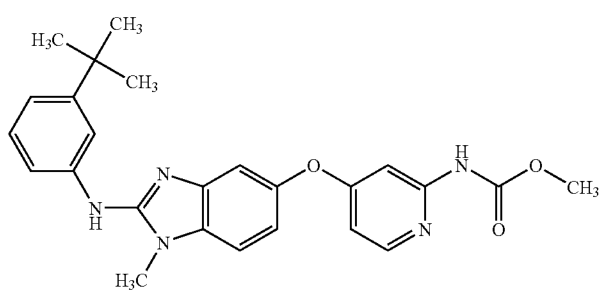 [SMILES: COC(=O)Nc1cc(Oc2ccc3c(c2)nc(Nc2cccc(C(C)(C)C)c2)n3C)ccn1] | methyl 4-({2-[(3-tert-butylphenyl)amino]-1-methyl-1H-benzimidazol-5-yl}oxy)pyridin-2-ylcarbamate | 446.5 |
| 368 | 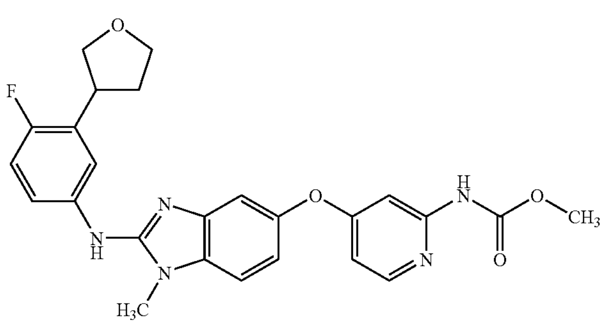 [SMILES: COC(=O)Nc1cc(Oc2ccc3c(c2)nc(Nc2ccc(F)c(C4CCOC4)c2)n3C)ccn1] | methyl 4-({2-[(4-fluoro-3-tetrahydrofuran-3-ylphenyl)amino]-1-methyl-1H-benzimidazol-5-yl}oxy)pyridin-2-ylcarbamate | 478.5 |

TABLE 1-continued

| Ex. | Structure | Name | MH+ |
| --- | --- | --- | --- |
| 369 | 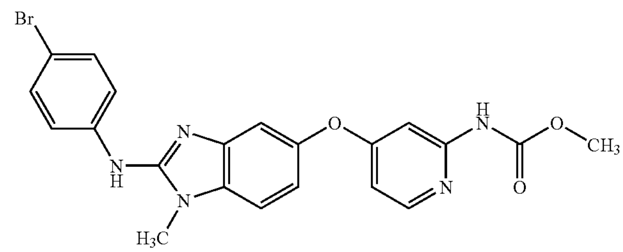 | methyl 4-({2-[(4-bromophenyl)-amino]-1-methyl-1H-benzimidazol-5-yl}oxy)pyridin-2-ylcarbamate | 469.3 |
| 370 | 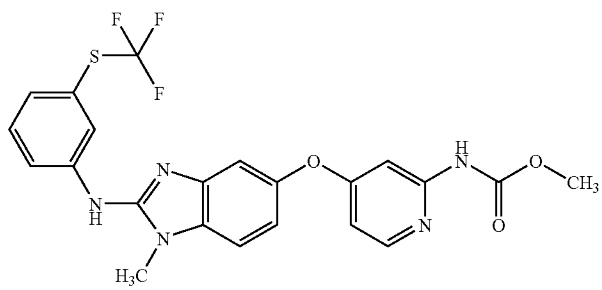 [SMILES: COC(=O)Nc1cc(Oc2ccc3c(c2)nc(Nc2cccc(SC(F)(F)F)c2)n3C)ccn1] | methyl 4-{[1-methyl-2-({3-[(trifluoro-methyl)thio]phenyl}amino)-1H-benzimidazol-5-yl]oxy}pyridin-2-yl-carbamate | 490.5 |
| 371 | 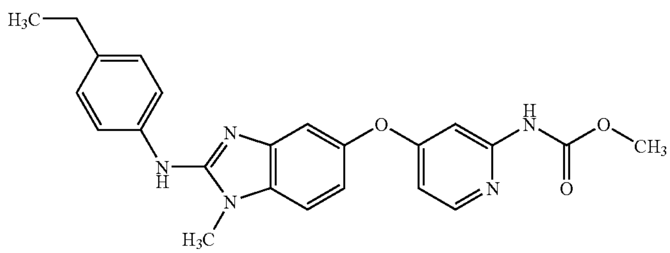 | methyl 4-({2-[(4-ethylphenyl)-amino]-1-methyl-1H-benzimidazol-5-yl}oxy)pyridin-2-ylcarbamate | 418.5 |
| 372 | 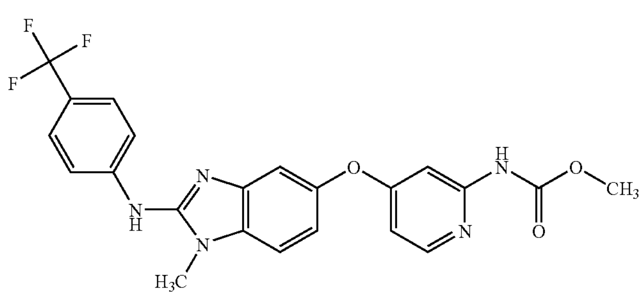 [SMILES: COC(=O)Nc1cc(Oc2ccc3c(c2)nc(Nc2ccc(C(F)(F)F)cc2)n3C)ccn1] | methyl 4-[(1-methyl-2-{[4-(trifluoro-methyl)phenyl]amino}-1H-benzimidazol-5-yl)oxy]pyridin-2-yl-carbamate | 458.4 |
| 373 | 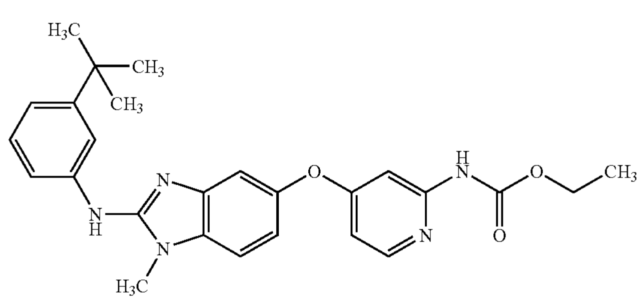 [SMILES: CCOC(=O)Nc1cc(Oc2ccc3c(c2)nc(Nc2cccc(C(C)(C)C)c2)n3C)ccn1] | ethyl 4-({2-{(3-tert-butylphenyl)-amino]-1-methyl-1H-benzimidazol-5-yl}oxy)pyridin-2-ylcarbamate | 460.5 |

TABLE 1-continued

| Ex. | Structure | Name | MH+ |
|---|---|---|---|
| 374 | 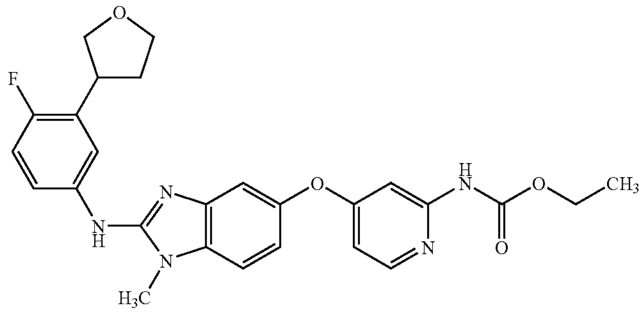 | ethyl 4-({2-[(4-fluoro-3-tetrahydrofuran-3-ylphenyl)amino]-1-methyl-1H-benzimidazol-5-yl}oxy)pyridin-2-ylcarbamate | 492.5 |
| 375 | 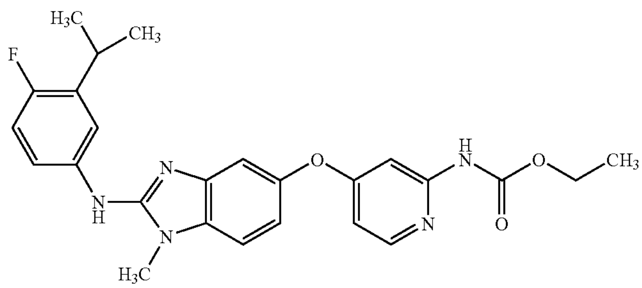 [SMILES: CCOC(=O)Nc1cc(Oc2ccc3c(c2)nc(Nc2ccc(F)c(C(C)C)c2)n3C)ccn1] | ethyl 4-({2-[(4-fluoro-3-isopropylphenyl)amino]-1-methyl-1H-benzimidazol-5-yl}oxy)pyridin-2-yl-carbamate | 464.5 |
| 376 | 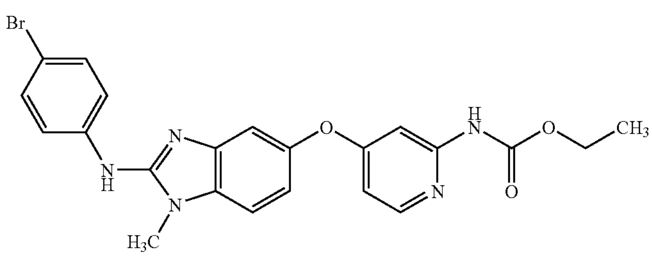 [SMILES: CCOC(=O)Nc1cc(Oc2ccc3c(c2)nc(Nc2ccc(Br)cc2)n3C)ccn1] | ethyl 4-({2-[(4-bromophenyl)amino]-1-methyl-1H-benzimidazol-5-yl}-oxy)pyridin-2-ylcarbamate | 483.3 |
| 377 | 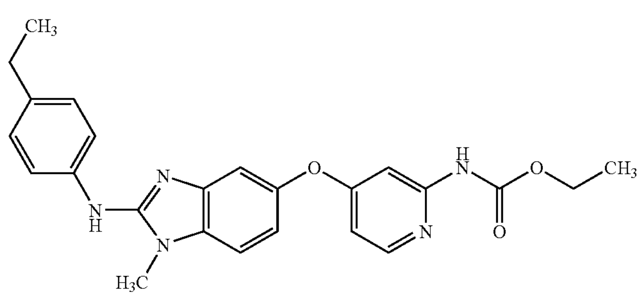 [SMILES: CCOC(=O)Nc1cc(Oc2ccc3c(c2)nc(Nc2ccc(CC)cc2)n3C)ccn1] | ethyl 4-({2-[(4-ethylphenyl)amino]-1-methyl-1H-benzimidazol-5-yl}-oxy)pyridin-2-ylcarbamate | 432.5 |
| 378 | 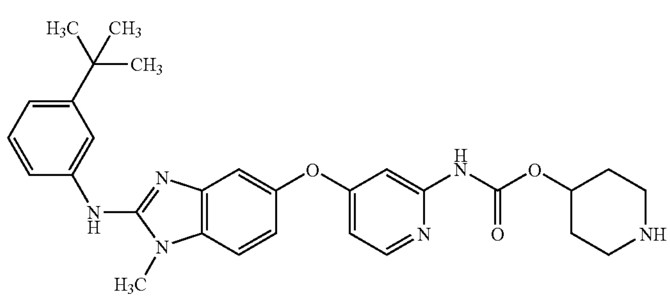 [SMILES: Cn1c(Nc2cccc(C(C)(C)C)c2)nc2cc(Oc3ccnc(NC(=O)OC4CCNCC4)c3)ccc21] | piperidin-4-yl 4-({2-[(3-tert-butylphenyl)amino]-1-methyl-1H-benzimidazol-5-yl}oxy)pyridin-2-yl-carbamate | 515.6 |

TABLE 1-continued

| Ex. | Structure | Name | MH+ |
|---|---|---|---|
| 379 | 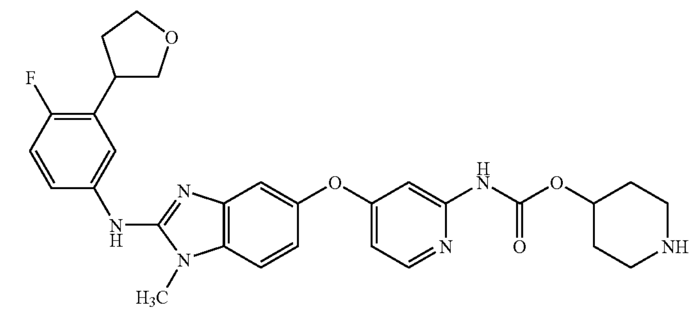 [SMILES: Cn1c(Nc2ccc(F)c(C3CCOC3)c2)nc2cc(Oc3ccnc(NC(=O)OC4CCNCC4)c3)ccc21] | piperidin-4-yl 4-({2-[(4-fluoro-3-tetrahydrofuran-3-ylphenyl)amino]-1-methyl-1H-benzimidazol-5-yl}-oxy)pyridin-2-ylcarbamate | 547.6 |
| 380 | 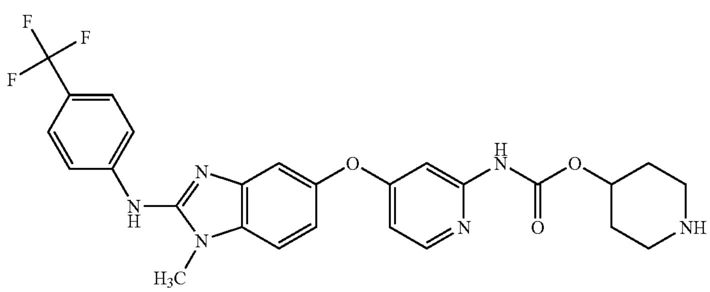 [SMILES: Cn1c(Nc2ccc(C(F)(F)F)cc2)nc2cc(Oc3ccnc(NC(=O)OC4CCNCC4)c3)ccc21] | piperidin-4-yl 4-[(1-methyl-2-{[4-(trifluoromethyl)phenyl]amino}-1H-benzimidazol-5-yl)oxy]pyridin-2-ylcarbamate | 527.5 |
| 381 | 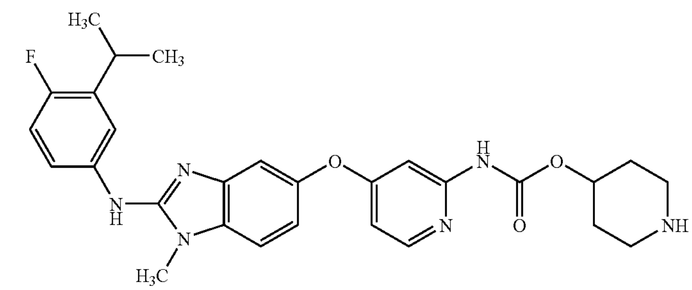 | piperidin-4-yl 4-({2-[(4-fluoro-3-isopropylphenyl)amino]-1-methyl-1H-benzimidazol-5-yl}oxy)pyridin-2-ylcarbamate | 519.6 |
| 382 | 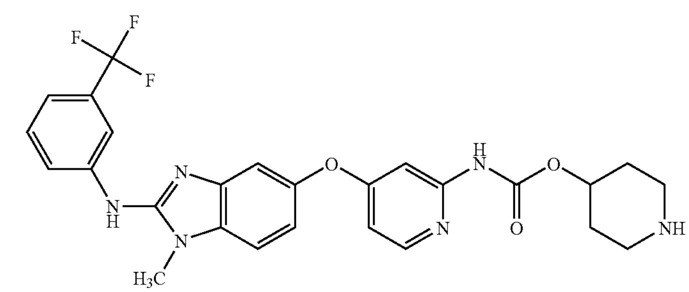 [SMILES: Cn1c(Nc2cccc(C(F)(F)F)c2)nc2cc(Oc3ccnc(NC(=O)OC4CCNCC4)c3)ccc21] | piperidin-4-yl 4-[(1-methyl-2-{[3-(trifluoromethyl)phenyl]amino}-1H-benzimidazol-5-yl)oxy]pyridin-2-ylcarbamate | 527.5 |
| 383 | 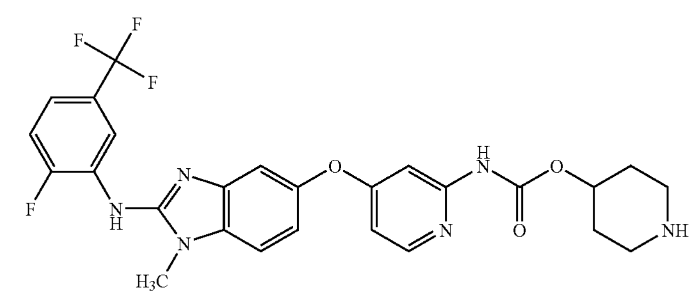 [SMILES: Cn1c(Nc2cc(C(F)(F)F)ccc2F)nc2cc(Oc3ccnc(NC(=O)OC4CCNCC4)c3)ccc21] | piperidin-4-yl 4-[(2-{[2-fluoro-5-(trifluoromethyl)phenyl]amino}-1-methyl-1H-benzimidazol-5-yl)-oxy]pyridin-2-ylcarbamate | 545.5 |

TABLE 1-continued

| Ex. | Structure | Name | MH+ |
|---|---|---|---|
| 384 | 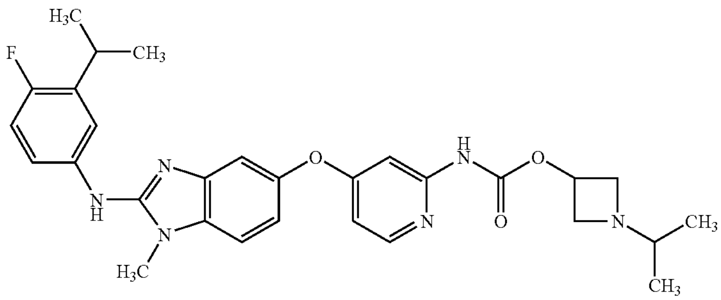 [SMILES: CC(C)c1cc(Nc2nc3cc(Oc4ccnc(NC(=O)OC5CN(C(C)C)C5)c4)ccc3n2C)ccc1F] | 1-isopropylazetidin-3-yl 4-({2-[(4-fluoro-3-isopropylphenyl)amino]-1-methyl-1H-benzimidazol-5-yl}-oxy)pyridin-2-ylcarbamate | 533.6 |
| 385 | 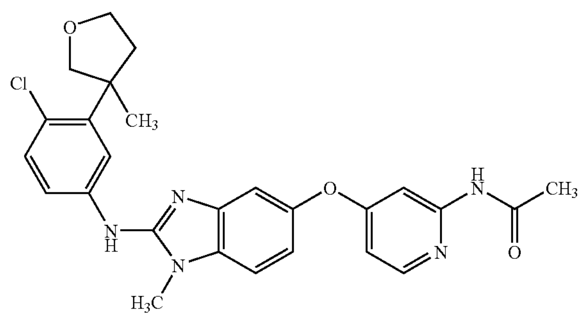 [SMILES: CC(=O)Nc1cc(Oc2ccc3c(c2)nc(Nc2ccc(Cl)c(C4(C)CCOC4)c2)n3C)ccn1] | N-{4-[(2-{[4-chloro-3-(3-methyl-tetrahydrofuran-3-yl)phenyl]amino}-1-methyl-1H-benzimidazol-5-yl)-oxy]pyridin-2-yl}acetamide | 493 |
| 386 | 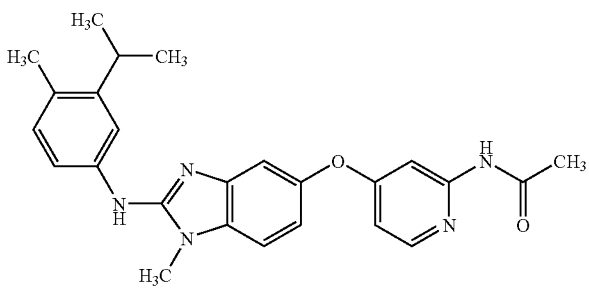 [SMILES: CC(=O)Nc1cc(Oc2ccc3c(c2)nc(Nc2ccc(C)c(C(C)C)c2)n3C)ccn1] | N-[4-({2-[(3-isopropyl-4-methyl-phenyl)amino]-1-methyl-1H-benzimidazol-5-yl}oxy)pyridin-2-yl]-acetamide | 430.5 |
| 387 | 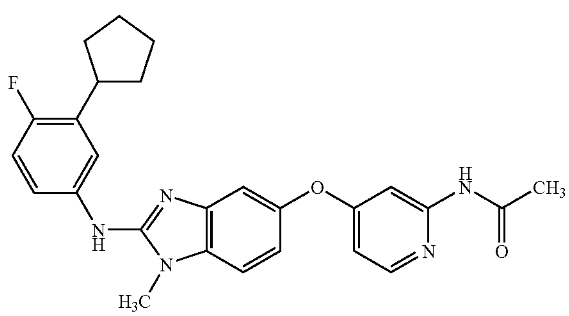 [SMILES: CC(=O)Nc1cc(Oc2ccc3c(c2)nc(Nc2ccc(F)c(C4CCCC4)c2)n3C)ccn1] | N-[4-({2-[(3-cyclopentyl-4-fluoro-phenyl)amino]-1-methyl-1H-benzimidazol-5-yl}oxy)pyridin-2-yl]-acetamide | 460.5 |
| 388 | 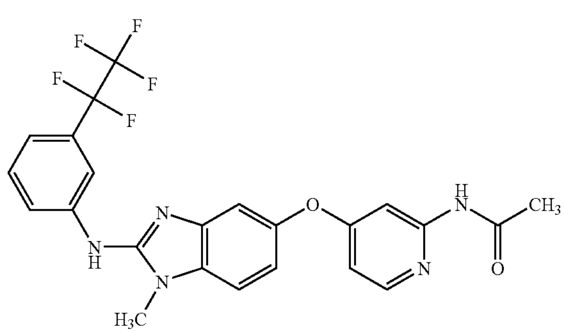 [SMILES: CC(=O)Nc1cc(Oc2ccc3c(c2)nc(Nc2cccc(C(F)(F)C(F)(F)F)c2)n3C)ccn1] | N-{4-[(1-methyl-2-{[3-(pentafluoro-ethyl)phenyl]amino}-1H-benzimidazol-5-yl)oxy]pyridin-2-yl}-acetamide | 492.4 |

TABLE 1-continued

| Ex. | Structure | Name | MH+ |
|---|---|---|---|
| 389 | 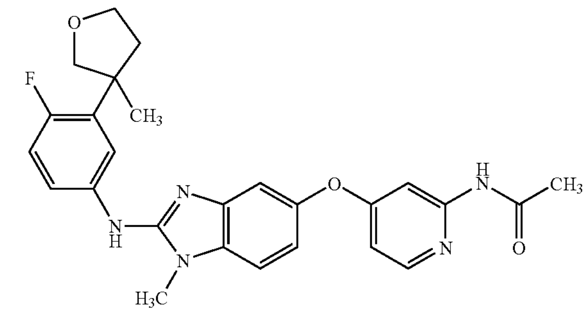 [SMILES: CC(=O)Nc1cc(Oc2ccc3c(c2)nc(Nc2ccc(F)c(C4(C)CCOC4)c2)n3C)ccn1] | N-{4-[(2-{[4-fluoro-3-(3-methyl-tetrahydrofuran-3-yl)phenyl]amino}-1-methyl-1H-benzimidazol-5-yl)-oxy]pyridin-2-yl}acetamide | 476.5 |
| 390 | 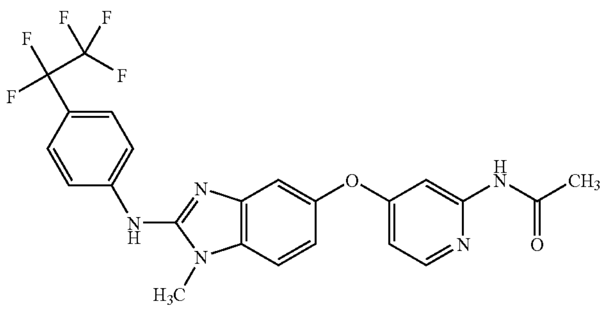 [SMILES: CC(=O)Nc1cc(Oc2ccc3c(c2)nc(Nc2ccc(C(F)(F)C(F)(F)F)cc2)n3C)ccn1] | N-{4-[(1-methyl-2-{[4-(pentafluoro-ethyl)phenyl]amino}-1H-benzimidazol-5-yl)oxy]pyridin-2-yl}-acetamide | 492.4 |
| 391 | 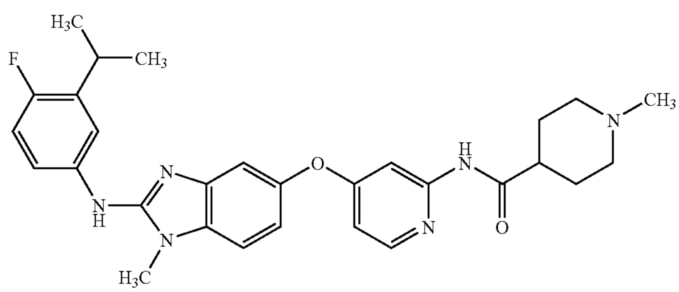 | N-[4-({2-[(4-fluoro-3-isopropyl-phenyl)amino]-1-methyl-1H-benzimidazol-5-yl}oxy)pyridin-2-yl]-1-methylpiperidine-4-carboxamide | 517.6 |
| 392 | 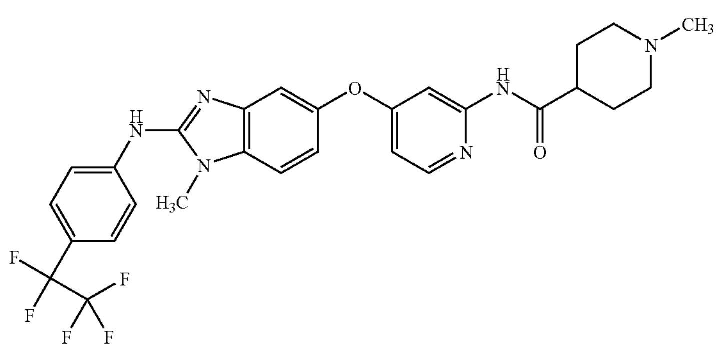 [SMILES: CN1CCC(C(=O)Nc2cc(Oc3ccc4c(c3)nc(Nc3ccc(C(F)(F)C(F)(F)F)cc3)n4C)ccn2)CC1] | 1-methyl-N-{4-[(1-methyl-2-{[4-(pentafluoroethyl)phenyl]amino}-1H-benzimidazol-5-yl)oxy]pyridin-2-yl}piperidine-4-carboxamide | 575.6 |
| 393 | 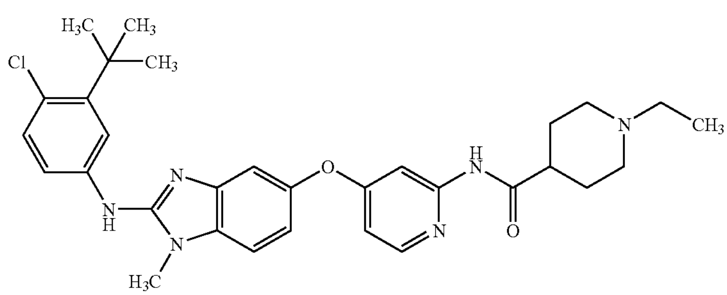 [SMILES: CCN1CCC(C(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-1-ethylpiperidine-4-carboxamide | 562.1 |

TABLE 1-continued

| Ex. | Structure | Name | MH+ |
|---|---|---|---|
| 394 | 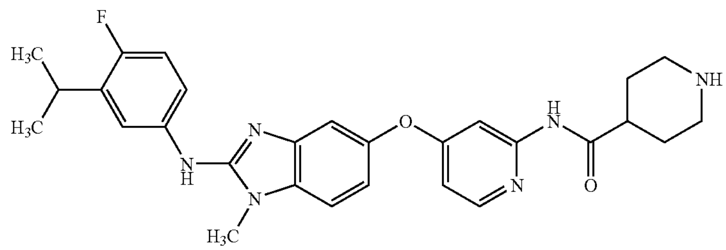 [SMILES: CC(C)c1cc(Nc2nc3cc(Oc4ccnc(NC(=O)C5CCNCC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-piperidine-4-carboxamide | 503.6 |
| 395 | 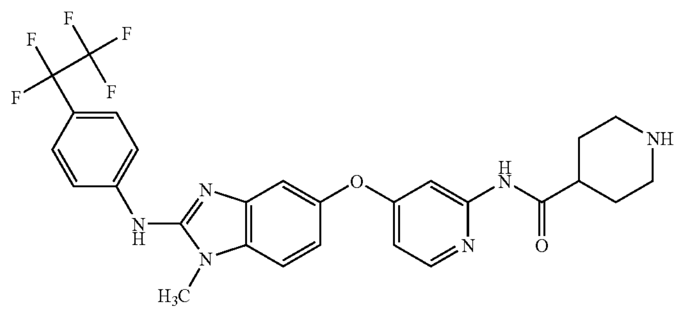 [SMILES: Cn1c(Nc2ccc(C(F)(F)C(F)(F)F)cc2)nc2cc(Oc3ccnc(NC(=O)C4CCNCC4)c3)ccc21] | N-{4-[(1-methyl-2-{[4-(pentafluoro-ethyl)phenyl]amino}-1H-benzimidazol-5-yl)oxy]pyridin-2-yl}-piperidine-4-carboxamide | 561.5 |
| 396 | 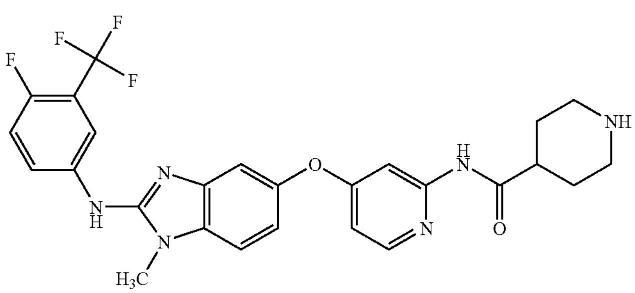 [SMILES: Cn1c(Nc2ccc(F)c(C(F)(F)F)c2)nc2cc(Oc3ccnc(NC(=O)C4CCNCC4)c3)ccc21] | N-{4-[(2-{[4-fluoro-3-(trifluoro-methyl)phenyl]amino}-1-methyl-1H-benzimidazol-5-yl)oxy]pyridin-2-yl}-piperidine-4-carboxamide | 529.5 |
| 397 | 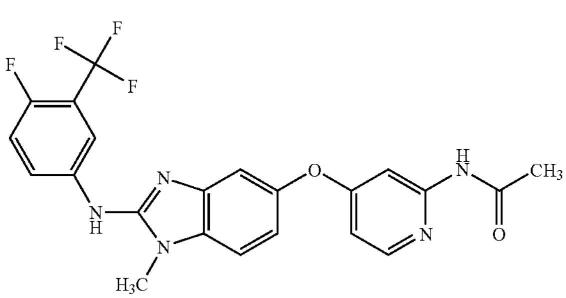 [SMILES: CC(=O)Nc1cc(Oc2ccc3c(c2)nc(Nc2ccc(F)c(C(F)(F)F)c2)n3C)ccn1] | N-{4-[(2-{[4-fluoro-3-(trifluoro-methyl)phenyl]amino}-1-methyl-1H-benzimidazol-5-yl)oxy]pyridin-2-yl}-acetamide | 460.4 |

TABLE 1-continued

| Ex. | Structure | Name | MH+ |
| --- | --- | --- | --- |
| 398 | 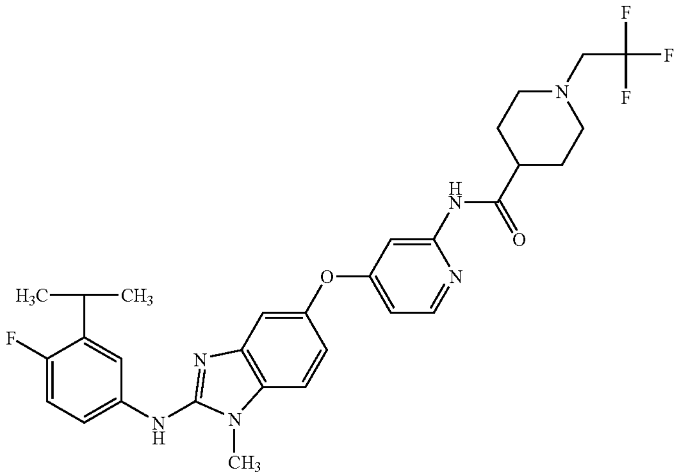 [SMILES: CC(C)c1cc(Nc2nc3cc(Oc4ccnc(NC(=O)C5CCN(CC(F)(F)F)CC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-1-(2,2,2-trifluoroethyl)piperidine-4-carboxamide | 585.6 |
| 399 | 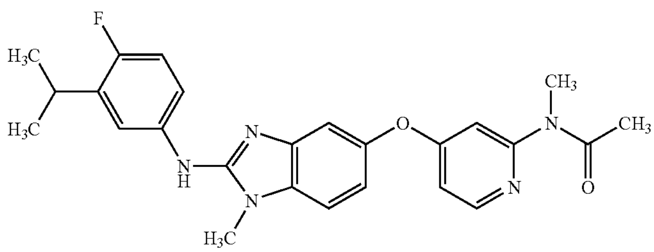 [SMILES: CC(=O)N(C)c1cc(Oc2ccc3c(c2)nc(Nc2ccc(F)c(C(C)C)c2)n3C)ccn1] | N-[4-({2-[(4-fluoro-3-isopropyl-phenyl)amino]-1-methyl-1H-benzimidazol-5-yl}oxy)pyridin-2-yl]-N-methylacetamide | 448.5 |
| 400 | 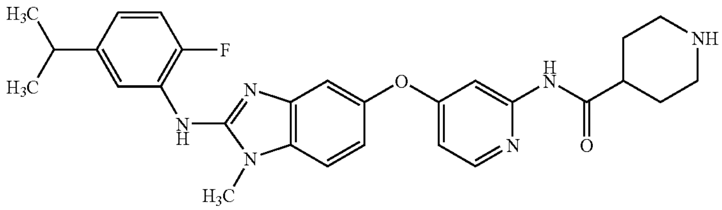 [SMILES: CC(C)c1ccc(F)c(Nc2nc3cc(Oc4ccnc(NC(=O)C5CCNCC5)c4)ccc3n2C)c1] | N-[4-({2-[(2-fluoro-5-isopropyl-phenyl)amino]-1-methyl-1H-benzimidazol-5-yl}oxy)pyridin-2-yl]-piperidine-4-carboxamide | 503.6 |
| 401 | 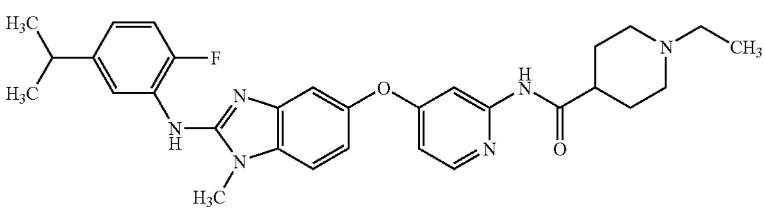 [SMILES: CCN1CCC(C(=O)Nc2cc(Oc3ccc4c(c3)nc(Nc3cc(C(C)C)ccc3F)n4C)ccn2)CC1] | 1-ethyl-N-[4-({2-[(2-fluoro-5-isopropylphenyl)amino]-1-methyl-1H-benzimidazol-5-yl}oxy)pyridin-2-yl]piperidine-4-carboxamide | 531.6 |
| 402 | 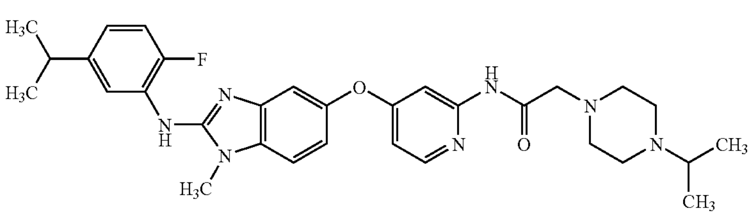 [SMILES: CC(C)c1ccc(F)c(Nc2nc3cc(Oc4ccnc(NC(=O)CN5CCN(C(C)C)CC5)c4)ccc3n2C)c1] | N-[4-({2-[(2-fluoro-5-isopropyl-phenyl)amino]-1-methyl-1H-benzimidazol-5-yl}oxy)pyridin-2-yl]-2-(4-isopropylpiperazin-1-yl)-acetamide | 560.7 |
| 403 | 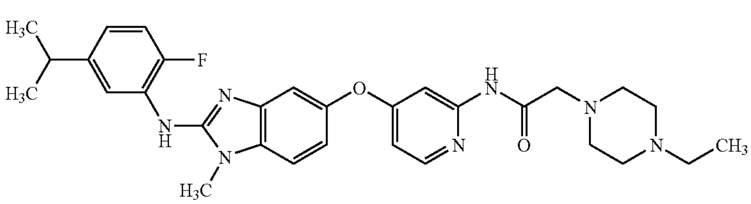 [SMILES: CCN1CCN(CC(=O)Nc2cc(Oc3ccc4c(c3)nc(Nc3cc(C(C)C)ccc3F)n4C)ccn2)CC1] | 2-(4-ethylpiperazin-1-yl)-N-[4-({2-[(2-fluoro-5-isopropylphenyl)-amino]-1-methyl-1H-benzimidazol-5-yl}oxy)pyridin-2-yl]acetamide | 546.7 |

TABLE 1-continued

| Ex. | Structure | Name | MH+ |
|---|---|---|---|
| 404 | 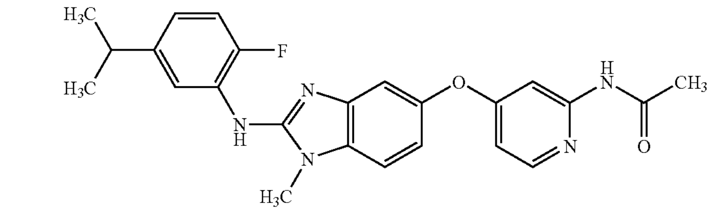 [SMILES: CC(=O)Nc1cc(Oc2ccc3c(c2)nc(Nc2cc(C(C)C)ccc2F)n3C)ccn1] | N-[4-({2-[(2-fluoro-5-isopropyl-phenyl)amino]-1-methyl-1H-benzimidazol-5-yl}oxy)pyridin-2-yl]-acetamide | 434.5 |
| 405 | 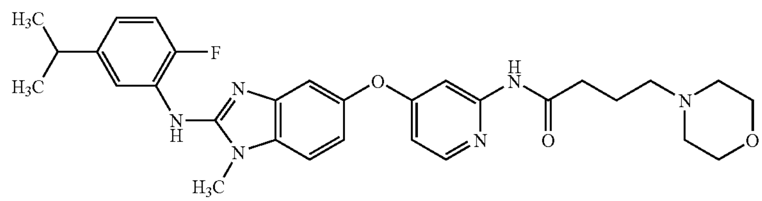 [SMILES: CC(C)c1ccc(F)c(Nc2nc3cc(Oc4ccnc(NC(=O)CCCN5CCOCC5)c4)ccc3n2C)c1] | N-[4-({2-[(2-fluoro-5-isopropyl-phenyl)amino]-1-methyl-1H-benzimidazol-5-yl}oxy)pyridin-2-yl]-4-morpholin-4-ylbutanamide | 547.6 |
| 406 | 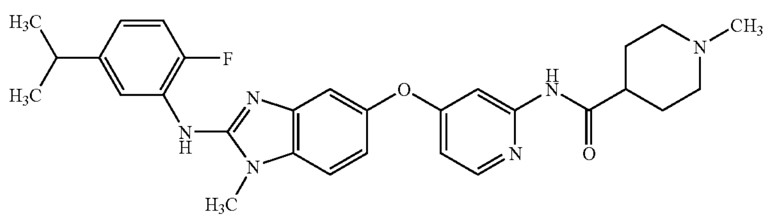 [SMILES: CC(C)c1ccc(F)c(Nc2nc3cc(Oc4ccnc(NC(=O)C5CCN(C)CC5)c4)ccc3n2C)c1] | N-[4-({2-[(2-fluoro-5-isopropyl-phenyl)amino]-1-methyl-1H-benzimidazol-5-yl}oxy)pyridin-2-yl]-1-methylpiperidine-4-carboxamide | 517.6 |
| 407 | Chiral | 2-[(2R,6S)-2,6-dimethylmorpholin-4-yl]-N-[4-({2-[(2-fluoro-5-isopropyl-phenyl)amino]-1-methyl-1H-benzimidazol-5-yl}oxy)pyridin-2-yl]-acetamide | 547.6 |
| 408 | 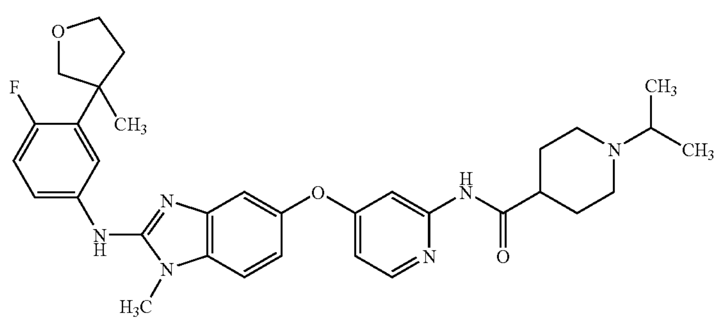 [SMILES: CC(C)N1CCC(C(=O)Nc2cc(Oc3ccc4c(c3)nc(Nc3ccc(F)c(C5(C)CCOC5)c3)n4C)ccn2)CC1] | N-{4-[(2-{[4-fluoro-3-(3-methyl-tetrahydrofuran-3-yl)phenyl]amino}-1-methyl-1H-benzimidazol-5-yl)oxy]pyridin-2-yl}-1-isopropyl-piperidine-4-carboxamide | 587.7 |
| 409 | 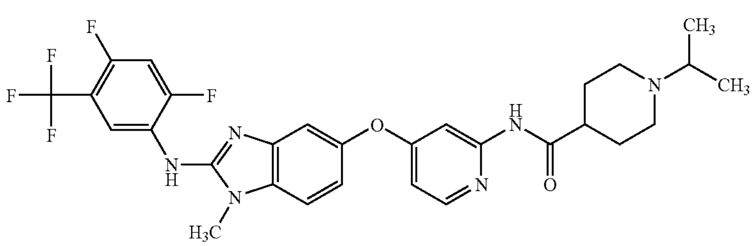 [SMILES: CC(C)N1CCC(C(=O)Nc2cc(Oc3ccc4c(c3)nc(Nc3cc(C(F)(F)F)c(F)cc3F)n4C)ccn2)CC1] | N-{4-[(2-{[2,4-difluoro-5-(trifluoro-methyl)phenyl]amino}-1-methyl-1H-benzimidazol-5-yl)oxy]pyridin-2-yl}-1-isopropylpiperidine-4-carboxamide | 589.6 |

TABLE 1-continued

| Ex. | Structure | Name | MH+ |
| --- | --- | --- | --- |
| 410 | 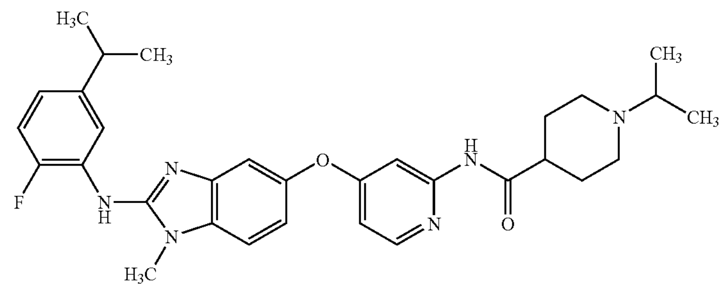 [SMILES: CC(C)c1ccc(F)c(Nc2nc3cc(Oc4ccnc(NC(=O)C5CCN(C(C)C)CC5)c4)ccc3n2C)c1] | N-[4-({2-[(2-fluoro-5-isopropyl-phenyl)amino]-1-methyl-1H-benzimidazol-5-yl}oxy)pyridin-2-yl]-1-isopropylpiperidine-4-carboxamide | 545.7 |
| 411 | 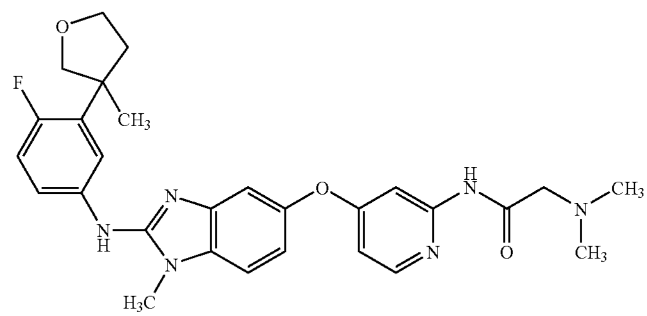 [SMILES: CN(C)CC(=O)Nc1cc(Oc2ccc3c(c2)nc(Nc2ccc(F)c(C4(C)CCOC4)c2)n3C)ccn1] | N~1~-{4-[(2-{[4-fluoro-3-(3-methyl-tetrahydrofuran-3-yl)phenyl]amino}-1-methyl-1H-benzimidazol-5-yl)-oxy]pyridin-2-yl}-N~2~,N~2~-dimethylglycinamide | 519.6 |
| 412 | 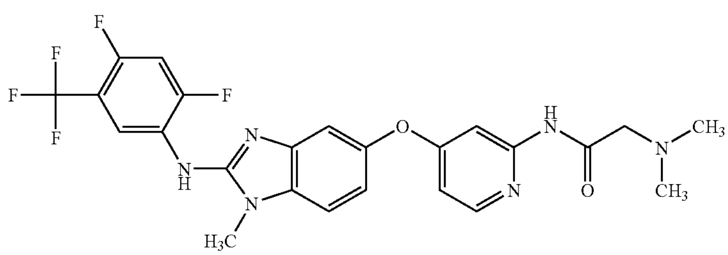 [SMILES: CN(C)CC(=O)Nc1cc(Oc2ccc3c(c2)nc(Nc2cc(C(F)(F)F)c(F)cc2F)n3C)ccn1] | N~1~-{4-[(2-{[2,4-difluoro-5-(trifluoromethyl)phenyl]amino}-1-methyl-1H-benzimidazol-5-yl)-oxy]pyridin-2-yl}-N~2~,N~2~-dimethylglycinamide | 521.5 |
| 413 | 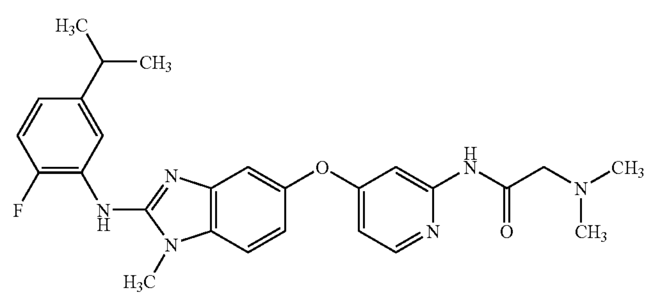 [SMILES: CC(C)c1ccc(F)c(Nc2nc3cc(Oc4ccnc(NC(=O)CN(C)C)c4)ccc3n2C)c1] | N~1~-[4-({2-[(2-fluoro-5-isopropyl-phenyl)amino]-1-methyl-1H-benzimidazol-5-yl}oxy)pyridin-2-yl]-N~2~,N~2~-dimethylglycinamide | 477.6 |
| 414 | 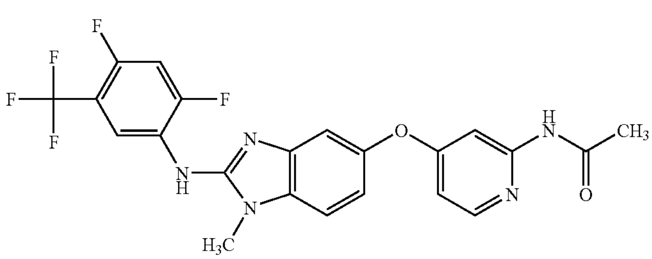 [SMILES: CC(=O)Nc1cc(Oc2ccc3c(c2)nc(Nc2cc(C(F)(F)F)c(F)cc2F)n3C)ccn1] | N-{4-[(2-{[2,4-difluoro-5-(trifluoro-methyl)phenyl]amino}-1-methyl-1H-benzimidazol-5-yl)oxy]pyridin-2-yl}-acetamide | 478.4 |

TABLE 1-continued

| Ex. | Structure | Name | MH+ |
|---|---|---|---|
| 415 | 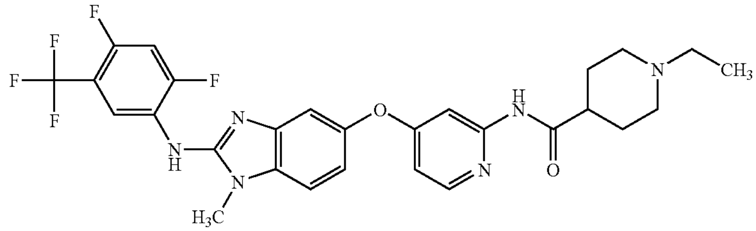 [SMILES: CCN1CCC(C(=O)Nc2cc(Oc3ccc4c(c3)nc(Nc3cc(C(F)(F)F)c(F)cc3F)n4C)ccn2)CC1] | N-{4-[(2-{[2,4-difluoro-5-(trifluoromethyl)phenyl]amino}-1-methyl-1H-benzimidazol-5-yl)oxy]pyridin-2-yl}-1-ethylpiperidine-4-carboxamide | 575.6 |
| 416 | 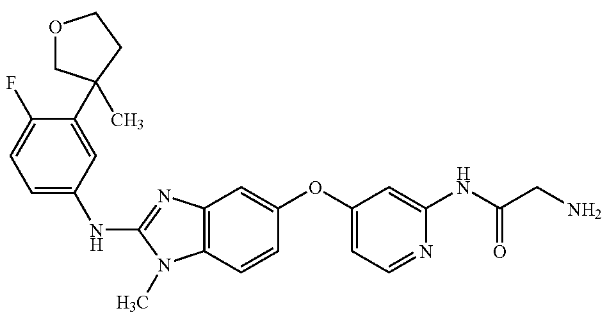 [SMILES: Cn1c(Nc2ccc(F)c(C3(C)CCOC3)c2)nc2cc(Oc3ccnc(NC(=O)CN)c3)ccc21] | N~1~-{4-[(2-{[4-fluoro-3-(3-methyltetrahydrofuran-3-yl)phenyl]amino}-1-methyl-1H-benzimidazol-5-yl)oxy]pyridin-2-yl}glycinamide | 491.5 |
| 417 | 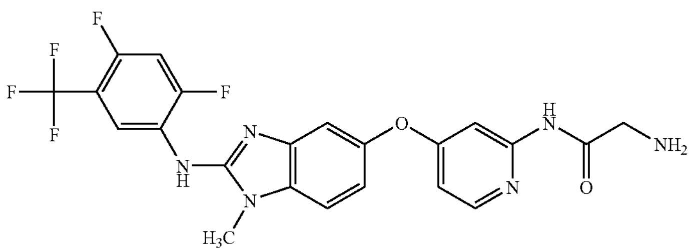 [SMILES: Cn1c(Nc2cc(C(F)(F)F)c(F)cc2F)nc2cc(Oc3ccnc(NC(=O)CN)c3)ccc21] | N~1~-{4-[(2-{[2,4-difluoro-5-(trifluoromethyl)phenyl]amino}-1-methyl-1H-benzimidazol-5-yl)oxy]pyridin-2-yl}glycinamide | 493.4 |
| 418 | 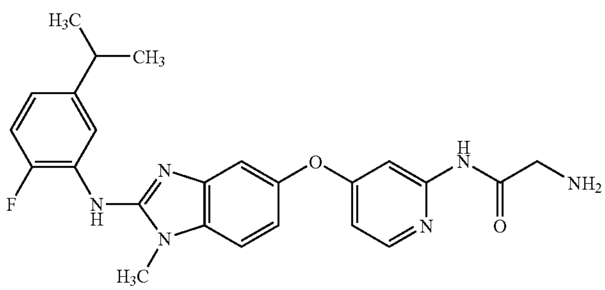 [SMILES: CC(C)c1ccc(F)c(Nc2nc3cc(Oc4ccnc(NC(=O)CN)c4)ccc3n2C)c1] | N~1~-[4-({2-[(2-fluoro-5-isopropylphenyl)amino]-1-methyl-1H-benzimidazol-5-yl}oxy)pyridin-2-yl]glycinamide | 449.5 |
| 419 | 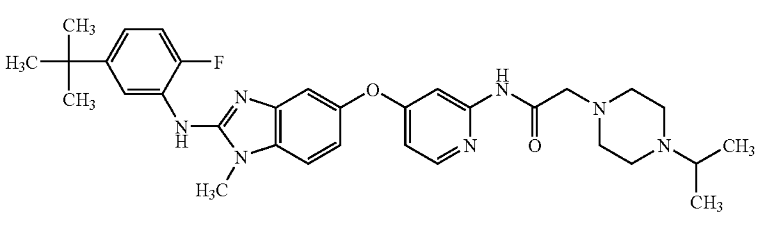 [SMILES: CC(C)N1CCN(CC(=O)Nc2cc(Oc3ccc4c(c3)nc(Nc3cc(C(C)(C)C)ccc3F)n4C)ccn2)CC1] | N-[4-({2-[(5-tert-butyl-2-fluorophenyl)amino]-1-methyl-1H-benzimidazol-5-yl}oxy)pyridin-2-yl]-2-(4-isopropylpiperazin-1-yl)acetamide | 574.7 |
| 420 | 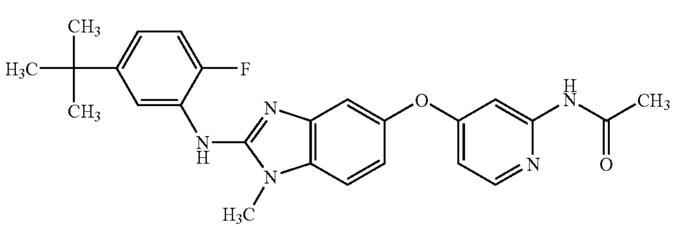 [SMILES: CC(=O)Nc1cc(Oc2ccc3c(c2)nc(Nc2cc(C(C)(C)C)ccc2F)n3C)ccn1] | N-[4-({2-[(5-tert-butyl-2-fluorophenyl)amino]-1-methyl-1H-benzimidazol-5-yl}oxy)pyridin-2-yl]acetamide | 448.5 |

TABLE 1-continued

| Ex. | Structure | Name | MH+ |
|---|---|---|---|
| 421 | 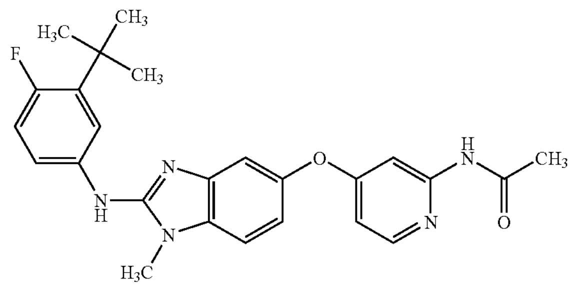 [SMILES: CC(=O)Nc1cc(Oc2ccc3c(c2)nc(Nc2ccc(F)c(C(C)(C)C)c2)n3C)ccn1] | N-[4-({2-[(3-tert-butyl-4-fluoro-phenyl)amino]-1-methyl-1H-benzimidazol-5-yl}oxy)pyridin-2-yl]-acetamide | 448.5 |
| 422 | 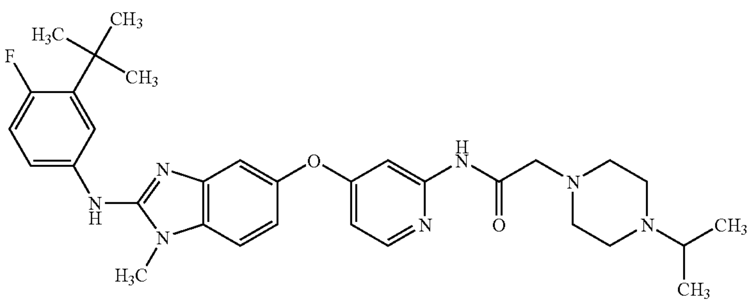 [SMILES: CC(C)N1CCN(CC(=O)Nc2cc(Oc3ccc4c(c3)nc(Nc3ccc(F)c(C(C)(C)C)c3)n4C)ccn2)CC1] | N-[4-({2-[(3-tert-butyl-4-fluoro-phenyl)amino]-1-methyl-1H-benzimidazol-5-yl}oxy)pyridin-2-yl]-2-(4-isopropylpiperazin-1-yl)-acetamide | 574.7 |
| 423 | 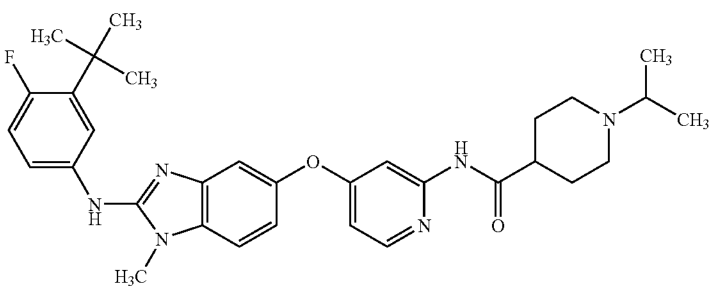 [SMILES: CC(C)N1CCC(C(=O)Nc2cc(Oc3ccc4c(c3)nc(Nc3ccc(F)c(C(C)(C)C)c3)n4C)ccn2)CC1] | N-[4-({2-[(3-tert-butyl-4-fluoro-phenyl)amino]-1-methyl-1H-benzimidazol-5-yl}oxy)pyridin-2-yl]-1-isopropylpiperidine-4-carboxamide | 559.7 |
| 424 | 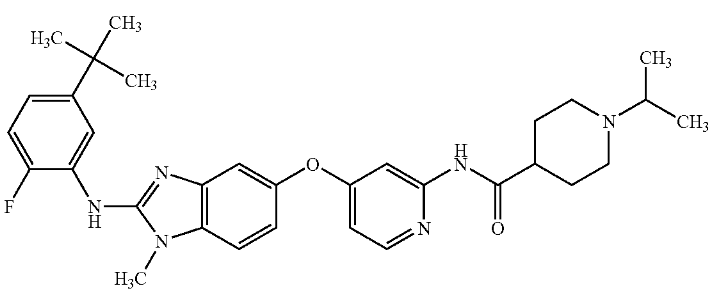 [SMILES: CC(C)N1CCC(C(=O)Nc2cc(Oc3ccc4c(c3)nc(Nc3cc(C(C)(C)C)ccc3F)n4C)ccn2)CC1] | N-[4-({2-[(5-tert-butyl-2-fluoro-phenyl)amino]-1-methyl-1H-benzimidazol-5-yl}oxy)pyridin-2-yl]-1-isopropylpiperidine-4-carboxamide | 559.7 |
| 425 | 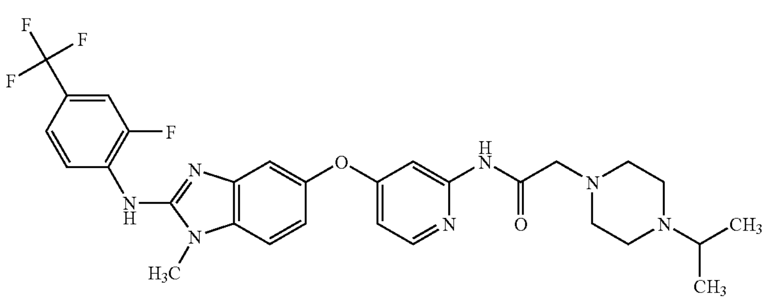 [SMILES: CC(C)N1CCN(CC(=O)Nc2cc(Oc3ccc4c(c3)nc(Nc3ccc(C(F)(F)F)cc3F)n4C)ccn2)CC1] | N-{4-[(2-{[2-fluoro-4-(trifluoro-methyl)phenyl]amino}-1-methyl-1H-benzimidazol-5-yl)oxy]pyridin-2-yl}-2-(4-isopropylpiperazin-1-yl)-acetamide | 586.6 |

TABLE 1-continued

| Ex. | Structure | Name | MH+ |
|---|---|---|---|
| 426 | 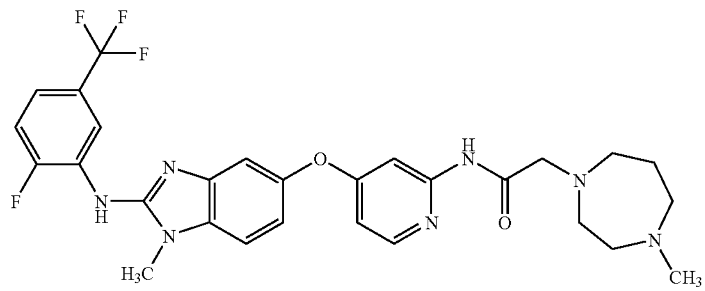 [SMILES: CN1CCCN(CC(=O)Nc2cc(Oc3ccc4c(c3)nc(Nc3cc(C(F)(F)F)ccc3F)n4C)ccn2)CC1] | N-{4-[(2-{[2-fluoro-5-(trifluoromethyl)phenyl]amino}-1-methyl-1H-benzimidazol-5-yl)oxy]pyridin-2-yl}-2-(4-methyl-1,4-diazepan-1-yl)-acetamide | 572.6 |
| 427 | 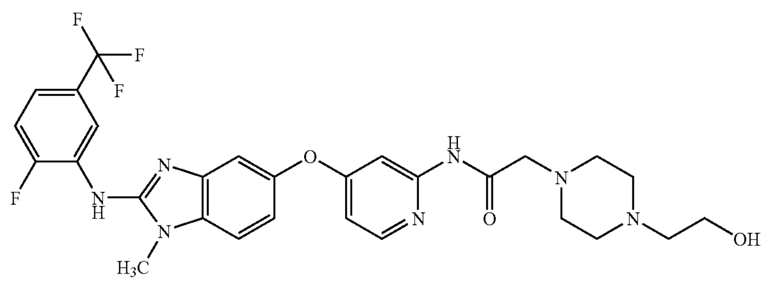 [SMILES: Cn1c(Nc2cc(C(F)(F)F)ccc2F)nc2cc(Oc3ccnc(NC(=O)CN4CCN(CCO)CC4)c3)ccc21] | N-{4-[(2-{[2-fluoro-5-(trifluoromethyl)phenyl]amino}-1-methyl-1H-benzimidazol-5-yl)oxy]pyridin-2-yl}-2-[4-(2-hydroxyethyl)piperazin-1-yl]acetamide | 588.6 |
| 428 | 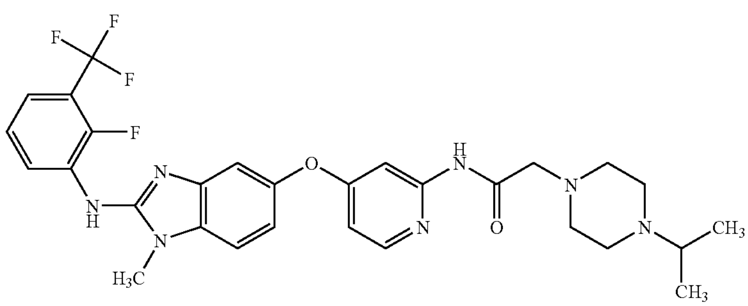 [SMILES: CC(C)N1CCN(CC(=O)Nc2cc(Oc3ccc4c(c3)nc(Nc3cccc(C(F)(F)F)c3F)n4C)ccn2)CC1] | N-{4-[(2-{[2-fluoro-3-(trifluoromethyl)phenyl]amino}-1-methyl-1H-benzimidazol-5-yl)oxy]pyridin-2-yl}-2-(4-isopropylpiperazin-1-yl)-acetamide | 586.6 |
| 429 | 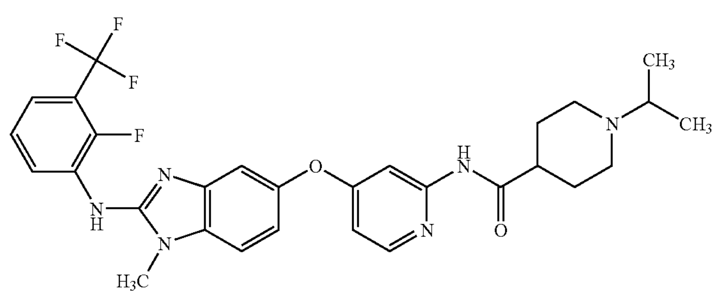 [SMILES: CC(C)N1CCC(C(=O)Nc2cc(Oc3ccc4c(c3)nc(Nc3cccc(C(F)(F)F)c3F)n4C)ccn2)CC1] | N-{4-[(2-{[2-fluoro-3-(trifluoromethyl)phenyl]amino}-1-methyl-1H-benzimidazol-5-yl)oxy]pyridin-2-yl}-1-isopropylpiperidine-4-carboxamide | 571.6 |
| 430 | 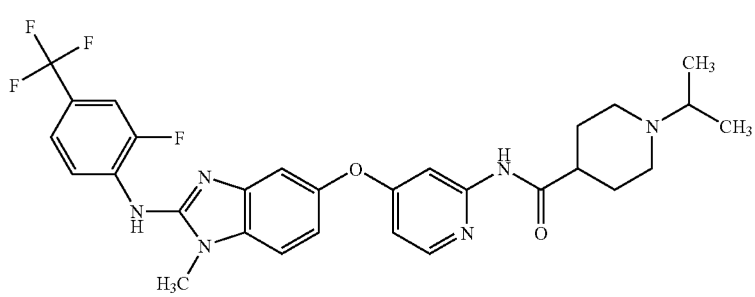 [SMILES: CC(C)N1CCC(C(=O)Nc2cc(Oc3ccc4c(c3)nc(Nc3ccc(C(F)(F)F)cc3F)n4C)ccn2)CC1] | N-{4-[(2-{[2-fluoro-4-(trifluoromethyl)phenyl]amino}-1-methyl-1H-benzimidazol-5-yl)oxy]pyridin-2-yl}-1-isopropylpiperidine-4-carboxamide | 571.6 |

TABLE 1-continued

| Ex. | Structure | Name | MH+ |
|---|---|---|---|
| 431 | 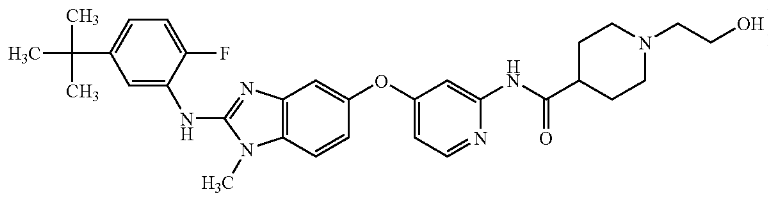 [SMILES: Cn1c(Nc2cc(C(C)(C)C)ccc2F)nc2cc(Oc3ccnc(NC(=O)C4CCN(CCO)CC4)c3)ccc21] | N-[4-({2-[(5-tert-butyl-2-fluoro-phenyl)amino]-1-methyl-1H-benzimidazol-5-yl}oxy)pyridin-2-yl]-1-(2-hydroxyethyl)piperidine-4-carboxamide | 561.7 |
| 432 | 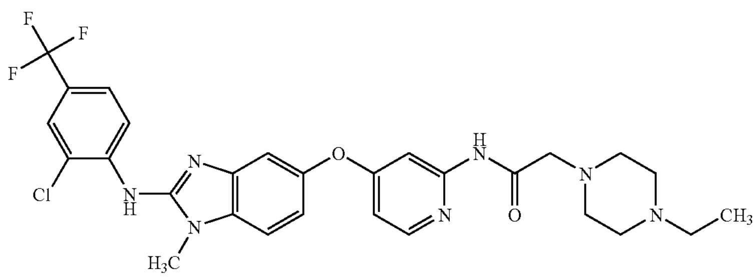 [SMILES: CCN1CCN(CC(=O)Nc2cc(Oc3ccc4c(c3)nc(Nc3ccc(C(F)(F)F)cc3Cl)n4C)ccn2)CC1] | N-{4-[(2-{[2-chloro-4-(trifluoro-methyl)phenyl]amino}-1-methyl-1H-benzimidazol-5-yl)oxy]pyridin-2-yl}-2-(4-ethylpiperazin-1-yl)acetamide | 589 |
| 433 | 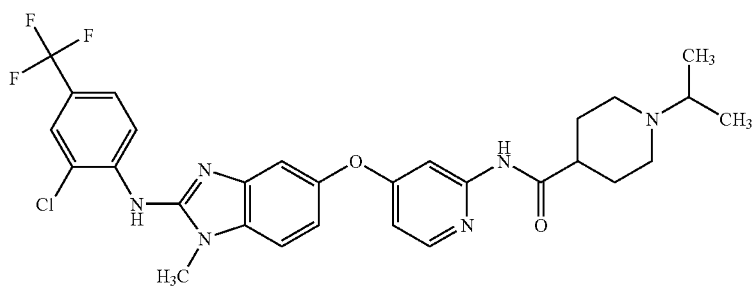 [SMILES: CC(C)N1CCC(C(=O)Nc2cc(Oc3ccc4c(c3)nc(Nc3ccc(C(F)(F)F)cc3Cl)n4C)ccn2)CC1] | N-{4-[(2-{[2-chloro-4-(trifluoro-methyl)phenyl]amino}-1-methyl-1H-benzimidazol-5-yl)oxy]pyridin-2-yl}-1-isopropylpiperidine-4-carboxamide | 588 |
| 434 | 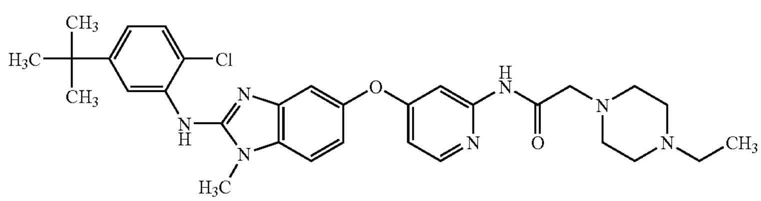 [SMILES: CCN1CCN(CC(=O)Nc2cc(Oc3ccc4c(c3)nc(Nc3cc(C(C)(C)C)ccc3Cl)n4C)ccn2)CC1] | N-[4-({2-[(5-tert-butyl-2-chloro-phenyl)amino]-1-methyl-1H-benzimidazol-5-yl}oxy)pyridin-2-yl]-2-(4-ethylpiperazin-1-yl)acetamide | 577.1 |
| 435 | 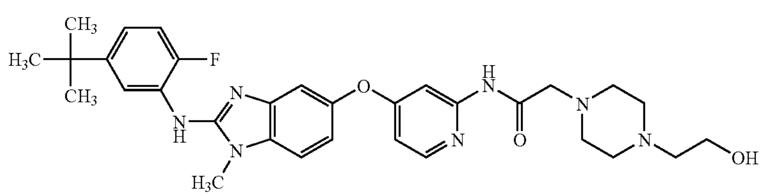 [SMILES: Cn1c(Nc2cc(C(C)(C)C)ccc2F)nc2cc(Oc3ccnc(NC(=O)CN4CCN(CCO)CC4)c3)ccc21] | N-[4-({2-[(5-tert-butyl-2-fluoro-phenyl)amino]-1-methyl-1H-benzimidazol-5-yl}oxy)pyridin-2-yl]-2-[4-(2-hydroxyethyl)piperazin-1-yl]acetamide | 576.7 |
| 436 | 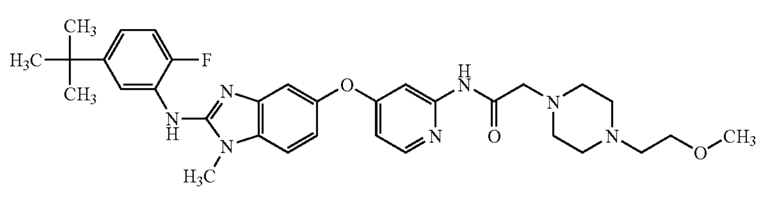 [SMILES: COCCN1CCN(CC(=O)Nc2cc(Oc3ccc4c(c3)nc(Nc3cc(C(C)(C)C)ccc3F)n4C)ccn2)CC1] | N-[4-({2-[(5-tert-butyl-2-fluoro-phenyl)amino]-1-methyl-1H-benzimidazol-5-yl}oxy)pyridin-2-yl]-2-[4-(2-methoxyethyl)piperazin-1-yl]acetamide | 590.7 |

TABLE 1-continued

| Ex. | Structure | Name | MH+ |
|---|---|---|---|
| 437 | 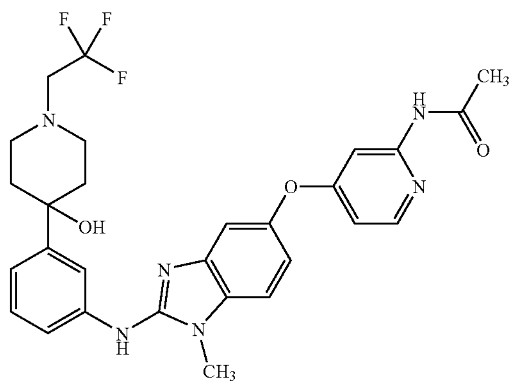 [SMILES: CC(=O)Nc1cc(Oc2ccc3c(c2)nc(Nc2cccc(C4(O)CCN(CC(F)(F)F)CC4)c2)n3C)ccn1] | N-(4-{[2-({3-[4-hydroxy-1-(2,2,2-trifluoroethyl)piperidin-4-yl]-phenyl}amino)-1-methyl-1H-benzimidazol-5-yl]oxy}pyridin-2-yl)-acetamide | 555.5 |
| 438 | 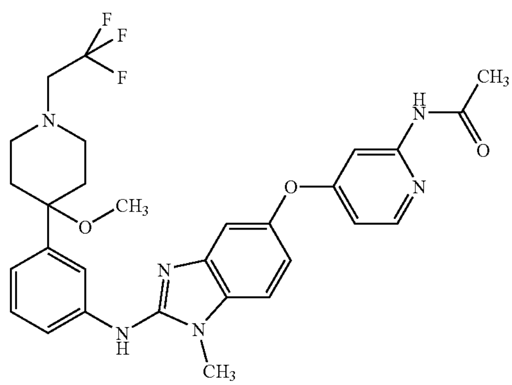 [SMILES: COC1(c2cccc(Nc3nc4cc(Oc5ccnc(NC(C)=O)c5)ccc4n3C)c2)CCN(CC(F)(F)F)CC1] | N-(4-{[2-({3-[4-methoxy-1-(2,2,2-trifluoroethyl)piperidin-4-yl]-phenyl}amino)-1-methyl-1H-benzimidazol-5-yl]oxy}pyridin-2-yl)-acetamide | 569.5 |
| 439 | 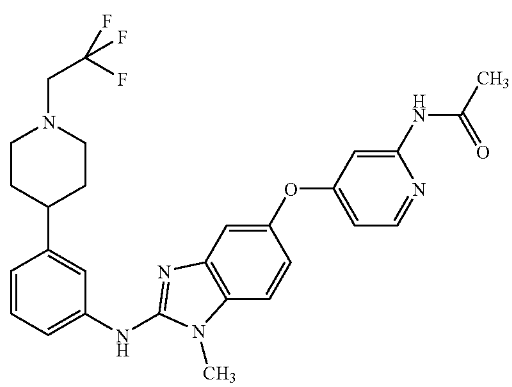 [SMILES: CC(=O)Nc1cc(Oc2ccc3c(c2)nc(Nc2cccc(C4CCN(CC(F)(F)F)CC4)c2)n3C)ccn1] | N-(4-{[1-methyl-2-({3-[1-(2,2,2-trifluoroethyl)piperidin-4-yl]-phenyl}amino)-1H-benzimidazol-5-yl]oxy}pyridin-2-yl)acetamide | 539.6 |
| 440 | 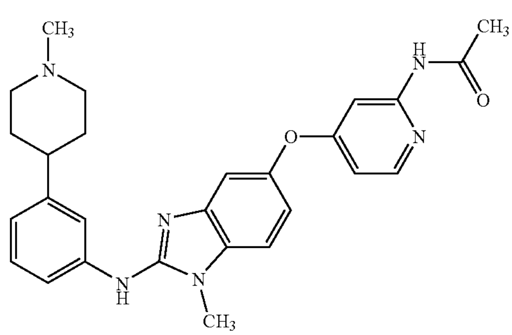 [SMILES: CC(=O)Nc1cc(Oc2ccc3c(c2)nc(Nc2cccc(C4CCN(C)CC4)c2)n3C)ccn1] | N-{4-[(1-methyl-2-{[3-(1-methyl-piperidin-4-yl)phenyl]amino}-1H-benzimidazol-5-yl)oxy]pyridin-2-yl}acetamide | 471.6 |

TABLE 1-continued

| Ex. | Structure | Name | MH+ |
|---|---|---|---|
| 441 | 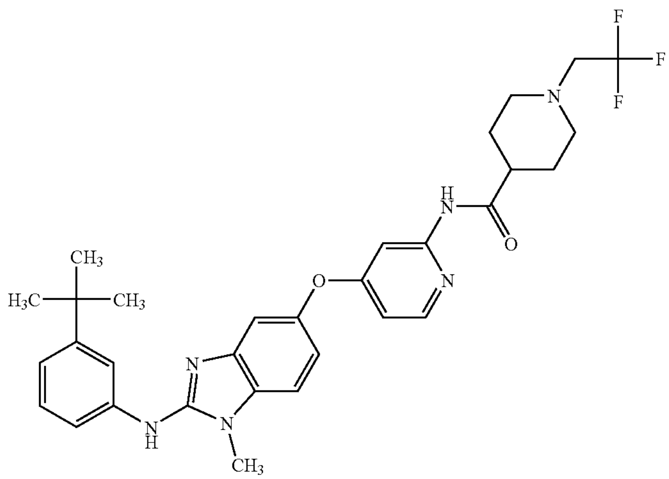 [SMILES: Cn1c(Nc2cccc(C(C)(C)C)c2)nc2cc(Oc3ccnc(NC(=O)C4CCN(CC(F)(F)F)CC4)c3)ccc21] | N-[4-({2-[(3-tert-butylphenyl)amino]-1-methyl-1H-benzimidazol-5-yl}-oxy)pyridin-2-yl]-1-(2,2,2-trifluoro-ethyl)piperidine-4-carboxamide | 581.7 |
| 442 | 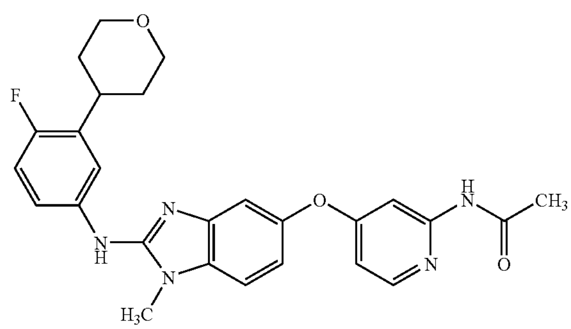 [SMILES: CC(=O)Nc1cc(Oc2ccc3c(c2)nc(Nc2ccc(F)c(C4CCOCC4)c2)n3C)ccn1] | N-[4-({2-[(4-fluoro-3-tetrahydro-2H-pyran-4-ylphenyl)amino]-1-methyl-1H-benzimidazol-5-yl}oxy)pyridin-2-yl]acetamide | 476.3 |
| 443 | 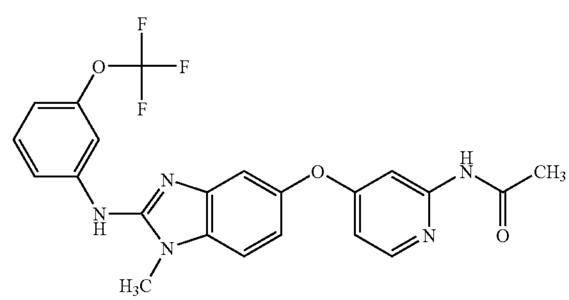 [SMILES: CC(=O)Nc1cc(Oc2ccc3c(c2)nc(Nc2cccc(OC(F)(F)F)c2)n3C)ccn1] | N-{4-[(1-methyl-2-{[3-(trifluoro-methoxy)phenyl]amino}-1H-benzimidazol-5-yl)oxy]pyridin-2-yl}-acetamide | 458.3 |
| 444 | 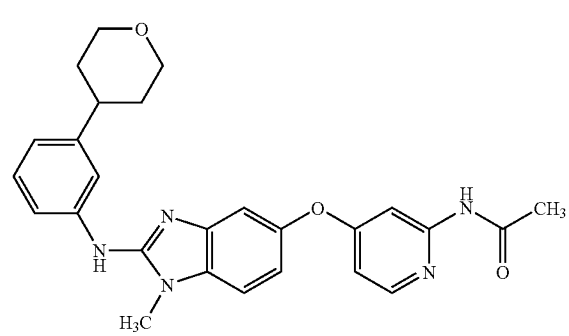 [SMILES: CC(=O)Nc1cc(Oc2ccc3c(c2)nc(Nc2cccc(C4CCOCC4)c2)n3C)ccn1] | N-[4-({1-methyl-2-[(3-tetrahydro-2H-pyran-4-ylphenyl)amino]-1H-benzimidazol-5-yl}oxy)pyridin-2-yl]-acetamide | 458.3 |

TABLE 1-continued

| Ex. | Structure | Name | MH+ |
|---|---|---|---|
| 445 | Chiral | (3R)-1-isopropyl-N-{4-[(1-methyl-2-{[4-(trifluoromethyl)phenyl]amino}-1H-benzimidazol-5-yl)oxy]pyridin-2-yl}pyrrolidine-3-carboxamide | 359.6 |
| 446 | Chiral | (3R)-N-[4-({2-[(4-fluoro-3-isopropylphenyl)amino]-1-methyl-1H-benzimidazol-5-yl}oxy)pyridin-2-yl]-1-isopropylpyrrolidine-3-carboxamide | 531.2 |
| 447 | Chiral | (3R)-N-[4-({2-[(2-fluoro-5-isopropylphenyl)amino]-1-methyl-1H-benzimidazol-5-yl}oxy)pyridin-2-yl]-1-isopropylpyrrolidine-3-carboxamide | 531.2 |
| 448 | Chiral | (3R)-N-[4-({2-[(5-tert-butyl-2-fluorophenyl)amino]-1-methyl-1H-benzimidazol-5-yl}oxy)pyridin-2-yl]-1-isopropylpyrrolidine-3-carboxamide | 545.2 |
| 449 | Chiral | (3R)-N-{4-[(2-{[2-fluoro-5-(trifluoromethyl)phenyl]amino}-1-methyl-1H-benzimidazol-5-yl)oxy]pyridin-2-yl}-1-isopropylpyrrolidine-3-carboxamide | 557.1 |

TABLE 1-continued

| Ex. | Structure | Name | MH+ |
|---|---|---|---|
| 450 | 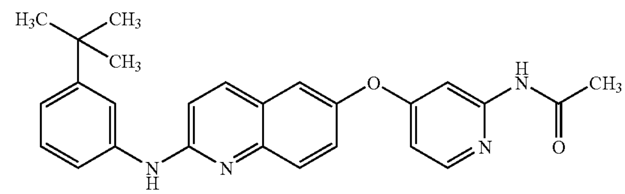 [SMILES: CC(=O)Nc1cc(Oc2ccc3nc(Nc4cccc(C(C)(C)C)c4)ccc3c2)ccn1] | N-[4-({2-[(3-tert-butylphenyl)-amino]quinolin-6-yl}oxy)pyridin-2-yl]acetamide | 427.5 |
| 451 | 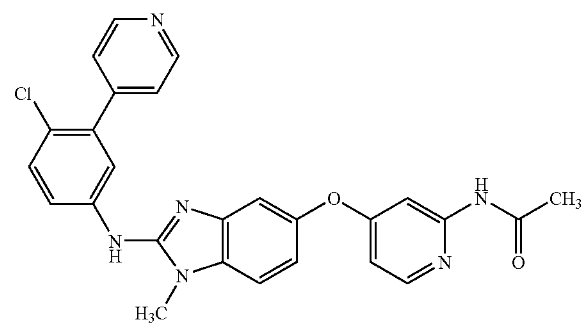 [SMILES: CC(=O)Nc1cc(Oc2ccc3c(c2)nc(Nc2ccc(Cl)c(-c4ccncc4)c2)n3C)ccn1] | N-[4-({2-[(4-chloro-3-pyridin-4-yl)phenyl)amino]-1-methyl-1H-benzimidazol-5-yl}oxy)pyridin-2-yl]acetamide | 485.9 |
| 452 | 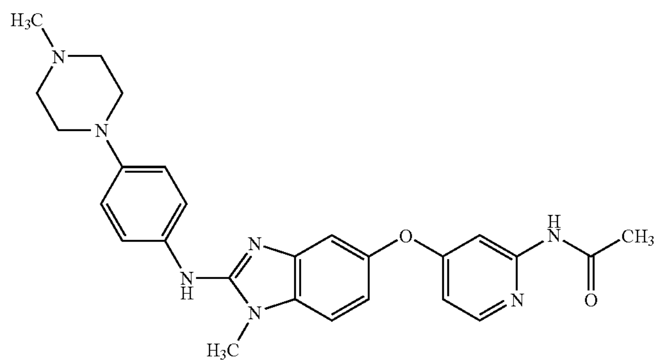 [SMILES: CC(=O)Nc1cc(Oc2ccc3c(c2)nc(Nc2ccc(N4CCN(C)CC4)cc2)n3C)ccn1] | N-{4-[(1-methyl-2-{[4-(4-methylpiperazin-1-yl)phenyl]-amino}-1H-benzimidazol-5-yl)-oxy]pyridin-2-yl}acetamide | 472.6 |
| 453 | 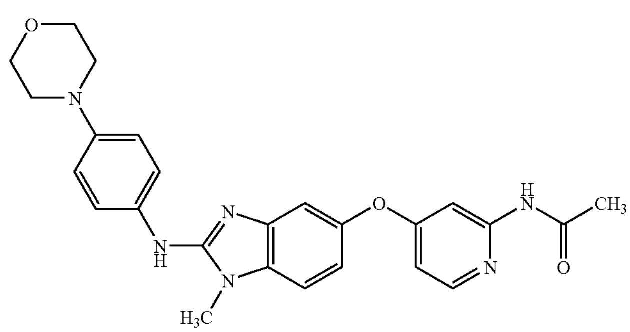 [SMILES: CC(=O)Nc1cc(Oc2ccc3c(c2)nc(Nc2ccc(N4CCOCC4)cc2)n3C)ccn1] | N-[4-({1-methyl-2-[(4-morpholin-4-ylphenyl)amino]-1H-benzimidazol-5-yl}oxy)pyridin-2-yl]acetamide | 459.5 |
| 454 | 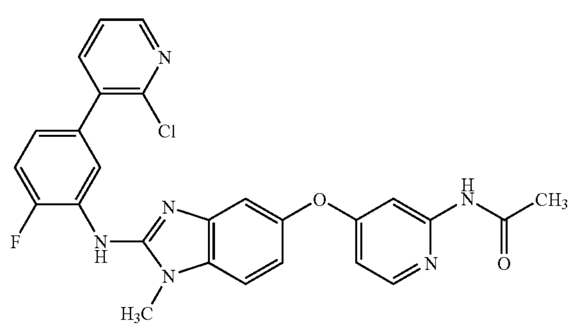 [SMILES: CC(=O)Nc1cc(Oc2ccc3c(c2)nc(Nc2cc(-c4cccnc4Cl)ccc2F)n3C)ccn1] | N-{4-[(2-{[5-(2-chloropyridin-3-yl)-2-fluorophenyl]amino}-1-methyl-1H-benzimidazol-5-yl)-oxy]pyridin-2-yl}acetamide | 503.9 |

TABLE 1-continued

| Ex. | Structure | Name | MH+ |
|---|---|---|---|
| 455 | 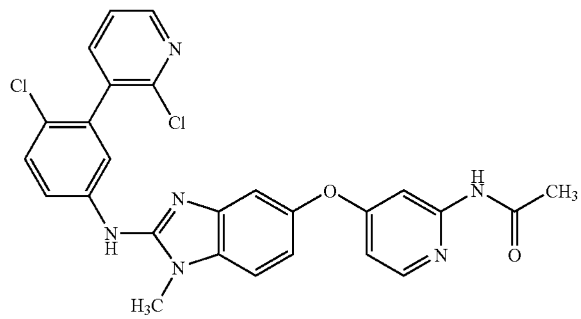 [SMILES: CC(=O)Nc1cc(Oc2ccc3c(c2)nc(Nc2ccc(Cl)c(-c4cccnc4Cl)c2)n3C)ccn1] | N-{4-[(2-{[4-chloro-3-(2-chloro-pyridin-3-yl)phenyl]amino}-1-methyl-1H-benzimidazol-5-yl)oxy]pyridin-2-yl}acetamide | 520.4 |
| 456 | 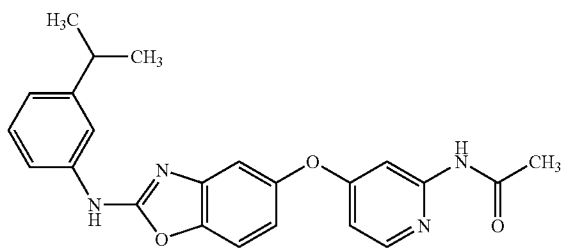 [SMILES: CC(=O)Nc1cc(Oc2ccc3oc(Nc4cccc(C(C)C)c4)nc3c2)ccn1] | N-[4-({2-[(3-isopropylphenyl)-amino]-1,3-benzoxazol-5-yl}-oxy)pyridin-2-yl]acetamide | 403.5 |
| 457 | 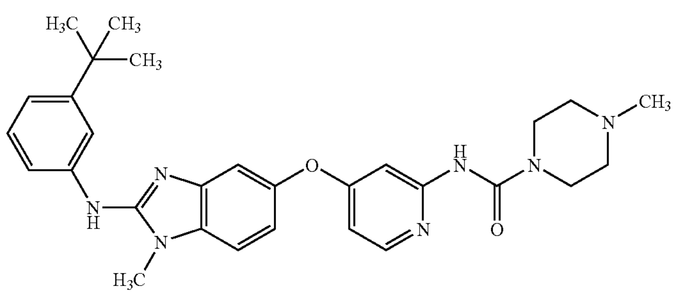 [SMILES: CN1CCN(C(=O)Nc2cc(Oc3ccc4c(c3)nc(Nc3cccc(C(C)(C)C)c3)n4C)ccn2)CC1] | N-[4-({2-[(3-tert-butylphenyl)-amino]-1-methyl-1H-benzimidazol-5-yl}oxy)pyridin-2-yl]-4-methylpiperazine-1-carboxamide | 514.6 |
| 458 | 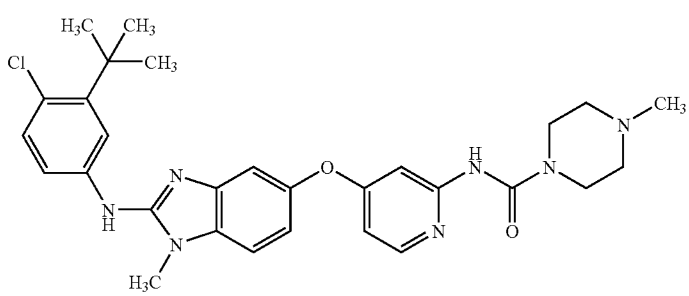 [SMILES: CN1CCN(C(=O)Nc2cc(Oc3ccc4c(c3)nc(Nc3ccc(Cl)c(C(C)(C)C)c3)n4C)ccn2)CC1] | N-[4-({2-[(3-tert-butyl-4-chloro-phenyl)amino]-1-methyl-1H-benzimidazol-5-yl}oxy)pyridin-2-yl]-4-methylpiperazine-1-carboxamide | 549.1 |
| 459 | 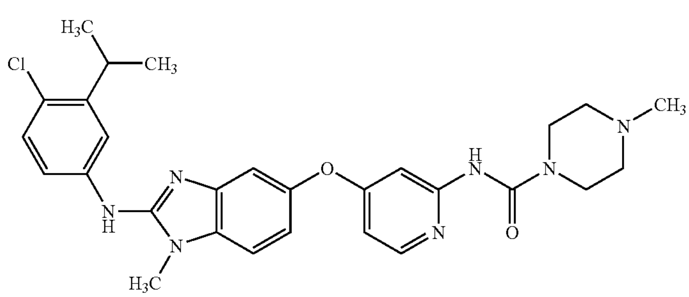 [SMILES: CC(C)c1cc(Nc2nc3cc(Oc4ccnc(NC(=O)N5CCN(C)CC5)c4)ccc3n2C)ccc1Cl] | N-[4-({2-[(4-chloro-3-isopropyl-phenyl)amino]-1-methyl-1H-benzimidazol-5-yl}oxy)pyridin-2-yl]-4-methylpiperazine-1-carboxamide | 535.1 |

TABLE 1-continued

| Ex. | Structure | Name | MH+ |
|---|---|---|---|
| 460 | 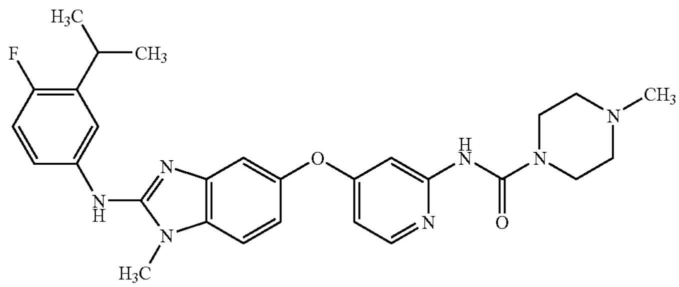 [SMILES: CC(C)c1cc(Nc2nc3cc(Oc4ccnc(NC(=O)N5CCN(C)CC5)c4)ccc3n2C)ccc1F] | N-[4-({2-[(4-fluoro-3-isopropyl-phenyl)amino]-1-methyl-1H-benzimidazol-5-yl}oxy)pyridin-2-yl]-4-methylpiperazine-1-carboxamide | 518.6 |
| 461 | 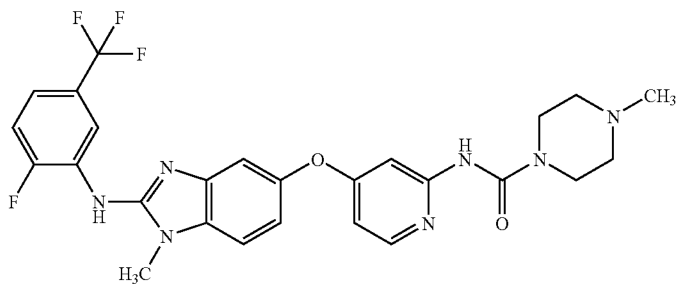 [SMILES: CN1CCN(C(=O)Nc2cc(Oc3ccc4c(c3)nc(Nc3cc(C(F)(F)F)ccc3F)n4C)ccn2)CC1] | N-{4-[(2-{[2-fluoro-5-(trifluoro-methyl)phenyl]amino}-1-methyl-1H-benzimidazol-5-yl)oxy]-pyridin-2-yl}-4-methylpiperazine-1-carboxamide | 544.5 |
| 462 | 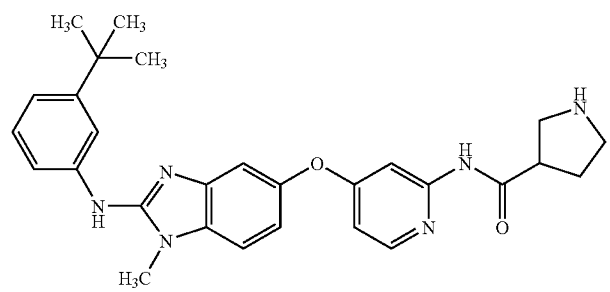 [SMILES: Cn1c(Nc2cccc(C(C)(C)C)c2)nc2cc(Oc3ccnc(NC(=O)C4CCNC4)c3)ccc21] | N-[4-({2-[(3-tert-butylphenyl)-amino]-1-methyl-1H-benzimidazol-5-yl}oxy)pyridin-2-yl]pyrrolidine-3-carboxamide | 485.6 |
| 463 | 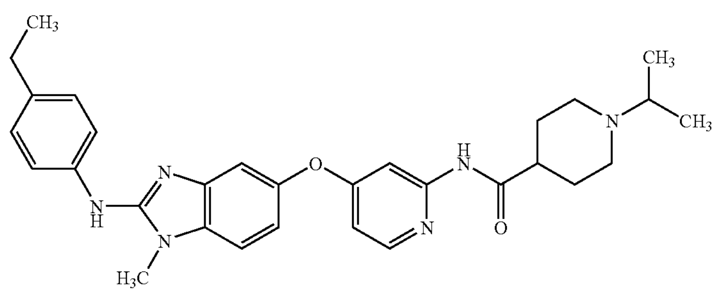 [SMILES: CCc1ccc(Nc2nc3cc(Oc4ccnc(NC(=O)C5CCN(C(C)C)CC5)c4)ccc3n2C)cc1] | N-[4-({2-[(4-ethylphenyl)amino]-1-methyl-1H-benzimidazol-5-yl}oxy)pyridin-2-yl]-1-isopropyl-piperidine-4-carboxamide | 513.7 |
| 464 | 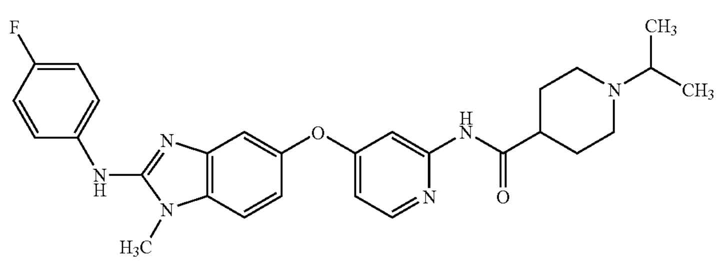 [SMILES: CC(C)N1CCC(C(=O)Nc2cc(Oc3ccc4c(c3)nc(Nc3ccc(F)cc3)n4C)ccn2)CC1] | N-[4-({2-[(4-fluorophenyl)amino]-1-methyl-1H-benzimidazol-5-yl}oxy)pyridin-2-yl]-1-isopropyl-piperidine-4-carboxamide | 503.6 |

TABLE 1-continued

| Ex. | Structure | Name | MH+ |
|---|---|---|---|
| 465 | 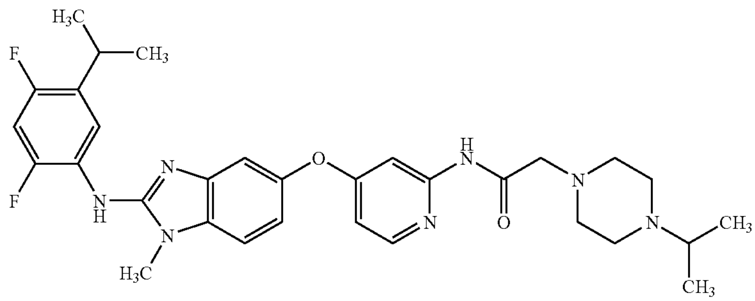 [SMILES: CC(C)c1cc(Nc2nc3cc(Oc4ccnc(NC(=O)CN5CCN(C(C)C)CC5)c4)ccc3n2C)c(F)cc1F] | N-[4-({2-[(2,4-difluoro-5-isopropylphenyl)amino]-1-methyl-1H-benzimidazol-5-yl}-oxy)pyridin-2-yl]-2-(4-isopropyl-piperazin-1-yl)acetamide | 578.7 |
| 466 | 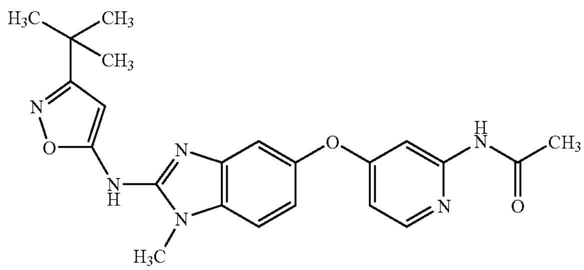 [SMILES: CC(=O)Nc1cc(Oc2ccc3c(c2)nc(Nc2cc(C(C)(C)C)no2)n3C)ccn1] | N-[4-({2-[(3-tert-butylisoxazol-5-yl)amino]-1-methyl-1H-benzimidazol-5-yl}oxy)pyridin-2-yl]acetamide | 421.5 |
| 467 | 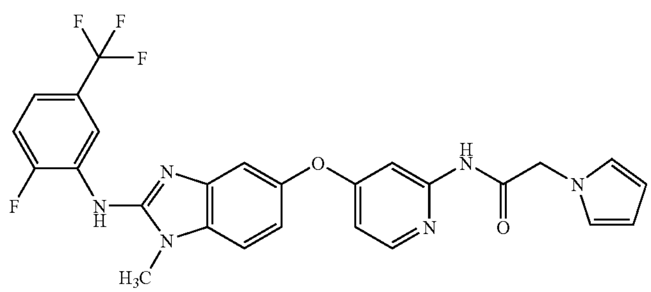 | N-{4-[(2-{[2-fluoro-5-(trifluoro-methyl)phenyl]amino}-1-methyl-1H-benzimidazol-5-yl)oxy]-pyridin-2-yl}-2-(1H-pyrrol-1-yl)-acetamide | 525.5 |
| 468 | 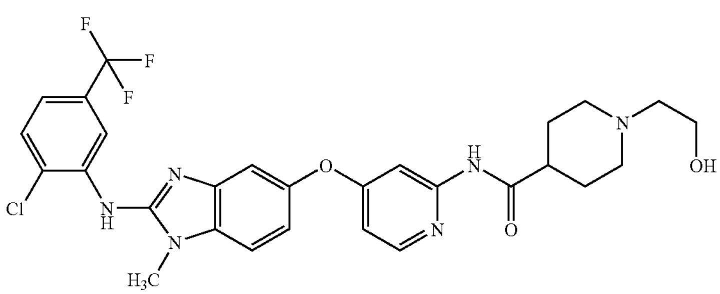 [SMILES: Cn1c(Nc2cc(C(F)(F)F)ccc2Cl)nc2cc(Oc3ccnc(NC(=O)C4CCN(CCO)CC4)c3)ccc21] | N-{4-[(2-{[2-chloro-5-(trifluoro-methyl)phenyl]amino}-1-methyl-1H-benzimidazol-5-yl)oxy]-pyridin-2-yl}-1-(2-hydroxy-ethyl)piperidine-4-carboxamide | 590.0 |
| 469 Chiral | | N-{4-[(2-{[2-fluoro-5-(trifluoro-methyl)phenyl]amino}-1-methyl-1H-benzimidazol-5-yl)oxy]-pyridin-2-yl}-2-[(3R)-3-hydroxy-pyrrolidin-1-yl]acetamide | 545.5 |

TABLE 1-continued

| Ex. | Structure | Name | MH+ |
|---|---|---|---|
| 470 | 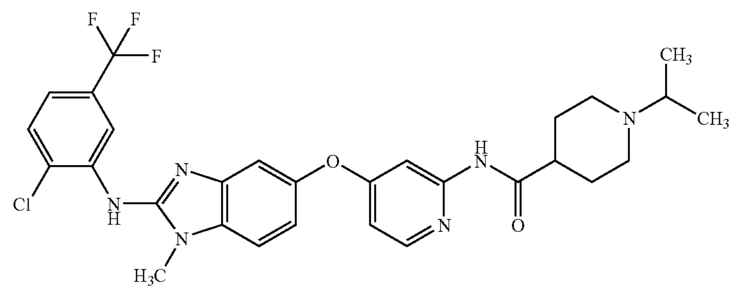 [SMILES: CC(C)N1CCC(C(=O)Nc2cc(Oc3ccc4c(c3)nc(Nc3cc(C(F)(F)F)ccc3Cl)n4C)ccn2)CC1] | N-{4-[(2-{[2-chloro-5-(trifluoro-methyl)phenyl]amino}-1-methyl-1H-benzimidazol-5-yl)oxy]-pyridin-2-yl}-1-isopropyl-piperidine-4-carboxamide | 588.0 |
| 471 | Chiral | 2-[(3R)-3-(dimethylamino)-pyrrolidin-1-yl]-N-{4-[(2-{[2-fluoro-5-(trifluoromethyl)-phenyl]amino}-1-methyl-1H-benzimidazol-5-yl)oxy]pyridin-2-yl}acetamide | 572.6 |
| 472 | 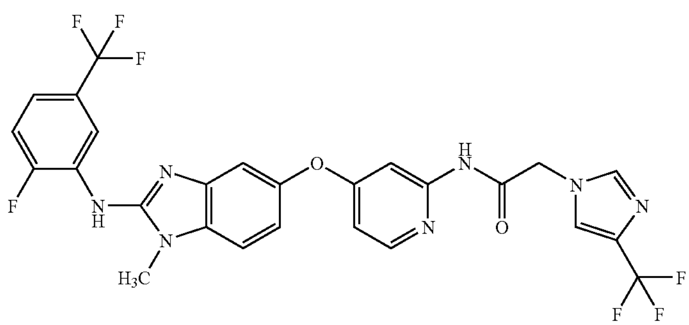 [SMILES: Cn1c(Nc2cc(C(F)(F)F)ccc2F)nc2cc(Oc3ccnc(NC(=O)Cn4cnc(C(F)(F)F)c4)c3)ccc21] | N-{4-[(2-{[2-fluoro-5-(trifluoro-methyl)phenyl]amino}-1-methyl-1H-benzimidazol-5-yl)oxy]-pyridin-2-yl}-2-[4-(trifluoro-methyl)-1H-imidazol-1-yl]-acetamide | 594.5 |
| 473 | 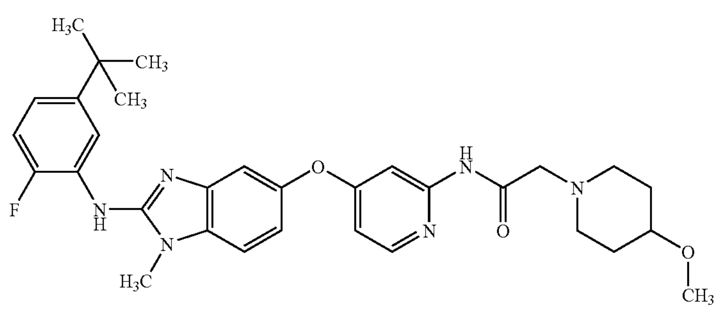 [SMILES: COC1CCN(CC(=O)Nc2cc(Oc3ccc4c(c3)nc(Nc3cc(C(C)(C)C)ccc3F)n4C)ccn2)CC1] | N-[4-({2-[(5-tert-butyl-2-fluoro-phenyl)amino]-1-methyl-1H-benzimidazol-5-yl}oxy)pyridin-2-yl]-2-(4-methoxypiperidin-1-yl)-acetamide | 561.7 |
| 474 | 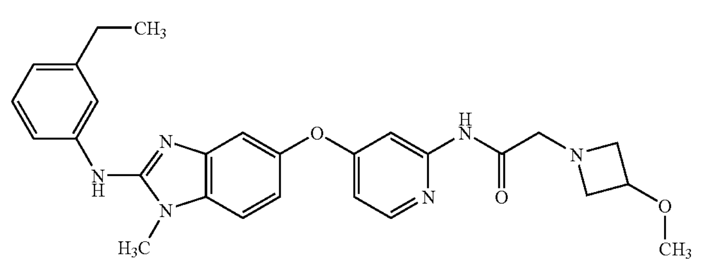 [SMILES: CCc1cccc(Nc2nc3cc(Oc4ccnc(NC(=O)CN5CC(OC)C5)c4)ccc3n2C)c1] | N-[4-({2-[(3-ethylphenyl)amino]-1-methyl-1H-benzimidazol-5-yl}oxy)pyridin-2-yl]-2-(3-methoxyazetidin-1-yl)acetamide | 487,6 |

TABLE 1-continued

| Ex. | Structure | Name | MH+ |
|---|---|---|---|
| 475 | 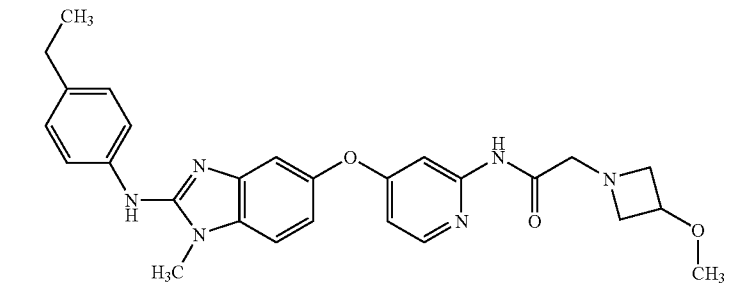 [SMILES: CCc1ccc(Nc2nc3cc(Oc4ccnc(NC(=O)CN5CC(OC)C5)c4)ccc3n2C)cc1] | N-[4-({2-[(4-ethylphenyl)amino]-1-methyl-1H-benzimidazol-5-yl}oxy)pyridin-2-yl]-2-(3-methoxyazetidin-1-yl)acetamide | 487.6 |
| 476 | 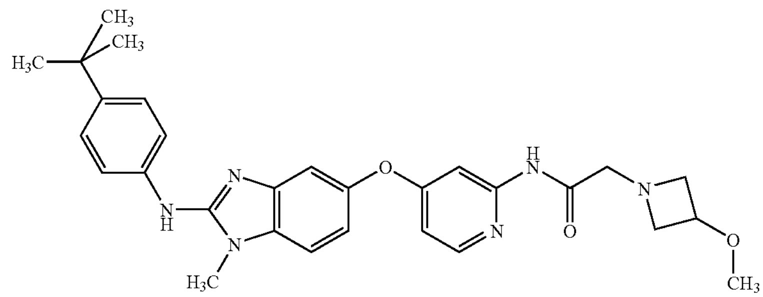 [SMILES: COC1CN(CC(=O)Nc2cc(Oc3ccc4c(c3)nc(Nc3ccc(C(C)(C)C)cc3)n4C)ccn2)C1] | N-[4-({2-[(4-tert-butylphenyl)-amino]-1-methyl-1H-benzimidazol-5-yl}oxy)pyridin-2-yl]-2-(3-methoxyazetidin-1-yl)-acetamide | 515.6 |
| 477 | 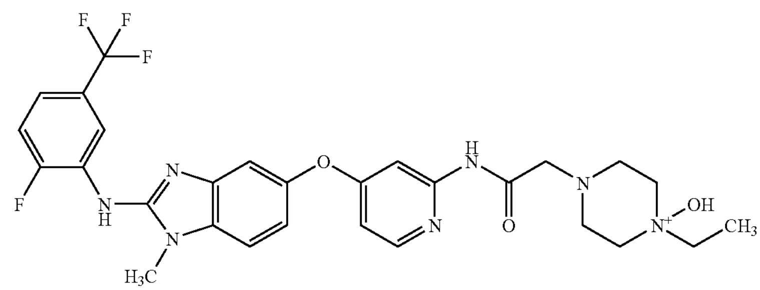 [SMILES: CC[N+]1(O)CCN(CC(=O)Nc2cc(Oc3ccc4c(c3)nc(Nc3cc(C(F)(F)F)ccc3F)n4C)ccn2)CC1] | 1-ethyl-4-[2-({4-[(2-{[2-fluoro-5-(trifluoromethyl)phenyl]amino}-1-methyl-1H-benzimidazol-5-yl)-oxy]pyridin-2-yl}amino)-2-oxoethyl]-1-hydroxypiperazin-1-ium | 589.6 |
| 478 | 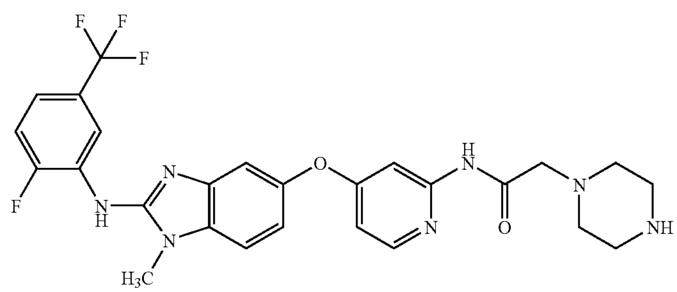 [SMILES: Cn1c(Nc2cc(C(F)(F)F)ccc2F)nc2cc(Oc3ccnc(NC(=O)CN4CCNCC4)c3)ccc21] | N-{4-[(2-{[2-fluoro-5-(trifluoro-methyl)phenyl]amino}-1-methyl-1H-benzimidazol-5-yl)oxy]-pyridin-2-yl}-2-piperazin-1-yl-acetamide | 544.5 |
| 479 | 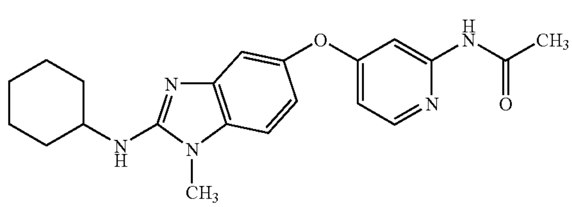 [SMILES: CC(=O)Nc1cc(Oc2ccc3c(c2)nc(NC2CCCCC2)n3C)ccn1] | N-(4-{[2-(cyclohexylamino)-1-methyl-1H-benzimidazol-5-yl]oxy}pyridin-2-yl)acetamide | 380.5 |
| 480 | 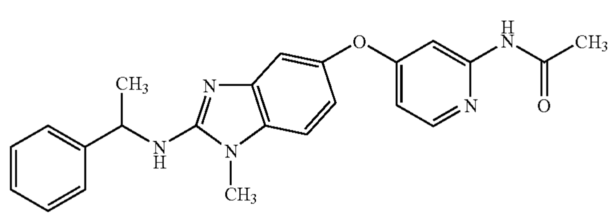 [SMILES: CC(=O)Nc1cc(Oc2ccc3c(c2)nc(NC(C)c2ccccc2)n3C)ccn1] | N-[4-({1-methyl-2-[(1-phenyl-ethyl)amino]-1H-benzimidazol-5-yl}oxy)pyridin-2-yl]acetamide | 402.5 |

TABLE 1-continued

| Ex. | Structure | Name | MH+ |
|---|---|---|---|
| 481 | 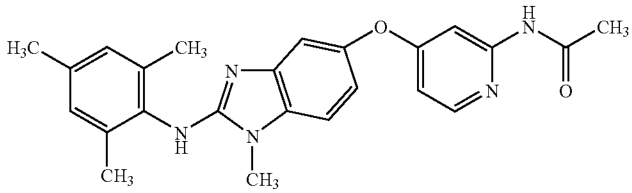 [SMILES: CC(=O)Nc1cc(Oc2ccc3c(c2)nc(Nc2c(C)cc(C)cc2C)n3C)ccn1] | N-(4-{[2-(mesitylamino)-1-methyl-1H-benzimidazol-5-yl]-oxy}pyridin-2-yl)acetamide | 416.5 |
| 482 | 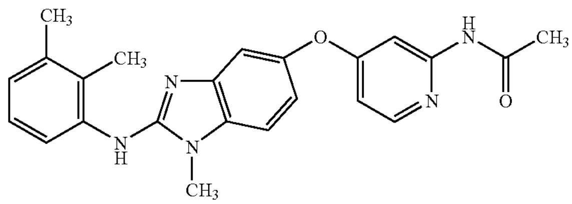 [SMILES: CC(=O)Nc1cc(Oc2ccc3c(c2)nc(Nc2cccc(C)c2C)n3C)ccn1] | N-[4-({2-[(2,3-dimethylphenyl)-amino]-1-methyl-1H-benzimidazol-5-yl}oxy)pyridin-2-yl]acetamide | 402.5 |
| 483 | 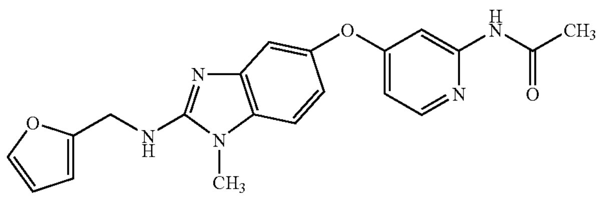 [SMILES: CC(=O)Nc1cc(Oc2ccc3c(c2)nc(NCc2ccco2)n3C)ccn1] | N-[4-({2-[(2-furylmethyl)amino]-1-methyl-1H-benzimidazol-5-yl}oxy)pyridin-2-yl]acetamide | 378.4 |
| 484 | 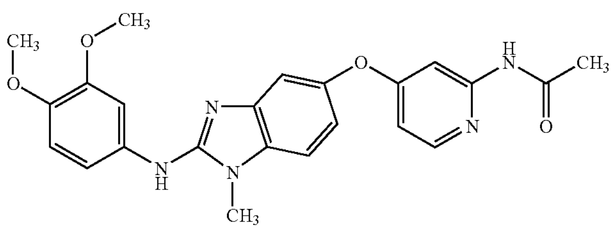 [SMILES: COc1ccc(Nc2nc3cc(Oc4ccnc(NC(C)=O)c4)ccc3n2C)cc1OC] | N-[4-({2-[(3,4-dimethoxyphenyl)-amino]-1-methyl-1H-benzimidazol-5-yl}oxy)pyridin-2-yl]acetamide | 434.5 |
| 485 | 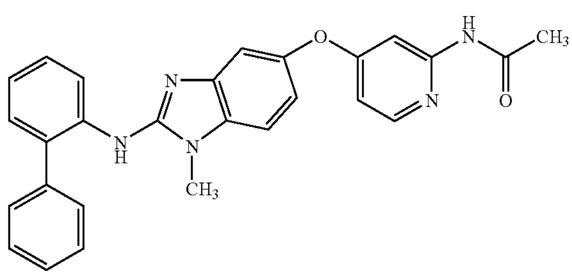 [SMILES: CC(=O)Nc1cc(Oc2ccc3c(c2)nc(Nc2ccccc2-c2ccccc2)n3C)ccn1] | N-(4-{[2-(1,1'-biphenyl-2-yl-amino)-1-methyl-1H-benzimidazol-5-yl]oxy}pyridin-2-yl)acetamide | 450.5 |
| 486 | 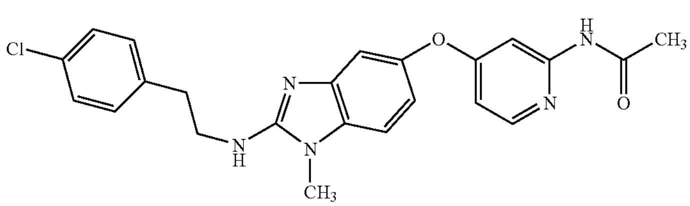 [SMILES: CC(=O)Nc1cc(Oc2ccc3c(c2)nc(NCCc2ccc(Cl)cc2)n3C)ccn1] | N-{4-[(2-{[2-(4-chlorophenyl)-ethyl]amino}-1-methyl-1H-benzimidazol-5-yl)oxy]pyridin-2-yl}acetamide | 436.9 |
| 487 | 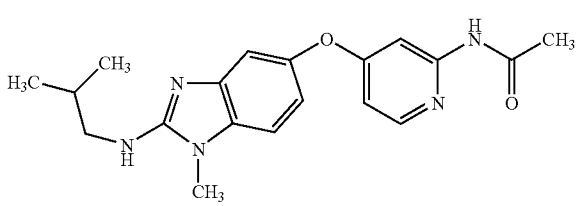 [SMILES: CC(=O)Nc1cc(Oc2ccc3c(c2)nc(NCC(C)C)n3C)ccn1] | N-(4-{[2-(isobutylamino)-1-methyl-1H-benzimidazol-5-yl]-oxy}pyridin-2-yl)acetamide | 354.4 |

TABLE 1-continued

| Ex. | Structure | Name | MH+ |
|---|---|---|---|
| 488 | 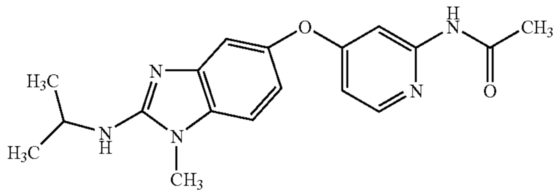 [SMILES: CC(=O)Nc1cc(Oc2ccc3c(c2)nc(NC(C)C)n3C)ccn1] | N-(4-{[2-(isopropylamino)-1-methyl-1H-benzimidazol-5-yl]-oxy}pyridin-2-yl)acetamide | 340.4 |
| 489 | 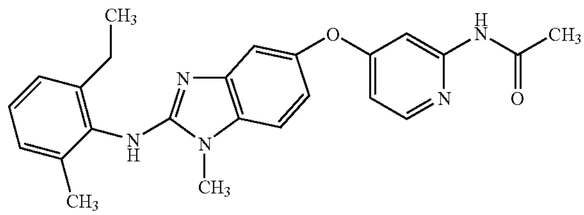 [SMILES: CCc1cccc(C)c1Nc1nc2cc(Oc3ccnc(NC(C)=O)c3)ccc2n1C] | N-[4-({2-[(2-ethyl-6-methyl-phenyl)amino]-1-methyl-1H-benzimidazol-5-yl}oxy)pyridin-2-yl]acetamide | 416.5 |
| 490 | 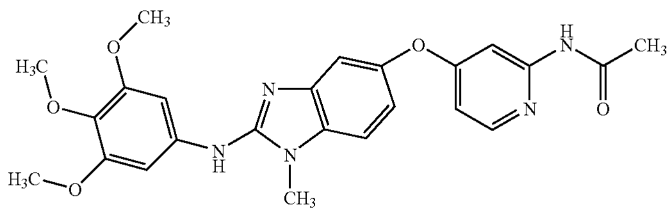 [SMILES: COc1cc(Nc2nc3cc(Oc4ccnc(NC(C)=O)c4)ccc3n2C)cc(OC)c1OC] | N-[4-({1-methyl-2-[(3,4,5-trimethoxyphenyl)amino]-1H-benzimidazol-5-yl}oxy)pyridin-2-yl]acetamide | 464.5 |
| 491 | 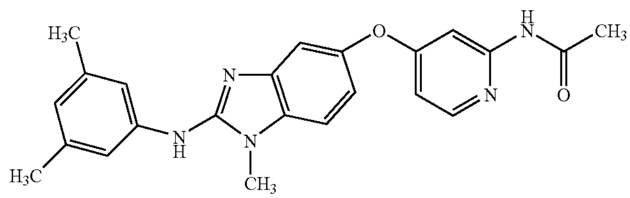 [SMILES: CC(=O)Nc1cc(Oc2ccc3c(c2)nc(Nc2cc(C)cc(C)c2)n3C)ccn1] | N-[4-({2-[(3,5-dimethylphenyl)-amino]-1-methyl-1H-benzimidazol-5-yl}-oxy)pyridin-2-yl]acetamide | 402.5 |
| 492 | 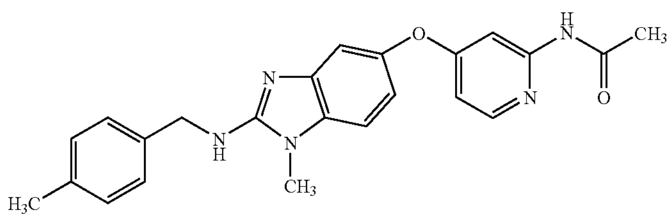 [SMILES: CC(=O)Nc1cc(Oc2ccc3c(c2)nc(NCc2ccc(C)cc2)n3C)ccn1] | N-[4-({1-methyl-2-[(4-methyl-benzyl)amino]-1H-benzimidazol-5-yl}oxy)pyridin-2-yl]acetamide | 402.5 |
| 493 | 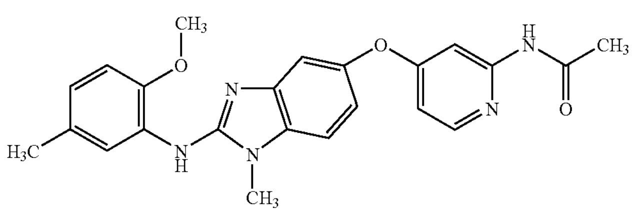 [SMILES: COc1ccc(C)cc1Nc1nc2cc(Oc3ccnc(NC(C)=O)c3)ccc2n1C] | N-[4-({2-[(2-methoxy-5-methyl-phenyl)amino]-1-methyl-1H-benzimidazol-5-yl}oxy)pyridin-2-yl]acetamide | 418.5 |
| 494 | 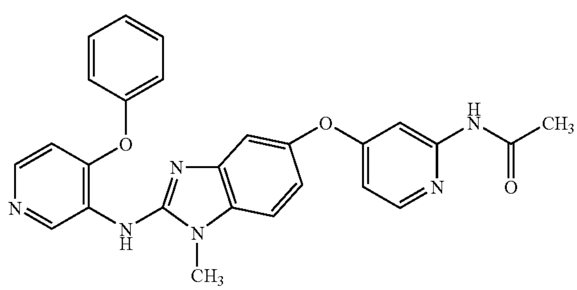 [SMILES: CC(=O)Nc1cc(Oc2ccc3c(c2)nc(Nc2cnccc2Oc2ccccc2)n3C)ccn1] | N-[4-({1-methyl-2-[(4-phenoxy-pyridin-3-yl)amino]-1H-benzimidazol-5-yl}oxy)pyridin-2-yl]acetamide | 467.5 |

TABLE 1-continued

| Ex. | Structure | Name | MH+ |
|---|---|---|---|
| 495 | 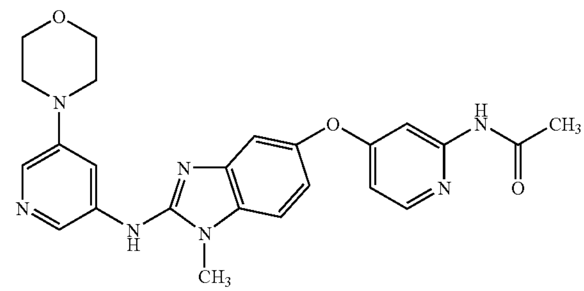 [SMILES: CC(=O)Nc1cc(Oc2ccc3c(c2)nc(Nc2cncc(N4CCOCC4)c2)n3C)ccn1] | N-[4-({1-methyl-2-[(5-morpholin-4-ylpyridin-3-yl)amino]-1H-benzimidazol-5-yl}oxy)pyridin-2-yl]acetamide | 460.5 |
| 496 | 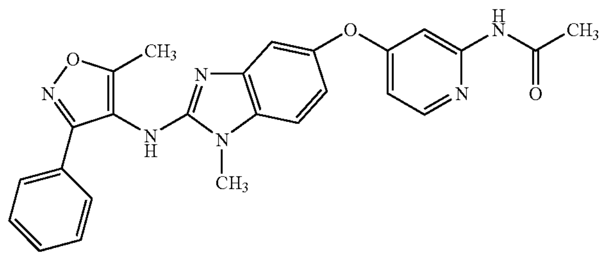 [SMILES: CC(=O)Nc1cc(Oc2ccc3c(c2)nc(Nc2c(-c4ccccc4)noc2C)n3C)ccn1] | N-[4-({1-methyl-2-[(5-methyl-3-phenylisoxazol-4-yl)amino]-1H-benzimidazol-5-yl}oxy)pyridin-2-yl]acetamide | 455.5 |
| 497 | 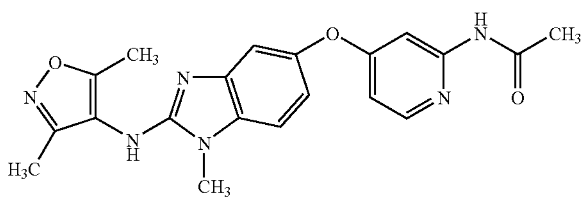 [SMILES: CC(=O)Nc1cc(Oc2ccc3c(c2)nc(Nc2c(C)noc2C)n3C)ccn1] | N-[4-({2-[(3,5-dimethylisoxazol-4-yl)amino]-1-methyl-1H-benzimidazol-5-yl}oxy)pyridin-2-yl]acetamide | 393.4 |
| 498 | 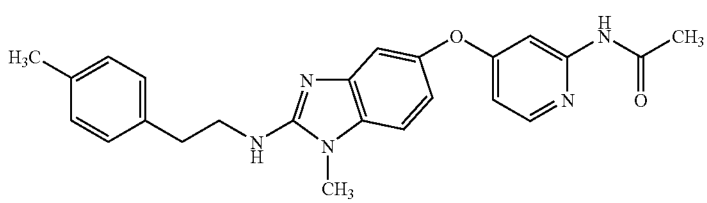 [SMILES: CC(=O)Nc1cc(Oc2ccc3c(c2)nc(NCCc2ccc(C)cc2)n3C)ccn1] | N-{4-[(1-methyl-2-{[2-(4-methylphenyl)ethyl]amino}-1H-benzimidazol-5-yl)oxy]pyridin-2-yl}acetamide | 416.5 |
| 499 | 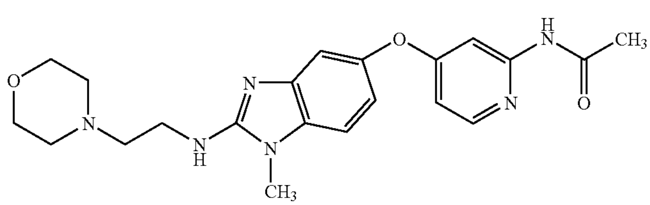 [SMILES: CC(=O)Nc1cc(Oc2ccc3c(c2)nc(NCCN2CCOCC2)n3C)ccn1] | N-[4-({1-methyl-2-[(2-morpholin-4-ylethyl)amino]-1H-benzimidazol-5-yl}oxy)pyridin-2-yl]acetamide | 411.5 |
| 500 | 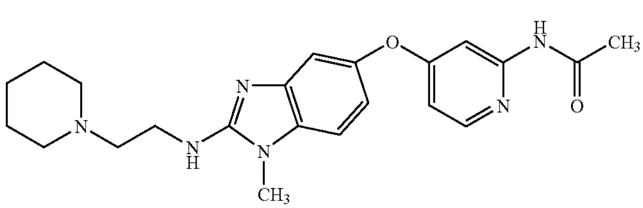 [SMILES: CC(=O)Nc1cc(Oc2ccc3c(c2)nc(NCCN2CCCCC2)n3C)ccn1] | N-[4-({1-methyl-2-[(2-piperidin-1-ylethyl)amino]-1H-benzimidazol-5-yl}oxy)pyridin-2-yl]acetamide | 409.5 |
| 501 | 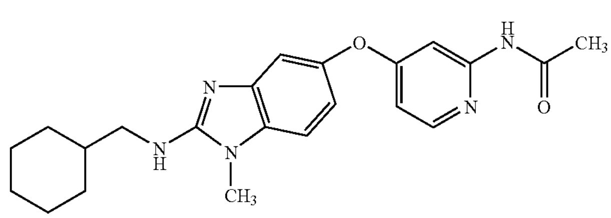 [SMILES: CC(=O)Nc1cc(Oc2ccc3c(c2)nc(NCC2CCCCC2)n3C)ccn1] | N-[4-({2-[(cyclohexylmethyl)amino]-1-methyl-1H-benzimidazol-5-yl}oxy)pyridin-2-yl]acetamide | 394.5 |

TABLE 1-continued

| Ex. | Structure | Name | MH+ |
|---|---|---|---|
| 502 | 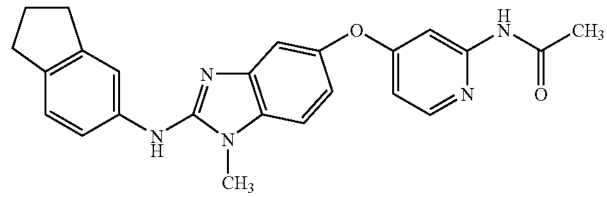 [SMILES: CC(=O)Nc1cc(Oc2ccc3c(c2)nc(Nc2ccc4c(c2)CCC4)n3C)ccn1] | N-(4-{[2-(2,3-dihydro-1H-inden-5-ylamino)-1-methyl-1H-benzimidazol-5-yl]oxy}pyridin-2-yl)acetamide | 414.5 |
| 503 | 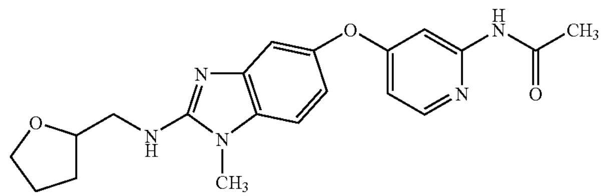 [SMILES: CC(=O)Nc1cc(Oc2ccc3c(c2)nc(NCC2CCCO2)n3C)ccn1] | N-[4-({1-methyl-2-[(tetrahydro-furan-2-ylmethyl)amino]-1H-benzimidazol-5-yl}oxy)pyridin-2-yl]acetamide | 382.4 |
| 504 | 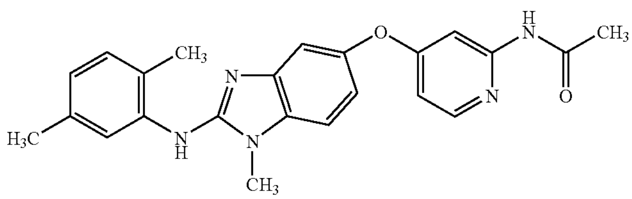 [SMILES: CC(=O)Nc1cc(Oc2ccc3c(c2)nc(Nc2cc(C)ccc2C)n3C)ccn1] | N-[4-({2-[(2,5-dimethylphenyl)-amino]-1-methyl-1H-benzimidazol-5-yl}oxy)pyridin-2-yl]acetamide | 402.5 |
| 505 | 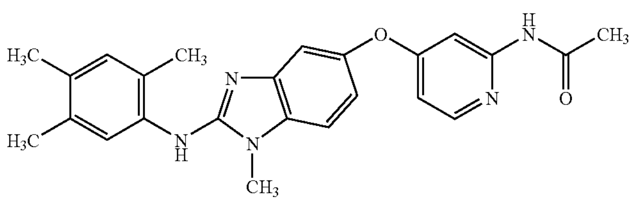 [SMILES: CC(=O)Nc1cc(Oc2ccc3c(c2)nc(Nc2cc(C)c(C)cc2C)n3C)ccn1] | N-[4-({1-methyl-2-[(2,4,5-trimethylphenyl)amino]-1H-benzimidazol-5-yl}oxy)pyridin-2-yl]acetamide | 416.5 |
| 506 | 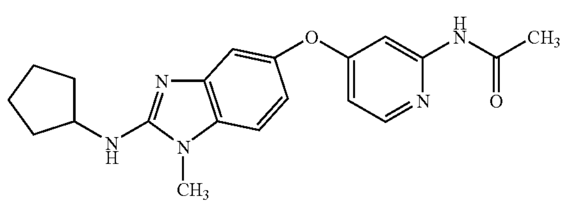 [SMILES: CC(=O)Nc1cc(Oc2ccc3c(c2)nc(NC2CCCC2)n3C)ccn1] | N-(4-{[2-(cyclopentylamino)-1-methyl-1H-benzimidazol-5-yl]oxy}pyridin-2-yl)acetamide | 366.4 |
| 507 | 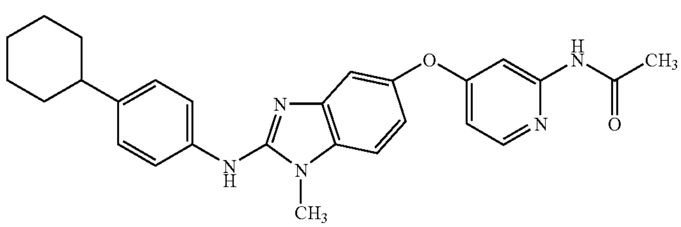 [SMILES: CC(=O)Nc1cc(Oc2ccc3c(c2)nc(Nc2ccc(C4CCCCC4)cc2)n3C)ccn1] | N-[4-({2-[(4-cyclohexylphenyl)-amino]-1-methyl-1H-benzimidazol-5-yl}oxy)pyridin-2-yl]acetamide | 456.6 |
| 508 | 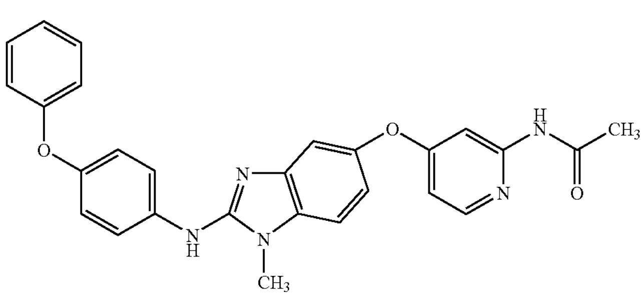 [SMILES: CC(=O)Nc1cc(Oc2ccc3c(c2)nc(Nc2ccc(Oc4ccccc4)cc2)n3C)ccn1] | N-[4-({1-methyl-2-[(4-phenoxy-phenyl)amino]-1H-benzimidazol-5-yl}oxy)pyridin-2-yl]acetamide | 466.5 |

TABLE 1-continued

| Ex. | Structure | Name | MH+ |
| --- | --- | --- | --- |
| 509 | 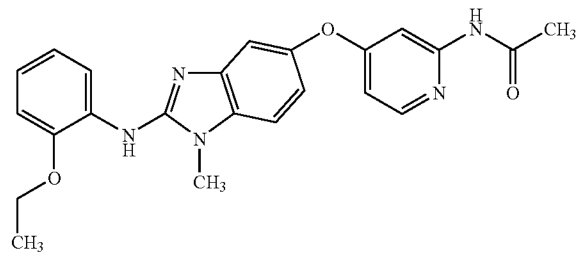 [SMILES: CCOc1ccccc1Nc1nc2cc(Oc3ccnc(NC(C)=O)c3)ccc2n1C] | N-[4-({2-[(2-ethoxyphenyl)-amino]-1-methyl-1H-benzimidazol-5-yl}oxy)pyridin-2-yl]acetamide | 418.5 |
| 510 | 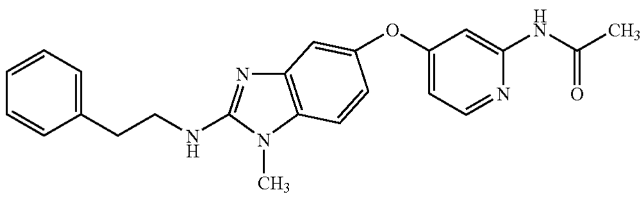 [SMILES: CC(=O)Nc1cc(Oc2ccc3c(c2)nc(NCCc2ccccc2)n3C)ccn1] | N-[4-({1-methyl-2-[(2-phenyl-ethyl)amino]-1H-benzimidazol-5-yl}oxy)pyridin-2-yl]acetamide | 402.5 |
| 511 | 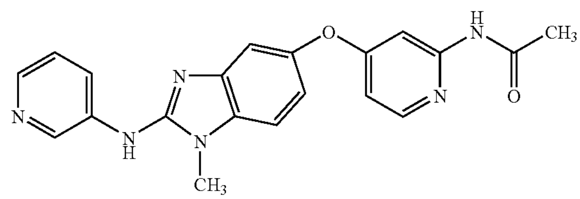 [SMILES: CC(=O)Nc1cc(Oc2ccc3c(c2)nc(Nc2cccnc2)n3C)ccn1] | N-(4-{[1-methyl-2-(pyridin-3-yl-amino)-1H-benzimidazol-5-yl]-oxy}pyridin-2-yl)acetamide | 375.4 |
| 512 | 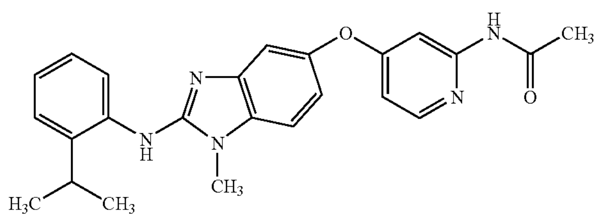 [SMILES: CC(=O)Nc1cc(Oc2ccc3c(c2)nc(Nc2ccccc2C(C)C)n3C)ccn1] | N-[4-({2-[(2-isopropylphenyl)-amino]-1-methyl-1H-benzimidazol-5-yl}oxy)pyridin-2-yl]acetamide | 416.5 |
| 513 | 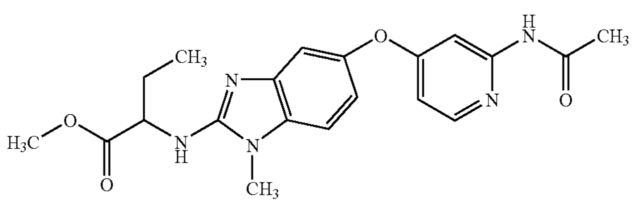 [SMILES: CCC(Nc1nc2cc(Oc3ccnc(NC(C)=O)c3)ccc2n1C)C(=O)OC] | methyl 2-[(5-{[2-(acetylamino)pyridin-4-yl]oxy}-1-methyl-1H-benzimidazol-2-yl)amino]butanoate | 398.4 |
| 514 | 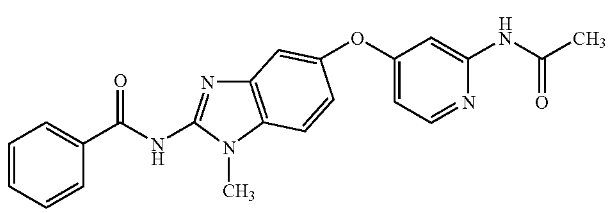 [SMILES: CC(=O)Nc1cc(Oc2ccc3c(c2)nc(NC(=O)c2ccccc2)n3C)ccn1] | N-(5-{[2-(acetylamino)pyridin-4-yl]oxy}-1-methyl-1H-benzimidazol-2-yl)benzamide | 402.4 |
| 515 | 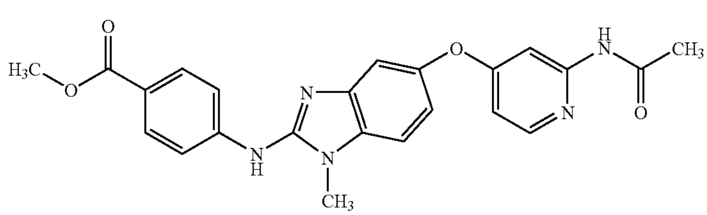 [SMILES: COC(=O)c1ccc(Nc2nc3cc(Oc4ccnc(NC(C)=O)c4)ccc3n2C)cc1] | methyl 4-[(5-{[2-(acetylamino)-pyridin-4-yl]oxy}-1-methyl-1H-benzimidazol-2-yl)amino]-benzoate | 432.4 |

EXAMPLE 516

Raf/Mek Filtration Assay

Buffers
Assay buffer: 50 mM Tris, pH 7.5, 15 mM MgCl$_2$, 0.1 mM EDTA, 1 mM DTT
Wash buffer: 25 mM Hepes, pH 7.4, 50 mM sodium pyrophosphate, 500 mM NaCl
Stop reagent: 30 mM EDTA
Materials

| | |
|---|---|
| Raf, active: | Upstate Biotech #14-352 |
| Mek, inactive: | Upstate Biotech #14-205 |
| $^{33}$P-ATP: | NEN Perkin Elmer #NEG 602 h |
| 96 well assay plates: | Falcon U-bottom polypropylene plates #35-1190 |
| Filter apparatus: | Millipore #MAVM 096 OR |
| 96 well filtration plates: | Millipore Immobilon 1 #MAIP NOB |
| Scintillation fluid: | Wallac OptiPhase "SuperMix" #1200-439 |

Assay Conditions
Raf approximately 120 pM
Mek approximately 60 nM
$^{33}$P-ATP 100 nM
Reaction time 45-60 minutes at room temperature
Assay Protocol
Raf and Mek were combined at 2× final concentrations in assay buffer (50 mM Tris, pH 7.5, 15 mM MgCl$_2$. 0.1 mM EDTA and 1 mM DTT) and dispensed 15 μl per well in polypropylene assay plates (Falcon U-bottom polypropylene 96 well assay plates #35-1190. Background levels are determined in wells containing Mek and DMSO without Raf.

To the Raf/Mek containing wells was added 3 μl of 10× of a raf kinase inhibitor test compound diluted in 100% DMSO. The raf kinase activity reaction was started by the addition of 12 μl per well of 2.5×$^{33}$P-ATP diluted in assay buffer. After 45-60 minutes, the reactions were stopped with the addition of 70 μl of stop reagent (30 mM EDTA). Filtration plates were pre-wetted for 5 min with 70% ethanol, and then rinsed by filtration with wash buffer. Samples (90 μl) from the reaction wells were then transferred to the filtration plates. The filtration plates were washed 6× with wash buffer using Millipore filtration apparatus. The plates were dried and 100 μl per well of scintillation fluid (Wallac OptiPhase "SuperMix" #1200-439) was added. The CPM is then determined using a Wallac Microbeta 1450 reader.

EXAMPLE 517

Assay 2

Biotinylated Raf Screen

In Vitro Raf Screen
The activity of various isoforms of Raf serine/threonine kinases (e.g., c-Raf, B-Raf and mutant B-Raf (V599E); see, for example, "Mechanism of Activation of the RAF-ERK Signaling Pathway by Oncogenic Mutations of B-RAF", *Cell* 116: 855-867 (Mar. 19, 2004); and "Dynamic Changes in C-Raf Phosphorylation and 14-3-3 Protein Binding in Response to Growth Factor Stimulation—Differential Roles Of 14-3-3 Protein Binding Sites", *Journal of Biological Chemistry* 279(14): 14074-14086 (Apr. 2, 2004)) can be measured by providing ATP, MEK substrate, and assaying the transfer of phosphate moiety to the MEK residue. Recombinant isoforms of Raf were obtained by purification from sf9 insect cells infected with a human Raf recombinant baculovirus expression vector. Recombinant kinase inactive MEK was expressed in *E. coli* and labeled with Biotin post purification. For each assay, test compounds were serially diluted in DMSO then mixed with Raf (0.50 nM) and kinase inactive biotin-MEK (50 nM) in reaction buffer plus ATP (1 μM). Reactions were subsequently incubated for 2 hours at room temperature and stopped by the addition of 0.5 M EDTA. Stopped reaction mixture was transferred to a neutradavin-coated plate (Pierce) and incubated for 1 hour. Phosphorylated product was measured with the DELFIA time-resolved fluorescence system (Wallac), using a rabbit anti-p-MEK (Cell Signaling) as the primary antibody and europium labeled anti-rabbit as the secondary antibody. Time resolved fluorescence was read on a Wallac 1232 DELFIA fluorometer. The concentration of each compound for 50% inhibition (IC$_{50}$) was calculated by non-linear regression using XL Fit data analysis software.

Using the procedures of Example 517, the compounds of Examples 1-466, 468-476 and 478 were shown to have a raf kinase inhibitory activity at an IC$_{50}$ of less than 10 μM.

While the preferred embodiments of the invention has been illustrated and described, it will be appreciated that various changes can be made therein without departing from the spirit and scope of the invention.

The embodiments of the invention in which an exclusive property or privilege is claimed are defined as follows:

1. A composition comprising an amount of a compound of formula (I):

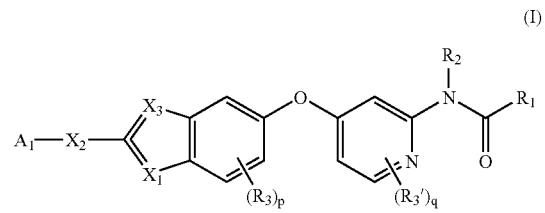

(I)

wherein, X$_1$ and X$_3$ are selected from N and —NR$_4$—, wherein R$_4$ is hydrogen or loweralkyl, provided that one of X$_1$ and X$_3$ must be N and the other of X$_1$ and X$_3$ must be —NR$_4$—;
X$_2$ is —NH— or —(CH$_2$)hd m—, wherein m is 0, 1, 2, 3 or 4;
A$_l$ is substituted or unsubstituted alkyl, cycloalkyl, heterocycloalkyl, aryl, polycyclic aryl, polycyclic arylalkyl, heteroaryl, biaryl, heteroarylaryl, or heteroarylheteroaryl;
R$_1$ is hydrogen or substituted loweralkyl, or substituted or unsubstituted alkoxyalkyl, loweralkyloxy, amino, aminoalkyl, cycloalkyl, heterocycloalkyl, aryl, heteroaryl, alkyloxyalkylheterocycloalkyl, heteroarylalkyl, cycloalkyloweralkyl, heterocycloalkyl -loweralkyl, loweralkylheterocycloalkyl, arylloweralkyl, heteroarylloweralkyl, alkyloxy -alkylheterocycloloweralkyl, or heteroarylloweralkyl;
R$_2$ is hydrogen or loweralkyl;
each R$_3$ and R$_3$' are independently selected from hydrogen, halogen, hydroxy, cyano, loweralkyl, or loweralkoxy; and
p and q are independently 0, 1, 2 or 3; or
a pharmaceutically acceptable salt thereof that is effective to inhibit Raf kinase activity in a human or animal subject when administered thereto, together with a pharmaceutically acceptable carrier.

2. A composition of claim 1 which further comprises at least one additional agent for the treatment of cancer selected from dacarbazine, irinotecan, topotecan, gemcitabine, 5-fluorouracil, leucovorin, carboplatin, cisplatin, taxanes, tezacitabine, cyclophosphamide, vinca alkaloids, imatinib, anthracyclines, rituximab, and trastuzumab.

3. A method for treating a cancer disorder in a human or animal subject, comprising administering to the human or animal subject a composition comprising an amount of a compound of claim 1 effective to inhibit Raf kinase activity in the human or animal subject, wherein said cancer disorder is melanoma, papillary thyroid cancer, cholangiocarcinoma, gallbladder carcinoma, colorectal cancer, pancreatic cancer, chronic myelogenous leukemia, prostate cancer, ovarian cancer, breast cancer, or lung cancer.

4. A method of claim 3 which further comprises administering to the human or animal subject at least one additional agent for the treatment of cancer.

5. A method of claim 4 in which the at least one additional agent for the treatment of cancer is selected from dacarbazine, irinotecan, topotecan, gemcitabine, 5-fluorouracil, leucovorin, carboplatin, cisplatin, taxanes, tezacitabine, cyclophosphamide, vinca alkaloids, imatinib, anthracyclines, rituximab and trastuzumab.

6. The composition of claim 1, wherein $X_1$ of the compound of formula (I) is —$NR_4$—.

7. The composition of claim 6, wherein $R_4$ is hydrogen.

8. The composition of claim 6, wherein $R_4$ is methyl.

9. The composition of claim 1, wherein $X_2$ of the compound of formula (I) is —NH—.

10. The composition of claim 1, wherein $A_1$ of the compound of formula (I) is selected from the group consisting of substituted or unsubstituted phenyl, pyridyl, pyrimidinyl, phenylalkyl, pyridylalkyl, pyrimidinylalkyl, heterocyclylcarbonylphenyl, heterocyclylphenyl, heterocyclylalkylphenyl, chlorophenyl, fluorophenyl, bromophenyl, iodophenyl, dihalophenyl, nitrophenyl, 4-bromophenyl, 4-chlorophenyl, alkylbenzoate, alkoxyphenyl, dialkoxyphenyl, dialkylphenyl, trialkylphenyl, thiophene, thiophene-2-carboxylate, alkylthiophenyl, trifluoromethylphenyl, acetylphenyl, sulfamoylphenyl, biphenyl, cyclohexylphenyl, phenyloxyphenyl, dialkylaminophenyl, alkylbromophenyl, alkylchlorophenyl, alkylfluorophenyl, trifluoromethylchlorophenyl, trifluoromethylbromophenyl indenyl, 2,3-dihydroindenyl, tetralinyl, trifluorophenyl, (trifluoromethyl)thiophenyl, alkoxybiphenyl, morpholinyl, N-piperazinyl, N-morpholinylalkyl, piperazinylalkyl, cyclohexylalkyl, indolyl, 2,3-dihydroindolyl, 1-acetyl-2,3-dihydroindolyl, cycloheptyl, bicyclo[2.2.1] hept-2-yl, hydroxyphenyl, hydroxyalkyiphenyl, pyrrolidinyl, pyrrolidin-l-yl, pyrrolidin-1-ylalkyl, 4- amino(imino)methylphenyl, isoxazolyl, indazolyl, adamantyl, bicyclohexyl, quinuclidinyl, imidazolyl, benzimidazolyl, imidazolylphenyl, phenylimidazolyl, phthalamido, napthyl, benzophenone, anilinyl, anisolyl, quinolinyl, quinolinonyl, phenylsulfonyl, phenylalkylsulfonyl, 9H-fluoren-l-yl, piperidin-l-yl, piperidin-l-ylalkyl, cyclopropyl, cyclopropylalkyl, pyrimidin-5-ylphenyl, quinolidinylphenyl, furanyl, furanylphenyl, N-methylpiperidin-4-yl, 4-diazepan-l-yl, hydroxypyrrolidin-l-yl, dialkylaminopyrrolidin-l-yl, 1,4'- bipiperidin-l'-yl, and (1,4'-bipiperidin-1'-ylcarbonyl)phenyl.

11. The composition of claim 1, wherein $A_1$ of the compound of formula (I) has the structure:

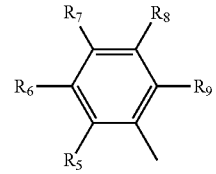

wherein $R_5$, $R_6$, $R_7$, $R_8$ and $R_9$ are independently selected from hydrogen, halo, loweralkyl, cyano, hydroxy, haloloweralkyl, loweralkyloxy, haloloweralkyloxy, loweralkylthio, haloloweralkylthio, and substituted or unsubstituted cycloalkyl, heterocycloalkyl, aryl, and heteroaryl.

12. The composition of claim 11, wherein $R_5$, $R_6$, $R_7$, $R_8$ and $R_9$ are independently selected from hydrogen, chloro, fluoro, methyl, ethyl, propyl, iso-propyl, butyl, tert-butyl, cyano, hydroxy, methyloxy, trifluoromethyl, trifluoromethoxy, trifluoromethylthio, acetyl, and substituted or unsubstituted phenyl, phenyloxy, furyl, tetrahydrofuranyl, tetrahydropyranyl, pyridinyl, trifluoromethylpiperidinyl, thiophenyl, piperazinyl, and morpholinyl.

13. The composition of claim 1, wherein $R_1$ of the compound of formula (I) has the structure:

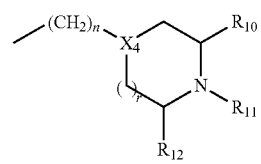

wherein n is 0, 1, 2, 3 or 4;
r is 1 or 2;
$X_4$ is —CH— or N;
$R_{10}$ and $R_{12}$ are independently selected from hydrogen, halo, loweralkyl, haloloweralkyl, hydroxyloweralkyl, loweralkyloxy, haloloweralkyloxy, loweralkylsulfonyl, haloloweralkylsulfonyl, and substituted or unsubstituted cycloalkyl, heterocycloalkyl, aryl, or heteroaryl; and
$R_{11}$ is hydrogen, loweralkyl, haloloweralkyl, hydroxyloweralkyl, loweralkyloxy, haloloweralkyloxy, loweralkyloxyloweralkyl, and substituted or unsubstituted cycloalkyl, heterocycloalkyl, aryl, or heteroaryl.

14. The composition of claim 13, wherein n of the compound of formula (I) is 1.

15. The composition of claim 13, wherein $R_{10}$ and $R_{12}$ of the compound of formula (I) are hydrogen or loweralkyl.

16. The composition of claim 13, wherein $R_{11}$ of the compound of formula (I) is loweralkyl.

* * * * *